US007449544B2

(12) United States Patent
Zheleva et al.

(10) Patent No.: US 7,449,544 B2
(45) Date of Patent: Nov. 11, 2008

(54) P21 PEPTIDES

(75) Inventors: Daniella I. Zheleva, Dundee (GB);
Peter Martin Fischer, Angus (GB);
Campbell McInnes, Dundee (GB);
Martin J. I. Andrews, Dundee (GB);
Weng C. Chan, Nottingham (GB); Gail E. Atkinson, Beverley (GB)

(73) Assignee: Cyclacel Limited, London (GB)

( * ) Notice: Subject to any disclaimer, the term of this patent is extended or adjusted under 35 U.S.C. 154(b) by 1 day.

(21) Appl. No.: 10/441,952

(22) Filed: May 19, 2003

(65) Prior Publication Data

US 2004/0176301 A1    Sep. 9, 2004

Related U.S. Application Data

(63) Continuation-in-part of application No. 09/726,470, filed on Nov. 29, 2000.

(30) Foreign Application Priority Data

Nov. 30, 1999  (GB) ................................. 9928323.6

(51) Int. Cl.
*C07K 5/12* (2006.01)
*C07K 5/02* (2006.01)
*C07K 1/00* (2006.01)
*C07K 1/107* (2006.01)
*A61K 38/12* (2006.01)

(52) U.S. Cl. ............................. 530/317; 514/9; 514/11; 530/332; 530/333; 530/345

(58) Field of Classification Search ....................... None
See application file for complete search history.

(56) References Cited

U.S. PATENT DOCUMENTS

| | | | | |
|---|---|---|---|---|
| 4,536,397 | A * | 8/1985 | Okumura et al. | 514/11 |
| 4,639,434 | A * | 1/1987 | Wenger et al. | 514/11 |
| 5,028,588 | A * | 7/1991 | Hoffman et al. | 514/6 |
| 5,240,910 | A * | 8/1993 | Lam et al. | 514/11 |
| 5,780,221 | A * | 7/1998 | Schumacher et al. | 435/5 |
| 5,811,512 | A * | 9/1998 | Hirschmann et al. | 530/311 |
| 5,837,684 | A * | 11/1998 | Orning et al. | 514/15 |
| 5,916,872 | A * | 6/1999 | Chang et al. | 514/9 |
| 5,962,408 | A * | 10/1999 | Orning et al. | 514/11 |
| 6,261,569 | B1 * | 7/2001 | Comis et al. | 424/204.1 |
| 2002/0142966 | A1 * | 10/2002 | Bair et al. | 514/16 |
| 2003/0036628 | A1 * | 2/2003 | Zheleva et al. | 530/327 |
| 2004/0053849 | A1 * | 3/2004 | Bair et al. | 514/16 |
| 2004/0077549 | A1 * | 4/2004 | Bair et al. | 514/16 |
| 2005/0153894 | A1 | 7/2005 | Zheleva et al. | |

FOREIGN PATENT DOCUMENTS

| | | |
|---|---|---|
| GB | 9928323.6 | 11/1999 |
| WO | WO-96/14334 A1 | 5/1996 |
| WO | WO-96/35715 A2 | 11/1996 |
| WO | WO-97/42222 A1 | 11/1997 |

OTHER PUBLICATIONS

Adams, Peter D., et al., "Identification of Cyclin-cdk2 Recognition Motif Present in Substrates and p21-Like Cyclin-Dependent Kinase Inhibitors," *Molecular and Cellular Biology*, vol. 16(12):6623-6633 (1996).
Adams, Peter D., et al., "Retinoblastoma Protein Contains a C-terminal Motif That Targets It for a Phosphorylation by Cyclin-cdk Complexes," *Molecular and Cellular Biology*, vol. 19(2):1068-1080 (1999).
Ball, Kathryn L., et al., "Cell-cycle arrest and inhibition of Cdk4 activity by small peptides based on the carboxy-terminal domain of p21$^{WAF1}$," *Current Biology*, vol. 7:71-80 (1996).
Bonfanti, Marina, et al., "p21$^{WAF1}$-derived Peptides Linked to an Internalization Peptide Inhibit Human Cancer Cell Growth," *Cancer Research*, vol. 57:1442-1446 (1997).
Brown, Nick R., et al., "The structural basis for specificity of substrate and recruitment peptides for cyclin-dependent kinases," *Nature Cell Biology*, vol. 1:438-443 (1999).
Chen, Junjie, et al., "Cyclin-Binding Motifs Are Essential for the Function of p21$^{CIP1}$," *Molecular and Cellular Biology*, vol. 16(9):4673-4682 (1996).
Chen, Ying-Nan P., et al., "Selective killing of transformed cells by cyclin/cyclin-dependent kinase 2 antagonists," *Proc. Natl. Acad. Sci. USA*, vol. 96:4325-4329 (1999).
Lin, Jiayuh, et al., Analysis of Wild-Type and Mutant p21$^{WAF-1}$ Gene Activities, *Molecular and Cellular Biology*, vol. 16(4):1786-1793 (1996).
Mutoh, Masato, et al., "A p21$^{Waf1/Cip1}$ Carboxyl-terminal Peptide Exhibited Cyclin-dependent Kinase-inhibitory Activity and Cytotoxicity When Introduced into Human Cells," *Cancer Research*, vol. 59:3480-3488 (1999).
Pin, Sokhom S., et al., "Analysis of Protein-Peptide Interaction by a Miniaturized Fluorescence Polarization Assay Using Cyclin-Dependent Kinase 2/Cyclin E as a Model System," *Analytical Biochemistry*, vol. 275:156-161 (1999).
Russo, Alicia A., et al., "Crystal structure of the p27Kip1 cyclin-dependent-kinase inhibitor bound to the cyclin A-Cdk2 complex," *Nature*, vol. 382:325-331 (1996).
Warbick, E., et al., "PCNA binding proteins in Drosophilia melanogaster: the analysis of a conserved PCNA binding domain," *Nucleic Acids Research*, 26(17):3925-3932 (1998).
Database PIR_73, ACS 39358, Feb. 25, 1994.
Database SwissProt_40, AC P38936, Dec. 15, 1995.
Database SPTREMBL_21, AC Q14010, Nov. 1, 1996.
Database PIR_73, AC I54380, Jul. 2, 1996.
Database SwissProt_40, AC O19002, Dec. 15, 1998.

* cited by examiner

*Primary Examiner*—Andrew D Kosar
(74) *Attorney, Agent, or Firm*—Lahive & Cockfield LLP; Giulio A. DeConti, Jr.; Cynthia L. Kanik

(57) ABSTRACT

The present invention relates to p21 derived peptides capable of inhibiting CDK/cyclin complexes, particularly cyclins A or E/CDK2, by modifying the interaction with their substrates. The peptides are derived from a C-terminal region of p21 and display selectivity for cyclin/CDK2 inhibition over cyclin/CDK4 inhibition. Variants of such peptides particularly involving certain alanine replacements are shown to be particularly potent.

9 Claims, 6 Drawing Sheets

P21 PEPTIDES

RELATED APPLICATIONS

This application is a continuation-in-part of U.S. Ser. No. 09/726,470, filed Nov. 29, 2000, and claims priority to Great Britain application Serial No. 9928323.6 filed Nov. 30, 1999, the contents each of which are entirely incorporated by reference.

BACKGROUND OF THE INVENTION

The present invention relates to substances and their therapeutic use, and in particular to specific regions of p21$^{WAF1}$ that bind to G1 and S phase specific cyclins, preferably ones activating CDK2 and to substances and mimetics based on this region. The invention also relates to assay methods and means for identifying substances useful for interfering with protein-protein interactions involving cyclins, particularly CDK/cyclin interactions and preferably capable of inhibiting CDK2 activity.

p21$^{WAF1}$ is an inhibitor of both the G1 cyclin dependent protein kinases (CDKs; which control the progression from G1 into S phase) (Harper et al., 1995) and proliferating cell nuclear antigen (PCNA; an essential DNA-replication factor) (Florez-Rozas et al., 1994; Waga et al., 1994). Thus, inhibition of the function of either CDKs or PCNA provides, in theory, two distinct avenues for drug discovery based on the activity of p21$^{WAF1}$. The PCNA binding function of p21$^{WAF1}$ can be mimicked by a 20-amino acid peptide derived from the C-terminal domain of p21$^{WAF1}$ and this peptide is sufficient partially to inhibit SV40 replication in vitro (Warbrick et al., 1995).

Despite its PCNA binding role, the primary function of the p21$^{WAF1}$ protein as a growth suppressor appears to be inhibition of the G1 cyclin-CDK complexes (Chen et al., 1995; Harper et al., 1995; Luo et al., 1995; Nakanishi et al., 1995b). Luo et al. (1995) reported the N-terminal domain of p21 composed of residues 1-75, to act as a CDK-inhibitor in vitro, inhibiting cyclin E-CDK2.

WO 97/42222 (Cyclacel Ltd) discloses peptide fragments of p21$^{WAF1}$ that interact with CDK4/cyclin D1. Thus it was observed that p21$_{(16-35)}$ and p21$_{(46-65)}$ bind to CDK4 and cyclin D1 respectively. Of these, only p21$_{(16-35)}$ was observed to inhibit CDK activity. p21$_{(141-160)}$ was observed to bind to CDK4 and cyclin D1 and to be a potent inhibitor of CDK4.

This data supported the known phenomenon of peptides including the sequence LFG as being the binding motif essential for the interaction of the p21 family with cyclins [Chen J et al.(1996), Lin J et al. and Russo A A et al.] and the further known properties of the amino-terminal half of p21 as being required for binding to CDK complex.

It should be borne in mind when considering the prior art discussed herein that unless otherwise explicitly stated the references to "motifs" is made with reference to papers that have made deductions and predictions based upon the activity of longer peptides usually consisting of at least 12 amino acids. Thus, the motifs are no more than conjecture based upon the a specific set of reactions. Such motifs provide no indication as to the actual length of peptide or modifications that could be made to retain and/or even enhance activity or specificity.

The sequence p21$_{(141-160)}$ (disclosed in WO97/42222 and Ball K. et al) in respect of cyclin D1/CDK4 inhibition was subjected to analysis in order to determine the minimum length of an inhibitory peptide upon which novel antiproliferative drugs could be designed. Observations of CDK4/cyclin D1 inhibitory activity led to the identification of an inhibitory motif comprising RRLIF (p21$_{(155-159)}$) (SEQ ID No. 5), the bold residues being described as essential for activity and the underlined residue contributing towards inhibitory activity. Further observations in these disclosures include the retention of inhibitory activity against cyclin D1-CDK4 by the peptide KRRLIFSK (p21$_{(154-161)}$) (SEQ ID No. 6) albeit at a concentration 1000 times greater than the parent sequence p21$_{141-160}$ and that the substitution of aspartic acid at position 149 of p21$_{141-160}$ by alanine surprisingly reduced the IC$_{50}$ of the full length peptide from 100 nM to 46 nM. Thus, although identifying the RRLIF (SEQ ID No. 5) motif as being important to cyclinD1/CDK4 inhibition, Ball et al. is inconclusive as to the actual minimum length peptide required for enhanced activity. The effect of the Asp149 to Ala substitution has not proven reproducible.

In summary, WO97/42222 and Ball et al teach that there are sequences within the carboxy terminal region of p21 that are capable of interacting with CDK4/cyclin D in a manner that is inhibitory to CDK4 and further involves specific binding to cyclin D. Though the peptide p21$_{(141-160)}$ is described as being preferred, an 8-mer comprising p21$_{(154-161)}$ (KRRLIFSK) (SEQ ID No. 6) was inhibitory, but at higher concentrations. Finally, alanine replacement at position 149 within p21$_{141-160}$ increased the inhibitory activity.

Thus, although the art indicates that this is an interesting region of p21 to investigate, no guidance is provided as to the identity of further fragments that would be preferably active against CDK4/cyclin D or any other CDK/cyclin enzymes.

Chen J et al. (Mol Cell Biol (1996) 16(9) 4673-4682) disclose a 12-mer corresponding to p21$_{17-24}$ as being a cyclin binding domain of p21. They further identify a less avid cyclin binding region as p21$_{150-161}$. Mutation and inhibition analysis demonstrated that the principal site of interaction with cyclin A was p21$_{17-24}$, being a better inhibitor than p21$_{150-161}$ consistent with its greater avidity for cyclins such that it can be detected by pull-down assay. Interaction of p21$_{150-161}$ could only "be inferred from competition for binding and kinase inhibition assays. The importance of the p21$_{150-161}$ in vivo was questioned due to the possibility of the relevant site being occupied by PCNA.

Adams D A et al. (Mol Cell Biol (1996) 16(12) 6623-6633) discloses N- and C-terminal regions of p21 that putatively bind to CDK2/cyclin. A 14-mer (p21$_{149-162}$) is disclosed as inhibiting the binding of cyclin A to E2F1 and the binding of cyclins A and E to GST-p21. An amino acid sequence containing 8 amino acid residues (PVKRRLDL) (SEQ ID No. 7), derived from the transcription factor E2F1 was shown to bind to cyclin A/E-CDK2 complexes. An alanine scan of the 8-mer identified, on a qualitative level that certain modified forms of the peptide retained this activity. Noteworthy is that deletion or alanine replacement of either terminal amino acid reduced or abolished the ability to compete with GST-E2F1 for cyclin A binding.

In a further paper, Adams D A et al. (Mol Cell Biol (1999) 19(2) 1068-1080) investigated the existence of an E2F1-like motif within pRB as a means to explain its interaction with cyclin A/CDK2. A single 10-mer, pRB869-878 was the shortest pRB derived peptide investigated.

In a subsequent paper, Chen et al. (Proc. Natn. Acad. Sci. (1999) 96, 4325-4329) disclosed two E2F1 derived 8-mers as possessing the ability to interact with the cyclin A/CDK2 complex, being PVKRRLFG (SEQ ID No. 8) and PVKRRLDL (SEQ ID No. 7). These peptides were tested in whole cell assays using membrane translocation carrier peptides HIV-TAT or Penetratin®.

Brown N R et al. (Nature Cell Biol. (1999) 1, 438-443) describe a crystal structure of the cyclin A3/phospho-CDK2 complex with an 11-mer derived from p107 including the RXLF SEQ ID No. 9) motif. Of the 11-mer, the region RRLFGE (SEQ ID No. 10), was found to be within the binding region of cyclin A forming interactions with M210, I213, W217, E220, L253 and Q254.

An aim of the present invention has been to identify further peptides derived from p21 that retain or improve upon the inhibitory activities described in the art, particularly with regard to substrate specificity and peptide chain length as described in detail below.

SUMMARY OF THE INVENTION

A first aspect of the present invention therefore relates to a p21 derived peptide of formula; DFYHSKRRLIF (SEQ ID No. 1) or such a peptide (i) bearing a further amino acid residue at either end; or, (ii) having up to 7 amino acid residues deleted from the N-terminal end; and variants thereof wherein at least one amino acid residue is replaced by an alternative natural or unnatural replacement amino acid residue, with the proviso that the motif XLXF (SEQ ID No. 11) is retained. The peptide of SEQ ID No. 1 corresponds to p21(149-159). In an embodiment of this aspect up to 5 amino acid residues are deleted from the N-terminal and the motif RXLXF (SEQ ID No. 12) is retained.

A second aspect of the present invention relates to a p21 derived peptide of formula; $X_1X_2X_3RX_4LX_5F$ (SEQ ID No. 2) wherein $X_1$, $X_3$, $X_4$ and $X_5$ are any amino acid and $X_2$ is serine or alanine; and variants thereof.

In one aspect, the invention pertains to a peptide of formula I: $N_1$DFYHSKRRLIF$N_2$ (formula I) (SEQ ID No. 4), comprising the motif XLXF (SEQ ID No. 11) wherein $N_1$ and $N_2$ are independently a natural or non-natural amino acid or nothing; or the peptide of formula I having up to 8 amino acid residues deleted from the N-terminal end; and variants thereof wherein at least one amino acid residue is replaced by an alternative natural or non-natural replacement amino acid residue, with the proviso that the motif XLXF(SEQ ID No. 11) is retained, wherein X refers to any natural or unnatural amino acid.

In one embodiment, $N_1$ and $N_2$ are independently selected from nothing and the polar residues C, N, Q, S, T and Y.

In one embodiment, $N_1$ is a natural or unnatural amino acid. In another embodiment, $N_1$ is threonine.

In one embodiment, $N_2$ is a natural or unnatural amino acid. In one embodiment, $N_1$ is serine.

In another embodiment, up to 6 amino acid residues are deleted from the N-terminal end of the peptide of formula I.

In another embodiment, from 3-5 amino acid residues are deleted from the N-terminal end of the peptide of formula I.

In yet another embodiment 4 amino acid residues are deleted from the N-terminal end of the peptide of formula I.

In one embodiment, $N_2$ is a natural or unnatural amino acid.

In another embodiment, $N_2$ is serine.

In yet another embodiment, 7 or 8 amino acid residues are deleted from the N-terminal end of the peptide of formula I.

In another aspect, the invention pertains to a peptide of formula DFYHSKRRLIF (SEQ ID No. 1), comprising the motif XLXF (SEQ ID No. 11), or such a peptide (i) bearing a further amino acid residue at either end; and, (ii) having up to 7 amino acid residues deleted from the N-terminal end; and variants thereof wherein at least one amino acid residue is replaced by an alternative natural or unnatural replacement amino acid residue, with the proviso that the motif XLXF (SEQ ID No. 11) is retained, wherein the peptide of SEQ ID No. 1 is modified by at least one of; deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives dual peptides, multimers of the peptides and any of said peptides in the D-stereomer form, or the order of the final two residues at the C-terminal end are reversed.

In one embodiment, the serine residue corresponding to p21(153Ser), is replaced by an alanine residue.

In another embodiment, a peptide is selected from;

| | |
|---|---|
| D F Y H S K R R L I F S, | (SEQ. ID NO: 13) |
| T D F Y H S K R R L I F,, | (SEQ ID NO: 14) |
| A F Y H S K R R L I F S, | (SEQ ID NO: 15) |
| D A Y H S K R R L I F S, | (SEQ ID NO: 16) |
| D F A H S K R R L I F S,, | (SEQ ID NO: 17) |
| D F Y A S K R R L I F S, | (SEQ ID NO: 18) |
| D F Y H A K R R L I F S, | (SEQ ID NO: 19) |
| D F Y H S A R R L I F S, | (SEQ ID NO: 20) |
| D F Y H S K R A L I F S, | (SEQ ID NO: 21) |
| D F Y H S K R R L A F S, | (SEQ ID NO: 22) |
| D F Y H S K R R L I F A, | (SEQ ID NO: 23) |
| F Y H S K R R L I F S, | (SEQ ID NO: 24) |
| Y H S K R R L I F S, | (SEQ ID NO: 25) |
| H S K R R L I F S, | (SEQ ID NO: 26) |

-continued

```
D F Y H S K R R L I F,                              (SEQ ID NO: 1)

F Y H S K R R L I F,                                (SEQ ID NO: 27)

Y H S K R R L I F,                                  (SEQ ID NO: 28)

H S K R R L I F,                                    (SEQ ID NO: 29)

S K R R L I F,                                      (SEQ ID NO: 30)

K R R L I F,                                        (SEQ ID NO: 31)

H- Arg- Leu- Ile- Phe  —NH2                         (SEQ ID NO. 32)

H- Arg- Arg- Leu- Ile- Phe  —NH2                    (SEQ ID NO. 33)

H- Lys- Arg- Arg- Leu- Ile- Phe  —NH2               (SEQ ID NO. 34)

H- Ala- Lys- Arg- Arg- Leu- Ile- Phe  —NH2          (SEQ ID NO. 35)

H- His- Ala- Lys- Arg- Arg- Leu- Ile- Phe  —NH2     (SEQ ID NO. 36)

H- Asn- Leu- Phe- Gly  —NH2                         (SEQ ID NO. 37)

H- Arg- Asn- Leu- Phe- Gly  —NH2                    (SEQ ID NO. 38)

H- Abu- Arg- Asn- Leu- Phe- Gly  —NH2               (SEQ ID NO. 39)

H- Ala- Abu- Arg- Asn- Leu- Phe- Gly  —NH2 and      (SEQ ID NO. 40)

H- Ser- Ala- Abu- Arg- Asn- Leu- Phe- Gly  —NH2     (SEQ ID NO. 41)
```

In still another aspect, the invention pertains to a peptide of formula II: $X_1X_2X_3RX_4LX_5F$ (formula II) (SEQ ID No. 2) wherein $X_1$, $X_3$, $X_4$ and $X_5$ may be any amino acid and $X_2$ is serine or alanine; and variants thereof.

In one embodiment, $X_5$ is selected from isoleucine and glycine.

In one embodiment, $X_1$ and $X_4$ are both basic amino acid residues and $X_3$ is a basic or polar residue.

In one embodiment, $X_1$ is histidine and $X_4$ is arginine, and $X_3$ is lysine or cysteine.

In another aspect the invention pertains to a peptide of formula: $X_1X_2X_3RX_4LX_5F$ (SEQ ID No. 2) wherein $X_1$, $X_3$, $X_4$ and $X_5$ may be any amino acid and $X_2$ is serine or alanine; and variants thereof, wherein the peptide is modified by at least one of a deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives, dual peptides, multimers of the peptides and any of said peptides in the D-stereomer form, or the order of the final two residues at the C-terminal end are reversed.

In yet another aspect, the invention pertains to a peptide of formula: $X_1X_2X_3RX_4LX_5F$ (SEQ ID No. 2) wherein $X_1$, $X_3$, $X_4$ and $X_5$ may be any amino acid and $X_2$ is serine or alanine; and variants thereof, wherein: (a) $X_1$ is deleted or is any amino acid, (b) $X_2$ is serine or alanine or a straight or branched chain amino acid, (c) $X_3$ is a basic amino acid or straight chain aliphatic amino acid, (d) R is unchanged or conservatively substituted (by basic amino acids), (e) $X_4$ is any amino acid that is capable of providing at least one site for participating in hydrogen bonding, (f) L is unchanged or conservatively substituted, (g) $X_5$ is any amino acid, or (h) F is unchanged or substituted by any aromatic amino acid.

In another aspect, the invention pertains to a peptide of formula: $X_1X_2X_3RX_4LX_5F$ (SEQ ID No. 463), wherein (a) $X_1$ is histidine, deleted or replaced by a natural or unnatural amino acid residue such as alanine, 3-pyridylalanine (Pya), 2-thienylalanine (Thi), homoserine (Hse), phenylalanine, or diaminobutyric acid (Dab), (b) $X_2$ is alanine or an alternative natural or unnatural amino acid residue having a smaller or slightly larger aromatic or aliphatic side chain, such as glycine, aminobutyric acid (Abu), norvaline (Nva), t-butylglycine(Bug), valine, isoleucine, phenylglycine (Phg) or phenylalanine, (c) $X_3$ is lysine or either a basic residue such as arginine or an uncharged natural or unnatural amino acid residue, such as norleucine (Nle), aminobutyric acid (Abu) or leucine, (d) arginine is replaced by either a basic residue such as lysine or an uncharged natural or unnatural amino acid residue, such as citrulline (Cit), homoserine, histidine, norleucine (Nle) or glutamine, (e) $X_4$ is arginine or a natural or unnatural amino acid residue, such as asparagine, proline, serine, aminoisobutyric acid (Aib) or sarcosine (Sar), or an amino acid residue capable of forming a cyclic linkage such as lysine or ornithine, (f) leucine is replaced with a natural or unnatural amino acid residue having a slightly larger aromatic or aliphatic side chain, such as norleucine, norvaline, cyclohexylalanine (Cha), phenylalanine or 1-naphthylalanine (1 Nal), (g) $X_5$ is isoleucine or an alternative natural or unnatural amino acid residue having a slightly larger aromatic or aliphatic side chain, such as norleucine, norvaline, cyclohexylalanine (Cha), phenylalanine or 1-naphthylalanine (1Nal), (h) phenylalanine is replaced with a natural or unnatural amino acid such as leucine, cyclohexylalanine (Cha), homophenylalanine (Hof), tyrosine, para-fluorophenylalanine (pFPhe), meta-fluorophenylalanine (mFPhe), trptophan, 1-naphthylalanine (1Nal), 2-naphthylalanine (2Nal), biphenylalanine (Bip) or (Tic), (i) $X_5$ and the terminal phenylalanine residue are reversed, or (j) the peptide is in cyclic form by the formation of a linkage between the side chain of $X_4$ and the C-terminus residue.

In one embodiment, $X_2$ is alanine.

In one embodiment, $X_5$ is isoleucine.

In another embodiment, a peptpide is selected from the group consisting of:

```
H S K R R L I F,                              (SEQ ID NO. 29)
H A K R R L I F,                              (SEQ ID NO. 42)
H S K R R L F G,                              (SEQ ID NO. 43)
H A K R R L F G,                              (SEQ ID NO. 44)
K A C R R L F G,                              (SEQ ID NO. 45)
K A C R R L I F,                              (SEQ ID NO. 46)
    X1   X2   X3   R    X4   L    X5   F                (SEQ ID NO. 464)
H-  His- Ala- Lys- Arg- Arg- Leu- Ile- Phe  -NH2 (SEQ ID NO. 36)
H-  Ala- Ala- Lys- Arg- Arg- Leu- Ile- Phe  -NH (SEQ ID NO. 47)
    H-   Ala- Lys- Arg- Arg- Leu- Ile- Phe  -NH2 (SEQ ID NO. 48)
H-  Pya- Ala- Lys- Arg- Arg- Leu- Ile- Phe  -NH2 (SEQ ID NO. 49)
H-  Thi- Ala- Lys- Arg- Arg- Leu- Ile- Phe  -NH2 (SEQ ID NO. 50)
H-  Hse- Ala- Lys- Arg- Arg- Leu- Ile- Phe  -NH2 (SEQ ID NO. 51)
H-  Phe- Ala- Lys- Arg- Arg- Leu- Ile- Phe  -NH2 (SEQ ID NO. 52)
H-  Dab- Ala- Lys- Arg- Arg- Leu- Ile- Phe  -NH2 (SEQ ID NO. 53)
H-  His- Gly- Lys- Arg- Arg- Leu- Ile- Phe  -NH2 (SEQ ID NO. 54)
H-  His- Abu- Lys- Arg- Arg- Leu- Ile- Phe  -NH2 (SEQ ID NO. 55)
H-  His- Nva- Lys- Arg- Arg- Leu- Ile- Phe  -NH2 (SEQ ID NO. 56)
H-  His- Bug- Lys- Arg- Arg- Leu- Ile- Phe  -NH2 (SEQ ID NO. 57)
H-  His- Val- Lys- Arg- Arg- Leu- Ile- Phe  -NH2 (SEQ ID NO. 58)
H-  His- Ile- Lys- Arg- Arg- Leu- Ile- Phe  -NH2 (SEQ ID NO. 59)
H-  His- Phg- Lys- Arg- Arg- Leu- Ile- Phe  -NH2 (SEQ ID NO. 60)
H-  His- Phe- Lys- Arg- Arg- Leu- Ile- Phe  -NH2 (SEQ ID NO. 61)
H-  His- Ala- Ala- Arg- Arg- Leu- Ile- Phe  -NH2 (SEQ ID NO. 62)
H-  His- Ala- Nle- Arg- Arg- Leu- Ile- Phe  -NH2 (SEQ ID NO. 63)
H-  His- Ala- Abu- Arg- Arg- Leu- Ile- Phe  -NH2 (SEQ ID NO. 64)
H-  His- Ala- Leu- Arg- Arg- Leu- Ile- Phe  -NH2 (SEQ ID NO. 65)
H-  His- Ala- Arg- Arg- Arg- Leu- Ile- Phe  -NH2 (SEQ ID NO. 66)
H-  His- Ala- Lys- Ala- Arg- Leu- Ile- Phe  -NH2 (SEQ ID NO. 67)
H-  His- Ala- Lys- Cit- Arg- Leu- Ile- Phe  -NH2 (SEQ ID NO. 68)
H-  His- Ala- Lys- Hse- Arg- Leu- Ile- Phe  -NH2 (SEQ ID NO. 69)
H-  His- Ala- Lys- His- Arg- Leu- Ile- Phe  -NH2 (SEQ ID NO 70)
H-  His- Ala- Lys- Nle- Arg- Leu- Ile- Phe  -NH2 (SEQ ID NO. 71)
H-  His- Ala- Lys- Gln- Arg- Leu- Ile- Phe  -NH2 (SEQ ID NO. 72)
H-  His- Ala- Lys- Lys- Arg- Leu- Ile- Phe  -NH2 (SEQ ID NO. 73)
H-  His- Ala- Lys- Arg- Ala- Leu- Ile- Phe  -NH2 (SEQ ID NO. 74)
H-  His- Ala- Lys- Arg- Asn- Leu- Ile- Phe  -NH2 (SEQ ID NO. 75)
H-  His- Ala- Lys- Arg- Pro- Leu- Ile- Phe  -NH2 (SEQ ID NO. 76)
H-  His- Ala- Lys- Arg- Ser- Leu- Ile- Phe  -NH2 (SEQ ID NO. 77)
H-  His- Ala- Lys- Arg- Aib- Leu- Ile- Phe  -NH2 (SEQ ID NO. 78)
```

-continued

| | | | | | | | | | |
|---|---|---|---|---|---|---|---|---|---|
| H- | His- | Ala- | Lys- | Arg- | Sar- | Leu- | Ile- | Phe | —NH2 (SEQ ID NO. 79) |
| H- | His- | Ala- | Lys- | Arg- | Cit- | Leu- | Ile- | Phe | —NH2 (SEQ ID NO. 80) |
| H- | His- | Ala- | Lys- | Arg- | Arg- | Ala- | Ile- | Phe | —NH2 (SEQ ID NO. 81) |
| H- | His- | Ala- | Lys- | Arg- | Arg- | leu- | Ile- | Phe | —NH2 (SEQ ID NO. 82) |
| H- | His- | Ala- | Lys- | Arg- | Arg- | Ile- | Ile- | Phe | —NH2 (SEQ ID NO. 83) |
| H- | His- | Ala- | Lys- | Arg- | Arg- | Val- | Ile- | Phe | —NH2 (SEQ ID NO. 84) |
| H- | His- | Ala- | Lys- | Arg- | Arg- | Nle- | Ile- | Phe | —NH2 (SEQ ID NO. 85) |
| H- | His- | Ala- | Lys- | Arg- | Arg- | Nva- | Ile- | Phe | —NH2 (SEQ ID NO. 86) |
| H- | His- | Ala- | Lys- | Arg- | Arg- | Cha- | Ile- | Phe | —NH2 (SEQ ID NO. 87) |
| H- | His- | Ala- | Lys- | Arg- | Arg- | Phe- | Ile- | Phe | —NH2 (SEQ ID NO. 88) |
| H- | His- | Ala- | Lys- | Arg- | Arg- | 1Nap- | Ile- | Phe | —NH2 (SEQ ID NO. 89) |
| H- | His- | Ala- | Lys- | Arg- | Arg- | Leu- | Ala- | Phe | —NH2 (SEQ ID NO. 90) |
| H- | His- | Ala- | Lys- | Arg- | Arg- | Leu- | Leu- | Phe | —NH2 (SEQ ID NO. 91) |
| H- | His- | Ala- | Lys- | Arg- | Arg- | Leu- | Val- | Phe | —NH2 (SEQ ID NO. 92) |
| H- | His- | Ala- | Lys- | Arg- | Arg- | Leu- | Nle- | Phe | —NH2 (SEQ ID NO. 93) |
| H- | His- | Ala- | Lys- | Arg- | Arg- | Leu- | Nva- | Phe | —NH2 (SEQ ID NO. 94) |
| H- | His- | Ala- | Lys- | Arg- | Arg- | Leu- | Cha- | Phe | —NH2 (SEQ ID NO. 95) |
| H- | His- | Ala- | Lys- | Arg- | Arg- | Leu- | Phe- | Phe | —NH2 (SEQ ID NO. 96) |
| H- | His- | Ala- | Lys- | Arg- | Arg- | Leu- | 1Nap- | Phe | —NH2 (SEQ ID NO. 97) |
| | H- | His- | Ala- | Lys- | Arg- | Arg- | Leu- | Phe | —NH2 (SEQ ID NO. 98) |
| H- | His- | Ala- | Lys- | Arg- | Arg- | Leu- | Ile- | Leu | —NH2 (SEQ ID NO. 99) |
| H- | His- | Ala- | Lys- | Arg- | Arg- | Leu- | Ile- | Cha | —NH2 (SEQ ID NO. 100) |
| H- | His- | Ala- | Lys- | Arg- | Arg- | Leu- | Ile- | Hof | —NH2 (SEQ ID NO. 101) |
| H- | His- | Ala- | Lys- | Arg- | Arg- | Leu- | Ile- | Tyr | —NH2 (SEQ ID NO. 102) |
| H- | His- | Ala- | Lys- | Arg- | Arg- | Leu- | Ile- | pFPhe | —NH2 (SEQ ID NO. 103) |
| H- | His- | Ala- | Lys- | Arg- | Arg- | Leu- | Ile- | mFPhe | —NH2 (SEQ ID NO. 104) |
| H- | His- | Ala- | Lys- | Arg- | Arg- | Leu- | Ile- | Trp | —NH2 (SEQ ID NO. 105) |
| H- | His- | Ala- | Lys- | Arg- | Arg- | Leu- | Ile- | 1Nap | —NH2 (SEQ ID NO. 106) |
| H- | His- | Ala- | Lys- | Arg- | Arg- | Leu- | Ile- | 2Nap | —NH2 (SEQ ID NO. 107) |
| H- | His- | Ala- | Lys- | Arg- | Arg- | Leu- | Ile- | Lys | —NH2 (SEQ ID NO. 108) |
| H- | His- | Ala- | Lys- | Arg- | Arg- | Leu- | Ile- | Tic | —NH2 (SEQ ID NO. 109) |
| H- | His | Ala | Lys | Arg | Arg | Leu | Ile | L-Pse | OH (SEQ ID NO. 110) |
| H- | His | Ala | Lys | Arg | Arg | Leu | Ile | D-Pse | OH (SEQ ID NO. 111) |
| H- | His | Ser | Lys | Arg | Arg | Leu | Ile | L-Pse | OH (SEQ ID NO. 112) |
| H- | His | Ser | Lys | Arg | Arg | Leu | Ile | D-Pse | OH (SEQ ID NO. 113) |
| H- | His | Ala | Lys | Arg | Arg | Leu | Ile | L-Psa | OH (SEQ ID NO. 114) |
| H- | His | Ala | Lys | Arg | Arg | Leu | Ile | D-Psa | OH (SEQ ID NO. 115) |
| H- | His | Ser | Lys | Arg | Arg | Leu | Ile | L-Psa | OH (SEQ ID NO. 116) |
| H- | His | Ser | Lys | Arg | Arg | Leu | Ile | D-Psa | OH (SEQ ID NO. 117) |
| H- | His | Ala | Lys | Arg | Arg | Leu | Ile | Dhp | OH (SEQ ID NO. 118) |

-continued

```
H-  His  Ser  Lys  Arg   Arg   Leu   Ile     Dhp    OH    (SEQ ID NO. 119)
H-  His  Ala  Lys  Arg   Arg   Leu   Ile     Pheol        (SEQ ID NO. 120)
H-  His  Ser  Lys  Arg   Arg   Leu   Ile     Pheol        (SEQ ID NO. 121)
H-  Ala- Ala- Abu- Arg-  Arg-  Leu-  Ile-    pFPhe  -NH2  (SEQ ID NO. 122)
H-  Ala- Ala- Lys- Arg-  Arg-  Leu-  Ile-    pFPhe  -NH2  (SEQ ID NO. 123)
H-  Ala- Ala- Lys- Arg-  Cit-  Leu-  Ile-    pFPhe  -NH2  (SEQ ID NO. 124)
H-  Ala- Ala- Lys- Arg-  Arg-  Leu-  Ala-    pFPhe  -NH2  (SEQ ID NO. 125)
H-  Ala- Ala- Abu- Arg-  Ser-  Leu-  Ile-    pFPhe  -NH2  (SEQ ID NO. 126)
H-  Ala- Ala- Lys- Gln-  Arg-  Leu-  Ile-    pFPhe  -NH2  (SEQ ID NO. 127)
H-  Ala- Ala- Lys- Arg-  Arg-  Leu-  Ile-    pFPhe  -NH2  (SEQ ID NO. 128)
H-  Gly- Ala- Lys- Arg-  Arg-  Leu-  Ile-    pFPhe  -NH2  (SEQ ID NO. 129)
H-  Ala- Ala- Lys- hArg- Arg-  Leu-  Ile-    pFPhe  -NH2  (SEQ ID NO. 130)
H-  Ala- Ala- Lys- Ser-  Arg-  Leu-  Ile-    pFPhe  -NH2  (SEQ ID NO. 131)
H-  Ala- Ala- Lys- Hse-  Arg-  Leu-  Ile-    pFPhe  -NH2  (SEQ ID NO. 132)
H-  Ala- Ala- Lys- Arg-  Lys-  Leu-  Ile-    pFPhe  -NH2  (SEQ ID NO. 133)
H-  Ala- Ala- Lys- Arg-  Orn-  Leu-  Ile-    pFPhe  -NH2  (SEQ ID NO. 134)
H-  Ala- Ala- Lys- Arg-  Gln-  Leu-  Ile-    pFPhe  -NH2  (SEQ ID NO. 135)
H-  Ala- Ala- Lys- Arg-  Hse-  Leu-  Ile-    pFPhe  -NH2  (SEQ ID NO. 136)
H-  Ala- Ala- Lys- Arg-  Thr-  Leu-  Ile-    pFPhe  -NH2  (SEQ ID NO. 137)
H-  Ala- Ala- Lys- Arg-  Nva-  Leu-  Ile-    pFPhe  -NH2  (SEQ ID NO. 138)
H-  Ala- Ala- Lys- Arg-  Arg-  Phg-  Ile-    pFPhe  -NH2  (SEQ ID NO. 139)
H-  Ala- Ala- Lys- Arg-  Arg-  Met-  Ile-    pFPhe  -NH2  (SEQ ID NO. 140)
H-  Ala- Ala- Lys- Arg-  Arg-  Ala-  Ile-    pFPhe  -NH2  (SEQ ID NO. 141)
H-  Ala- Ala- Lys- Arg-  Arg-  Hof-  Ile-    pFPhe  -NH2  (SEQ ID NO. 142)
H-  Ala- Ala- Lys- Arg-  Arg-  hLeu- Ile-    pFPhe  -NH2  (SEQ ID NO. 143)
H-  Ala- Ala- Lys- Arg-  Arg-  aIle- Ile-    pFPhe  -NH2  (SEQ ID NO. 144)
H-  Ala- Ala- Lys- Arg-  Arg-  Leu-  Gly-    pFPhe  -NH2  (SEQ ID NO. 145)
H-  Ala- Ala- Lys- Arg-  Arg-  Leu-  βAla    pFPhe  -NH2  (SEQ ID NO. 146)
H-  Ala- Ala- Lys- Arg-  Arg-  Leu-  Phg-    pFPhe  -NH2  (SEQ ID NO. 147)
H-  Ala- Ala- Lys- Arg-  Arg-  Leu-  Aib-    pFPhe  -NH2  (SEQ ID NO. 148)
H-  Ala- Ala- Lys- Arg-  Arg-  Leu-  Sar-    pFPhe  -NH2  (SEQ ID NO. 149)
H-  Ala- Ala- Lys- Arg-  Arg-  Leu-  Pro-    pFPhe  -NH2  (SEQ ID NO. 150)
H-  Ala- Ala- Lys- Arg-  Arg-  Leu-  Bug-    pFPhe  -NH2  (SEQ ID NO. 151)
H-  Ala- Ala- Lys- Arg-  Arg-  Leu-  Ser-    pFPhe  -NH2  (SEQ ID NO. 152)
H-  Ala- Ala- Lys- Arg-  Arg-  Leu-  Asp-    pFPhe  -NH2  (SEQ ID NO. 153)
H-  Ala- Ala- Lys- Arg-  Arg-  Leu-  Asn-    pFPhe  -NH2  (SEQ ID NO. 154)
H-  Ala- Ala- Lys- Arg-  Arg-  Leu-  pFPhe-  Phe    -NH2  (SEQ ID NO. 155)
H-  Ala- Ala- Lys- Arg-  Arg-  Leu-  diClPhe Phe    -NH2  (SEQ ID NO. 156)
H-  Ala- Ala- Lys- Arg-  Arg-  Leu-  pClPhe- Phe    -NH2  (SEQ ID NO. 157)
H-  Ala- Ala- Lys- Arg-  Arg-  Leu-  mClPhe  Phe    -NH2  (SEQ ID NO. 158)
```

-continued

| | | | | | | | | |
|---|---|---|---|---|---|---|---|---|
| H- | Ala- | Ala- | Lys- | Arg- | Arg- | Leu- | oClPhe- | Phe | —NH2 (SEQ ID NO. 159) |
| H- | Ala- | Ala- | Lys- | Arg- | Arg- | Leu- | pIPhe- | Phe | —NH2 (SEQ ID NO. 160) |
| H- | Ala- | Ala- | Lys- | Arg- | Arg- | Leu- | TyrMe- | Phe | —NH2 (SEQ ID NO. 161) |
| H- | Ala- | Ala- | Lys- | Arg- | Arg- | Leu- | Thi- | Phe | —NH2 (SEQ ID NO. 162) |
| H- | Ala- | Ala- | Lys- | Arg- | Arg- | Leu- | Pya- | Phe | —NH2 (SEQ ID NO. 163) |
| H- | Ala- | Ala- | Lys- | Arg- | Arg- | Leu- | Ile- | diClPhe | —NH2 (SEQ ID NO. 164) |
| H- | Ala- | Ala- | Lys- | Arg- | Arg- | Leu- | Ile- | pClPhe | —NH2 (SEQ ID NO. 165) |
| H- | Ala- | Ala- | Lys- | Arg- | Arg- | Leu- | Ile- | mClPhe | —NH2 (SEQ ID NO. 166) |
| H- | Ala- | Ala- | Lys- | Arg- | Arg- | Leu- | Ile- | oClPhe | —NH2 (SEQ ID NO. 167) |
| H- | Ala- | Ala- | Lys- | Arg- | Arg- | Leu- | Ile- | Phg | —NH2 (SEQ ID NO. 168) |
| H- | Ala- | Ala- | Lys- | Arg- | Arg- | Leu- | Ile- | TyrMe | —NH2 (SEQ ID NO. 169) |
| H- | Ala- | Ala- | Lys- | Arg- | Arg- | Leu- | Ile- | Thi | —NH2 (SEQ ID NO. 170) |
| H- | Ala- | Ala- | Lys- | Arg- | Arg- | Leu- | Ile- | Pya | —NH2 (SEQ ID NO. 171) |
| H- | Ala- | Ala- | Lys- | Arg- | Arg- | Leu- | Ile- | Inc | —NH2 (SEQ ID NO. 172) | and the cyclic peptides:

5,8-cyclo-[H-His-Ala-Lys-Arg-Lys-Leu-Phe-Gly]  (SEQ ID NO. 173)

5,8-cyclo-[H-His-Ala-Lys-Arg-Orn-Leu-Phe-Gly]  (SEQ ID NO. 174)

In another aspect, the invention pertains to a peptide of the formula III or IV; H'$X_2$K'$R_1$$R_2$L'$X_5$F (formula III) (SEQ ID No. 175) or H'$X_2$K'$R_1$$R_2$L'F$X_5$ (formula IV) (SEQ ID No. 176) or a variant thereof, wherein:
H' is nothing, His, D-His, Ala, Thi, Hse, Phe, or Dab;
$X_2$ is Ala, Ser, Abu, Val;
K' is Lys, Arg, or Abu;
$R_1$ is Arg, Lys, or Gln; and
$R_2$ is Arg, forms a cyclic peptide with the C-terminal residue, Ser, or Cit;
L' is Leu or Ile;
$X_5$ is Ile, Leu, Gly, or Ala; and
F' is Phe, para-fluoroPhe, meta-fluoroPhe, L-Psa, 2-Nap, Dhp, or D-Psa.

In one embodiment, $X_2$ is alanine.

In one embodiment, $X_5$ isoleucine.

In another embodiment, the invention pertains to a peptide of the formula IV H'$X_2$K'$R_1$$R_2$L'F'$X_5$ (SEQ ID No. 472).

In another embodiment, the peptide is in a cyclic form by virtue of a linkage between the C-terminal residue and the residue 3 upstream to it.

In another embodiment, $X_2$ is Ala and $X_5$ is Ile.

In yet another embodiment, F' is para-fluoro-Phe and H' is Ala or nothing.

In another embodiment, K' is Abu; $R_1$ is Gln; $R_2$ is Cit or Ser; and $X_5$ is Ala.

In still another embodiment, a peptide is selected from the group consisting of:

| | | | | | | | | |
|---|---|---|---|---|---|---|---|---|
| H- | his- | Ala- | Lys- | Arg- | Arg- | Leu- | Ile- | Phe | —NH2 (SEQ ID NO. 36) |
| H- | Ala- | Ala- | Lys- | Arg- | Arg- | Leu- | Ile- | Phe | —NH2 (SEQ ID NO. 47) |
| H- | | Ala- | Lys- | Arg- | Arg- | Leu- | Ile- | Phe | —NH2 (SEQ ID NO. 48) |
| H- | Thi- | Ala- | Lys- | Arg- | Arg- | Leu- | Ile- | Phe | —NH2 (SEQ ID NO. 50) |
| H- | Hse- | Ala- | Lys- | Arg- | Arg- | Leu- | Ile- | Phe | —NH2 (SEQ ID NO. 51) |
| H- | Phe- | Ala- | Lys- | Arg- | Arg- | Leu- | Ile- | Phe | —NH2 (SEQ ID NO. 52) |
| H- | Dab- | Ala- | Lys- | Arg- | Arg- | Leu- | Ile- | Phe | —NH2 (SEQ ID NO. 53) |
| H- | His- | Abu- | Lys- | Arg- | Arg- | Leu- | Ile- | Phe | —NH2 (SEQ ID NO. 55) |
| H- | His- | Val- | Lys- | Arg- | Arg- | Leu- | Ile- | Phe | —NH2 (SEQ ID NO. 58) |
| H- | His- | Ala- | Arg- | Arg- | Arg- | Leu- | Ile- | Phe | —NH2 (SEQ ID NO. 66) |

-continued

| | | | | | | | | | |
|---|---|---|---|---|---|---|---|---|---|
| H- | His- | Ala- | Lys- | Arg- | Arg- | Ile- | Ile- | Phe | —NH2 (SEQ ID NO. 83) |
| H- | His- | Ala- | Lys- | Arg- | Arg- | Leu- | Leu- | Phe | —NH2 (SEQ ID NO. 91) |
| H- | His- | Ala- | Lys- | Arg- | Arg- | Leu- | Ile- | pFPhe | —NH2 (SEQ ID NO. 103) |
| H- | His- | Ala- | Lys- | Arg- | Arg- | Leu- | Ile- | 2Nap | —NH2 (SEQ ID NO. 107) |
| H- | His | Ala | Lys | Arg | Arg | Leu | Ile | D-Psa | OH (SEQ ID NO. 115) |
| H- | His | Ser | Lys | Arg | Arg | Leu | Ile | Dhp | OH (SEQ ID NO. 119) |
| H- | Ala- | Ala- | Abu- | Arg- | Arg- | Leu- | Ile- | pFPhe | —NH2 (SEQ ID NO. 122) |
| H- | Ala- | Ala- | Lys- | Arg- | Arg- | Leu- | Ile- | pFPhe | —NH2 (SEQ ID NO. 123) |
| H- | Ala- | Ala- | Lys- | Arg- | Cit- | Leu- | Ile- | pFPhe | —NH2 (SEQ ID NO. 124) |
| H- | Ala- | Ala- | Lys- | Arg- | Arg- | Leu- | Ala- | pFPhe | —NH2 (SEQ ID NO. 125) |
| H- | Ala- | Ala- | Abu- | Arg- | Ser- | Leu- | Ile- | pFPhe | —NH2 (SEQ ID NO. 126) |
| H- | Ala- | Ala- | Lys- | Gln- | Arg- | Leu- | Ile- | pFPhe | —NH2 (SEQ ID NO. 127) |
| H- | | Ala- | Lys- | Arg- | Arg- | Leu- | Ile- | pFPhe | —NH2 (SEQ ID NO. 177) |

In another aspect, the invention pertains to an assay for identifying candidate substances capable of binding to a cyclin associated with a G1 control CDK enzyme and/or inhibition of said enzyme, comprising; (a) bringing into contact i) a p21 derived peptide as defined in claim 1, ii) said cyclin or portion thereof or cyclin groove, iii) said CDK or portion thereof and iv) said candidate substance, under conditions wherein, in the absence of the candidate substance being an inhibitor of the cyclin/CDK interaction, the p21 derived peptide would bind to said cyclin or portion thereof or cyclin groove, and (b) monitoring any change in the expected binding of the p21 derived peptide and the cyclin or portion thereof or cyclin groove.

In yet another aspect, the invention pertains to an assay for the identification of compounds that interact with a cyclin or a cyclin when complexed with the physiologically relevant CDK, comprising; (a) incubating a candidate compound and peptide of formula I: $X_1X_2X_3RX_4LX_5F$ (formula II) (SEQ ID No. 2) wherein $X_1$, $X_3$, $X_4$ and $X_5$ may be any amino acid and $X_2$ is serine or alanine; and variants thereof or a peptide of the formula III or IV: H'X'$_2$K'R$_1$R$_2$L'X'$_5$F' (formula III) (SEQ ID No. 471) or H'X'$_2$K'R$_1$R$_2$L° F'X'$_5$ (formula IV) (SEQ ID No. 472) or a variant thereof, wherein H' is His, nothing, D-His, Ala, Thi, Hse, Phe, or Dab; X'$_2$ is Ala, Ser, Abu, Val; K' is Lys, Arg, or Abu; R$_1$ is Arg, Lys, or Gln; and R$_2$ is Arg, forms a cyclic peptide with the C-terminal residue, Ser, or Cit; L' is Leu or Ile; X'$_5$ is Ile, Leu, Gly, or Ala; F' is Phe, para-fluoroPhe, meta-fluoroPhe, L-Psa, 2-Nap,Dhp, or D-Psa and a cyclin or cyclin/CDK complex; (b) detecting binding of either the candidate compound or the peptide of formula II or III with cyclin.

In another aspect, the invention pertains to an assay for candidate compounds that interact with a cyclin by virtue of forming associations with at least two of the amino acids corresponding to the cyclin A amino acids L253, I206 and R211.

In yet another aspect of the invention, the candidate compound additionally forms associations with at least one of the amino acids corresponding to the cyclin A amino acids E223, E224, D284, D283, L253, I206 and R211.

In one embodiment, the candidate additionally forms associations with at least one of the amino acids corresponding to the cyclin A amino acids W217, V219, V221, S408, E411, Y225, I213, L214, G257, R250, Q254, T207 and L214.

In still another aspect, the candidate compound additionally forms associations with at least one of the amino acids corresponding to the cyclin A amino acids G222, Y225, I281, E223, E220, V279, A212, V215, L218, Q406, S408, M210, L253, L218, I239, V256 and M200.

In one embodiment, the cyclin is selected from cyclin A, cyclin E or cyclin D.

In another embodiment, the cyclin is cyclin A.

In one embodiment, the assay comprises use of a three dimensional model of a cyclin and a candidate compound.

In another embodiment, at least one of the assay components is bound to a solid phase.

In still another embodiment, the p21 derived peptide is labeled such as to emit a signal when bound to said cyclin.

In another embodiment, the cyclin is labeled such as to emit a signal when bound to the p21 derived peptide.

In one embodiment, one of the assay components is labeled with a fluorescence emitter and the signal is detected using fluorescence polarization techniques.

In another aspect, the invention pertains to a method of using a cyclin in a drug screening assay comprising: (a) selecting a candidate compound by performing rational drug design with a three-dimensional model of said cyclin, wherein said selecting is performed in conjunction with computer modeling; (b) contacting the candidate compound with the cyclin; and (c) detecting the binding affinity of the candidate compound for the cyclin groove; wherein a potential drug is selected on the basis of its having a greater affinity for the cyclin groove than that of a peptide of formula II: $X_1X_2X_3RX_4LX_5F$ (formula II) (SEQ ID No. 2) wherein $X_1$, $X_3$, $X_4$ and $X_5$ may be any amino acid and $X_2$ is serine or alanine; and variants thereof or a peptide of formula III or IV: H'X'$_2$K'R$_1$R$_2$L'X'$_5$F' (formula III) (SEQ ID No. 471) or H'X'$_2$K'R$_1$R$_2$L'F'X'$_5$ (formula IV) (SEQ ID No. 472) or a variant thereof, wherein H' is His, nothing, D-His, Ala, Thi, Hse, Phe, or Dab; X'$_2$ is Ala, Ser, Abu, Val; K' is Lys, Arg, or Abu; R$_1$ is Arg, Lys, or Gln; and R$_2$ is Arg, forms a cyclic peptide with the C-terminal residue, Ser, or Cit; L' is Leu or Ile; X'$_5$ is Ile, Leu, Gly, or Ala; F' is Phe, para-fluoroPhe, meta-fluoroPhe, L-Psa, 2-Nap, Dhp, or D-Psa.

In another aspect, the invention pertains to a method of using a cyclin in a drug screening assay comprising: (a) selecting a candidate compound by performing rational drug design with a three-dimensional model of said cyclin, wherein said selecting is performed in conjunction with computer modeling; (b) contacting the candidate compound with the cyclin; and (c) detecting whether said the candidate compound forms associations with at least the amino acids corresponding to the cyclin A amino acids L253, I206 and R211.

In one embodiment, the method further comprises detection of whether the candidate compound additionally forms associations with at least one of the amino acids corresponding to the cyclin A amino acids E223, E224, D284, D283, L253, I206 and R211.

In another embodiment, the method further comprises detection of whether the candidate compound additionally forms associations with at least one of the amino acids corresponding to the cyclin A amino acids W217, V219, V221, S408, E411, Y225, I213, L214, G257, R250, Q254, T207 and L214.

In another embodiment, the method further comprises detection of whether the candidate compound additionally forms associations with at least one of the amino acids corresponding to the cyclin A amino acids G222, Y225, I281, E223, E220, V279, A212, V215, L218, Q406, S408, M210, L253, L218, I239, V256 and M200.

In another aspect, the invention pertains to an assay for identifying candidate substances capable of inhibiting CDK in a cell, comprising;

(a) contacting a cell comprising a cyclin or portion thereof or cyclin groove, and a CDK or portion thereof, with a candidate substance under conditions where, in the absence of the candidate substance, the cyclin or portion thereof or cyclin groove and CDK or portion thereof would interact, and (b) monitoring any change in the activity of the CDK or portion thereof, wherein inhibition of CDK activity is indicated by one or more of: G0 and/o G1/S cell cycle arrest; cell cycle-related apoptosis; suppression of E2F transcription factor activity; hypophosphorylation of cellular pRb; and in vitro anti-proliferative effects.

In still another aspect, the invention pertains to use of a peptide in the preparation of a medicament for use in (a) inhibition of CDK2 or (b) in the treatment of proliferative disorders such as cancers and leukaemias where inhibition of CDK2 would be beneficial.

DETAILED DESCRIPTION OF THE INVENTION

Figure 1:
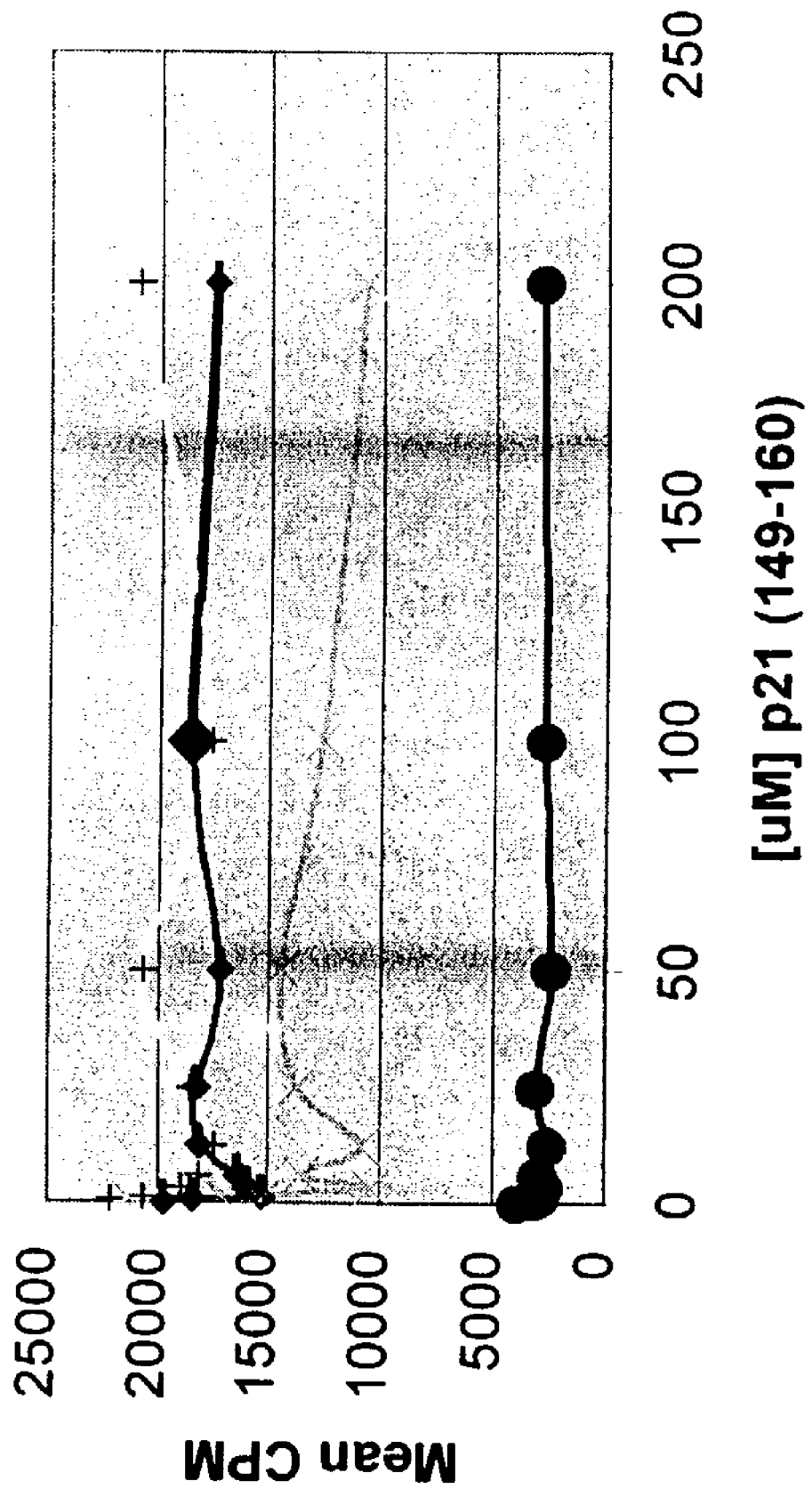
FIG. 1 shows the effect of p21 (149-160) on CDK2-Cyclin E induced phopshorylation of different concentrations Histone 1. Yellow line (+ marks)—1 mg/ml Histone 1, purple line (diamonds), 0.7 mg/ml Histone 1, blue line (x marks)—0.25 mg/ml Histone 1 and brown line (closed circles)—0.1 mg/ml Histone 1.

Although the peptides of the first aspect and in some embodiments of the second aspect, include the described CDK4-inhibitory motif RRLIF (SEQ ID NO: 5), the peptides of the present invention have been shown to display preferential selectivity for CDK2 over CDK4 in contrast to those described in Ball et al.(supra) who concluded that such p21 carboxy-terminal peptides "do not have high specific activity for CDK2 inhibition, they are potent inhibitors of CDK4 activity". Thus, Ball et al. do not focus upon this region for further development for preferential CDK2 inhibitors, indeed p21$_{141-160}$ was shown by these authors to be 40 times more active against cyclinD1/CDK4 than cyclinE/CDK2. Thus, further surprising advantages of the above peptides relate to their specificity particularly for G1 control CDK's, such as CDK2/cyclinE and CDK2/cyclin A, as opposed to mitotic control enzymes including CDK's such as CDK1/cyclin B or A and protein kinase Cα (PKCα).

Further evidence of the unexpected observation that these peptides display activity against CDK4 and CDK2 is that Ball et al. described how N-terminal truncation of p21$_{141-160}$ reduced CDK4/cyclin D1 inhibitory activity. The disclosure therein of RRLIF (SEQ ID No. 5) as being the CDK4-inhibitory motif was made on a theoretical basis rather than a demonstration that a peptide of that size would retain inhibitory activity. Furthermore, of the prior art disclosures discussed above, only two 8-mer peptides have been shown to be active against cyclin A/CDK2, these being the E2F1 derived peptides PVKRRLFG (SEQ ID No. 8) and PVKRRLDL (SEQ ID No. 7). Thus, the present invention has demonstrated, in contrast to the information available in the art, that shorter, in some cases more specific and/or potent inhibitors of cyclin-CDK, especially cyclin E/CDK2 and cyclin A/CDK2 interaction may derived from within the sequence p21$_{141-160}$.

In one embodiment of the first aspect of the invention, the peptide may include a further amino acid residue at either the N- or C-terminus. The further residue is preferably selected from the polar residues C, N, Q, S, T and Y, and is preferably threonine when added to the N-terminus and serine, when added to the C-terminus. These last recited preferred embodiments correspond to the sequences 148-159 and 149-160 of p21 respectively. In an alternative embodiment, up to 7 amino acid residues may be deleted from the N-terminal end of formula I. Such truncation may therefore give rise to peptides corresponding to p21(150-159), p21(151-159), p21(152-159), p21(153-159), p21(154-159) p21(155-159) and p21 (156-159) or wherein an additional serine residue is added to the C-terminal end to p21(150-160), p21(151-160), p21(152-

160), p21(153-160), p21(154-160), p21(155-160) and p21(156-160). Preferably, from 2 to 7 residues are deleted, most preferably seven are deleted. In each of these preferred embodiments it is preferable that, when present the serine residue corresponding to p21(153) is replaced by an alanine residue.

Considering the second aspect of the invention, peptides and variants of the formula $X_1X_2X_3RX_4LX_5F$ (SEQ ID No. 465) include peptides where one or more of:
(a) X1 may be deleted or may be any amino acid,
(b) X2 may be serine or alanine or a straight or branched chain amino acid,
(c) X3 may be a basic amino acid or straight or branched chain aliphatic amino acid,
(d) R may be unchanged or conservatively substituted (by basic amino acids),
(e) X4 may be any amino acid that is capable of providing at least one site for participating in hydrogen bonding,
(f) L may be unchanged or conservatively substituted,
(g) X5 may be any amino acid, or
(h) F may be unchanged or substituted by any aromatic amino acid.

More particularly, $X_2$ is preferably alanine as this provides a significant increase in the efficacy of the peptide and $X_5$ is preferably a non-polar amino acid residue, more preferably isoleucine or glycine, most preferably isoleucine. Of the remaining groups, $X_1$, $X_3$ and $X_4$, $X_1$ and $X_4$ are both preferably basic amino acid residue, $X_1$ is more preferably histidine and $X_4$ more preferably arginine. $X_3$ may be a basic or polar residue, preferably lysine or cysteine. A preferred peptide in accordance with the second aspect is that of SEQ ID No.3;

$HX_2KRRLX_5F$ (SEQ ID No. 3)

wherein $X_2$ and $X_5$ have the same meanings and preferences as above. When $X_2$ is serine and $X_5$ isoleucine the peptide corresponds to the sequence 152-159 of p21 and may hereinafter be referred to as p21(152-159). A further aspect of the invention therefore relates to a peptide $HX_2KRRLX_5F$ (SEQ ID No. 3) and variants thereof, especially, wherein at least one amino acid residue is replaced by an alternative natural or unnatural replacement amino acid residue.

As used herein the term "variant" is used to include the peptides of SEQ ID Nos 1, 2 and 3 being modified by at least one of; deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives, dual peptides, multimers of the peptides and any of said peptides in the D-stereoisomer form or the order of the final two residues at the C-terminus residues are reversed; provided that such variants retain the activity of the parent peptide. As used hereinafter, the term "substitution" is used as to mean "replacement" i.e. substitution of an amino acid residue means its replacement e.g. with a different natural or non-natural amino acid residue.

Preferably, the variants involve the replacement of an amino acid residue by one or more, preferably one, of those selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Such variants may arise from homologous substitution i.e. like-for-like substitution such as basic for basic, acidic for acidic, polar for polar etc. Non-homologous substitution may also occur i.e. from one class of residue to another or alternatively involving the inclusion of unnatural amino acids such as ornithine, diaminobutyric acid, norleucine, pyriylalanine, thienylalanine, naphthylalanine and phenylglycine.

As used herein, amino acids are classified according to the following classes;
basic; H, K, R
acidic; D, E
non-polar; A, F, G, I, L, M, P, V, W
polar; C, N, Q, S, T, Y,
(using the internationally accepted amino acid single letter codes)

and homologous and non-homologous substitution is defined using these classes. Thus, homologous substitution is used to refer to substitution from within the same class, whereas non-homologous substitution refers to substitution from a different class or by an unnatural amino acid.

The variants may also arise from replacement of an amino acid residue by an unnatural amino acid residue that may be homologous or non-homologous with that it is replacing. Such unnatural amino acid residues may be selected from;- alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid$^\#$, 7-amino heptanoic acid*, L-methionine sulfone$^{\#*}$, L-norleucine*, L-norvaline*, p-nitro-L-phenylalanine*, L-hydroxyproline$^\#$, L-thioproline*, methyl derivatives of phenylalanine (Phe) such as 4-methyl-Phe*, pentamethyl-Phe*, L-Phe (4-amino)$^\#$, L-Tyr (methyl)*, L-Phe (4-isopropyl)*, L-Tic (1,2,3,4-tetrahydroisoquinoline-3-carboxyl acid)*, L-diaminopropionic acid$^\#$ and L-Phe (4-benzyl)*. The notation * has been utilised for the purpose of the discussion above, to indicate the hydrophobic nature of the derivative whereas # has been utilised to indicate the hydrophilic nature of the derivative, #* indicates amphipathic characteristics. The structures and accepted three letter codes of some of these and other unnatural amino acids are given in the Examples section.

With particular reference to the first aspect of the invention (SEQ ID No. 1), a variant peptide may involve the replacement of an amino acid residue by an alanine residue. In the first aspect of the present invention, such substitution preferably takes place at any of positions 150, 151, 152, 153, 154, 158 or 160 which all display a greater selectivity for CDK2/cyclin E inhibition than CDK4/cyclin D1 inhibition as described below. Most preferably, such alanine replacement occurs at position 153 where in addition to an increase in selectivity, the observed $IC_{50}$ is at least two orders of magnitude greater that for the corresponding parent peptide ($p21_{149-160}$). In respect of the second aspect of the invention, it is also preferable that amino acid replacement is by an alanine residue, most preferably at the 153 position ($X_2$). Furthermore, in respect of this aspect of the invention, the variant may include the deletion of the N-terminal asparagine residue resulting in the peptide corresponding to p21(150-159). According the first aspect, a preferable peptide is one including a serine residue at the C-terminus such as the peptide D F Y H A K R R L I F S (SEQ ID No. 19)

As discussed above, variants also include inversion of the two C-terminal amino acid residues and cyclic peptides, both of which are preferred independently as well as when taken together or in combination with any other variant. When such a variant is applied to the second or third aspects of the invention, it is to the exclusion of the peptide PVKRRLFG (SEQ ID No. 8), unless in cyclic form.

With regard to cyclic peptides, these are preferably formed by linkage between the C-terminal amino acid residue and any upstream amino acid residue, preferably 3 amino acid residues upstream to it. Those skilled in the art will be aware as to the nature of such cyclic linkages. In some instances the participating amino acids may require modification in order to facilitate such linkage. In the context of the present invention, cyclic peptides are most conveniently prepared using variants wherein the two C-terminal amino acids are reversed, I and F when considering the first aspect of the invention, $X_5$ and the terminal phenylalanine residue in the second aspect etc. resulting in a linkage between I or $X_5$ and an upstream residue. In such circumstances the terminal amino acid residue (I or $X_5$) is preferably modified to be glycine, the upstream amino acid residue preferably being modified to be lysine or ornithine.

Thus, in accordance with the first aspect of the invention, the peptide may be selected from:

```
D F Y H A K R R L I F S,                          (SEQ ID No. 19)

T D F Y H S K R R L I F,                          (SEQ ID No. 14)

A F Y H S K R R L I F S,                          (SEQ ID No. 15)

D A Y H S K R R L I F S,                          (SEQ ID No. 16)

D F A H S K R R L I F S,                          (SEQ ID No. 17)

D F Y A S K R R L I F S,                          (SEQ ID No. 18)

D F Y H A K R R L I F S,                          (SEQ ID No. 19)

D F Y H S A R R L I F S,                          (SEQ ID No. 20)

D F Y H S K R A L I F S,                          (SEQ ID No. 21)

D F Y H S K R R L A F S,                          (SEQ ID No. 22)

D F Y H S K R R L I F A,                          (SEQ ID No. 23)

F Y H S K R R L I F S,                            (SEQ ID No. 24)

Y H S K R R L I F S,                              (SEQ ID No. 25)

H S K R R L I F S,                                (SEQ ID No. 26)

D F Y H S K R R L I F,                            (SEQ ID No. 1)

F Y H S K R R L I F,                              (SEQ ID No. 27)

Y H S K R R L I F,                                (SEQ ID No. 28)

H S K R R L I F,                                  (SEQ ID No. 29)

S K R R L I F,                                    (SEQ ID No. 30)

K R R L I F,                                      (SEQ ID No. 31)

H- Arg- Leu- Ile- Phe  —NH2                       (SEQ ID NO. 32)

H- Arg- Arg- Leu- Ile- Phe  —NH2                  (SEQ ID NO. 33)

H- Lys- Arg- Arg- Leu- Ile- Phe  —NH2             (SEQ ID NO. 34)

H- Ala- Lys- Arg- Arg- Leu- Ile- Phe  —NH2        (SEQ ID NO. 35)

H- His- Ala- Lys- Arg- Arg- Leu- Ile- Phe  —NH2   (SEQ ID NO. 36)

H- Asn- Leu- Phe- Gly  —NH2                       (SEQ ID NO. 37)

H- Arg- Asn- Leu- Phe- Gly  —NH2                  (SEQ ID NO. 38)

H- Abu- Arg- Asn- Leu- Phe- Gly  —NH2             (SEQ ID NO. 39)

H- Ala- Abu- Arg- Asn- Leu- Phe- Gly  —NH2 and    (SEQ ID NO. 40)

H- Ser- Ala- Abu- Arg- Asn- Leu- Phe- Gly  —NH2   (SEQ ID NO. 41)
```

Considering $X_1X_2X_3RX_4LX_5F$ (SEQ ID No. 2), preferred peptides and variants thereof may include any one of or optionally at least one or more of the following;

(a) $X_1$ is histidine, deleted or replaced by a natural or unnatural amino acid residue-such as alanine, 3-pyridylalanine (Pya), 2-thienylalanine (Thi), homoserine (Hse), phenylalanine, or diaminobutyric acid (Dab), (b) $X_2$ is alanine or an alternative natural or unnatural amino acid residue having a smaller or slightly larger aromatic or aliphatic side chain, such as glycine, aminobutyric acid (Abu), norvaline (Nva), t-butylglycine(Bug), valine, isoleucine, phenylglycine (Phg) or phenylalanine, (c) $X_3$ is lysine or either a basic residue such as arginine or an uncharged natural or unnatural amino acid residue, such as norleucine (Nle), aminobutyric acid (Abu) or leucine, (d) arginine is replaced by either a basic residue such as lysine or an uncharged natural or unnatural amino acid residue, such as citrulline (Cit), homoserine, histidine, norleucine (Nle) or glutamine, (e) $X_4$ is or a natural or unnatural amino acid residue, such as asparagine, proline, serine, aminoisobutyric acid (Aib) or sarcosine (Sar), or an amino acid residue capable of forming a cyclic linkage such as lysine or ornithine, (f) leucine is replaced with a natural or unnatural amino acid residue having a slightly larger aromatic or aliphatic side chain, such as norleucine, norvaline, cyclohexylalanine (Cha), phenylalanine or 1-naphthylalanine (1Nal), (g) $X_5$ is isoleucine or an alternative natural or unnatural amino acid residue having a slightly larger aromatic or aliphatic side chain, such as norleucine, norvaline, cyclohexylalanine (Cha), phenylalanine or 1-naphthylalanine (1Nal), (h) phenylalanine is replaced with a natural or unnatural amino acid such as leucine, cyclohexylalanine (Cha), homophenylalanine (Hof), tyrosine, para-fluorophenylalanine (pFPhe), meta-fluorophenylalanine (mFPhe), trptophan, 1-naphthylalanine (1Nal), 2-naphthylalanine (2Nal), biphenylalanine(Bip) or (Tic), (i) $X_5$ and the terminal phenylalanine residue are reversed, or (j) the peptide is in cyclic form by for example, the formation of a linkage between the side chain of $X_4$ and the C-terminus residue.

In accordance with the second embodiment of the invention, the peptide may be selected from;

| | | | | | | | | |
|---|---|---|---|---|---|---|---|---|
| H S K R R L I F, | | | | | | | | (SEQ ID No. 29) |
| H A K R R L I F, | | | | | | | | (SEQ ID No. 42) |
| H S K R R L F G, | | | | | | | | (SEQ ID No. 43) |
| H A K R R L F G, | | | | | | | | (SEQ ID No. 44) |
| K A C R R L F G, | | | | | | | | (SEQ ID No. 45) |
| K A C R R L I F, | | | | | | | | (SEQ ID No. 46) |
| X1 | X2 | X3 | R | X4 | L | X5 | F | (SEQ ID No. 2) |
| H- His- | Ala- | Lys- | Arg- | Arg- | Leu- | Ile- | Phe | —NH2 (SEQ ID No. 36) |
| H- Ala- | Ala- | Lys- | Arg- | Arg- | Leu- | Ile- | Phe | —NH2 (SEQ ID No. 47) |
| H- | Ala- | Lys- | Arg- | Arg- | Leu- | Ile- | Phe | —NH2 (SEQ ID No. 48) |
| H- Pya- | Ala- | Lys- | Arg- | Arg- | Leu- | Ile- | Phe | —NH2 (SEQ ID No. 49) |
| H- Thi- | Ala- | Lys- | Arg- | Arg- | Leu- | Ile- | Phe | —NH2 (SEQ ID No. 50) |
| H- Hse- | Ala- | Lys- | Arg- | Arg- | Leu- | Ile- | Phe | —NH2 (SEQ ID No. 51) |
| H- Phe- | Ala- | Lys- | Arg- | Arg- | Leu- | Ile- | Phe | —NH2 (SEQ ID No. 52) |
| H- Dab- | Ala- | Lys- | Arg- | Arg- | Leu- | Ile- | Phe | —NH2 (SEQ ID No. 53) |
| H- His- | Ala- | Lys- | Arg- | Arg- | Leu- | Ile- | Phe | —NH2 (SEQ ID No. 36) |
| H- His- | Gly- | Lys- | Arg- | Arg- | Leu- | Ile- | Phe | —NH2 (SEQ ID No. 54) |
| H- His- | Abu- | Lys- | Arg- | Arg- | Leu- | Ile- | Phe | —NH2 (SEQ ID No. 55) |
| H- His- | Nva- | Lys- | Arg- | Arg- | Leu- | Ile- | Phe | —NH2 (SEQ ID No. 56) |
| H- His- | Bug- | Lys- | Arg- | Arg- | Leu- | Ile- | Phe | —NH2 (SEQ ID No. 57) |
| H- His- | Val- | Lys- | Arg- | Arg- | Leu- | Ile- | Phe | —NH2 (SEQ ID No. 58) |
| H- His- | Ile- | Lys- | Arg- | Arg- | Leu- | Ile- | Phe | —NH2 (SEQ ID No. 59) |
| H- His- | Phg- | Lys- | Arg- | Arg- | Leu- | Ile- | Phe | —NH2 (SEQ ID No. 60) |
| H- His- | Phe- | Lys- | Arg- | Arg- | Leu- | Ile- | Phe | —NH2 (SEQ ID No. 61) |
| H- His- | Ala- | Lys- | Arg- | Arg- | Leu- | Ile- | Phe | —NH2 (SEQ ID No. 36) |

-continued

```
H- His- Ala- Ala- Arg- Arg- Leu- Ile- Phe  -NH2 (SEQ ID No. 62)
H- His- Ala- Nle- Arg- Arg- Leu- Ile- Phe  -NH2 (SEQ ID No. 63)
H- His- Ala- Abu- Arg- Arg- Leu- Ile- Phe  -NH2 (SEQ ID No. 64)
H- His- Ala- Leu- Arg- Arg- Leu- Ile- Phe  -NH2 (SEQ ID No. 65)
H- His- Ala- Arg- Arg- Arg- Leu- Ile- Phe  -NH2 (SEQ ID No. 66)
H- His- Ala- Lys- Arg- Arg- Leu- Ile- Phe  -NH2 (SEQ ID No. 36)
H- His- Ala- Lys- Ala- Arg- Leu- Ile- Phe  -NH2 (SEQ ID No. 67)
H- His- Ala- Lys- Cit- Arg- Leu- Ile- Phe  -NH2 (SEQ ID No. 68)
H- His- Ala- Lys- Hse- Arg- Leu- Ile- Phe  -NH2 (SEQ ID No. 69
H- His- Ala- Lys- His- Arg- Leu- Ile- Phe  -NH2 (SEQ ID No. 70)
H- His- Ala- Lys- Nle- Arg- Leu- Ile- Phe  -NH2 (SEQ ID No. 71)
H- His- Ala- Lys- Gln- Arg- Leu- Ile- Phe  -NH2 (SEQ ID No. 72)
H- His- Ala- Lys- Lys- Arg- Leu- Ile- Phe  -NH2 (SEQ ID No. 73)
H- His- Ala- Lys- Arg- Arg- Leu- Ile- Phe  -NH2 (SEQ ID No. 36)
H- His- Ala- Lys- Arg- Ala- Leu- Ile- Phe  -NH2 (SEQ ID No. 74)
H- His- Ala- Lys- Arg- Asn- Leu- Ile- Phe  -NH2 (SEQ ID No. 75)
H- His- Ala- Lys- Arg- Pro- Leu- Ile- Phe  -NH2 (SEQ ID No. 76)
H- His- Ala- Lys- Arg- Ser- Leu- Ile- Phe  -NH2 (SEQ ID No. 77)
H- His- Ala- Lys- Arg- Aib- Leu- Ile- Phe  -NH2 (SEQ ID No. 78)
H- His- Ala- Lys- Arg- Sar- Leu- Ile- Phe  -NH2 (SEQ ID No. 79)
H- His- Ala- Lys- Arg- Cit- Leu- Ile- Phe  -NH2 (SEQ ID No. 80)
H- His- Ala- Lys- Arg- Arg- Leu- Ile- Phe  -NH2 (SEQ ID No. 36)
H- His- Ala- Lys- Arg- Arg- Ala- Ile- Phe  -NH2 (SEQ ID No. 81)
H- His- Ala- Lys- Arg- Arg- leu  Ile- Phe  -NH2 (SEQ ID No. 82)
H- His- Ala- Lys- Arg- Arg- Ile- Ile- Phe  -NH2 (SEQ ID No. 83)
H- His- Ala- Lys- Arg- Arg- Val- Ile- Phe  -NH2 (SEQ ID No. 84)
H- His- Ala- Lys- Arg- Arg- Nle- Ile- Phe  -NH2 (SEQ ID No. 85)
H- His- Ala- Lys- Arg- Arg- Nva- Ile- Phe  -NH2 (SEQ ID No. 86)
H- His- Ala- Lys- Arg- Arg- Cha- Ile- Phe  -NH2 (SEQ ID No. 87)
H- His- Ala- Lys- Arg- Arg- Phe- Ile- Phe  -NH2 (SEQ ID No. 88)
H- His- Ala- Lys- Arg- Arg- 1Nap- Ile- Phe -NH2 (SEQ ID No. 89)
H- His- Ala- Lys- Arg- Arg- Leu- Ile- Phe  -NH2 (SEQ ID No. 36)
H- His- Ala- Lys- Arg- Arg- Leu- Ala- Phe  -NH2 (SEQ ID No. 90)
H- His- Ala- Lys- Arg- Arg- Leu- Leu- Phe  -NH2 (SEQ ID No. 91)
H- His- Ala- Lys- Arg- Arg- Leu- Val- Phe  -NH2 (SEQ ID No. 92)
H- His- Ala- Lys- Arg- Arg- Leu- Nle- Phe  -NH2 (SEQ ID No. 93)
H- His- Ala- Lys- Arg- Arg- Leu- Nva- Phe  -NH2 (SEQ ID No. 94)
H- His- Ala- Lys- Arg- Arg- Leu- Cha- Phe  -NH2 (SEQ ID No. 95)
H- His- Ala- Lys- Arg- Arg- Leu- Phe- Phe  -NH2 (SEQ ID No. 96)
H- His- Ala- Lys- Arg- Arg- Leu- 1Nap- Phe -NH2 (SEQ ID No. 97)
```

```
                              -continued
        H-   His- Ala- Lys-  Arg- Arg- Leu-  Phe    -NH2  (SEQ ID No. 98)

H-   His- Ala- Lys   Arg- Arg- Leu-  Ile-   Phe   -NH2  (SEQ ID No. 36)

H-   His- Ala- Lys-  Arg- Arg- Leu-  Ile-   Leu   -NH2  (SEQ ID No. 99)

H-   His- Ala- Lys-  Arg- Arg- Leu-  Ile-   Cha   -NH2  (SEQ ID No. 100)

H-   His- Ala- Lys-  Arg- Arg- Leu-  Ile-   Hof   -NH2  (SEQ ID No. 101)

H-   His- Ala- Lys-  Arg- Arg- Leu-  Ile-   Tyr   -NH2  (SEQ ID No. 102)

H-   His- Ala- Lys-  Arg- Arg- Leu-  Ile-   pFPhe -NH2  (SEQ ID No. 103)

H-   His- Ala- Lys-  Arg- Arg- Leu-  Ile-   mFPhe -NH2  (SEQ ID No. 104)

H-   His- Ala- Lys-  Arg- Arg- Leu-  Ile-   Trp   -NH2  (SEQ ID No. 105)

H-   His- Ala- Lys-  Arg- Arg- Leu-  Ile-   1Nap  -NH2  (SEQ ID No. 106)

H-   His- Ala- Lys-  Arg- Arg- Leu-  Ile-   2Nap  -NH2  (SEQ ID No. 107)

H-   His- Ala- Lys-  Arg- Arg- Leu-  Ile-   Lys   -NH2  (SEQ ID No. 108)

H-   His- Ala- Lys-  Arg- Arg- Leu-  Ile-   Tic   -NH2  (SEQ ID No. 109)

H-   His- Ala- Lys-  Arg- Arg- Leu-  Ile-   Phe   -NH2  (SEQ ID No. 36)

H-   His  Ala  Lys   Arg  Arg  Leu   Ile    L-Pse  OH   (SEQ ID No. 110)

H-   His  Ala  Lys   Arg  Arg  Leu   Ile    D-Pse  OH   (SEQ ID No. 111)

H-   His  Ser  Lys   Arg  Arg  Leu   Ile    L-Pse  OH   (SEQ ID No. 112)

H-   His  Ser  Lys   Arg  Arg  Leu   Ile    D-Pse  OH   (SEQ ID No. 113)

H-   His  Ala  Lys   Arg  Arg  Leu   Ile    L-Psa  OH   (SEQ ID No. 114)

H-   His  Ala  Lys   Arg  Arg  Leu   Ile    D-Psa  OH   (SEQ ID No. 115)

H-   His  Ser  Lys   Arg  Arg  Leu   Ile    L-Psa  OH   (SEQ ID No. 116)

H-   His  Ser  Lys   Arg  Arg  Leu   Ile    D-Psa  OH   (SEQ ID No. 117)

H-   His  Ala  Lys   Arg  Arg  Leu   Ile    Dhp    OH   (SEQ ID No. 118)

H-   His  Ser  Lys   Arg  Arg  Leu   Ile    Dhp    OH   (SEQ ID No. 119)

H-   His  Ala  Lys   Arg  Arg  Leu   Ile    Pheol       (SEQ ID No. 120)

H-   His  Ser  Lys   Arg  Arg  Leu   Ile    Pheol       (SEQ ID No. 121)

H-   His- Ala- Lys-  Arg- Arg- Leu-  Ile-   Phe   -NH2  (SEQ ID No. 36)

H-   Ala- Ala- Abu-  Arg- Arg- Leu-  Ile-   pFPhe -NH2  (SEQ ID No. 122)

H-   Ala- Ala- Lys-  Arg- Arg- Leu-  Ile-   pFPhe -NH2  (SEQ ID No. 123)

H-   Ala- Ala- Lys-  Arg- Cit- Leu-  Ile-   pFPhe -NH2  (SEQ ID No. 124)

H-   Ala- Ala- Lys-  Arg- Arg- Leu-  Ala-   pFPhe -NH2  (SEQ ID No. 125)

H-   Ala- Ala- Abu-  Arg- Ser- Leu-  Ile-   pFPhe -NH2  (SEQ ID No. 126)

H-   Ala- Ala- Lys-  Gln- Arg- Leu-  Ile-   pFPhe -NH2  (SEQ ID No. 127)

H-   Ala- Ala- Lys-  Arg- Arg- Leu-  Ile-   pFPhe -NH2  (SEQ ID No. 128)

H-   Gly- Ala- Lys-  Arg- Arg- Leu-  Ile-   pFPhe -NH2  (SEQ ID No. 129)

H-   Ala- Ala- Lys-  hArg- Arg- Leu- Ile-   pFPhe -NH2  (SEQ ID No. 130)

H-   Ala- Ala- Lys-  Ser- Arg- Leu-  Ile-   pFPhe -NH2  (SEQ ID No. 131)

H-   Ala- Ala- Lys-  Hse- Arg- Leu-  Ile-   pFPhe -NH2  (SEQ ID No. 132)

H-   Ala- Ala- Lys-  Arg- Lys- Leu-  Ile-   pFPhe -NH2  (SEQ ID No. 133)

H-   Ala- Ala- Lys-  Arg- Orn- Leu-  Ile-   pFPhe -NH2  (SEQ ID No. 134)
```

```
                      -continued
H- Ala- Ala- Lys- Arg- Gln- Leu- Ile-  pFPhe   -NH2 (SEQ ID No. 135)

H- Ala- Ala- Lys- Arg- Hse- Leu- Ile-  pFPhe   -NH2 (SEQ ID No. 136)

H- Ala- Ala- Lys- Arg- Thr- Leu- Ile-  pFPhe   -NH2 (SEQ ID No. 137)

H- Ala- Ala- Lys- Arg- Nva- Leu- Ile-  pFPhe   -NH2 (SEQ ID No. 138)

H- Ala- Ala- Lys- Arg- Arg- Phg- Ile-  pFPhe   -NH2 (SEQ ID No. 139)

H- Ala- Ala- Lys- Arg- Arg- Met- Ile-  pFPhe   -NH2 (SEQ ID No. 140)

H- Ala- Ala- Lys- Arg- Arg- Ala- Ile-  pFPhe   -NH2 (SEQ ID No. 141)

H- Ala- Ala- Lys- Arg- Arg- Hof- Ile-  pFPhe   -NH2 (SEQ ID No. 142)

H- Ala- Ala- Lys- Arg- Arg- hLeu- Ile- pFPhe   -NH2 (SEQ ID No. 143)

H- Ala- Ala- Lys- Arg- Arg- aIle- Ile- pFPhe   -NH2 (SEQ ID No. 144)

H- Ala- Ala- Lys- Arg- Arg- Leu- Gly-  pFPhe   -NH2 (SEQ ID No. 145)

H- Ala- Ala- Lys- Arg- Arg- Leu- βAla   pFPhe   -NH2 (SEQ ID No. 146)

H- Ala- Ala- Lys- Arg- Arg- Leu- Phg-  pFPhe   -NH2 (SEQ ID No. 147)

H- Ala- Ala- Lys- Arg- Arg- Leu- Aib-  pFPhe   -NH2 (SEQ ID No. 148)

H- Ala- Ala- Lys- Arg- Arg- Leu- Sar-  pFPhe   -NH2 (SEQ ID No. 149)

H- Ala- Ala- Lys- Arg- Arg- Leu- Pro-  pFPhe   -NH2 (SEQ ID No. 150)

H- Ala- Ala- Lys- Arg- Arg- Leu- Bug-  pFPhe   -NH2 (SEQ ID No. 151)

H- Ala- Ala- Lys- Arg- Arg- Leu- Ser-  pFPhe   -NH2 (SEQ ID No. 152)

H- Ala- Ala- Lys- Arg- Arg- Leu- Asp-  pFPhe   -NH2 (SEQ ID No. 153)

H- Ala- Ala- Lys- Arg- Arg- Leu- Asn-  pFPhe   -NH2 (SEQ ID No. 154)

H- Ala- Ala- Lys- Arg- Arg- Leu- pFPhe-  Phe    -NH2 (SEQ ID No. 155)

H- Ala- Ala- Lys- Arg- Arg- Leu- diClPhe Phe    -NH2 (SEQ ID No. 156)

H- Ala- Ala- Lys- Arg- Arg- Leu- pClPhe- Phe    -NH2 (SEQ ID No. 157)

H- Ala- Ala- Lys- Arg- Arg- Leu- mClPhe  Phe    -NH2 (SEQ ID No. 158)

H- Ala- Ala- Lys- Arg- Arg- Leu- oClPhe- Phe    -NH2 (SEQ ID No. 159)

H- Ala- Ala- Lys- Arg- Arg- Leu- pIPhe-  Phe    -NH2 (SEQ ID No. 160)

H- Ala- Ala- Lys- Arg- Arg- Leu- TyrMe-  Phe    -NH2 (SEQ ID No. 161)

H- Ala- Ala- Lys- Arg- Arg- Leu- Thi-    Phe    -NH2 (SEQ ID No. 162)

H- Ala- Ala- Lys- Arg- Arg- Leu- Pya-    Phe    -NH2 (SEQ ID No. 163)

H- Ala- Ala- Lys- Arg- Arg- Leu- Ile-   diClPhe -NH2 (SEQ ID No. 164)

H- Ala- Ala- Lys- Arg- Arg- Leu- Ile-   pClPhe  -NH2 (SEQ ID No. 165)

H- Ala- Ala- Lys- Arg- Arg- Leu- Ile-   mClPhe  -NH2 (SEQ ID No. 166)

H- Ala- Ala- Lys- Arg- Arg- Leu- Ile-   oClPhe  -NH2 (SEQ ID No. 167)

H- Ala- Ala- Lys- Arg- Arg- Leu- Ile-   Phg     -NH2 (SEQ ID No. 168)

H- Ala- Ala- Lys- Arg- Arg- Leu- Ile-   TyrMe   -NH2 (SEQ ID No. 169)

H- Ala- Ala- Lys- Arg- Arg- Leu- Ile-   Thi     -NH2 (SEQ ID No. 170)

H- Ala- Ala- Lys- Arg- Arg- Leu- Ile-   Pya     -NH2 (SEQ ID No. 171)

H- Ala- Ala- Lys- Arg- Arg- Leu- Ile-   Inc     -NH2 (SEQ ID No. 172)
``` and the cyclic peptides;

```
5,8-cyclo-[H-His-Ala-Lys-Arg-Lys-Leu-Phe-Gly]  (SEQ ID No. 173)

5,8-cyclo-[H-His-Ala-Lys-Arg-Orn-Leu-Phe-Gly]  (SEQ ID No. 174)
```

In another preferred embodiment, the invention relates to a peptide selected from the following:

```
H  Ala Ala Abu  Arg Ser Leu  Ile      pFPhe  NH2   (SEQ ID No. 126)

H  Ala Ala Abu  Arg Ser Leu  Ile      Gly    NH2   (SEQ ID No. 290)

H  Ala Ala Abu  Arg Ser Leu  mClPhe   pFPhe  NH2   (SEQ ID No. 291)

H  Ala Ala Abu  Arg Ser Leu  mClPhe   Gly    NH2   (SEQ ID No. 292)
```

With particular reference to SEQ ID No. 3, a variant peptide may additionally involve the replacement of an amino acid residue by an alanine residue, the deletion of $X_1$ or the reversal of $X_5$ and the terminal phenylalanine residue. These options are also applicable to the peptide SEQ ID No 3 which may therefore, by way of example result in the peptides $X_2KRRLX_5F$ (SEQ ID No. 181) and $HX_2KRRLFX_5$ (SEQ ID No. 182). Most preferably, the peptide is H A K R R L I F (SEQ ID No. 42). Further variants those discussed below.

More preferably with respect to H $X_2$ K R R L $X_5$F (SEQ ID No. 469) preferred peptides and variants thereof may include any one of or optionally at least one or more of the following;
(a) His is unchanged, deleted or replaced by D-His, Ala, Thi, Hse, Phe, or Dab,
(b) $X_2$ is Ala unchanged or replaced by Ser, Abu Bug or Val,
(c) Lys is unchanged or replaced by Arg or Abu,
(d) Arg is unchanged or replaced by Lys, Cit, or Gln,
(e) Arg is unchanged or modified to form a cyclic peptide with the C-terminal residue, or replaced by Cit or Ser,
(f) Leu is unchanged or replaced by Ile,
(g) $X_5$ is Ile unchanged, replaced by Leu or Gly if reversed with Phe,
(h) Phe is unchanged or replaced by para-fluoroPhe, meta-fluoroPhe, L-Psa, 2-Nap or Dhp,
(i) the two C-terminal residue are reversed, or
(j) the peptide is in cyclic form by virtue of a linkage between the C-terminal residue and the residue 3 upstream to it.

Especially preferred are peptides wherein $X_2$ is Ala and $X_5$ is Ile, incorporating more than one of the above variations particularly where Phe is replaced by para-fluoro-Phe and His is replaced by Ala or is deleted. Of such peptides, especially preferred are those that include further modifications where:
(a) Lys is replaced by Abu,
(b) the first Arg residue is replaced by Gln and
(c) the second Arg residue is replaced by Cit or Ser and,
(d) Ile is replaced by Ala.

Thus, preferred peptides in accordance with the preferred sequence H A K R R L I F (SEQ ID No. 42) include;

```
His152
H- his- Ala- Lys- Arg- Arg- Leu- Ile- Phe   -NH2 (SEQ ID No. 183)

H- Ala- Ala- Lys- Arg- Arg- Leu- Ile- Phe   -NH2 (SEQ ID No. 47)

H-  Ala- Lys- Arg- Arg- Leu- Ile- Phe   -NH2 (SEQ ID No. 48)

H- Thi- Ala- Lys- Arg- Arg- Leu- Ile- Phe   -NH2 (SEQ ID No. 50)

H- Hse- Ala- Lys- Arg- Arg- Leu- Ile- Phe   -NH2 (SEQ ID No. 51)

H- Phe- Ala- Lys- Arg- Arg- Leu- Ile- Phe   -NH2 (SEQ ID No. 52)

H- Dab- Ala- Lys- Arg- Arg- Leu- Ile- Phe   -NH2 (SEQ ID No. 53)

Ala153
H- His- Abu- Lys- Arg- Arg- Leu- Ile- Phe   -NH2 (SEQ ID No. 55)

H- His- Val- Lys- Arg- Arg- Leu- Ile- Phe   -NH2 (SEQ ID No. 58)

Lys154
H- His- Ala- Arg- Arg- Arg- Leu- Ile- Phe   -NH2 (SEQ ID No. 66)

Leu157
H- His- Ala- Lys- Arg- Arg- Ile- Ile- Phe   -NH2 (SEQ ID No. 83)

Ile158
H- His- Ala- Lys- Arg- Arg- Leu- Leu- Phe   -NH2 (SEQ ID No. 91)

Phe159
H- His- Ala- Lys- Arg- Arg- Leu- Ile- pFPhe -NH2 (SEQ ID No. 103)
```

```
                                    -continued
H-  His-  Ala-  Lys-  Arg-  Arg-  Leu-  Ile-  2Nap   -NH2   (SEQ ID No. 107)

H-  His   Ala   Lys   Arg   Arg   Leu   Ile   D-Psa  OH     (SEQ ID No. 115)

H-  His   Ser   Lys   Arg   Arg   Leu   Ile   Dhp    OH     (SEQ ID No. 119)

Multiples
H-  Ala-  Ala-  Abu-  Arg-  Arg-  Leu-  Ile-  pFPhe  -NH2   (SEQ ID No. 122)

H-  Ala-  Ala-  Lys-  Arg-  Arg-  Leu-  Ile-  pFPhe  -NH2   (SEQ ID No. 123)

H-  Ala-  Ala-  Lys-  Arg-  Cit-  Leu-  Ile-  pFPhe  -NH2   (SEQ ID No. 124)

H-  Ala-  Ala-  Lys-  Arg-  Arg-  Leu-  Ala-  pFPhe  -NH2   (SEQ ID No. 125)

H-  Ala-  Ala-  Abu-  Arg-  Ser-  Leu-  Ile-  pFPhe  -NH2   (SEQ ID No. 126)

H-  Ala-  Ala-  Lys-  Gln-  Arg-  Leu-  Ile-  pFPhe  -NH2   (SEQ ID No. 127)

H-    Ala-  Lys-  Arg-  Arg-  Leu-  Ile-  pFPhe  -NH2   (SEQ ID No. 177)
```

The three letter notations appearing above are in accordance with IUPAC convention. The structure of various unnatural amino acid derivatives are provided in the introduction to the Examples, further expansion on nomenclature being given above.

The peptides of the present invention may be subjected to a further modification that is beneficial in the context of the present invention being conversion of the free carboxyl group of the carboxy terminal amino acid residue, to a carboxamide group. By way of example, when the peptide is of SEQ ID No.1 the carboxy terminal phenylalanine residue may have its carboxyl group converted into a carboxamide group. This modification is believed to enhance the stability of the peptide. Thus, the C-terminal amino acid residue may be in the form —C(O)—NRR', wherein R and R' are each independently selected from hydrogen, C1-6 alkyl, C1-6 alkylene or C1-6 alkynyl (collectively referred to "alk"), aryl such as benzyl or alkaryl, each optionally substituted by heteroatoms such as O, S or N. Preferably at least one of R or R' is hydrogen, most preferably, they are both hydrogen. Thus, the present invention therefore encompasses the peptides wherein the C-terminal amino acid residue is in the carboxyl or carboxamide form.

In one preferred embodiment, the invention relates to peptides of formula V $$RX_6X_7X_8X_9 \qquad \text{(formula V)(SEQ ID No. 293)}$$

wherein
$X_6$ is arginine, serine or lysine;
$X_7$ is leucine, isoleucine or valine;
$X_8$ is asparagine, alanine, glycine or isoleucine; and
$X_9$ is phenylalanine;

or variants thereof.

More preferably, the invention relates to peptides of formula V (SEQ ID No. 293) or variants thereof wherein the peptide is modified by at least one of a deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives, dual peptides, multimers of the peptides and any of said peptides in the D-stereomer form, or the order of the final two residues at the C-terminal end are reversed.

Even more preferably still, the invention relates to peptides of formula V (SEQ ID No. 293), or variants thereof, wherein:

(a) R is unchanged or conservatively substituted (by a basic amino acid), (b) $X_6$ is substituted by any amino acid capable of providing at least one site for participating in hydrogen bonding, (c) $X_7$ is unchanged or conservatively substituted, (d) $X_8$ is unchanged or conservatively substituted, (e) $X_9$ is unchanged or substituted by any aromatic amino acid.

In another preferred embodiment, the invention relates to peptides of formula V (SEQ ID No. 293), or variants thereof, wherein:

(a) R is replaced by either a basic residue such as lysine or an uncharged natural or unnatural amino acid residue, such as citrulline (Cit), homoserine, histidine, norleucine (Nle), or glutamine, (b) $X_6$ is replaced by a natural or unnatural amino acid residue such as asparagine, proline, aminoisobutyric acid (Aib) or sarcosine (Sar), or an amino acid residue capable of forming a cyclic linkage such as ornithine, (c) $X_7$ is replaced with a natural or unnatural amino acid residue having a slightly larger aromatic or aliphatic side chain, such as norleucine, norvaline, cyclohexylalanine (Cha), phenylalanine or 1-naphthylalanine (1Nal), (d) $X_8$ is replaced with a natural or unnatural amino acid residue having a slightly larger aromatic or aliphatic side chain, such as norleucine, norvaline, cyclohexylalanine (Cha), phenylalanine or 1-naphthylalanine (1Nal), (e) $X_9$ is replaced with a natural or unnatural amino acid such as leucine, cyclohexylalanine (Cha), homophenylalanine (Hof), tyrosine, para-fluorophenylalanine (pFPhe), meta-fluorophenylalanine (mFPhe), trptophan, 1-naphthylalanine (1Nal), 2-naphthylalanine (2Nal), meta-chlorophenylalanine (mClPhe),biphenylalanine(Bip) or (Tic).

In one preferred embodiment, the invention relates to peptides of formula V $$RX_6X_7X_8X_9 \qquad \text{(formula V) (SEQ ID No. 293)}$$

wherein
$X_6$ is arginine, serine or lysine;
$X_7$ is leucine, isoleucine or valine;
$X_8$ is asparagine, alanine, glycine or isoleucine; and
$X_9$ is phenylalanine;

or variants thereof.

More preferably, the invention relates to peptides of formula V or variants thereof wherein the peptide is modified by at least one of a deletion, addition or substitution of one or more amino acid residues, or by substitution of one or more natural amino acid residues by the corresponding D-stereomer or by a non-natural amino acid residue, chemical derivatives of the peptides, cyclic peptides derived from the peptides or from the peptide derivatives, dual peptides, multimers of the peptides and any of said peptides in the D-stereomer form, or the order of the final two residues at the C-terminal end are reversed.

Even more preferably still, the invention relates to peptides of formula V, or variants thereof, wherein: (a) R is unchanged or conservatively substituted (by a basic amino acid), (b) $X_6$ is substituted by any amino acid capable of providing at least one site for participating in hydrogen bonding, (c) $X_7$ is unchanged or conservatively substituted, (d) $X_8$ is unchanged or conservatively substituted, (e) $X_9$ is unchanged or substituted by any aromatic amino acid.

In another preferred embodiment, the invention relates to peptides of formula V (SEQ ID No. 293), or variants thereof, wherein:
(a) R is replaced by either a basic residue such as lysine or an uncharged natural or unnatural amino acid residue, such as citrulline (Cit), homoserine, histidine, norleucine (Nle), or glutamine,
(d) $X_6$ is replaced by a natural or unnatural amino acid residue such as asparagine, proline, aminoisobutyric acid (Aib) or sarcosine (Sar), or an amino acid residue capable of forming a cyclic linkage such as ornithine,
(e) $X_7$ is replaced with a natural or unnatural amino acid residue having a slightly larger aromatic or aliphatic side chain, such as norleucine, norvaline, cyclohexylalanine (Cha), phenylalanine or 1-naphthylalanine (1Nal),
(d) $X_8$ is replaced with a natural or unnatural amino acid residue having a slightly larger aromatic or aliphatic side chain, such as norleucine, norvaline, cyclohexylalanine (Cha), phenylalanine or 1-naphthylalanine (1Nal),
(e) $X_9$ is replaced with a natural or unnatural amino acid such as leucine, cyclohexylalanine (Cha), homophenylalanine (Hof), tyrosine, para-fluorophenylalanine (pFPhe), meta-fluorophenylalanine (mFPhe), trptophan, 1-naphthylalanine (1Nal), 2-naphthylalanine (2Nal), meta-chlorophenylalanine (mClPhe), biphenylalanine(Bip) or (Tic).

In one particularly preferred embodiment, the invention relates to peptides of formula V (SEQ ID No. 293), or variants thereof, wherein the N-terminal is acylated.

In another particularly preferred embodiment, the invention relates to peptides of formula V, or variants thereof, wherein R is substituted by citrulline.

Even more preferably, the invention relates to peptides of formula V (SEQ ID No. 293), or variants thereof, which are selected from the following:

```
H-  Arg  Arg  Leu  Asn  Phe   NH2 (SEQ ID No. 294)
H-  Arg  Arg  Leu  Asn  pFF   NH2 (SEQ ID No. 295)
H-  Arg  Arg  Leu  Asn  mClF  NH2 (SEQ ID No. 296)
H-  Arg  Arg  Leu  Ala  Phe   NH2 (SEQ ID No. 297)
H-  Arg  Arg  Leu  Ala  pFF   NH2 (SEQ ID No. 298)
H-  Arg  Arg  Leu  Ala  mClF  NH2 (SEQ ID No. 299)
H-  Arg  Arg  Leu  Gly  Phe   NH2 (SEQ ID No. 300)
H-  Arg  Arg  Leu  Gly  pFF   NH2 (SEQ ID No. 301)
H-  Arg  Arg  Leu  Gly  mClF  NH2 (SEQ ID No. 302)
H-  Arg  Arg  Ile  Asn  Phe   NH2 (SEQ ID No. 303)
H-  Arg  Arg  Ile  Asn  pFF   NH2 (SEQ ID No. 304)
H-  Arg  Arg  Ile  Asn  mClF  NH2 (SEQ ID No. 305)
H-  Arg  Arg  Ile  Ala  Phe   NH2 (SEQ ID No. 306)
H-  Arg  Arg  Ile  Ala  pFF   NH2 (SEQ ID No. 307)
H-  Arg  Arg  Ile  Ala  mClF  NH2 (SEQ ID No. 308)
H-  Arg  Arg  Ile  Gly  Phe   NH2 (SEQ ID No. 309)
H-  Arg  Arg  Ile  Gly  pFF   NH2 (SEQ ID No. 310)
H-  Arg  Arg  Ile  Gly  mClF  NH2 (SEQ ID No. 311)
H-  Arg  Arg  Val  Asn  Phe   NH2 (SEQ ID No. 312)
H-  Arg  Arg  Val  Asn  pFF   NH2 (SEQ ID No. 313)
H-  Arg  Arg  Val  Asn  mClF  NH2 (SEQ ID No. 314)
H-  Arg  Arg  Val  Ala  Phe   NH2 (SEQ ID No. 315)
H-  Arg  Arg  Val  Ala  pFF   NH2 (SEQ ID No. 316)
H-  Arg  Arg  Val  Ala  mClF  NH2 (SEQ ID No. 317)
H-  Arg  Arg  Val  Gly  Phe   NH2 (SEQ ID No. 318)
H-  Arg  Arg  Val  Gly  pFF   NH2 (SEQ ID No. 319)
H-  Arg  Arg  Val  Gly  mClF  NH2 (SEQ ID No. 320)
H-  Arg  Ser  Leu  Asn  Phe   NH2 (SEQ ID No. 321)
H-  Arg  Ser  Leu  Asn  pFF   NH2 (SEQ ID No. 322)
H-  Arg  Ser  Leu  Asn  mClF  NH2 (SEQ ID No. 323)
H-  Arg  Ser  Leu  Ala  Phe   NH2 (SEQ ID No. 324)
H-  Arg  Ser  Leu  Ala  pFF   NH2 (SEQ ID No. 325)
H-  Arg  Ser  Leu  Ala  mClF  NH2 (SEQ ID No. 326)
H-  Arg  Ser  Leu  Gly  Phe   NH2 (SEQ ID No. 327)
H-  Arg  Ser  Leu  Gly  pFF   NH2 (SEQ ID No. 328)
H-  Arg  Ser  Leu  Gly  mClF  NH2 (SEQ ID No. 329)
H-  Arg  Ser  Ile  Asn  Phe   NH2 (SEQ ID No. 330)
H-  Arg  Ser  Ile  Asn  pFF   NH2 (SEQ ID No. 331)
H-  Arg  Ser  Ile  Asn  mClF  NH2 (SEQ ID No. 332)
H-  Arg  Ser  Ile  Ala  Phe   NH2 (SEQ ID No. 333)
H-  Arg  Ser  Ile  Ala  pFF   NH2 (SEQ ID No. 334)
H-  Arg  Ser  Ile  Ala  mClF  NH2 (SEQ ID No. 335)
H-  Arg  Ser  Ile  Gly  Phe   NH2 (SEQ ID No. 336)
H-  Arg  Ser  Ile  Gly  pFF   NH2 (SEQ ID No. 337)
H-  Arg  Ser  Ile  Gly  mClF  NH2 (SEQ ID No. 338)
H-  Arg  Ser  Val  Asn  Phe   NH2 (SEQ ID No. 339)
H-  Arg  Ser  Val  Asn  pFF   NH2 (SEQ ID No. 340)
H-  Arg  Ser  Val  Asn  mClF  NH2 (SEQ ID No. 341)
H-  Arg  Ser  Val  Ala  Phe   NH2 (SEQ ID No. 342)
H-  Arg  Ser  Val  Ala  pFF   NH2 (SEQ ID No. 343)
```

```
H-  Arg  Ser  Val  Ala  mClF  NH2  (SEQ ID No. 344)
H-  Arg  Ser  Val  Gly  Phe   NH2  (SEQ ID No. 345)
H-  Arg  Ser  Val  Gly  pFF   NH2  (SEQ ID No. 346)
H-  Arg  Ser  Val  Gly  mClF  NH2  (SEQ ID No. 347)
H-  Arg  Lys  Leu  Asn  Phe   NH2  (SEQ ID No. 348)
H-  Arg  Lys  Leu  Asn  pFF   NH2  (SEQ ID No. 349)
H-  Arg  Lys  Leu  Asn  mClF  NH2  (SEQ ID No. 350)
H-  Arg  Lys  Leu  Ala  Phe   NH2  (SEQ ID No. 351)
H-  Arg  Lys  Leu  Ala  pFF   NH2  (SEQ ID No. 352)
H-  Arg  Lys  Leu  Ala  mClF  NH2  (SEQ ID No. 353)
H-  Arg  Lys  Leu  Gly  Phe   NH2  (SEQ ID No. 354)
H-  Arg  Lys  Leu  Gly  pFF   NH2  (SEQ ID No. 355)
H-  Arg  Lys  Leu  Gly  mClF  NH2  (SEQ ID No. 356)
H-  Arg  Lys  Ile  Asn  Phe   NH2  (SEQ ID No. 357)
H-  Arg  Lys  Ile  Asn  pFF   NH2  (SEQ ID No. 358)
H-  Arg  Lys  Ile  Asn  mClF  NH2  (SEQ ID No. 359)
H-  Arg  Lys  Ile  Ala  Phe   NH2  (SEQ ID No. 360)
H-  Arg  Lys  Ile  Ala  pFF   NH2  (SEQ ID No. 361)
H-  Arg  Lys  Ile  Ala  mClF  NH2  (SEQ ID No. 362)
H-  Arg  Lys  Ile  Gly  Phe   NH2  (SEQ ID No. 363)
H-  Arg  Lys  Ile  Gly  pFF   NH2  (SEQ ID No. 364)
H-  Arg  Lys  Ile  Gly  mClF  NH2  (SEQ ID No. 365)
H-  Arg  Lys  Val  Asn  Phe   NH2  (SEQ ID No. 366)
H-  Arg  Lys  Val  Asn  pFF   NH2  (SEQ ID No. 367)
H-  Arg  Lys  Val  Asn  mClF  NH2  (SEQ ID No. 368)
H-  Arg  Lys  Val  Ala  Phe   NH2  (SEQ ID No. 369)
H-  Arg  Lys  Val  Ala  pFF   NH2  (SEQ ID No. 370)
H-  Arg  Lys  Val  Ala  mClF  NH2  (SEQ ID No. 371)
H-  Arg  Lys  Val  Gly  Phe   NH2  (SEQ ID No. 372)
H-  Arg  Lys  Val  Gly  pFF   NH2  (SEQ ID No. 373)
H-  Arg  Lys  Val  Gly  mClF  NH2  (SEQ ID No. 374)
H-  Arg  Arg  Leu  Ile  pFF   NH2  (SEQ ID No. 375)
H-  Cit  Cit  Leu  Ile  pFF   NH2  (SEQ ID No. 376)
H-  Arg  Arg  Leu  Ile  Phe   NH2  (SEQ ID No. 377)
```

More preferably still, the invention relates to peptides of formula V which are selected from the following:

```
H-  Arg  Arg  Leu  Asn  Phe   NH2  (SEQ ID No. 294)
H-  Arg  Arg  Leu  Asn  pFF   NH2  (SEQ ID No. 295)
H-  Arg  Arg  Leu  Asn  mClF  NH2  (SEQ ID No. 296)
H-  Arg  Arg  Leu  Ala  pFF   NH2  (SEQ ID No. 298)
H-  Arg  Arg  Leu  Ala  mClF  NH2  (SEQ ID No. 299)
H-  Arg  Arg  Leu  Gly  pFF   NH2  (SEQ ID No. 301)
H-  Arg  Arg  Leu  Gly  mClF  NH2  (SEQ ID No. 302)
H-  Arg  Arg  Ile  Asn  pFF   NH2  (SEQ ID No. 304)
H-  Arg  Arg  Ile  Asn  mClF  NH2  (SEQ ID No. 305)
H-  Arg  Arg  Ile  Ala  pFF   NH2  (SEQ ID No. 307)
H-  Arg  Arg  Ile  Ala  mClF  NH2  (SEQ ID No. 308)
H-  Arg  Lys  Leu  Asn  mClF  NH2  (SEQ ID No. 350)
H-  Arg  Lys  Leu  Ala  pFF   NH2  (SEQ ID No. 352)
H-  Arg  Lys  Leu  Ala  mClF  NH2  (SEQ ID No. 353)
H-  Arg  Lys  Leu  Gly  pFF   NH2  (SEQ ID No. 355)
H-  Arg  Lys  Ile  Asn  pFF   NH2  (SEQ ID No. 358)
H-  Arg  Arg  Leu  Ile  pFF   NH2  (SEQ ID No. 375)
```

In one especially preferred embodiment, the peptides of formula V are selected from the following:

```
H-  Arg  Arg  Leu  Asn  Phe   NH2  (SEQ ID No. 294)
H-  Arg  Arg  Leu  Asn  pFF   NH2  (SEQ ID No. 295)
H-  Arg  Arg  Leu  Asn  mClF  NH2  (SEQ ID No. 296)
H-  Arg  Arg  Leu  Ala  pFF   NH2  (SEQ ID No. 298)
H-  Arg  Arg  Ile  Asn  pFF   NH2  (SEQ ID No. 304)
H-  Arg  Arg  Ile  Ala  pFF   NH2  (SEQ ID No. 307)
H-  Arg  Lys  Leu  Ala  pFF   NH2  (SEQ ID No. 352)
H-  Arg  Arg  Leu  Asn  pFF   NH2  (SEQ ID No. 295)
H-  Arg  Arg  Ile  Asn  pFF   NH2  (SEQ ID No. 304)
H-  Arg  Arg  Leu  Ile  pFF   NH2  (SEQ ID No. 375)
```

The present invention further encompasses the above described peptides of the first, second and third aspects, their use in the inhibition of CDK2, their use in the treatment of proliferative disorders such as cancers and leukaemias where inhibition of CDK2 would be beneficial and their use in the preparation of medicaments for such use. Such preparation including their use in assays for further candidate compound as described herein. The embodiments described as being preferred in the context of the peptides of the invention apply equally to their use.

Assays

A further embodiment of the present invention relates to assays for candidate substances that are capable of modifying the cyclin interaction with CDK's, especially CDK2 and CDK4. Such assays are based upon the observation that the peptides of the invention, despite not including the generally considered "cyclin binding motif" as discussed in Example 9, have been shown to bind to cyclin. Furthermore, it has been shown that the peptides of the second and further aspects of the invention competitively inhibit the binding of a peptide of the first aspect of the invention. Thus, such assays may involve incubating a candidate substance with a cyclin and a peptide of the invention and detecting either the candidate-cyclin complex or free (unbound) peptide of the invention. An example of the latter would involve the peptide of the invention being labeled such as to emit a signal when bound to a CDK. The reduction in said signal being indicative of the candidate substance binding to, or inhibiting peptide-cyclin interaction.

Suitable candidate substances include peptides, especially of from about 5 to 30 or 10 to 25 amino acids in size, based on the sequence of the various domains of p21, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for p21 or cyclin binding regions thereof. Furthermore, combinatorial libraries, single-compound collections of synthetic or natural organic molecules, peptide and peptide mimetics, defined chemical entities, oligonucleotides, and natural product libraries may be screened for activity as modulators of cyclin/CDK/regulatory protein complex interactions in assays such as those described below. The candidate substances may be used in an initial screen in batches of, for example, 10 substances per reaction, and the substances of those batches which show inhibition tested individually. Candidate substances which show activity in in vitro screens such as those described below can then be tested in whole cell systems, such as mammalian cells.

Thus the present invention further relates to an assay for the identification of compounds that interact with cyclin A, cyclin E or cyclin D (hereinafter "a cyclin") or these cyclins when complexed with the physiologically relevant CDK, comprising;

(a) incubating a candidate compound and a peptide of the formula $X_1X_2X_3RX_4LX_5F$ (SEQ ID No. 464) or more preferably of formula $HX_2KRRLX_5F$ (SEQ ID No. 470) or variants thereof as defined above, and a cyclin or cyclin/CDK complex, (b) detecting binding of either the candidate compound or the peptide of formula $X_1X_2X_3RX_4LX_5F$ (SEQ ID No. 464)/ $HX_2KRRLX_5F$ (SEQ ID No. 470) with the cyclin.

The assays of the present invention (discussed hereinafter with reference to cyclin A) encompass screening for candidate compounds that bind a cyclin "recruitment center" or "cyclin groove" discussed above in respect of the prior art but herein defined in greater detail with reference to the amino acid sequence of preferably human cyclin A or of partially homologous and functionally equivalent mammmalian cyclins. The substrate recruitment site from previously described cyclin A/peptide complexes consists mainly of residues of the α1 (particularly residues 207-225) and α3 (particularly residues 250-269) helices, which form a shallow groove on the surface, comprised predominantly of hydrophobic residues. This is discussed in greater detail in Russo A A et al. (Nature (1996) 382, 325-331) with respect to p27/cyclin A. From the X-ray structure assigned to the p27/cyclin A/CDK2 provided therein it is possible to conclude that the sequence SACRNLFG (SEQ ID No. 178) of p27 that interacts with cyclin A does so through the following interaction residues of cyclin A:

| p27 residue | Cyclin A residues |
|---|---|
| S | E220, E224 |
| A | W217, E220, V221, E224, I281 |
| C | Y280, I281, D283 |
| R | D216, W217, E220, Q254 |
| N | Q254, T285, Y286 |
| L | I213, L214, W217, Q254 |
| F | M210, I213, R250, G251, K252, L253, Q254 |
| G | T285 |

These residues are largely conserved in the A, B, E and D1 cyclins.

Through analysis of the interaction of the p21 peptides of the present invention with cyclin A, further distinct amino acid residues of cyclin A have been identified as being important in the interaction between cyclin A and p21, especially with respect to the inhibitory activity the peptides of the present invention display against CDK2.

The cyclin A amino acids believed to be important for interaction with the p21 derived peptides of the present invention include:

| | Cyclin A residues | | |
|---|---|---|---|
| p21 residue | Major Interaction | Intermediate Interaction | Minor Interaction |
| H | E223, E224 | W217, V219, V221 S408, E411 | G222, Y225, I281 |
| A | | Y225 | E223 |
| K | D284 | | E220, V279 |
| R | | I213 | A212, V215, L218 Q406, S408 |
| R | D283 | I213, L214 | M210, L253 |
| L | L253 | G257 | L218, I239, V256 |
| I | | R250, Q254 | |
| F | I206, R211 | T207, L214 | M200 |

The present invention therefore includes assays for candidate compounds that interact with cyclin A by virtue of forming associations with at least two of the amino acid residues L253, I206 and R211 of cyclin A or the corresponding homologous amino acids of cyclin D or cyclin E.

In a further preferred assay, the candidate compound may form associations with at least E223, E224, D284, D283, L253, I206 and R211 of cyclin A or the corresponding homologous amino acids of cyclin D or cyclin E.

In a preferred assay, the candidate compound may form further associations with W217, V219, V221, S408, E411, Y225, I213, L214, G257, R250, Q254, T207 and L214 of cyclin A or the corresponding homologous amino acids of cyclin D or cyclin E.

In a more preferred assay, the candidate compound may form further associations with G222, Y225, I281, E223, E220, V279, A212, V215, L218, Q406, S408, M210, L253, L218, I239, V256 and M200 of cyclin A or the corresponding homologous amino acids of cyclin D or cyclin E.

As used in this context the phrase "forming associations" is used to include any form of interaction a binding peptide may make with a peptide ligand. These include electrostatic interactions, hydrogen bonds, or hydrophobic/lipophilic interactions through Van der Waals's forces or aromatic stacking, etc.

Also, as used herein in the context of assays of the present invention, the term "cyclin" is used to refer to cyclin A, cyclin D or cyclin E, or regions thereof that incorporate the "cyclin groove" as hereinbefore described. Thus, an assay may be performed in accordance with the present invention if it utilises the a full length cyclin protein or a region sufficient to allow the cyclin groove to exist, for example amino acids 173-432 or 199-306 of human cyclin A.

Figure 4:
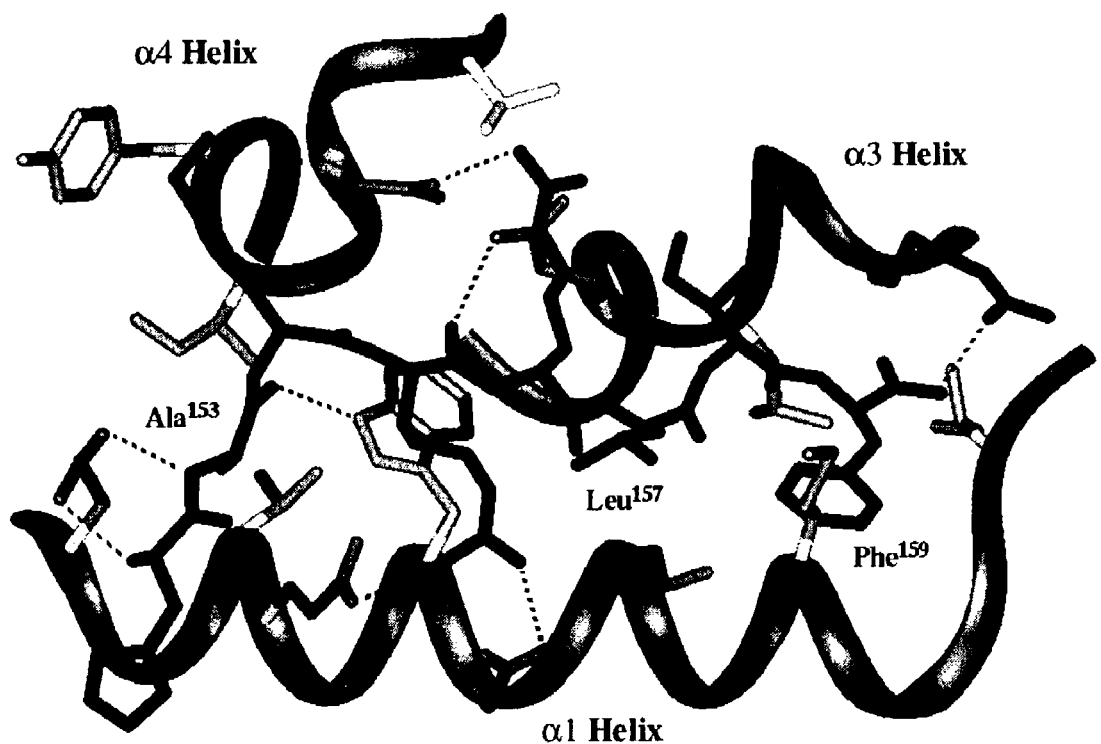
FIG. 4 shows the 3-D structure of the peptide H-His-Ala-Lys-Arg-Arg-Leu-Ile-Phe-NH$_2$ (SEQ ID NO. 36)/cyclin A complex was generated using molecular docking techniques. The peptide structure is represented in black, while only the residues of the cyclin groove that make intermolecular contacts with the peptide are shown. The backbone of cyclin A is represented by the grey ribbon.

Thus, by utilising the peptides of the present invention especially those of the preferred embodiments in competitive binding assays with candidate compounds, further compounds that interact at this site may be identified and assigned utility in the control of the cell cycle by virtue of controlling, preferably inhibiting CDK2 and/or CDK4 activity. Such assays may be performed in vitro or virtually i.e. by using a three dimensional model or preferably, a computer generated model of a complex of a peptide of the present invention and cyclin A. Using such a model, candidate compounds may be designed based upon the specific interactions between the peptides of the present invention and cyclin A, the relevant bond angles and orientation between those components of the peptides of the present invention that interact both directly and indirectly with the cyclin groove. By way of example, FIG. 4 shows the interaction between the peptide HAKRRLIF (SEQ ID No. 42) and Cyclin A. From using the three dimensional model computer generated by this interaction it has been possible to identify the cyclin A amino acid residues that interact with the peptides of the present invention, particularly with HAKRRLIF (SEQ ID No. 42) as outlined above and discussed in greater detail in the examples.

In an embodiment, the cyclin groove includes about residues 173-432 of human cyclin A. In another embodiment, the cyclin groove includes about residues 199-306 of human cyclin A. In a preferred embodiment, the cyclin groove includes about residues 207-225 and about residues 250-269 and about residues 274-282 of human cyclin A. In another embodiment, the cyclin groove includes one or more of: about residues 207-225; about residues 250-269; and about residues 274-282 of human cyclin A. In another embodiment, the cyclin groove includes two or more of: about residues 207-225; about residues 250-269; and about residues 274-282 of human cyclin A As used herein the term "three dimensional model" includes both crystal structures as determined by X-ray diffraction analysis, solution structures determined by nuclear magnetic resonance spectroscopy as well as computer generated models. Such computer generated models may be created on the basis of a physically determined structure of a peptide of the present invention bound to cyclin A or on the basis of the known crystal structure of cyclin A, modified (by the constraints provided by the software) to accommodate a peptide of formula I. Suitable software suitable of the generation of such computer generated three dimensional models include AFFINITY, CATALYST and LUDI (Molecular Simulations, Inc.).

Such three dimensional models may be used in a program of rational drug design to generate further candidate compounds that will bind to cyclin A. As used herein the term "rational drug design" is used to signify the process wherein structural information about a ligand-receptor interaction is used to design and propose modified ligand candidate compounds possessing improved fit with the receptor site in terms of geometry and chemical complementarity and hence improved biological and pharmaceutical properties, such properties including, e.g., increased receptor affinity (potency) and simplified chemical structure. Such candidate compounds may be further compounds or synthetic organic molecules. The preferred peptides for use in these aspects of the invention are identical to those designated as preferred with respect to the first and second aspects of the invention, most especially those of the formula $HX_2KRRLX_5F$ (SEQ ID No.470) and of those particularly the peptide HAKRRLIF (SEQ ID No. 42). In a preferred embodiment, rational drug design is focused upon the four C-terminal amino acids $RLX_5F$ (SEQ ID No. 184) or $RLFX_5$ (SEQ ID No. 185) or variants thereof as discussed above with respect to SEQ ID No. 3.

Using techniques known in the art, crystal or solution structures of cyclin A bound to a peptide of the present invention may be generated, these too may be used in a programme of rational drug design as discussed above.

Crystals of the p21 derived peptides of the present invention complexed with cyclin A can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used.

Once a crystal of the present invention is grown, X-ray diffraction data can be collected. Crystals can be characterized by using X-rays produced in a conventional source (such as a sealed tube or a rotating anode) or using a synchrotron source. Methods of characterization include, but are not limited to, precision photography, oscillation photography, diffractometer data collection, and Se-Met multiwavelength anamalous dispersion data.

Once the three-dimensional structure of a protein-ligand complex formed between a p21 derived peptide of the present invention and cyclin A is determined, a candidate compound may be examined through the use of computer modeling using a docking program such as GRAM, DOCK or AUTODOCK [Dunbrack et al., 1997, Folding & Design 2:R27-42]. This procedure can include computer fitting of candidate compounds to the ligand binding site to ascertain how well the shape and the chemical structure of the candidate compound will complement the binding site. [Bugg et al., *Scientific American*, December:92-98 (1993); West et al; 1 *TIPS*, 16:67-74 (1995)]. Computer programs can also be employed to estimate the attraction, repulsion and steric hindrance of the two binding partners (i.e. the ligand-binding site and the candidate compound). Generally the tighter the fit, the lower the steric hindrances, and the greater the attractive forces, the more potent the potential drug since these properties are consistent with a tighter binding constant. Furthermore, the more specificity in the design of a potential drug the more likely that the drug will not interact as well with other proteins. This will minimize potential side-effects due to unwanted interactions with other proteins.

Initially candidate compounds can be selected for their structural similarity to a p21 derived peptide of the present invention such as HAKRRLIF (SEQ ID No. 42), the four C-terminal amino acids thereof $RLX_5F$ (SEQ ID No. 184) or $RLFX_5$ (SEQ ID No. 185); or variants or a region thereof. The structural analog can then be systematically modified by computer modeling programs or by inspection until one or more promising candidate compounds are identified. A candidate compound could be obtained by initially screening a random peptide library produced by recombinant bacteriophage for example [Scott and Smith, *Science*, 249:386-390 (1990); Cwirla et al., *Proc. Natl. Acad. Sci.*, 87:6378-6382 (1990); Devlin et al., *Science*, 249:404-406 (1990)]. A peptide selected in this manner would then be systematically modified by computer modeling programs as described above, and then treated analogously to a structural analog as described below.

Once a candidate compound is identified it can be either selected from a library of chemicals as are commercially available or, alternatively, the candidate compound or antagonist may be synthesized de novo. As mentioned above, the de novo synthesis of one or even a relatively small group of specific compounds is reasonable in the art of drug design. The candidate compound can be placed into a standard binding assay with cyclin A together with a peptide of the present invention and its relative activity assessed.

In such an assay, cyclin A may be attached to a solid support. Methods for placing such a binding domain on the solid support are well known in the art and include such things as linking biotin to the ligand binding domain and linking avidin to the solid support. The solid support can be washed to remove unreacted species. A solution of a labeled candidate compound alone or together with a peptide of the present invention can be contacted with the solid support. The solid support is washed again to remove the candidate compound/peptide not bound to the support. The amount of labeled candidate compound remaining with the solid support and thereby bound to the ligand binding domain may be determined. Alternatively, or in addition, the dissociation constant between the labeled candidate compound and cyclin A can be determined. Alternatively, if a peptide of the present invention is used, it may be labeled and the decrease in bound labeled peptide used an indication of the relative activity of the candidate compound. Suitable labels are exemplified in our WO00/50896 (the contents of which are hereby incorporated by reference) which describes suitable fluorescent labels for use in fluorescent polarisation assays for protein/protein and protein/non-protein binding reactions. Such assay techniques are of use in the assays and methods of the present invention.

When suitable candidate compounds are identified, a supplemental crystal may be grown comprising a protein-candidate complex formed between cyclin A and the potential drug. Preferably the crystal effectively diffracts X-rays for the determination of the atomic coordinates of the protein-candidate complex to a resolution of greater than 5.0 Angstroms, more preferably greater than 3.0 Angstroms, and even more preferably greater than 2.0 Angstroms. The three-dimensional structure of the supplemental crystal may be determined by Molecular Replacement Analysis. Molecular replacement involves using a known three-dimensional structure as a search model to determine the structure of a closely related molecule or protein-candidate complex in a new crystal form. The measured X-ray diffraction properties of the new crystal are compared with the search model structure to compute the position and orientation of the protein in the new crystal. Computer programs that can be used include: X-PLOR (Bruger X-PLOR v.3.1Manual, New Haven: Yale University (1993B)) and AMORE [J. Navaza, Acta Crystallographics ASO, 157-163 (1994)]. Once the position and orientation are known an electron density map can be calculated using the search model to provide X-ray phases. Thereafter, the electron density is inspected for structural differences and the search model is modified to conform to the new structure.

Candidates whose cyclin A binding capability has thus been verified biochemically can then form the basis for additional rounds of drug design through structure determination, model refinement, synthesis, and biochemical screening all as discussed above, until lead compounds of the desired potency and selectivity are identified. The candidate drug is then contacted with a cell that expresses cyclin A. A candidate drug is identified as a drug when it inhibits CDK2 and/or CDK4 in the cell. The cell can either by isolated from an animal, including a transformed cultured cell; or alternatively can be present in a living animal.

In such assays, and as alternative embodiments of the herein described assays, a functional end-point may be monitored as an indication of efficacy in preference to the detection of cyclin binding. Such end-points include: G0 and/or G1/S cell cycle arrest (using flow cytometry), cell cycle-related apoptosis (sub-G0 population by fluorescence-activated cell sorting, FACS; or TUNEL assay), suppression of E2F transcription factor activity (e.g. using a cellular E2F reporter gene assay), hypophosphorylation of cellular pRb (using Western blot analysis of cell lysates with relevant phospho-specific antibodies), or generally in vitro anti-proliferative effects.

Thus, a further related aspect of the present invention relates to a three dimensional model of a peptide of the formula $X_1X_2X_3RX_4LX_5F$ (SEQ ID No. 464) or preferably $HX_2KRRLX_5F$ (SEQ ID No. 470): or variants thereof as defined above and cyclin A.

The invention further includes a method of using a three-dimensional model of cyclin A and a peptide of the present invention in a drug screening assay comprising;
(a) selecting a candidate compound by performing rational drug design with the three-dimensional model, wherein said selecting is performed in conjunction with computer modeling;
(b) contacting said candidate compound with cyclin A, and
(c) detecting the binding of the candidate compound; wherein a potential drug is selected on the basis of the candidate compound having a similar or greater affinity for cyclin A than that of a standard p21 derived peptide.

In a preferred embodiment the standard p21 derived peptide has the general formula $HX_2KRRLX_5F$ (SEQ ID No. 470): as defined above. Preferably, the three dimensional model is a computer generated model.

The peptides of the invention and substances identified or identifiable by the assay methods of the invention may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular or transdermal administration. Typically, each protein may be administered at a dose of from 0.01 to 30 mg/kg body weight, preferably from 0.1 to 10 mg/kg, more preferably from 0.1 to 1 mg/kg body weight.

Pharmaceutically acceptable salts of the peptides of the invention include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

EXAMPLES

Abbreviations

The nomenclature for amino acid and peptide derivatives conforms with IUPAC-IUB rules (*J. Peptide Sci.* 1999, 5, 465-471). D-amino acids are indicated by lower-case abbreviations, e.g. Ala for L-alanine, ala for D-alanine. Non-standard abbreviations for amino-acid residues are as follows:

| | | |
|---|---|---|
| Abu | 2-Aminobutyric acid | 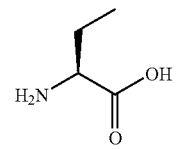 |
| Aib | Aminoisobutyric acid | 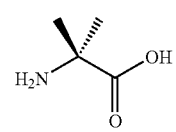 |
| Ahx | ε-Aminohexanoic acid | 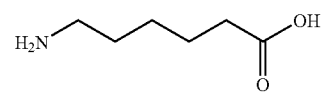 |
| hArg | Homoarginine | 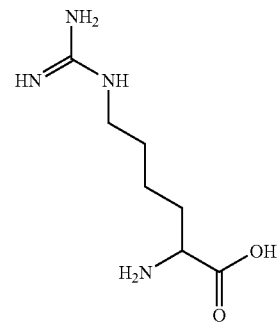 |
| Bug | t-Butylglycine | 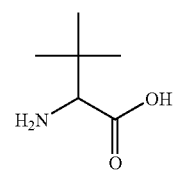 |
| oClPhe | o-Chlorophenylalanine | 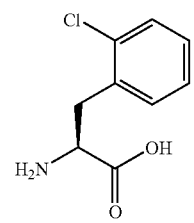 |

-continued
| | | |
|---|---|---|
| mClPhe | m-Chlorophenylalanine | 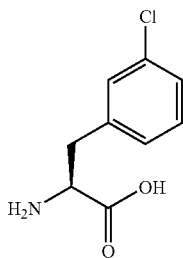 |
| pClPhe | p-Chlorophenylalanine | 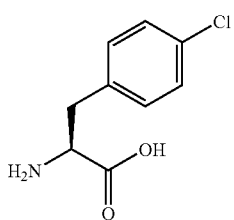 |
| Cha | Cyclohexylalanine |  |
| DiClPhe | m,p-Dichlorophenylalanine | 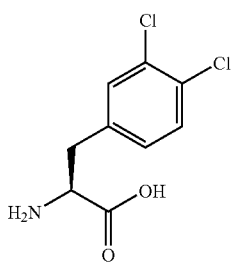 |
| Cit | Citrulline | 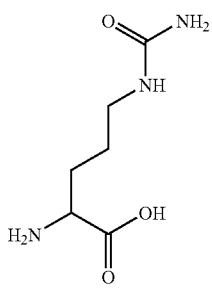 |
| Dhp | Dehydrophenylalanine | 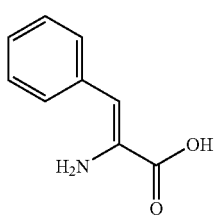 |

-continued
| | | |
|---|---|---|
| Dab | 1,3-Diaminobutyric acid | 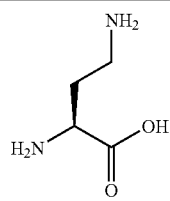 |
| mFPhe | m-Fluorophenylalanine | 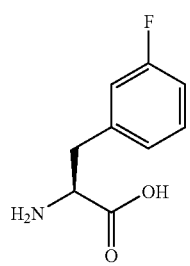 |
| pFPhe | p-Fluorophenylalanine | 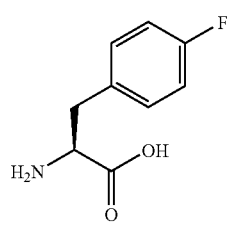 |
| Hof | Homophenylalanine | 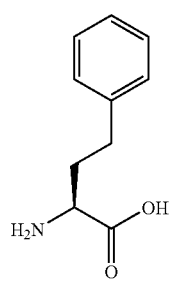 |
| Hse<br>aIle | Homoserine<br>allo-Isoleucine | 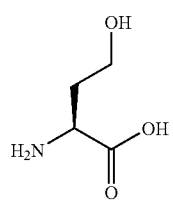 |
| Inc | 2-Indolecarboxylic acid | 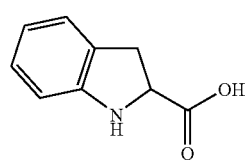 |
| pIPhe | p-Iodophenylalanine | 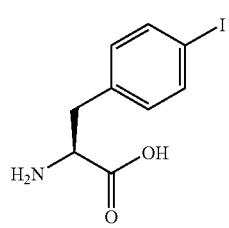 |

-continued
| | | |
|---|---|---|
| 1Nap | 1-Naphthylalanine | 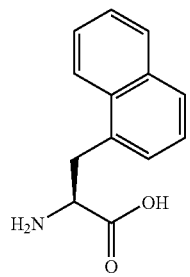 |
| 2Nap | 2-Naphthylalanine | 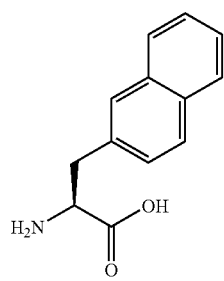 |
| Nle | Norleucine | 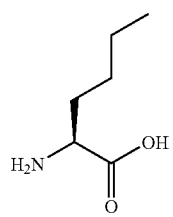 |
| Nva | Norvaline | 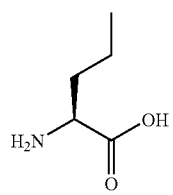 |
| Pheol | Phenylalaninol | 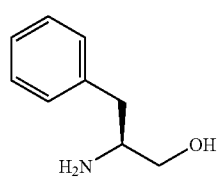 |
| Phg | Phenylglycine | 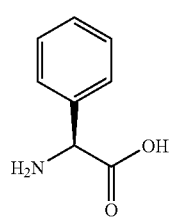 |
| Psa | O-Acetylphenylserine | 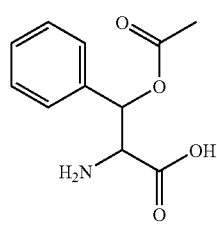 |

-continued

| | | |
|---|---|---|
| Pse | Phenylserine | 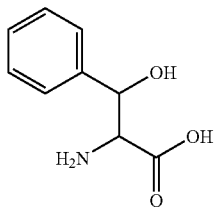 |
| Pya | 3-Pyridylalanine | 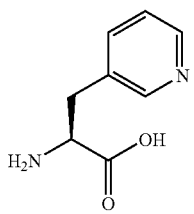 |
| Sar | Sarcosine | 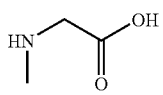 |
| Thi | 2-Thienylalanine | 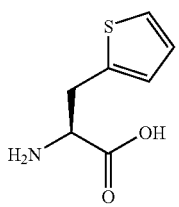 |
| Tic | 1,2,3,4-Tetrahydroisoquinoline-3-carboxylic acid | 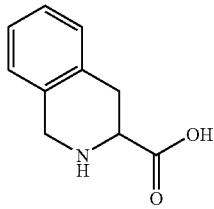 |
| Tyr(Me) | O-Methyltyrosine | 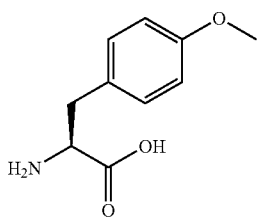 |

Other abbreviations used:

| | |
|---|---|
| Boc | t-Butyloxycarbonyl |
| BSA | Bovine serum albumin |
| CDK | Cyclin-dependent kinase |
| DE MALDI-TOF MS | Delayed extraction matrix-assisted laser desorption ionisation time-of-flight mass spectrometry |
| DMF | Dimethylformamide |
| ES-MS | Electrospray ionisation mass spectrometry |
| FAB-MS | Fast atom bombardment mass spectrometry |
| Fmoc | Fluoren-9-ylmethoxycarbonyl |
| Fmoc-ONSu | Fmoc N-hydroxysuccinimidyl ester |
| HBTU | 2-(1H-Benzotriazole-1-yl)-1,1,3,3-tetramethyluronium hexafluorophosphate |
| HOBt | 1-Hydroxybenzotriazole |
| $IC_{50}$ | Concentration at which 50% inhibition is observed |
| Mtt | 4-Methyltrityl |
| NMP | N-methylpyrrolidinone |
| Pbf | 2,2,4,6,7-Pentamethyldihydrobenzofuran-5-sulfonyl |
| Pmc | 2,2,5,7,8-Pentamethylchroman-6-sulfonyl |
| PyBOP | Benzotriazole-1-yl-oxy-tris-pyrrolidino-phosphonium hexafluorophosphate |
| RP-HPLC | Reversed-phase high-performance liquid chromatography |
| TBTU | 2-(1H-Benzotriazole-1-yl)-1,1,3,3-tetramethyluronium tetrafluoroborate |
| TFA | Trifluoroacetic acid |
| THF | Tetrahydrofuran |

-continued

| TLC | Thin layer chromatography |
| Trt | Trityl |

Example 1

Peptide Inhibitors of Rb Phosphorylation by G1 CDKs

Experimental Procedures

Unless otherwise indicated, the peptides in the examples below were assembled using a Multipin Peptide Synthesis Kit (Chiron Technologies, Clayton, VIC, Australia; Valerio, R. M.; Bray, A. M.; Maeji, N. J. *Intl. J. Peptide Protein Res.* 1994, 44, 158-165 & Valerio et al., 1993) or an automated peptide synthesiser (ABI 433A). In either case, the solid-phase linker was 4-(2',4-dimethoxyphenyl-Fmoc-aminomethyl)phenoxyacetamido (Rink amide linker; Rink, H. *Tetrahedron Lett.* 1987, 28, 3787-3790 & Fields et al. 1990). Standard solid-phase chemistry based on the Fmoc protecting group (Atherton, E.; Sheppard, R. C. Solid phase peptide synthesis: a practical approach; IRL Press at Oxford University Press: Oxford, 1989) was employed using PyBOP- HBTU- or TBTU-mediated acylation chemistry in the presence of HOBt and $Pr_2^iNEt$, in either NMP or DMF. Repetitive Fmoc-deprotection was achieved with piperidine. The following amino acid side-chain protecting groups were used: Asp(OBu$^t$), Glu(OBu$^t$), His(Trt), Lys(Boc), Arg(Pmc), Hse(Bu$^t$), Ser(Bu$^t$), Dab(Boc), Asn(Trt), Gln(Trt), Trp(Boc). Peptides were side-chain deprotected and cleaved from the synthesis support using either of the following acidolysis mixtures: a) 2.5:2.5:95 (v/v/v) $Pr_3^iSiH$, $H_2O$, $CF_3COOH$, b) 0.75:0.5:0.5:0.25:10 (w/v/v/v/v) PhOH, PhSMe, $H_2O$, $HSCH_2CH_2SH$, $CF_3COOH$ (King et al., 1990). Cleavage/deprotection was allowed to proceed for 2.5 h under $N_2$, before evaporation in vacuo, precipitation from $Et_2O$, and drying. All peptides were purified by preparative RP-HPLC or solid phase extraction (on octadecylsilane cartridges), isolated by lyophilisation, and were analyzed by analytical RP-HPLC and mass spectrometry (Dynamo DE MALDI-TOF spectrometer, ThermoBioAnalysis).

Peptide synthesis. Peptides were assembled using a Multipin Peptide Synthesis Kit (Chiron Technologies, Clayton, VIC, Australia) (Valerio et al., 1993). Standard solid-phase chemistry based on the Fmoc protecting group was employed (Fields et al., 1990). Peptides were side-chain deprotected and cleaved from the synthesis support using methods as described (King et al., 1990). All peptides were purified by preparative reversed-phase HPLC or solid phase extraction, isolated by lyophilisation, and were analyzed by analytical HPLC and mass spectrometry (Dynamo DE MALDI-TOF spectrometer, ThermoBioAnalysis).

Example 2

Production of Recombinant Proteins

PKCα-6×His (6×His tag disclosed as SEQ ID NO: 462), CDK4-6×His (6×His tag disclosed as SEQ ID NO: 462), CDK2-6×His/Cyclin E-6×His (6×His tags disclosed as SEQ ID NO: 462), CDK1-6×His/Cyclin B-6×His (6×His tags disclosed as SEQ ID NO: 462) -His-tagged CDK2/Cyclin E and CDK1/Cyclin B were co-expressed and PKCα, and CDK4 were singularly expressed in Sf9 insect cells infected with the appropriate baculovirus constructs. The cells were harvested two days after infection by low speed centrifugation and the proteins were purified from the insect cell pellets by Metal-chelate chromatography. Briefly, the insect cell pellet was lysed in Buffer A (10 mM Tris-HCl, pH 8.0, 150 mM NaCl, 0.02% NP40 and 5 mM β-marcaptoethanol, 1 mM NaF. 1 mM Na3VO4 and Protease Inhibitors Cocktail (Sigma) containing AEBSF, pepstatin A, E 64, bestatin, leupeptin) by sonication. The soluble fraction was cleared by centrifugation and loaded onto Ni-NTA-Agarose (Quiagen). Non bound proteins were washed off with 300 mM NaCl, 5-15 mM Imidazole in Buffer A and the bound proteins were eluted with 250 mM Imidazole in Buffer A. The purified proteins were extensively dialyzed against Storage buffer (20 mM HEPES pH 7.4, 50 mM NaCl, 2 mM DTT, 1 mM EDTA, 1 mM EGTA, 0.02% NP40, 10% v/v Glycerol) aliquoted and stored at −70° C.

PKC-α-6×His (6×His tag disclosed as SEQ ID NO: 462) was purified the same way but using different buffers-50 mM NaH2PO4, pH 8.0 and 0.05% Triton X-100 instead of Tris and NP40 respectively.

Cyclin D1 and p21 were expressed in *E coli* BL21 (DE3) using PET expression vectors. BL21 (DE3) was grown at 37° C. with shaking (200 rpm) to mid-log phase (OD600 nm=0.6). Expression was induced by the addition of IPTG at a final concentration of 1 mM, and the culture was incubated for a further 3 h. The bacteria were than harvested by centrifugation, and the cell pellet was resuspended in 50 mM Tris-HCl, pH 7.5, 10% sucrose. Both proteins were purified from inclusion bodes. Briefly, the bacterial cells were lysed by treatment with lysosyme and sonication. The insoluble fraction was pelleted by centrifugation. The inclusion bodies were purified by repetitive washing of the insoluble fraction with 50 mM Tris-Hcl pH 8.0, 2 mM EDTA, 100 mM NaCl and 0.5% Triton X-100. Purified inclusion bodies were solubilized with the same buffer, containing 6M urea. The proteins were refolded by slow dilution with 25 mM Tris-HCl pH 8.0, 100 mM NaCl, 2 mM DTT, 1 mM EDTA, 0.2% NP40. After concentration by ultrafiltration (Amicon concentration unit) the purified proteins were aliquoted and stored at −70° C.

GST-Rb—An *E coli* expression construct containing the hyperphosphorylation domain of pRb (amino acids 773-924) was purified on a Glutathione-Sepharose column according to the manufacturers instructions (Pharmacia). For the 96-well format "in vitro" kinase assay GST-Rb was used immobilized on Glutathione-Sepharose beads.

Example 3

Enzyme Assays

CDK4/Cyclin D1, CDK2/Cyclin E, CDIK1/Cyclin B Kinase Assays

Phosphorylation of GST-Rb

GST-Rb phosphorylation, induced by CDK4/Cyclin D1, CDK2/Cyclin E or CDK1/Cyclin B was determined by incorporation of radio-labeled phosphate in GST-Rb(772-928) using radiolabelled ATP in 96-well format in vitro kinase assay. The phosphorylation reaction mixture (total volume 40 µl) consisted of 50 mM HEPES pH 7.4, 20 mM MgCl2, 5 mM EGTA, 2 mM DTT, 20 mM β-glycerophosphate, 2 mM NaF, 1 nM Na3VO4, Protease Inhibitors Cocktail (Sigma, see above), BSA 0.5 mg/ml, 1 µg purified enzyme complex, 10 µl of GST-Rb-Sepharose beads, 100 µM ATP, 0.2 µCi $^{32}$P-ATP.

The reaction was carried out for 30 min at 30° C. at constant shaking. At the end of this period 100 μl of 50 mM HEPES, pH 7.4 and 1 mM ATP were added to each well and the total volume was transferred onto GFC filtered plate. The plate was washed 5 times with 200 μl of 50 mM HEPES, pH 7.4 and 1 mM ATP. To each well were added 50 μl scintillant liquid and the radioactivity of the samples was measured on Scintilation counter (Topcount, HP). The IC50 values of different peptides were calculated using GraFit software.

Phosphorylation of Histone

Histone 1 phosphorylation induced by CDK2/Cyclin E and CDK1/Cyclin B was measured using similar method. The concentration of Histone 1 in the kinase reaction was 1 mg/ml (unless different stated). The kinase reaction was stopped by 75 mM Phosphoric acid (100 μl per well) and the reaction mixture was transferred onto P81 plates. The plates were washed 3 times with 200 μl 75 mM orthophosphoric acid.

Protein Kinase C (PKC)α Assay

PKCα kinase activity was measured by the incorporation of radio-labeled phosphate in Histone 3. The reaction mixture (total volume 65 μl) consist of 50 mM Tris-HCl, 1 mM Calcium acetate, 3 mM DTT, 0.03 mg/ml Phosphatidylserine, 2.4 μg/ml PMA, 0.04% NP40, 12 mM Mg/Cl, purified PKCα-100 ng, Histone 3, 0.2 mg/ml, 100 μM ATP, 0.2 μCi [γ-$^{32}$P]-ATP. The reaction was carried over 15 min at 37° C. in microplate shaker and was stopped by adding 10 μl 75 mM orthophosphoric acid and placing the plate on ice. 50 μl of the reaction mixture was transferred onto P81 filterplate and after washing off the free radioactive phosphate (3 times with 200 μl 75 mM orthophosphoric acid per well) 50 μl of scintillation liquid (Microscint 40) were added to each well and the radioactivity was measured on Scintillation counter (Topcount, HP).

ERK-2 (MAP Kinase) Assay

ERK-2 kinase activity was measured by the incorporation of radio-labeled phosphate into Myelin Basic Protein (MBP), catalyzed by purified mouse ERK2 (Upstate Biotechnologies). The reaction mixture (total volume 50 μl) consisted of 20 mM MOPS, pH 7.0, 25 mM β-glycerophosphate, 5 mM EGTA, 1 mM DTT, 1 mM $Na_3VO_4$, 10 mM MgCl, 100 μM ATP, 0.2 μCi [γ-$^{32}$P]-ATP.

CDK2/Cyclin A

CDK2/cyclin A kinase assays were performed in 96-well plates using recombinant CDK2/cyclin A. Assay buffer consisted of 25 mM β-glycerophosphate, 20 mM MOPS, 5 mM EGTA, 1 mM DTT, 1 mM $NaVO_3$, pH 7.4, into which was added 2-4 μg of CDK2/cyclin A with substrate pRb(773-928). The reaction was initiated by addition of Mg/ATP mix (15 mM $MgCl_2$, 100 μM ATP with 30-50 kBq per well of [γ-$^{32}$P]-ATP) and mixtures incubated for 10-30 min, as required, at 30° C. Reactions were stopped on ice, followed by filtration through p81 filterplates (Whatman Polyfiltronics, Kent, UK). After washing 3 times with 75 mM orthophosphoric acid, plates were dried, scintillant added and incorporated radioactivity measured in a scintillation counter (TopCount, Packard Instruments, Pangbourne, Berks, UK).

Competitive Cyclin D1/Cyclin A Binding Assay (ELISA).

Biotinylated p21 (149-159)-DFYHSKRRLIF (SEQ ID No. 1) was immobilized on Streptavidin coated 96-well plates (PIERCE). Different amounts of a competitor peptide were mixed with Cyclin D1/Cyclin A and than loaded onto the plate with immobilized biotinylated p21 (149-159). The amount of bound Cyclin D1/Cyclin A was immunodetected and quantified by Turbo-ELISA reagent (PIERCE). The IC 50 values (a concentration of the competitor peptide which inhibits 50% of Biotin-p21 (149-159)-Cyclin D1/Cyclin A binding) were calculated using GraFit software.

Cyclin A Binding Assay

Streptavidin-coated plates (Reacti-Bind™, Pierce) were washed three times with TBS/BSA buffer (25 mM Tris•HCl, 150 mM NaCl pH 7.5, 0.05% Tween-20, 0.1% BSA; 200 μL) for 2 min each. A 10 mM stock solution of biotinyl-Ahx-His-Ala-Lys-Arg-Arg-Leu-Ile-Phe-$NH_2$ (SEQ ID No. 186) was diluted to 0.5 μM with TBS/BSA buffer. This was added to each well (100 μL). The plate was incubated for 1 h at room temperature with constant shaking. The plate was washed once quickly with TBS/BSA buffer (200 μL), followed by three more washes with TBS/BSA buffer (200 μL) for 5 min each. Serial dilutions of test peptides were prepared in a new plate (50 μL in each well). Cyclin A was diluted to 5 μg/50 μL with TBS/BSA buffer and this was then added to each well (50 μL). The solutions were mixed thoroughly with a pipette (5-6 times), before being incubated for 30 min at room temperature. This reaction mixture was then transferred to the biotinylated peptide:streptavidin-coated plate and incubated for 1 h at room temperature with constant shaking. The plate was washed once quickly with TBS/BSA buffer (200 μL), followed by three more washes with TBS/BSA buffer (200 μL) for 5 min each. The cyclin A antibody (Santa Cruz polyclonal) solution was diluted 1:200 with TBS/BSA buffer and this was then added to each well of the plate (100 μL. The plate was incubated for 1 h at room temperature with constant shaking. The plate was washed once quickly with TBS/BSA buffer (200 μl), followed by three more washes with TBS/BSA buffer (200 μL) for 5 min each. The anti-rabbit secondary antibody (goat anti-rabbit IgG peroxidase conjugate) was diluted 1:10,000 with TBS/BSA and this was then added to each well of the plate (100 μL). The plate was incubated for 1 h at room temperature with constant shaking. The plate was washed once quickly with TBS/BSA buffer (200 μL), followed by three more washes with TBS/BSA buffer (200 μL) for 5 min each. To each well was added the TMB-ELISA reagent (Pierce 1-Step™ Turbo TMB-ELISA; 100 μL) and the plate incubated for 1 min with constant shaking. The reaction was then quenched by the addition of 2 M aqueous $H_2SO_4$ (100 μL, each well). The UV absorbance of the each solution was measured spectrophotometrically at 450 nm. $IC_{50}$ values were calculated from dose-response curves.

Example 4

Molecular Modelling

The structure co-ordinates of the ternary complex of CDK2/cyclin A/p27$^{KIP1}$ were obtained from the RCSB (accession code 1JSU) and used as the starting point for generating a bound complex of H-His-Ala-Lys-Arg-Arg-Leu-Ile-Phe-$NH_2$ (SEQ ID No. 36). The peptide was modelled by replacing the residues of the corresponding p27 peptide and manipulating the torsion angles of the Leu-Ile-Phe hydrophobic motif to approximate the bound positioning of the Leu and Phe residues. This structure was then docked into the cyclin groove using the Affinity program (Molecular Simulations, San Diego, Calif.). This molecular docking routine, which incorporates a full molecular mechanics approach, allows for flexibility both in the ligand and in the side chains and backbone of the receptor. For these calculations the side chains and non-α carbons of the cyclin groove were allowed to sample a range of conformational space during optimisation of the peptide/protein complex. The calculation was performed using the CVFF force field, in a two-step process using an implicitly derived solvation model and geometric hydrogen bond restraints. For the initial phase of the calculation, the peptide was minimised into the groove using a simple non-bonded method where the Coulombic and Van der Waals terms are scaled to zero and 0.1, respectively. The subsequent refinement phase involved conformational sampling using molecular dynamics calculated over 5 ps in 100 fs stages, where the temperature is scaled from 500 K to 300 K. The calculation was completed by a final minimisation over 1,000 steps using the Polak-Ribiere Conjugate Gradient method.

Example 5

Structure-Activity Relationships of p21(145-164) Peptides with Respect to Inhibition of Cyclin E/CDK2 and Cyclin D1/CDK4

Previous studies have shown that a 20-residue peptide, derived from the C-terminus of p21$^{WAF1}$ (residues 141-160) binds to CDK4 and cyclin D1 and is able to inhibit in vitro kinase activity of the CDK4/cyclin D1 complex (Ball, K. L.; Lain, S.; Fåhraeus, R.; Smythe, C.; Lane, D. P. *Curr Biol.* 1996, 7, 71-80). In order to define the pharmacophore region of the p21$^{WAF1}$ C-terminus, 12mer overlapping peptides covering the region of p21(145-164) were synthesized. The in vitro effect of these peptides on CDK4/cyclin D1 and CDK2/cyclin E kinase activity in terms of inhibition of phosphorylation of GST-pRb was investigated.

A shorter sequence being a 12 amino acid peptide DFYHS-KRRLIFS-p21 (149-160) (SEQ ID No. 13) was found to have very similar activity as the original 20-mer peptide of Ball et al. with respect to in vitro inhibitory activity in vitro CDK4-Cyclin D1 kinase.

A detailed SAR analysis of p21 (149-160) was done in 96-well format CDK4-Cyclin D1 kinase assay using different peptide derivatives—truncations and alanine substitutions. In order to determine the relative importance of each position of the 12 amino acid peptide which contained the binding domain, p21(149-160) derivatives were synthesized in which each residue was sequentially substituted with Ala. The effect of the peptide mutations on their kinase inhibitory activity was then tested. Ala substitution of Phe$^{150}$, Tyr$^{151}$, His$^{152}$, Ile$^{158}$, and Ser$^{160}$ did not change significantly the CDK2/cyclin E inhibitory activity of p21(149-160). Substitution of Ser$^{153}$ with Ala increased 100-fold the inhibitory potency of p21(149-160) towards CDK2/cyclin E. The results are shown in Table 1.

SAR of p21 (149-160) in CDK2/Cyclin E Kinase Assay.

P21 (141-160) peptide was shown to inhibit CDK2-Cyclin E induced phosphorylation of GST-Rb (Ball et al., 1995) at concentration 40 times its IC50 of CDK4/cyclin D1. The results herein show that a truncated form—p21 (149-160) and variants thereof, retain very good potency to inhibit the CDK2-Cyclin E induced phosphorylation of GST-Rb and in many cases the peptides were shown to be preferentially inhibitory of CDK2 as opposed to CDK4. Detailed SAR of p21 (149-160) were determined in CDK2-Cyclin E in vitro kinase assay. The data are shown in Table 1.

A comparison between the SAR of p21 (149-160) in CDK2-Cyclin E and CDK4-Cyclin D1 kinase assays shows a higher inhibitory activity towards CDK2-Cyclin E than to CDK4-Cyclin D1. Alanine mutation of Ser153 increases 100 fold the potency of the peptide to inhibit the CDK2-Cyclin E but has little effect on CDK4-Cyclin D1 induced phosphorylation of GST-Rb. For both inhibitory activities of p21 (149-160) the most important residues are Arg155, Leu 157 and Phe 159. The CDK4-Cyclin D1 inhibitory activity of p21 (149-160) tolerates less changes than the CDK2-Cyclin E one.

Using identical assays, the sequence p21(148-159) was shown to be active against both CDK2/cyclin E and CDK4/cyclin D1.

TABLE 1

Structure-activity relationships of p21 (145-164) peptides with respect to Inhibition of cyclin E/CDK2 and cyclin D1/CDK4

| P21$^{wafl}$ Sequence$^a$ | Seq ID No. | Formula | MS$^b$ $M_r$ | [M + H] |
|---|---|---|---|---|
| 145    150    155    160    165 | | | | |
| T S M T D F Y H S K R R L I F S K R K P | 187 | | | |
| T S M T D F Y H S K R R | 188 | C$_{65}$H$_{102}$N$_{22}$O$_{19}$S | 1527.71 | 1530.3 |
| S M T D F Y H S K R R L | 189 | C$_{67}$H$_{106}$N$_{22}$O$_{18}$S | 1539.76 | 1541.66 |
| M T D F Y H S K R R L I | 190 | C$_{70}$H$_{112}$N$_{22}$O$_{17}$S | 1565.84 | 1569.5 |
| T D F Y H S K R R L I F | 191 | C$_{74}$H$_{112}$N$_{22}$O$_{17}$ | 1581.82 | 1583.9 |
| D F Y H S K R R L I F S | 192 | C$_{73}$H$_{110}$N$_{2}$20$_{17}$ | 1567.79 | 1569.7 |
| F Y H S K R R L I F S K | 193 | C$_{75}$H$_{117}$N$_{23}$O$_{15}$ | 1580.88 | 1580.4 |
| Y H S K R R L I F S K R | 194 | C$_{72}$H$_{120}$N$_{26}$O$_{15}$ | 1589.89 | 1592.0 |
| H S K R R L I F S K R K | 195 | C$_{69}$H$_{123}$N$_{27}$O$_{14}$ | 1554.89 | 1556.9 |
| S K R R L I F S K R K P | 196 | C$_{68}$H$_{123}$N$_{25}$O$_{14}$ | 1514.86 | 1518.7 |
| A F Y H S K R R L I F S | 197 | C$_{72}$H$_{110}$N$_{22}$O$_{15}$ | 1523.78 | 1526.0 |
| D A Y H S K R R L I F S | 198 | C$_{67}$H$_{106}$N$_{22}$O$_{17}$ | 1491.70 | 1494.8 |

TABLE 1-continued

Structure-activity relationships of p21 (145-164) peptides with respect to Inhibition of cyclin E/CDK2 and cyclin D1/CDK4

| Sequence | # | Formula | | |
|---|---|---|---|---|
| D F A H S K R R L I F S | 199 | $C_{67}H_{106}N_{22}O_{16}$ | 1475.70 | 1482.2 |
| D F Y A S K R R L I F S | 200 | $C_{70}H_{108}N_{20}O_{17}$ | 1501.73 | 1506.6 |
| D F Y H A K R R L I F S | 201 | $C_{73}H_{110}N_{22}O_{16}$ | 1551.79 | 1554.2 |
| D F Y H S A R R L I F S | 202 | $C_{70}H_{103}N_{21}O_{17}$ | 1510.7 | 1512.9 |
| D F Y H S K A R L I F S | 203 | $C_{70}H_{103}N_{19}O_{17}$ | 1482.68 | 1485.7 |
| D F Y H S K R A L I F S | 204 | $C_{70}H_{103}N_{19}O_{18}$ | 1483.68 | 1488.9 |
| D F Y H S K R R A I F S | 205 | $C_{70}H_{104}N_{22}O_{17}$ | 1525.71 | 1529.0 |
| D F Y H S K R R L A F S | 206 | $C_{70}H_{104}N_{22}O_{18}$ | 1526.71 | 1527.9 |
| D F Y H S K R R L I A S | 207 | $C_{67}H_{106}N_{22}O_{17}$ | 1491.70 | 1495.0 |
| D F Y H S K R R L I F A | 208 | $C_{73}H_{110}N_{22}O_{16}$ | 1551.79 | 1551.1 |
| F Y H S K R R L I F S | 209 | $C_{69}H_{105}N_{21}O_{14}$ | 1452.71 | 1450.2 |
| Y H S K R R L I F S | 210 | $C_{60}H_{96}N_{20}O_{13}$ | 1305.53 | 1304.0 |
| H S K R R L I F S | 211 | $C_{51}H_{87}N_{19}O_{11}$ | 1142.36 | 1141.0 |
| D F Y H S K R R L I F | 212 | $C_{70}H_{105}N_{21}O_{13}$ | 1480.72 | 1476.5 |
| D F Y H S K R R L I | 213 | $C_{61}H_{96}N_{20}O_{14}$ | 1333.54 | 1331.2 |
| D F Y H S K R R L | 214 | $C_{55}H_{85}N_{19}O_{13}$ | 1220.38 | 1219.6 |
| D F Y H S K R R | 215 | $C_{49}H_{74}N_{18}O_{12}$ | 1107.23 | 1106.9 |
| D F Y H S K R | 216 | $C_{41}H_{62}N_{14}O_{11}$ | 951.04 | 950.8 |
| D F Y H S K | 217 | $C_{17}H_{30}N_{10}O_{10}$ | 794.85 | 794.4 |
| F Y H S K R R L I F | 218 | $C_{66}H_{100}N_{20}O_{12}$ | 1365.63 | 1362.6 |
| F Y H S K R R L I | 219 | $C_{57}H_{91}N_{19}O_{11}$ | 1218.45 | 1218.2 |
| F Y H S K R R L | 220 | $C_{51}H_{80}N_{18}O_{10}$ | 1105.3 | 1104.5 |
| F Y H S K R R | 221 | $C_{45}H_{69}N_{18}O_{10}$ | 992.14 | 994.3 |
| F Y H S K R | 222 | $C_{39}H_{57}N_{13}O_{8}$ | 835.95 | 838.2 |
| Y H S K R R L I F | 223 | $C_{57}H_{91}N_{19}O_{11}$ | 1218.45 | 1218.8 |
| Y H S K R R L I | 224 | $C_{48}H_{82}N_{18}O_{10}$ | 1071.28 | 1072.4 |
| Y H S K R R L | 225 | $C_{42}H_{71}N_{17}O_{9}$ | 958.12 | 960.4 |
| Y H S K R R | 226 | $C_{36}H_{60}N_{16}O_{8}$ | 844.96 | 847.4 |
| Y H S K R | 227 | $C_{30}H_{48}N_{12}O_{7}$ | 688.78 | 691.2 |
| H S K R R L I F | 228 | $C_{48}H_{82}N_{18}O_{9}$ | 1055.28 | 1056.5 |
| S K R R L I F | 229 | $C_{42}H_{75}N_{15}O_{8}$ | 918.14 | 919.3 |
| K R R L I F | 34 | $C_{39}H_{70}N_{14}O_{6}$ | 831.06 | 823.2 |
| H S K R R L I | 230 | $C_{39}H_{73}N_{17}O_{8}$ | 908.11 | 909.0 |
| H S K R R L | 231 | $C_{33}H_{62}N_{16}O_{8}$ | 794.95 | 797.5 |
| K R R L I F S K | 232 | $C_{48}H_{87}N_{17}O_{9}$ | 1046.31 | 1047.9 |

TABLE 1-continued

Structure-activity relationships of p21 (145-164) peptides with respect to Inhibition of cyclin E/CDK2 and cyclin D1/CDK4

| Seq ID No. | RP-HPLC$^c$ $T_r$ (min) | Purity (%) | Cyclin E/CDK2 IC$_{30}$ (μM) | % Inhibition | Cyclin D1/CDK4 IC$_{30}$ (μM) | % Inhibition |
|---|---|---|---|---|---|---|
| 188 | 11.0 | 55.7 | — | 35 | — | 30 |
| 189 | 11.5 | 73.5 | — | 40 | — | 18 |
| 190 | 12.2 | 93.5 | — | 35 | — | 11 |
| 191 | 13.3 | 76.9 | 2.2 ± 0.4 | 85 | 15 ± 3 | 72 |
| 192 | 12.8 | 92.7 | 4.5 ± 0.5 | 80 | 20 ± 2 | 70 |
| 193 | 12.0 | 89.4 | 26 ± 6.2 | 70 | 41 ± 10 | 70 |
| 194 | 11.2 | 90.3 | 17.6 ± 6.9 | 80 | 45 ± 10 | 60 |
| 195 | 10.7 | 20.0 | 8.7 ± 2.5 | 90 | 34 ± 6 | 80 |
| 196 | 10.7 | 87.9 | 46 ± 33 | 70 | — | 40 |
| 197 | 12.7 | 92.3 | 11 ± 2 | 70 | 22 ± 4 | 72 |
| 198 | 12.2 | 80.8 | 5.9 ± 0.4 | 85 | 37 ± 6 | 76 |
| 199 | 12.5 | 91.2 | 5.3 ± 0.6 | 80 | 121 ± 31 | 56 |
| 200 | 13.0 | 79.1 | 5.1 ± 0.5 | 80 | 73 ± 42 | 60 |
| 201 | 12.9 | 97.8 | 0.04 ± 0.005 | 80 | 10 | 52 |
| 202 | 13.8 | 91.6 | 12.9 ± 2.4 | 80 | 200 | 50 |
| 203 | 13.3 | 72.9 | — | 25 | — | 30 |
| 204 | 13.2 | 78.6 | 30 ± 8 | 70 | — | 30 |
| 205 | 12.1 | 94.5 | — | 30 | — | 30 |
| 206 | 12.0 | 94.8 | 14 ± 3 | 80 | 53 ± 20 | 61 |
| 207 | 11.3 | 89.6 | — | 20 | — | 35 |
| 208 | 13.1 | 93.0 | 5.4 ± 1.1 | 70 | 40 | 60 |
| 209 | 12.6 | 83.2 | 6.8 ± 1.0 | 80 | 22 ± 5 | 70 |
| 210 | 12.2 | 81.8 | 7.3 ± 0.8 | 80 | 20 ± 1 | 70 |
| 211 | 12.0 | 94.4 | 3.4 ± 0.2 | 80 | 32 ± 6 | 65 |
| 212 | 13.5 | 94.6 | 2 ± 0.2 | 75 | 13 ± 2 | 70 |
| 213 | 12.1 | 89.0 | — | 35 | — | 20 |
| 214 | 10.6 | 98.0 | 200 | 50 | — | 10 |
| 215 | 9.8 | 96.4 | — | 40 | — | 10 |
| 216 | 9.6 | 89.8 | 200 | 50 | — | — |
| 217 | 9.5 | 96.9 | 200 | 45 | — | 10 |
| 218 | 13.3 | 85.5 | 5.8 ± 1 | 80 | 19 ± 3 | 70 |
| 219 | 9.6 | 68.2 | — | 45 | — | 20 |
| 220 | 10.4 | 86.9 | >200 | 48 | — | 20 |
| 221 | 9.2 | 83.6 | >200 | 45 | — | 20 |
| 222 | 8.9 | 92.4 | — | 20 | — | 10 |
| 223 | 12.9 | 94.3 | 7 ± 2 | 80 | 16 ± 1 | 70 |
| 224 | 10.9 | 82.5 | >200 | 45 | — | 15 |
| 225 | 9.2 | 95.8 | >200 | 30 | — | 10 |
| 226 | 7.4 | 87.2 | — | 40 | — | 10 |
| 227 | 7.0 | 66.9 | — | 25 | — | 10 |
| 228 | 12.7 | 81.8 | 3.4 ± 1 | 80 | 21 ± 4 | 72 |
| 229 | 8.2 | 93.4 | 7.7 ± 0.5 | 80 | 54 | 72 |
| 34 | 7.4 | 99.1 | 1.1 ± 1.3 | 80 | >200 | 72 |
| 230 | 10.6 | 86.7 | — | 35 | — | 10 |
| 231 | 8.7 | 89.9 | >200 | 45 | — | — |
| 232 | 11.3 | 94.2 | >200 | 60 | — | 20 |

$^a$All peptides were synthesised with free amino termini and as the C-terminal carboxamides
$^b$DE MALDI-TOF MS, positive mode, α-cyano-4-hydroxycinnamic acid matrix, calibration using authentic peptides in the appropriate m/z range
$^c$Vydac218TP54, 1 mL/min, 25° C., 0-60% MeCN in 0.1% aq CF$_3$COOH over 20 min, purity by integration at λ = 214 nm
$^c$Standard kinase assay procedures [ATP] = 100 μM

Example 6

Specificity of Enzyme Inhibition

Effect of p21 (149-160) on CDK2-Cyclin E Induced Phosphorylation of Histone 1.

p21(149-160) was tested for inhibitory activity in a CDK2/cyclin E kinase assay with histone H1 as a substrate. The peptide was completely inactive as an inhibitor of CDK2/cyclin E-induced phosphorylation of histone H1 (FIG. 1).

Figure 2:
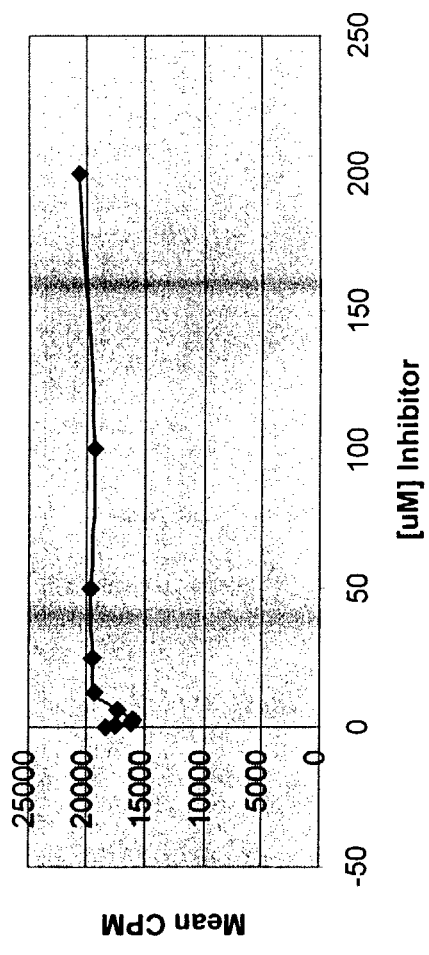
FIG. 2 shows that p21 (141-160)153A is a strong inhibitor of GST-Rb phopshorylation but not of Histone 1 phosphorylation induced by CDK2-Cyclin E kinase complex.
Figure 2:
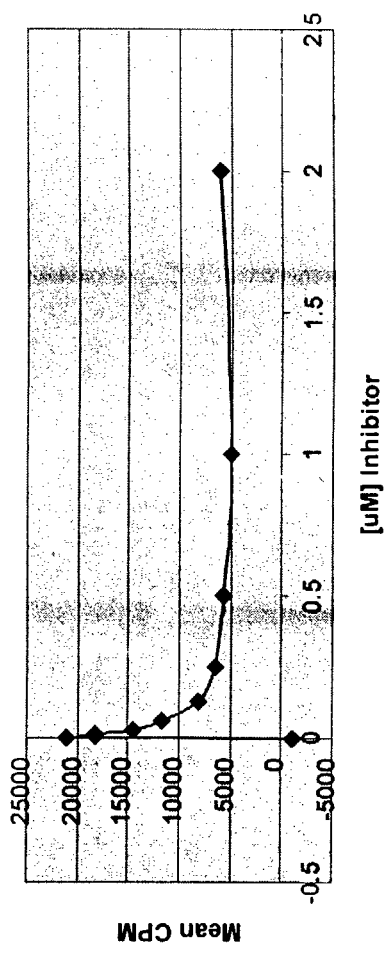

One possible mechanism for inhibitory action is competition of the peptide with the substrate for binding to the kinase complex. If this is so, the peptide inhibitory activity will depend on the substrate concentration. The $IC_{50}$ of p21(149-160) in the presence of different concentrations of histone H1 was determined and p21(149-160) did not inhibit CDK2/cyclin E-induced phosphorylation of histone H1 at any of the substrate concentrations used. The most potent inhibitor of CDK2/cyclin E phosphorylation of GST-pRb (i.e. p21(149-160)Ser153Ala) was also tested for its ability to inhibit histone H1 phosphorylation induced by the same kinase complex (FIG. 2). Even this powerful inhibitor of the GST-pRb phosphorylation was completely inactive in inhibition of the phosphorylation of histone H1 induced by CDK2/cyclin E kinase complex. Full-length p21$^{WAF1}$, on the other hand, inhibited strongly both the CDK2/cyclin E- and CDK4/cyclin D1-induced phosphorylation of GST-pRb and histone H1. The substrate-specific effect of p21(149-160) and its derivatives strongly suggests a mechanism of competitive binding of the peptide inhibitors and pRb to CDK2/cyclin E and CDK4/cyclin D1. The fact that p21(149-160) and its derivatives did not inhibit significantly the CDK1/cyclin B-induced phosphorylation of GST-pRb (see below) excludes a possibility of direct binding of the peptide to the substrate.

Effect of p21 (149-160) and its Derivatives on CDK1-Cyclin B Kinase Activity.

p21(149-160) and its derivatives were tested for ability to inhibit CDK1/cyclin B kinase activity in phosphorylating histone H1 or GST-pRb (Table 2). p21(149-160) and its Ala mutant p21(149-160) Ser153Ala did not have any significant effect on the CDK1/cyclin B-induced phosphorylation of histone H1. None of the tested peptides were able to inhibit significantly the CDK1/cyclin B-induced phosphorylation of GST-pRb and only the highest peptide concentrations used (200 µM) had a marginal inhibitory effect on CDK1/cyclin B kinase activity. When tested in the "pull-down" assay, immobilised p21(149-160) was unable to precipitate cyclin B either as a monomer, or as a complex with CDK1. These data coincide with the very poor inhibitory activity of the original 20 mer p21(141-160) peptide (Ball, K. L.; Lain, S.; Fåhraeus, R.; Smythe, C.; Lane, D. P. *Curr. Biol.* 1996, 7, 71-80) and the full-length p21$^{WAF1}$ protein towards CDK1/cyclin B complex (Harper, J. W.; Elledge, S. J.; Keyomarsi, K.; Dynlacht, B.; Tsai, L. H.; Zhang, P.; Dobrowolski, S.; Bai, C.; Connell-Crowley, L.; Swindell, E.; et al. *Molec. Biol. Cell* 1995, 6, 387-400) and show that p21(149-160) and its derivatives retain the selectivity of the full-length protein.

TABLE 2

Inhibition of CDK1-Cyclin B induced phosphorylation of Histone 1 and GST-Rb by p21 derived peptides.

| Peptide | Sequence | IC50 [µM] | IC50 [µM] |
|---|---|---|---|
| P21 (149-160) | DFYHSKRRLIFS (SEQ ID No. 13) | >200 | 200 |
| P21 (149-160)153A | DFYHAKRRLIFS (SEQ ID No. 19) | 200 | >200 |
| P21 (149-159) | DFYHSKRRLIF (SEQ ID No. 1) | Not tested | >200 |

Effect of Purified P21$^{WAF1}$ on CDK4-Cyclin D1 and CDK2-Cyclin E Kinase Activity In order to evaluate the selectivity, specificity and potency of p21 (149-160) and its derivatives we compared their effect with the one of purified p21 on kinase activity of CDK2-Cyclin E and CDK4-Cyclin D1. The IC 50 values characterizing the inhibition of CDK4-Cyclin D1 and CDK2-Cyclin E induced phosphorylation of GST-Rb and CDK2-Cyclin E induced phosphorylation of Histone 1 by purified p21$^{WAF1}$ are shown in Table 3. The IC 50 of the most active peptide—p21 (149-160) 153A for CDK2-Cyclin E induced phosphorylation of GST-Rb was 40 nM which is approximately 50 fold higher than the IC 50 value for p21$^{WAF1}$. Purified p21 though, inhibited strongly the CDK2-Cyclin E induced phosphorylation of GST-Rb as well as Histone 1. The peptides derived from p21$^{WAF1}$-p21 (149-160) and p21 (149-160) 153A peptides specifically inhibit the GST-Rb phosphorylation, but do not inhibit the Histone 1 phosphorylation induced by CDK2-Cyclin E. This substrate specific effect of p21 (149-160) and its derivatives strongly suggest a mechanism of competitive binding of the peptide inhibitors and Rb to CDK2-Cyclin E or CDK4-Cyclin D1. The fact that p21 (149-160) and its derivatives did not inhibit significantly the CDK1-Cyclin B induced phosphorylation of GST-Rb excludes a possibility for direct binding of the peptide to the substrate (see Table 2).

TABLE 3

Inhibition of CDK4-Cyclin D1 and CDK2-Cyclin E kinase activity by purified p21$^{WAF1}$

| Kinase complex | Substrate | Inhibition by p21$^{WAF1}$ IC50 [nM] |
|---|---|---|
| CDK4-Cyclin D1 | GST-Rb(772-928) | 6.5 ± 0.8 |
| CDK2-Cyclin E | GST-Rb(772-928) | 0.7 ± 0.2 |
| CDK2-Cyclin E | Histone 1 | 1.8 ± 0.4 |

Example 7

P21 (149-160) and Its Derivatives Do Not Inhibit PKCα and ERK2 Kinase Activity In Vitro To investigate further the specificity of p21 (149-160) and its derivatives we investigated the effect of the strongest inhibitors of CDK2-Cyclin E and CDK4-Cyclin D1 complexes on PKCα and ERK2 kinase activity (Table 4). None of the tested peptides (at concentrations up to 100 μM) had any inhibitory effect on PKCα phosphorylation of Histone 3 or ERK2 phosphorylation of Myelin Basic Protein. These results demonstrate further the selectivity of the inhibitory effect of the peptides derived from p21 C-terminus.

nus), p27 and p57 kinase inhibitors (see FIG. 2 in Adams et al.). When the substrate recognition motif was mutated in p107 (Rb related protein) or E2F1 their phosphorylation by CDK2-Cyclin A was prevented (Adams et al., 1996).

Our p21 (149-160) SAR data clearly show though that two amino acids outside of ZXRL (SEQ ID No. 233) motif are very important for the kinase inhibitory activity of p21 (C-ter-

TABLE 4

Effect of p21$^{WAF1}$-derived peptides on PKCα and ERK2 kinase activity (activities against CDK2/cyclin E and CDK4/cyclin D1 included for comparison)

| Peptide | Sequence[a] | SEQ ID No. | IC$_{50}$ (mM) CDK4-D1 | IC$_{50}$ (mM) CDK2-E | IC$_{50}$ (mM) PKCα | IC$_{50}$ (mM) ERK2 |
|---|---|---|---|---|---|---|
| p21 (148-159) | TDFYHSKRRLIF | 191 | 15 | 2.2 | >100 | >100 |
| p21 (149-160) | DFYHSKRRLIFS | 192 | 20 | 4.5 | >100 | >100 |
| p21 (149-160) | S153ADFYHAKRRLIFS | 201 | 10 | 0.04 | >100 | >100 |
| p21 (149-159) | DFYHSKRRLIF | 212 | 13 | 2 | >100 | >100 |
| p21 (150-159) | FYHSKRRLIF | 218 | 19 | 5.8 | >100 | >100 |
| p21 (151-159) | YHSKRRLIF | 223 | 16 | 7 | >100 | >100 |
| p21 (152-159) | HSKRRLIF | 228 | 21 | 3.4 | >100 | >100 |

[a]All peptides were synthesized with free amino termini and the C-terminal carboxamides Example 8

P21 (149-159) Binds to the Cyclin, but Does Not Bind to the CDK Sub-Unit of CDK/Cyclin Complex. Binding of the Peptide to the Cyclin Does Not Disrupt the Complex.

Figure 3:
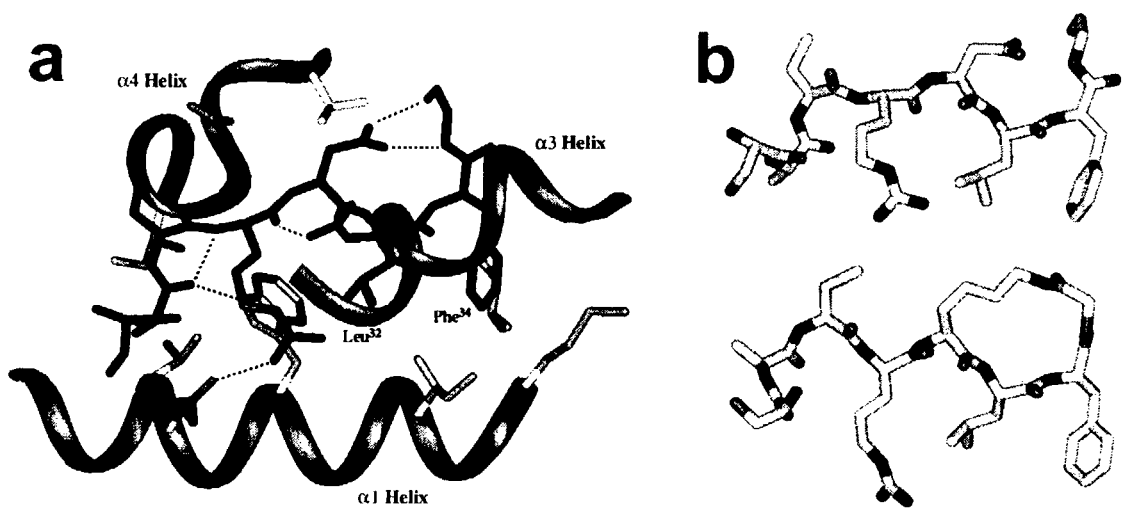
FIG. 3(a) shows interactions of p27($^{27}$Ser-Ala-Cys-Arg-Asn-Leu-Phe-Gly$^{34}$ (SEQ ID NO. 178) segment with cyclin A groove (Russo, A. A.; Jeffrey, P. D.; Patten, A. K.; Massague, J.; Pavletich, N. P. Nature 1996, 382, 325-31). Panel B shows conformation of the same segment (top) compared with modeled cyclic Ser-Ala-Cys-Arg-Lys-Leu-Phe-Gly (SEQ ID NO. 179) peptide (bottom).

A biotinylated version of p21(149-159) was used in "pull-down" experiments with the purified CDK sub-units, CDK2, CDK4, cyclin A, cyclin D1, and with the complexes of CDK2/cyclinA or CDK4/cyclin D1 kinases, in order to determine the binding partner of the peptide. The biotinylated peptide was pre-immobilised on streptavidin-agarose beads. FIG. 3 shows the profiles of the "pulled down" proteins, after SDS-PAGE, Western blotting and immunodetection. -It was found that p21(149-159) bound to cyclin A and cyclin D1, but failed to interact with CDK2 or CDK4 in the absence of their respective cyclin partners. Both CDK2 and CDK4 were "pulled down", however, with biotinylated p21(149-159)—streptavidin-agarose beads when they were in a complex with cyclin A or cyclin D1, respectively. Similar results were obtained with cyclin E and CDK2/cyclin E complex. These results suggest that binding of biotinylated p21(149-160) to the cyclin subunit does not disrupt the CDK/cyclin complex. Such a method may be utilised either alone or together with a candidate substance to identify cyclin binding moieties and/or inhibitors of cyclin-CDK interaction.

Example 9

Comparison Between Peptides, Containing ZRXL Substrate Recognition Motif

Adams et al., (1996) identified a motif—ZXRL (SEQ ID No. 233) which is present in many CDK2/Cyclin A (E) substrates—E2F family transcription factors and pRb family proteins; the same motif is present in p21 (N- and C-termiminus) derived peptide—A153 (which increases the potency approximately 100 fold) and F159 (which is vital for the kinase inhibition). To evaluate the importance of these flanking the ZXRL (SEQ ID NO: 233) motif regions we designed peptides, hybrids between p21 (152-159) and LDL motif (derived from E2F family transcription factors) or LFG motif (derived from p21 N-terminus, p27 and p57 kinase inhibitors), between p21 (16-23) and LIF motif (derived from p21 C-terminus) and between p21 (152-159)A153 and LFG motif. Their ability to inhibit CDK2/Cyclin E, CDK2/Cyclin A or CDK4/Cyclin D1 phosphorylation of pRb was compared with the one of the original peptides derived form p21-N and C-terminus, p27, E2F1 and p107 (Table 5).

The main results as presented in Table 5 below, are:

1. All peptides inhibited CDK2-Cyclin and were much less potent toward CDK4/Cyclin D1 kinase activity.
2. CDK2/Cyclin A and CDK2/Cyclin E were inhibited with similar potency by the 8-mers with the exception of HAKRRLIF (SEQ ID No. 42) and KAURRLIF (SEQ ID No. 234) which were 10 fold more potent toward CDK2/Cyclin A than to CDK2/Cyclin E kinase activity.
3. In the context of eight amino acid peptides alanine substitution of Ser153 led to significant increase of the kinase inhibitory potency of p21 (152-159)-100, 10 and 4 fold toward CDK2/Cyclin A, CDK2/Cyclin E and CDK4/Cyclin D1 phosphorylation of pRb respectively.
4. The most potent inhibitors of pRb phosphorylation contain Ala on the second position and LIF motif; they are followed by the peptides containing Ala on the second position and LFG motif (with the exception of the p27 derived peptide which contain Gln instead of Arg on the 5$^{th}$ position), Ser and LFG, and Ser and LIF containing peptides. The least potent were LDL containing peptides.

These results manifest the importance of Ala and LIF motif for the kinase inhibitory potency of the peptides.

Competitive Binding of Peptides, Containing Different Motifs (LIF, LFG, LDL) to Cyclin A or Cyclin D1.

The next important question was if these peptides share the same kinase inhibitory mechanism (bind to the same Cyclin docking site). To answer this question we developed a competitive binding assay where the influence of the 8-mers on Cyclin A (D1)-p21 (149-159) binding was studied (See Materials and Methods for more details).

The results from Cyclin D1 competitive binding assay are summarized on Table 6. For easy comparison, the data for CDK4/Cyclin D1 kinase inhibitory activity of the peptides are given in the same table.

to compete with Biotin-DFYHSKRRLIF (SEQ ID NO. 1) for binding to Cyclin D1. The only exception of this rule is p27 derived peptide—SAURNLFG (SEQ ID NO. 41), where one of the important Arg residues is replaced with Asn. These results suggest that LFG and LIF peptides bind to the same site of Cyclin D1.

The results for Cyclin A competitive binding and CDK2/Cyclin A kinase inhibition of the peptides, containing LIF, LFG and LDL motifs are also shown in Table 5. There is a very good correlation between the CDK2/Cyclin A inhibition and Cyclin A binding capabilities of the tested peptides. The

TABLE 5

Kinase inhibitory activity of LDL, LIF and LFG containing peptides, derived from E2F, p107, p21 N- and C-terminus and p27.

| | | | Kinase Inhibition | | | | | | | | Competitive binding[b] | |
|---|---|---|---|---|---|---|---|---|---|---|---|---|
| | | | Cyclin A/CDK2 | | Cyclin E/CDK2 | | Cyclin D1/CDK4 | | Cyclin D1/CDK6 | | Cyclin A | Cyclin D1 |
| Peptide | Sequence[a] | Seq ID No. | $IC_{50}$ (µM) | % Inhibition | $IC_{50}$ (µM) | % Inhibition | $IC_{50}$ (µM) | % Inhibition | $IC_{50}$ (µM) | % Inhibition | $IC_{50}$ (µM) | $IC_{50}$ (µM) |
| P21 C-terminus | HSKRRLIF | 228 | 3.4 | 80 | 3.4 | 80 | 21 | 72 | n/d | n/d | N/d | 48 |
| P21 C-terminus (S153A) | HAKRRLIF | 36 | 0.021 | 88 | 0.35 | 81 | 6 | 82 | 5.8 | 100 | 0.3 | 13 |
| P21 C-terminius-LFG hybrid | HSKRRLFG | 235 | 1.4 | 78 | 1.6 | 82 | n/a | 42 | n/d | n/d | 4.4 | >200 |
| P21 C-terminus-LDL hybrid | HSKRRLDL | 236 | 5.4 | 78 | 39 | 74 | n/a | 24 | n/d | n/d | 5.8 | >200 |
| P21 C-terminus (S153A) LFG | HAKRRLFG | 237 | 0.67 | 78 | 0.9 | 82 | 30 | 70 | n/d | n/d | 0.35 | 33 |
| E2F1 | PVKRRLDL | 238 | 1.2 | 80 | 2.1 | 74 | 99 | 58 | n/d | n/d | 1.2 | >100 |
| P27 | SAURNLFG | 41 | 6.1 | 80 | 2 | 82 | n/a | 46 | n/d | n/d | 3.8 | >200 |
| P107 | SAKRRLFG | 239 | 0.73 | 75 | 0.5 | 86 | 17 | 78 | n/d | n/d | 0.51 | 24 |
| P21 N-terminus | KAURRLFG | 240 | 0.54 | 80 | 0.074 | 86 | 42 | 66 | n/d | n/d | 0.75 | 134 |
| P21 N-terminus-LIF hybrid | KAURRLIF | 234 | 0.062 | 70 | 1.2 | 78 | 13 | 83 | n/d | n/d | 0.3 | 20 |

[a]All peptides were synthesised with free amino termini and as the C-terminal carboxamides
[b]Using the immobilised p21 (149-159) peptide biotinyl-Ahx-Asp-Phe-Tyr-His-Ser-Lys-Arg-Arg-Leu-Ile-Phe-NH (Seq. I.D. No. 241)

We have demonstrated a very good agreement between the CDK4/Cyclin D1 kinase inhibition and Cyclin D1 competitive binding capabilities of the tested peptides. The highest potency to inhibit CDK4/Cyclin D1 phosphorylation of pRb and to compete with Biotinylated p21-(149-159) for binding to Cyclin D1 has HAKRRLIF (SEQ ID NO. 42) peptide. These results suggest a mode of kinase inhibition via binding to the cyclin and coincide well with our previous results from 'pull down' experiments showing that the p21 (C-terminus) peptides bind to the Cyclins but not to the CDKs.

Thus, peptides containing the LDL motif (HSKRRLDL (SEQ ID NO. 236) and PVKRRLDL (SEQ ID NO. 238) were not able to inhibit CDK4/Cyclin D1 or to compete with Biotin-DFYHSKRRLIF (SEQ ID NO. 1) for binding to Cyclin D1. However, peptides, containing LFG motif and Ala on second position were able to inhibit CDK4/Cyclin D1 and most potent inhibitor and strongest binding competitor was HAKRRLIF (SEQ ID NO. 36) peptide.

Specificity and Selectivity of HAKRRLIF (SEQ ID NO. 42) Kinase Inhibitory Activity.

Similarly to p21 (149-160) its derivative p21 (152-159) S153A was not able to inhibit Histone phosphorylation by CDK2/Cyclin A(E) complexes (data not shown). HAKRRLIF (SEQ ID NO. 42) was not effective as an inhibitor in CDK1/Cyclin B in vitro kinase assay with Histone or Rb as substrates. HAKRRLIF (SEQ ID NO. 42) did not inhibit PKCα induced phosphorylation of Histones.

Thus, we have defined a 8-amino acid peptide derived for p21 (C-terminus) with a single point mutation—S153A which has significantly higher kinase inhibitory activity than the original sequence. HAKRRLIF (SEQ ID NO. 42) inhibited most strongly CDK2/Cyclin A phosphorylation of pRb— with IC 50 of 20 nM. The inhibitory activity of the peptide correlates with its ability to bind the cyclin sub-unit. HAKRRLIF (SEQ ID NO. 42) is very selective and specific kinase inhibitor—it inhibits specifically only the pRb phosphorylation activity of G1 CDK/Cyclins and does not inhibit the mitotic CDK/Cyclins—CDK1/Cyclin B (or A), or PKC α. HAKRRLIF (SEQ ID NO. 42) has much higher specificity and selectivity than the full length p21 protein, which inhibits the Histone phosphorylation of CDK2/Cyclin kinases complexes and has some activity toward CDK1/Cyclin B.

favourable for cyclin binding. This peptide contains a C-terminal Phe, which case was found considerably to enhance the kinase inhibitory and cyclin-binding activity in the case of the p21-derived peptides.

TABLE 6

Competitive cyclin A binding of p21- and pRb(866-880)/pRb(870-877) peptides

| Compound | SEQ ID No. | Formula | MS[a] $M_r$ | [M + R] | RP-HPLC[b] $t_R$ (min) | Purity (%) | Competitive Cyclin A Binding IC$_{50}$ (µM) immobilised pRb peptide[c] | immobilised P21 peptide[d] |
|---|---|---|---|---|---|---|---|---|
| H-His-Ala-Lys-Arg-Arg-Leu-Ile-Phe-NH$_2$ | 36 | | | | | | 0.2 | 0.02 |
| H-Asp Phe Tyr His Ala Lys Arg Arg Leu Ile Phe NH$_2$ | 242 | C$_{70}$H$_{105}$N$_{23}$O$_{14}$ | 1464.7 | 1466.0 | 15.8[i] | >95 | 0.1 | n/d |
| H-Ser-Asn-Pro-Pro-Lys-Pro-Leu-Lys-Lys-Leu-Arg-Phe-Asp-Ile-Glu-NH$_2$ | 243 | C$_{70}$H$_{117}$N$_{23}$O$_{21}$ | 1781.1 | 1780.0 | 18.1[ii] | >95 | 35 | 48 |
| H-Lys-Pro-Leu-Lys-Lys-Lue-Arg-Phe-NH$_2$ | 244 | C$_{50}$H$_{105}$N$_{23}$O$_{8}$ | 1028.3 | 1026.0 | 17.00[iii] | >95 | 0.6 | 24 |
| GST-pRb(772-298)[e] | | | | | | | n/d | 9 |

[a]DE MALDI-TOF MS, positive mode, α-cyano-4-hydroxycinnamic acid matric, calibration on authenic H-His-Ala-Lys-Arg-Arg-Leu-Ile-Phe-NH$_2$ (SEQ ID No. 36)
[b]Vaydac 218TP54, 1 mL/min, 25° C., λ = 214 nm; [i]0-40%, [ii]15-25%, [iii]10.5-20.5%, MeCN in 0.1% aq CF$_3$CooH over 20 min
[c]Competitive cyclin A binding assay using immobilized biotinyl Ahx-His-Ala-Lys-Arg-Arg Leu Ile Phe-NH$_2$ (SEQ ID No. 245)
[d]Competitive cyclin A binding assay using immobilized biotinyl
[e]Recombinant protein Example 10

Competitive Cyclin A Binding of p21- and pRb(866-880)/pRb(870-877) Peptides

It has been shown (Adams, P. D.; Li, X.; Sellers, W. R.; Baker, K. B.; Leng, X.; Harper, J. W.; Taya, Y.; Kaelin, W. G. J. *Molec. Cell Biol.* 1999, 19, 1068-1080) that pRb contains a cyclin-binding motif in its C-terminus and that this motif is required for the protein's phosphorylation. To test if the mechanism of kinase inhibition of the p21(152-159) Ser153Ala peptide was indeed via competition with pRb for binding to the cyclin subunit, two synthetic pRb-derived peptides—pRb(866-880) and pRb(870-877), as well as the recombinant GST-pRb(772-928) used in the kinase assays (all containing the cyclin-binding motif) were compared with p21-derived peptides for binding to cyclin A. Table 6 shows that all three pRb-derived peptides were able to compete with the p21-derived peptides for binding to cyclin A, and vice versa. Interestingly, the longer synthetic peptide pRb(866-880) was less effective than its truncated version pRb(870-877). Probably the conformation of the latter peptide is more Example 11

Competitive Binding of p21$^{WAF1}$ and H-His-Ala-Lys-Arg-Arg-Leu-Ile-Phe-NH$_2$ (SEQ ID No. 36) to Cyclin A in the Presence and Absence of CDK2 p21$^{WAF1}$ contains two cyclin-binding sites, one each in its N- and C-terminus [(p21(19-23) and p21(154-159)], as well as a CDK2-binding site [p21(46-65)]. The cyclin A-binding affinities of full-length p21$^{WAF1}$ and the peptide containing only the C-terminal cyclin-binding motif were compared in the presence and absence of CDK2. This showed (Table 7) that recombinant p21$^{WAF1}$ had ca. 27-fold lower affinity than H-His-Ala-Lys-Arg-Arg-Leu-Ile-Phe-NH$_2$ (SEQ ID NO. 36) for cyclin A alone. When cyclin A was pre-complexed with CDK2, on the other hand, the apparent binding affinity of p21$^{WAF1}$ increased and was comparable to that of the octapeptide. The increased ability of p21$^{WAF1}$ to compete with the octapeptide for binding to CDK2-complexed cyclin A is most probably due to the contribution of the CDK-binding motif present in the former. On the other hand, the presence of CDK2 slightly decreased the apparent binding affinity of H-His-Ala-Lys-Arg-Arg-Leu-Ile-Phe-NH$_2$ (SEQ ID NO. 36) for cyclin A, which could be due to some conformational changes of the substrate recognition site on the cyclin sub-unit upon binding of CDK2.

TABLE 7

Competitive binding of p21$^{WAF1}$ and H-His-Ala-Lys-Arg-Arg-Leu-Ile-Phe-NH$_2$ (SEQ ID NO: 36) to cyclin A in the presence and absence of CDK2

| Protein | Test Ligand in Solution | SEQ ID No. | Comptetitve binding IC$_{50}$ (nM)[a] |
|---|---|---|---|
| Cyclin A | H-His-Ala-Lys-Arg Arg-Leu-Ile Phe-NH$_2$ | 36 | 14 |
| Cyclin A | human recombinant p21 $^{WAF1}$ | | 289 |
| Cyclin A/CDK2 complex | H-His Ala Lys-Arg-Arg-Leu-Ile-Phe-NH$_2$ | 36 | 28 |
| Cyclin A/CDK2 complex | human recombinant p21 $^{WAF1}$ | | 11 |

[a]Comptetive binding of cylin A or cyclin A/CDK2 complex using immobilized peptide biotinyl-Ahx-His-Ala-Lys-Arg-Arg-Leu-Ile-Phe-NH$_2$ (SEQ ID No. 186)

Examples 12-22

Structure-Activity Relationships of the p21(152-159) Ser153Ala Peptide (H-His-Ala-Lys-Ary-Ary-Leu-Ile-Phe-NH$_2$) (SEQ ID NO. 36)

For the purposes of the following examples, the reference peptide of the invention has been taken as HAKRRLIF (SEQ ID NO. 42) i.e. a preferred peptide of the invention in accordance with the third aspect. As such, the relative activity is expressed against this peptide and all relative activities approaching (over about 0.7) or greater than unity indicate peptides that may be classified as preferred. The comments provided in these Examples are made with this comparator in mind. It should however be borne in mind that even a peptide having a relative activity of <0.1, remains within the scope of the present invention by virtue of still being active in the context of the invention, such variants are variants upon the first or second embodiments as described above.

Example 12

Sensitivity to Chiral Changes

Each residue in turn was substituted by its chiral antipode and the resulting peptide analogues were tested for both CDK2/cyclin A kinase inhibition and competitive cyclin A binding in the presence of immobilised p21(152-159) Ser153Ala peptide. It was found that inversion of configuration at the C$^\alpha$ atoms was only tolerated (in terms of retention of biological activity) at the peptide's termini. Thus His$^{152}$ could be present as either the L- or D-amino acid without loss of potency. Some potency was lost for the corresponding change at position Ala$^{153}$. Lys$^{154}$-Ile$^{158}$ could not be substituted by the corresponding D-amino acids without near-complete loss of activity. Some activity was retained when Phe$^{159}$ was inverted. These results confirm the highly selective and specific binding mode of the lead peptide. The effects seen for the terminal residues probably reflect the fact that these residues are conformationally more flexible in solution than sequence-internal groups and can be brought into a productive binding mode upon binding.

Example 12

D-Amino Acid Substitutions Based on p21(152-159)Ser153Ala

| Compound | SEQ ID No. | Formula | MS[a] M$_r$ | [M + H] | RP-HPLC[b] t$_R$ (min) | Purity (%) | Relative activity Kinase Inhibition[c] | Cyclin A Binding[d] |
|---|---|---|---|---|---|---|---|---|
| H-His-Ala-Lys-Arg-<u>Arg</u>-Leu-Ile-Phe-NH$_2$ | 36 | C$_{48}$H$_{82}$N$_{21}$O$_8$ | 1039.3 | | | | 1 | 1 |
| H-*his*-Ala-Lys-Arg-Arg-Leu-Ile Phe-NH$_2$ | 183 | C$_{48}$H$_{82}$N$_{21}$O$_8$ | 1039.3 | 1039.1 | 15.4 | 96 | 1.7 | 0.9 |
| H-His-*ala*-Lys-Arg-Arg-Leu-Ile Phe-NH$_2$ | 246 | C$_{48}$H$_{82}$N$_{21}$O$_8$ | 1039.3 | 1042.5 | 15.3 | 98 | 0.3 | 0.6 |
| H-His-Ala-*lys*-Arg-Arg-Leu-Ile Phe-NH$_2$ | 247 | C$_{48}$H$_{82}$N$_{21}$O$_8$ | 1039.3 | 1042.9 | 15.6 | 100 | <0.1 | <0.1 |
| H-His-Ala-Lys-*arg*-Arg-Leu-Ile Phe-NH$_2$ | 248 | C$_{48}$H$_{82}$N$_{21}$O$_8$ | 1039.3 | 1041.6 | 15.2 | 99 | <0.1 | <0.1 |
| H-His-Ala-Lys-Arg-*arg*-Leu-Ile Phe-NH$_2$ | 249 | C$_{70}$H$_{105}$N$_{21}$O$_{14}$ | 1039.3 | 1041.1 | 15.2 | 99 | <0.1 | <0.1 |
| H-His-Ala-Lys-Arg-Arg-*leu*-Ile Phe-NH$_2$ | 82 | C$_{82}$H$_{137}$N$_{23}$O$_{21}$ | 1039.3 | 1041.0 | 17.6 | 100 | <0.1 | <0.1 |

| Compound | SEQ ID No. | Formula | MS[a] $M_r$ | [M + H] | RP-HPLC[b] $t_R$ (min) | Purity (%) | Relative activity Kinase Inhibition[c] | Cyclin A Binding[d] |
|---|---|---|---|---|---|---|---|---|
| H-His-Ala-Lys-Arg-Arg-Leu-*ile* Phe-NH$_2$ | 250 | C$_{50}$H$_{89}$N$_{15}$O$_8$ | 1039.3 | 1040.5 | 18.1 | 100 | <0.1 | <0.1 |
| H-His-Ala-Lys-Arg-Arg-Leu-Ile *phe*-NH$_2$ | 251 | C$_{48}$H$_{82}$N$_{21}$O$_8$ | 1039.3 | 1039.7 | 17.1 | 100 | 0.1 | 0.2 |

[a] DE MALDI-TOF MS, =ve mode, α-cayno-4-hydroxycinnamic acid matric, calibration on authentic H-His-Ala-Lys-Arg-Arg-Leu-IIe-Phe-NH$_2$ (SEQ ID No. 36)
[b] Vaydac 218TP54, 1 mL/min, 25° C.; 0-40%, MeCN in 0.1% aq TFA over 20 min, λ = 214 nm
[c] CDK2/cyclin A kinase assay, pRb substrate. [ATP] = 100 μM
[d] Competitive cyclin A binding assay using immobilized biotinyl Ahx-His Ala-Lys-Arg-Arg Leu Ile Phe-NH$_2$ (SEQ ID No. 186)

Residue Substitutions

Example 13

His[152]

This residue is comparatively insensitive to substitution. With the exception of Pya, all residue substitutions were either tolerated or even lead to enhanced binding and/or kinase inhibition potency. Furthermore, this residue can be truncated without significant loss in biological activity.

Example 13

Substitutions of His[152] Residue in p21(152-159)Ser153Ala

| Compound | SEQ ID No. | Formula | MS[a] $M_r$ | [M + H] | RP-HPLC[b] $t_R$ (min) | Purity (%) | Relative activity Kinase Inhibition[c] | Cyclin A Binding[d] |
|---|---|---|---|---|---|---|---|---|
| H-His-Ala-Lys-Arg-Arg-Leu-Ile-Phe-NH$_2$ | 36 | | | | | | 1 | 1 |
| H-*Ala*-Ala-Lys-Arg-Arg-Leu-Ile Phe-NH$_2$ | 47 | C$_{42}$H$_{80}$N$_{16}$O$_8$ | 973.2 | 975.4 | 15.4 | 98 | 1.8 | 2.5 |
| H-Ala-Lys-Arg-Arg-Leu-Ile-Phe-NH$_2$ | 48 | C$_{42}$H$_{75}$N$_{15}$O$_7$ | 902.1 | 901.0 | 15.5 | 100 | 1 | 0.3 |
| H-*Pya*-Ala-Lys-Arg-Arg-Leu-Ile Phe-NH$_2$ | 49 | C$_{42}$H$_{80}$N$_{15}$O$_7$ | 1049.3 | 1050.6 | 15.4 | 98 | <0.1 | 0.2 |
| H-*Thi*-Ala-Lys-Arg-Arg-Leu-Ile Phe-NH$_2$ | 50 | C$_{49}$H$_{82}$N$_{16}$O$_8$S | 1055.3 | 1055.5 | 16.3 | 100 | 2 | 0.2 |
| H-*Hse*-Ala-Lys-Arg-Arg-Leu-Ile Phe-NH$_2$ | 51 | C$_{46}$H$_{82}$N$_{16}$O$_9$ | 1003.3 | 1002.9 | 15.7 | 82 | 2 | 2 |
| H-*Phe*-Ala-Lys-Arg-Arg-Leu-Ile Phe-NH$_2$ | 52 | C$_{51}$H$_{84}$N$_{16}$O$_8$ | 1049.3 | 1052.3 | 16.3 | 100 | 3 | 1 |
| H-*Dab*-Ala-Lys-Arg-Arg-Leu-Ile Phe-NH$_2$ | 53 | C$_{46}$H$_{83}$N$_{17}$O$_8$ | 1002.3 | 1004.7 | 15.5 | 100 | 5 | 0.4 |

[a] DE MALDI-TOF MS, =ve mode, α-cayno-4-hydroxycinnamic acid matric, calibration on authentic H-His-Ala-Lys-Arg-Arg-Leu-IIe-Phe-NH$_2$ (SEQ ID No. 36)
[b] Vaydac 218TP54, 1 mL/min, 25° C.; 0-40%, MeCN in 0.1% aq TFA over 20 min, λ = 214 nm
[c] CDK2/cyclin A kinase assay, pRb substrate, [ATP] = 100 μM
[d] Competitive cyclin A binding assay using immobilized biotinyl Ahx-His Ala-Lys-Arg-Arg Leu Ile Phe-NH$_2$ (SEQ ID No. 186)

Example 14

Ala$^{153}$

This is the residue position where replacement of the native Ser with Ala resulted in a dramatic potency increase. Further potency enhancements are observed when short, straight-chain (Abu) or β-branched (Val, Bug) residues are introduced. Side chains containing more than three saturated carbon atoms in a straight chain are poorly tolerated.

Example 14

Substitutions of Ala$^{153}$ Residue in p21(152-159)Ser153Ala

| Compound | SEQ ID No. | Formula | MS$^a$ $M_r$ | [M + H] | RP-HPLC$^b$ tg(min) | Purity (%) | Relative activity Kinase Inhibition$^c$ | Cyclin A Binding$^d$ |
|---|---|---|---|---|---|---|---|---|
| H-His-Ala-Lys-Arg-Arg-Leu-Ile-Phe-NH$_2$ | 36 | | | | | | 1 | 1 |
| H-His-*Gly*-Lys-Arg-Arg-Leu-Ile-Phe-NH$_2$ | 54 | C$_{47}$H$_{80}$N$_{18}$O$_8$ | 1025.3 | 1026.8 | 15.2 | 98 | 0.1 | 0.1 |
| H-His-*Abu*-Lys-Arg-Arg-Leu-Ile-Phe-NH$_2$ | 55 | C$_{49}$H$_{84}$N$_{18}$O$_8$ | 1053.3 | 1055.2 | 15.8 | 100 | 5 | 1.3 |
| H-His-*Nva*-Lys-Arg-Arg-Leu-Ile-Phe-NH$_2$ | 56 | C$_{50}$H$_{86}$N$_{18}$O$_8$ | 1067.3 | 1069.1 | 16.0 | 100 | <0.1 | <0.1 |
| H-His-*Bug*-Lys-Arg-Arg-Leu-Ile-Phe-NH$_2$ | 57 | C$_{51}$H$_{83}$N$_{18}$O$_8$ | 1081.4 | 1082.7 | 15.9 | 100 | 0.2 | 1.2 |
| H-His-*Val*-Lys-Arg-Arg-Leu-Ile-Phe-NH$_2$ | 58 | C$_{50}$H$_{86}$N$_{18}$O$_8$ | 1067.3 | 1068.5 | 15.9 | 100 | 2 | 1.7 |
| H-His-*Ile*-Lys-Arg-Arg-Leu-Ile-Phe-NH$_2$ | 59 | C$_{51}$H$_{83}$N$_{18}$O$_8$ | 1081.4 | 1081.9 | 16.1 | 100 | 0.5 | 0.2 |
| H-His-*Phg*-Lys-Arg-Arg-Leu-Ile-Phe-NH$_2$ | 60 | C$_{53}$H$_{84}$N$_{18}$O$_8$ | 1101.4 | 1101.8 | 15.8, 16.1$^e$ | 100 | <0.1 | <0.1 |
| H-His-*Phe*-Lys-Arg-Arg-Leu-Ile-Phe-NH$_2$ | 61 | C$_{54}$H$_{86}$N$_{18}$O$_8$ | 1115.4 | 1115.8 | 16.5 | 100 | 0.5 | 0.2 |

$^a$DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
$^b$Vaydac 218TP54, 1 ml/min, 25° C.; 0-40%, MeCN in 0.1% aq TFA over 20 min, λ = 214 nm
$^c$CDK2 / cyclin A kinase assay, pRb substrate, [ATP] = 100 μM
$^d$Competitive cyclin A binding assay using immobilized biotinyl Ahx-His Ala-Lys-Arg-Arg Leu Ile Phe- NH$_2$ (SEQ ID No. 186)
$^e$Mixture of diastereomers (racemic Fmoc-Phg-Oh used)

Example 15

Lys$^{154}$

Various non-isosteric replacements are tolerated to some extent. A significant potency increase is observed when the conservative Lys-to-Arg replacement is made.

Example 15

Substitutions of Lys$^{154}$ Residue in p21(152-159)Ser153Ala

| Compound | SEQ ID No. | Formula | MS$^a$ $M_r$ | [M + H] | RP-HPLC$^b$ tg(min) | Purity (%) | Relative activity Kinase Inhibition$^c$ | Cyclin A Binding$^d$ |
|---|---|---|---|---|---|---|---|---|
| H-His-Ala-Lys-Arg-<u>Arg</u>-Leu-Ile-Phe-NH$_2$ | 36 | C$_{48}$H$_{82}$N$_{18}$O$_8$ | | | | | 1 | 1 |
| H-His-Ala-Ala-Arg-Arg-Leu-Ile-Phe-NH$_2$ | 62 | C$_{45}$H$_{75}$N$_{17}$O$_8$ | 982.2 | 983.6 | 15.6 | 99 | <0.1 | 0.5 |
| H-His-Ala-Nle-Arg-Arg-Leu-Ile-Phe-NH$_2$ | 63 | C$_{48}$H$_{81}$N$_{17}$O$_8$ | 1024.3 | 1022.9 | 16.8 | 97 | 0.3 | 0.2 |
| H-His-Ala-Abu-Arg-Arg-Leu-Ile-Phe-NH$_2$ | 64 | C$_{46}$H$_{77}$N$_{17}$O$_8$ | 996.2 | 997.4 | 16.1 | 100 | 0.8 | 0.2 |
| H-His-Ala-Leu-Arg-Arg-Leu-Ile-Phe-NH$_2$ | 65 | C$_{48}$H$_{81}$N$_{17}$O$_8$ | 1024.3 | 1025.5 | 16.8 | 97 | 0.1 | 1.4 |
| H-His-Ala-Arg-Arg-Arg-Leu-Ile-Phe-NH$_2$ | 66 | C$_{48}$H$_{82}$N$_{20}$O$_8$ | 1067.3 | 1067.9 | 15.5 | 94 | 5.7 | 1.5 |

$^a$DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
$^b$Vaydac 218TP54, 1 ml/min, 25° C.; 0-40%, MeCN in 0.1% aq TFA over 20 min, λ = 214 nm
$^c$CDK2 / cyclin A kinase assay, pRb substrate, [ATP] = 100 μM
$^d$Competitive cyclin A binding assay using immobilized biotinyl Ahx-His Ala-Lys-Arg-Arg Leu Ile Phe- NH$_2$ (SEQ ID No. 186)

Example 16

Arg$^{155}$

Only the conservative replacements with Cit and Lys are tolerated to some extent.

Example 16

Substitutions of Arg$^{155}$ Residue in p21(152-159)Ser153Ala

| Compound | SEQ ID No. | Formula | MS$^a$ $M_r$ | [M + H] | RP-HPLC$^b$ tg(min) | Purity (%) | Relative activity Kinase Inhibition$^c$ | Cyclin A Binding$^d$ |
|---|---|---|---|---|---|---|---|---|
| H-His-Ala-Lys-Arg-<u>Arg</u>-Leu-Ile-Phe-NH$_2$ | 36 | C$_{48}$H$_{82}$N$_{18}$O$_8$ | | | | | 1 | 1 |
| H-His-Ala-Lys-Ala-Arg-Leu-Ile-Phe-NH$_2$ | 67 | C$_{45}$H$_{75}$N$_{15}$O$_8$ | 954.2 | 954.9 | 16.0 | 95 | <0.1 | <0.1 |
| H-His-Ala-Lys-Cit-Arg-Leu-Ile-Phe-NH$_2$ | 68 | C$_{48}$H$_{81}$N$_{17}$O$_9$ | 1040.3 | 1053.5 | 12.5 | 94 | 0.2 | 0.2 |

-continued

| Compound | SEQ ID No. | Formula | MS[a] $M_r$ | [M + H] | RP-HPLC[b] tg(min) | Purity (%) | Relative activity Kinase Inhibition[c] | Cyclin A Binding[d] |
|---|---|---|---|---|---|---|---|---|
| H-His Ala-Lys-*Hse*-Arg-Leu-Ile Phe-NH$_2$ | 69 | $C_{46}H_{77}N_{15}O_9$ | 984.2 | 985.9 | 15.8 | 100 | <0.1. | <0.1 |
| H-His-Ala-Lys-*Nle*-Arg-Leu-Ile Phe-NH$_2$ | 71 | $C_{48}H_{81}N_{15}O_8$ | 996.3 | 998.4 | 18.1 | 86 | <0.1 | <0.1 |
| H-His-Ala-Lys-*Gln*-Arg-Leu-Ile Phe-NH$_2$ | 72 | $C_{47}H_{78}N_{16}O_9$ | 1011.2 | 1012.9 | 15.6 | 98 | <0.1 | <0.1 |
| H-His-Ala-Lys-*Lys*-Arg-Leu-Ile Phe-NH$_2$ | 73 | $C_{48}H_{82}N_{16}O_8$ | 1011.3 | 1011.8 | 15.3 | 100 | 0.8 | 0.1 |

[a]DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b]Vaydac 218TP54, 1 ml/min, 25° C.; 0–40%, MeCN in 0.1% aq TFA over 20 min, λ = 214 nm
[c]CDK2/cyclin A kinase assay, pRb substrate, [ATP] = 100 μM
[d]Competitive cyclin A binding assay using immobilized biotinyl Ahx-His Ala-Lys-Arg-Arg Leu Ile Phe-NH$_2$ (SEQ ID No. 186)

Example 17

Arg[156]

This residue was probed with replacements constraining the backbone dihedral angles in different ways (Ala, Pro, Aib, Sar), none of which were tolerated. Partially tolerated replacements with Cit or Ser indicate involvement in H-bonding.

Example 17

Substitutions of Arg[156] Residue in p21(152-159)Ser153Ala

| Compound | SEQ ID No. | Formula | MS[a] $M_r$ | [M + H] | RP-HPLC[b] tg(min) | Purity (%) | Relative activity Kinase Inhibition[c] | Cyclin A Binding[d] |
|---|---|---|---|---|---|---|---|---|
| H-His-Ala-Lys-Arg-Arg-Leu-Ile- Phe-NH$_2$ | 36 | $C_{48}H_{82}H_{18}O_8$ | | | | | 1 | 1 |
| H-His-Ala-Lys-Arg-*Ala*-Leu-Ile Phe-NH$_2$ | 74 | $C_{45}H_{75}H_{15}O_8$ | 954.2 | 954.9 | 16.1 | 100 | <0.1 | <0.1 |
| H-His-Ala-Lys-Arg-*Asn*-Leu-Ile Phe-NH$_2$ | 75 | $C_{46}H_{76}H_{16}O_9$ | 997.2 | 997.5 | 15.5 | 99 | <0.1 | <0.1 |
| H-His Ala-Lys-Arg-*Pro*-Leu-Ile Phe-NH$_2$ | 76 | $C_{47}H_{77}H_{15}O_8$ | 980.2 | 980.1 | 16.3 | 100 | <0.1 | <0.1 |
| H-His-Ala-Lys-Arg-*Ser*-Leu-Ile Phe-NH$_2$ | 77 | $C_{45}H_{75}H_{15}O_9$ | 970.2 | 970.2 | 16.1 | 100 | 0.7 | 0.2 |
| H-His-Ala-Lys-Arg-*Aib*-Leu-Ile Phe-NH$_2$ | 78 | $C_{46}H_{77}H_{15}O_8$ | 968.2 | 968.1 | 16.7 | 73 | <0.1 | <0.1 |
| H-His-Ala-Lys-Arg-*Sar*-Leu-Ile Phe-NH$_2$ | 79 | $C_{45}H_{75}H_{15}O_8$ | 954.2 | 955.4 | 16.5 | 100 | <0.1 | <0.1 |

-continued

| Compound | SEQ ID No. | Formula | MS[a] M_r | [M + H] | RP-HPLC[b] tg(min) | Purity (%) | Relative activity Kinase Inhibition[c] | Cyclin A Binding[d] |
|---|---|---|---|---|---|---|---|---|
| H-His-Ala-Lys-Arg-*Cit*-Leu-Ile-Phe-NH$_2$ | 80 | C$_{48}$H$_{81}$H$_{17}$O$_9$ | 1040.3 | 1041.42 | 15.67 | 100 | 0.3 | n/d |

[a] DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b] Vaydac 218TP54, 1 ml/min, 25° C.; 0–40%, MeCN in 0.1% aq TFA over 20 min, λ = 214 nm
[c] CDK2 / cyclin A kinase assay, pRb substrate, [ATP] = 100 µM
[d] Competitive cyclin A binding assay using immobilized biotinyl Ahx-His Ala-Lys-Arg-Arg Leu Ile Phe-NH$_2$ (SEQ ID No. 186)

Example 18

Leu[157]

This residue is very sensitive to replacement, even with nearly isosteric groups. Only the very conservative Leu-to-Ile replacement was tolerated somewhat.

Example 18

Substitutions of Leu[157] Residue in p21(152-159)Ser153Ala

| Compound | SEQ ID No. | Formula | MS[a] M_r | [M + H] | RP-HPLC[b] tg(min) | Purity (%) | Relative activity Kinase Inhibition[c] | Cyclin A Binding[d] |
|---|---|---|---|---|---|---|---|---|
| H-His-Ala-Lys-Arg-Arg-Leu-Ile-Phe-NH$_2$ | 36 | C$_{48}$H$_{82}$N$_{18}$O$_8$ | | | | | 1 | 1 |
| H-His-Ala-Lys-Arg-Arg-*Ala*-Ile-Phe-NH$_2$ | 81 | C$_{48}$H$_{82}$N$_{18}$O$_8$ | 997.2 | 996.9 | 13.9 | 100 | <0.1 | <0.1 |
| H-His-Ala-Lys-Arg-Arg-*leu*-Ile-Phe-NH$_2$ | 82 | C$_{48}$H$_{82}$N$_{18}$O$_8$ | 1039.3 | 1041.0 | 15.1 | 100 | <0.1 | <0.1 |
| H-His Ala-Lys-Arg-Arg-*Ile*-Ile-Phe-NH$_2$ | 83 | C$_{48}$H$_{82}$N$_{18}$O$_8$ | 1039.3 | 1041.1 | 14.4 | 100 | 1.5 | 0.2 |
| H-His-Ala-Lys-Arg-Arg-*Val*-Ile-Phe-NH$_2$ | 84 | C$_{47}$H$_{80}$N$_{18}$O$_8$ | 1025.3 | 1026.2 | 15.8 | 100 | <0.1 | <0.1 |
| H-His-Ala-Lys-Arg-Arg-*Nle*-Ile-Phe-NH$_2$ | 85 | C$_{48}$H$_{82}$N$_{18}$O$_8$ | 1039.3 | 1040.2 | 15.8 | 100 | <0.1 | <0.1 |
| H-His-Ala-Lys-Arg-Arg-*Nva*-Ile-Phe-NH$_2$ | 86 | C$_{47}$H$_{80}$N$_{18}$O$_8$ | 1025.3 | 1025.0 | 14.9 | 100 | <0.1 | <0.1 |
| H-His-Ala-Lys-Arg-Arg-*Cha*-Ile-Phe-NH$_2$ | 87 | C$_{51}$H$_{80}$N$_{18}$O$_8$ | 1079.4 | 1079.2 | 17.5 | 100 | <0.1 | <0.1 |
| H-His-Ala-Lys-Arg-Arg-*Phe*-Ile-Phe-NH$_2$ | 88 | C$_{51}$H$_{80}$N$_{18}$O$_8$ | 1073.3 | 1072.7 | 16.4 | 100 | <0.1 | <0.1 |
| H-His-Ala-Lys-Arg-Arg-*1Nap*-Ile-Phe-NH$_2$ | 89 | C$_{52}$H$_{82}$N$_{18}$O$_8$ | 1123.4 | 1122.5 | 17.9 | 100 | <0.1 | <0.1 |

[a] DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b] Vaydac 218TP54, 1 ml/min, 25° C.; 0–40%, MeCN in 0.1% aq TFA over 20 min, λ = 214 nm
[c] CDK2 / cyclin A kinase assay, pRb substrate, [ATP] = 100 µM
[d] Competitive cyclin A binding assay using immobilized biotinyl Ahx-His Ala-Lys-Arg-Arg Leu Ile Phe-NH$_2$ (SEQ ID No. 186)

Example 19

Ile[158]

All substitutions with aliphatic and aromatic residues were tolerated to some extent. However, excision of the Ile residue abolished activity. These results indicate that this residue is not crucial for activity but may be important as a spacer group between the flanking Leu and Phe groups.

Example 19

Substitutions of Ile[158] Residue in p21(152-159)Ser153Ala

| Compound | SEQ ID No. | Formula | MS[a] $M_r$ | MS[a] [M + H] | RP-HPLC[b] tg(min) | RP-HPLC[b] Purity (%) | Relative activity Kinase Inhibition[c] | Relative activity Cyclin A Binding[d] |
|---|---|---|---|---|---|---|---|---|
| H-His-Ala-Lys-Arg-Arg-Leu-Ile-Phe-NH$_2$ | 36 | $C_{48}H_{82}N_{18}O_8$ | | | | | 1 | 1 |
| H-His-Ala-Lys-Arg-Arg-Leu-Ala-Phe-NH$_2$ | 90 | $C_{45}H_{76}N_{18}O_8$ | 997.2 | 996.5 | 13.8 | 100 | 0.3 | 0.8 |
| H-His-Ala-Lys-Arg-Arg-Leu-Leu-Phe-NH$_2$ | 91 | $C_{48}H_{82}N_{18}O_8$ | 1039.3 | 1038.4 | 16.1 | 100 | 1.2 | 0.6 |
| H-His Ala-Lys-Arg-Arg-Leu-Val-Phe-NH$_2$ | 92 | $C_{47}H_{80}N_{18}O_8$ | 1025.3 | 1024.7 | 14.9 | 100 | 0.8 | 1.5 |
| H-His-Ala-Lys-Arg-Arg-Leu-Nle-Phe-NH$_2$ | 93 | $C_{48}H_{82}N_{18}O_8$ | 1039.3 | 1040.3 | 16.3 | 100 | 0.4 | 0.3 |
| H-His-Ala-Lys-Arg-Arg-Leu-Nva-Phe-NH$_2$ | 94 | $C_{47}H_{80}N_{18}O_8$ | 1025.3 | 1025.7 | 15.2 | 100 | 0.2 | 0.6 |
| H-His-Ala-Lys-Arg-Arg-Leu-Cha-Phe-NH$_2$ | 95 | $C_{51}H_{86}N_{18}O_8$ | 1079.4 | 1080.2 | 18.4 | 100 | 0.3 | 0.5 |
| H-His-Ala-Lys-Arg-Arg-Leu-Phe-Phe-NH$_2$ | 96 | $C_{51}H_{80}N_{18}O_8$ | 1073.3 | 1073.9 | 16.3 | 100 | 0.4 | 0.4 |
| H-His-Ala-Lys-Arg-Arg-Leu-1Nap-Phe-NH$_2$ | 97 | $C_{55}H_{82}N_{18}O_8$ | 1123.4 | 1122.9 | 18.2 | 100 | 0.5 | 0.5 |
| H-His-Ala-Lys-Arg-Arg-Leu-Phe-NH$_2$ | 98 | $C_{42}H_{71}N_{17}O_7$ | 926.1 | 924.8 | 13.8 | 100 | <0.1 | <0.1 |

[a]DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b]Vaydac 218TP54, 1 ml/min, 25° C.; 0–40%, MeCN in 0.1% aq TFA over 20 min, λ = 214 nm
[c]CDK2 / cyclin A kinase assay, pRb substrate, [ATP] = 100 μM
[d]Competitive cyclin A binding assay using immobilized biotinyl Ahx-His Ala-Lys-Arg-Arg Leu Ile Phe-NH$_2$ (SEQ ID No. 186)

Example 20

Phe[159]

Only certain replacements with aromatic residues were tolerated. Notably pFPhe substitution resulted in an analogue with enhanced cyclin A-binding affinity.

Example 20

Substitutions of Phe[159] Residue in p21(152-159)Ser153Ala

| Compound | SEQ ID No. | Formula | MS[a] $M_r$ | [M + H] | RP-HPLC[b] $t_g$(min) | Purity (%) | Relative activity Kinase Inhibition[c] | Cyclin A Binding[d] |
|---|---|---|---|---|---|---|---|---|
| H-His-Ala-Lys-Arg-<u>Arg</u>-Leu-Ile-Phe-NH$_2$ | 36 | $C_{48}H_{82}N_{18}O_8$ | | | | | 1 | 1 |
| H-His-Ala-Lys-Arg-Arg-Leu-Ile-Leu-NH$_2$ | 99 | $C_{45}H_{88}N_{18}O_8$ | 1005.3 | 1005.7 | 14.2 | 97 | 0.3 | <0.1 |
| H-His-Ala-Lys-Arg-Arg-Leu-Ile-Cha-NH$_2$ | 100 | $C_{48}H_{88}N_{18}O_8$ | 1045.3 | 1045.5 | 16.9 | 100 | <0.1 | <0.1 |
| H-His-Ala-Lys-Arg-Arg-Leu-Ile-Hof-NH$_2$ | 101 | $C_{49}H_{84}N_{18}O_8$ | 1053.3 | 1052.8 | 15.8 | 96 | <0.1 | <0.1 |
| H-His-Ala-Lys-Arg-Arg-Leu-Ile-Tyr-NH$_2$ | 102 | $C_{48}H_{82}N_{18}O_9$ | 1055.3 | 1054.6 | 13.3 | 100 | 0.3 | 0.2 |
| H-His-Ala-Lys-Arg-Arg-Leu-Ile-pFPhe-NH$_2$ | 103 | $C_{48}H_{81}N_{18}O_9$ | 1057.3 | 1055.8 | 16.0 | 100 | 1 | 5 |
| H-His-Ala-Lys-Arg-Arg-Leu-Ile-mFPhe-NH$_2$ | 104 | $C_{48}H_{81}N_{18}O_8$ | 1057.3 | 1055.5 | 16.2 | 100 | 0.8 | 0.8 |
| H-His-Ala-Lys-Arg-Arg-Leu-Ile-Trp-NH$_2$ | 105 | $C_{50}H_{83}N_{19}O_8$ | 1078.3 | 1076.1 | 15.6 | 98 | 0.3 | 0.1 |
| H-His-Ala-Lys-Arg-Arg-Leu-Ile-1Nap-NH$_2$ | 106 | $C_{52}H_{84}N_{18}O_8$ | 1089.3 | 1090.7 | 17.8 | 100 | 0.2 | <0.1 |
| H-His-Ala-Lys-Arg-Arg-Leu-Ile-2Nap-NH$_2$ | 107 | $C_{52}H_{84}N_{18}O_8$ | 1083.3 | 1090.6 | 18.0 | 100 | 1.2 | 0.7 |
| H-His-Ala-Lys-Arg-Arg-Leu-Ile-Lys-NH$_2$ | 108 | $C_{45}H_{85}N_{19}O_8$ | 1020.3 | 1021.5 | 11.6 | 66 | <0.1 | <0.1 |
| H-His-Ala-Lys-Arg-Arg-Leu-Ile-Tic-NH$_2$ | 109 | $C_{49}H_{82}N_{18}O_8$ | 1051.3 | 1052.3 | 15.6 | 91 | 0.3 | <0.1 |

[a]DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b]Vaydac 218TP54, 1 ml/min, 25° C.; 0–40%, MeCN in 0.1% aq TFA over 20 min, λ = 214 nm
[c]CDK2 / cyclin A kinase assay, pRb substrate, [ATP] = 100 μM
[d]Competitive cyclin A binding assay using immobilized biotinyl Ahx-His Ala-Lys-Arg-Arg Leu Ile Phe-NH$_2$ (SEQ ID No. 186)

Example 21

Substitutions of Phe[159] Residue in p21(152-159)Ser153Ala with Conformationally Defined Residues Fmoc-DL-threo-Pse-OH To a solution of H-DL-threo-Pse-OH (1 g, 5.5 mmol) in 5% aq Na$_2$CO$_3$ (13 mL, 6 mmol), was added a solution of Fmoc-ONSu (1.7 g, 5 mmol) in THF (13 mL) over a period of 30 min. The mixture was stirred vigorously for 5 h. The solvent was evaporated to dryness in vacuo. The residual white solid was dissolved in H$_2$O (150 mL) and was washed with Et$_2$O (2×100 mL). The aqueous phase was acidified to pH 2 with 0.2 M aq HCl and a precipitate was obtained, which was extracted into EtOAc (2×100 mL). The combined extracts were washed with aq KHSO$_4$ and brine, dried (MgSO$_4$) and concentrated in vacuo to afford a crude product (1.32 g, 65%). This was dissolved in the minimum volume of EtOAc and dripped into vigorously stirred hexane to afford, after filtration and drying, the title compound (1.27 g, 63%). M.p. 107-108° C. TLC (EtOAc/AcOH, 99:1): $R_f$=0.27. RP-HPLC (Vydac 218TP54, 1 mL/min, 50-100% MeCN in 0.1% aq $CF_3COOH$ over 20 min): $t_R$=7.2 min. $^1$H-NMR ($CDCl_3$, 250 MHz), δ. 7.75 (2H, d, J=7.6 Hz, Fmoc aromatic H), 7.42-7.49 (2h, M, Fmoc aromatic H), 7.27-7.39 (9H, m, aromatic H), 5.67 (1H, d, J=9.0 Hz, NH), 5.45 (1H, d, J=2.4 Hz, $C^\beta H$), 4.68 (1H, dd, J=2.5, 8.8 Hz, $C^\alpha H$), 4.27 (2H, m, Fmoc $CH_2$), 4.14 (1H, t, J=7.1 Hz, Fmoc CH); $^{13}$C-NMR ($CDCl_3$:$d_6$-DMSO, 62.9 MHz) δ. 172.28 (carbonyl C, acid), 155.98 (carbonyl C, urethane), 143.60, 143.54, 140.80 (quaternary C). 127.81, 127.28, 127.16, 126.71, 125.73, 124.99, 124.88, 119.53, 72.68 (CH), 66.45 ($CH_2$), 59.62, 46.69 (CH). HR-MS (FAB) calc. For $C_{24}H_{22}NO_5$ ($MH^+$): 404.149798. found 404.148369.

Ac-DL-threo-Pse-OH

To a cold solution (5° C.) of H-DL-threo-Pse-OH (1 g, 5.5 mmol) and $NaHCO_3$ (1.85 g, 22.1 mmol) in $H_2O$ (30 mL) was added $Ac_2O$ (1.6 mL, 16.6 mmol) dropwise over a period of 15 min. The mixture was stirred vigorously at room temperature overnight. It was extracted with EtOAc (100 mL). The aqueous phase was acidified to pH 2 with aq $KHSO_4$ and the product was extracted into EtOAc (3×100 mL), and NaCl was added to aid the process. The organic extracts were combined and washed with aq $KHSO_4$, brine, dried ($MgSO_4$) and concentrated in vacuo to afford the title compound as a white solid (0.9 g, 73%). M.p. 142-143° C.; ES-MS$^+$ m/z 224.2 ($MH^+$), calc. 224.2; TLC (MeOH/$CH_2Cl_2$/AcOH, 20:79:1): $R_f$=0.41; RP-HPLC (Vydac 218TP54, 1 mL/min, 20-60% MeCN in 0.1% aq $CF_3COOH$ over 25 min): $t_R$=3.6 min. $^1$H-NMR ($d_6$-DMSO, 250 MHz) δ. 12.49-12.60 (1H, br. S, $CO_2H$), 7.99 (1H, d, J=9.1 Hz, NH), 7.07-7.39 (5H, m, ArH), 5.76-5.90 (1H, br. S, OH), 5.14 (1H, d, J=2.9 Hz, $C^\beta H$), 4.48 (1H, dd, J=3.0, 9.1 Hz, $C^\alpha H$), 1.75 (3H, s, $CH_3$).

H-DL-threo-Pse-OMe.HCl

A stream of HCl gas was passed through a stirred suspension of H-DL-threo-Pse-OH (1 g, 5.5 mmol) in MeOH (30 mL) at 0° C. After ca. 30 min, dissolution was complete. Gas addition was continued for 2 h. The mixture was allowed to reach room temperature, sealed, and left to stand overnight. Solvent was removed in vacuo to afford the title compound as an off-white solid (1.07 g, 83%). M.p. 154-156° C. (dec.); ES-MS$^+$ m/z 195.9 ($MH^+$), calc. 196.2; RP-HPLC (Vydac 218TP54, 1 mL/min, 20-60% MeCN in 0.1% aq $CF_3COOH$ over 25 min): $t_R$=3.2 min; $^1$H-NMR ($d_6$-DMSO, 250 MHz) δ. 8.54, (3H, br. S, $NH_3^+$), 7.29-7.40 (5H, m, ArH), 5.03 (1H, d, J=5.6 Hz, $C^\beta H$), 4.16 (1H, m, $C^\alpha H$), 3.61 (3H, s, $CH_3$).

Ac-DL-threo-Pse-OMe

To a vigorously stirred solution of H-DL-threo-Pse-OMe-.HCl (0.5 g. 2.15 mmol) and NaOAc.($H_2O$)$_3$ (1.17 g, 8.6 mmol) in $H_2O$ (10 mL) at 5° C. was added $Ac_2O$ (0.6 mL, 6.45 mmol) dropwise over 15 min. A white precipitate was formed within 10 min, and stirring was continued for 16 h at room temperature. The mixture was extracted with EtOAc (2×100 mL), and the organic phase was separated and washed with aq $NaHCO_3$ (2×50 mL) and brine (100 mL). The organic phase was dried ($MgSO_4$), and evaporated to dryness in vacuo to afford th title compound as a white solid (0.36 g, 71. %). M.p. 176-179° C.; ES-MS$^+$ m/z 238.1 ($MH^+$), calcd. 238.2; TLC (MeOH/$CH_2Cl_2$, 1:5): $R_f$=0.69; RP-HPLC (Vydac 218TP54, 1 mL/min, 20-50% MeCN in 0.1% aq $CF_3COOH$ over 25 min): $t_R$=5.2 min. $^1$H-NMR ($d_6$-DMSO, 250 MHz) δ. 8.20 (1H, d, J=8.8 Hz, NH), 7.20-7.39 (5H, m, ArH), 5.88 (1H, d, J=4.6 Hz, OH), 5.09 (1H, m, $C^\beta H$), 4.54 (1H, dd, J=3,7 8.8 Hz, $C^\alpha H$), 3.61 (3H, s, $CO_2CH_3$), 1.76 (3H, s, $NHCOCH_3$).

Ac-L-threo-Pse-OH

To a suspension of Ac-DL-threo-Pse-OMe (100 mg, 0.42 mmol) in 0.05 M aq potassium phosphate buffer (14 mL) was added α-chymotrypsin (10 mg, 400 units). The pH was maintained at its initial value (pH 7-8) by the manual addition of 0.5 M phosphate buffer. The mixture was stirred vigorously overnight. It was extracted with EtOAc (3×50 mL) to remove Ac-D-threo-Pse-OMe. The aqueous phase was separated, acidified to pH 2 with 2 M aq HCl and extracted into EtOAc (3×100 mL). The organic extract was washed with brine, dried ($MgSO_4$), and evaporated to dryness in vacuo to afford a colourless oil (25 mg, 53%). The title compound was obtained as a white solid after lyophilisation from $H_2O$. M.p. 160-163; $[α]_D^{26}$+25.1° (c=1.0, AcOH); ES-MS$^+$ m/z 224.1 ($MH^+$), calcd. 224.2; RP-HPLC (Vydac 218TP54, 1 mL/min, 20-60% MeCN in 0.1% aq $CF_3COOH$ over 25 min): $t_R$=3.6 min; $^1$H-NMR ($d_6$-DMSO, 250 MHz) δ. 7.99 (1H, D, J=9.1 Hz, NH), 7.18-7.39 (5H, m, ArH), 5.14 (1H, d, J=3.0 Hz, $C^\beta H$), 4.48 (1H, dd, J=3.0, 9.1 Hz, $C^\alpha H$), 1.74 (3H, s, $CH_3$).

Ac-D-threo-Pse-OMe

From the above reaction, the initial EtOAc extract (150 mL) was washed with aq $NaHCO_3$ (2×50 mL) and brine (2×50 mL), dried and evaporated to dryness in vacuo to afford the title compound as a white solid (48 mg, 96%). RP-HPLC (Vydac 218TP54, 1 mL/min, 20-60% MeCN in 0.1% aq $CF_3COOH$ over 25 min): $t_R$=5.2 min).

Fmoc-L-threo-Pse-OH

A solution of Ac-L-threo-Pse-OH (40 mg, 0.18 mmol) in 6 M aqueous HCl (5 mL) was refluxed at 100° C. for 5 h. The solution was allowed to attain room temperature and the solvent was removed in vacuo. The residue was then dissolved in $H_2O$ and lyophilised to afford H-L-threo-Pse-OH.HCl as a white foam. To this was added a solution of 5% aq $Na_2CO_3$ (0.5 mL, 0.22 mmol). Effervescence occurred, and the solution was adjusted to pH 9 using a further equivalent of 5% aq $Na_2CO_3$ (0.5 mL). A solution of Fmoc-ONSu (60 mg, 0.18 mmol) in THF (1 mL) was then added over a period of 10 min. The mixture was stirred vigorously at room temperature for a further 5 h. The solvent was evaporated in vacuo, and the resulting white solid was dissolved in $H_2O$ (100 mL) and washed with diethyl ether (2×50 ml). The aqueous extract was acidified to pH 2 with 2 M aq HCl and a precipitate was obtained, which was extracted into EtOAc (3×60 ml). The organic extract was washed with aq $KHSO_4$ (100 mL) and brine (100 mL), dried ($MgSO_4$) and concentrated in vacuo to afford a crude product as a yellow oil (84 mg, quantitative). This was dissolved in the minimum volume of EtOAc and dripped into vigorously stirred hexane (120 mL) to afford, after filtration and drying, the title compound (47 mg, 65%) as a white crystalline solid. M.p. 127-129° C.;

[α]$_D^{22}$+27.9° (c=1.0, MeOH); ES-MS$^+$ m/z 404.3 (MH$^+$), calcd. 404.4; TLC (EtOAc/AcOH, 99:1); R$_f$=0.27; RP-HPLC (Vydac 218TP54, 1 mL/min, 50-100% MeCN in 0.1% aq CF$_3$COOH over 20 min): t$_R$ 7.2 min; $^1$H-NMR (d$_6$-DMSO, 250 MHz) δ. 7.88 (2H, d, J=7.5 Hz, Fmoc ArH), 7.67 (1H, d, J=7.2 Hz, Fmoc ArH), 7.63 (1H, d, J=7.5 Hz, Fmoc ArH), 7.31-7.43 (9H, m, ArH), 5.80 (1H, br. s, OH), 5.16 (1H, d, J=3.3 Hz, C$^β$H), 4.29 (1H, dd, J=3.3, 9.4 Hz, C$^α$H), 4.01-4.16 (3H, m, Fmoc CH, CH$_2$). HR-MS (FAB) calcd. for C$_{24}$H$_{22}$NO$_5$ (MH$^+$): 404.149798. found: 404.149850.

Fmoc-D-threo-Pse-OH

A solution of Ac-D-threo-Pse-OMe (150 mg, 0.63 mmol) in 6 M aq HCl (10 mL) was refluxed at 100° C. for 5 h. The solution was allowed to attain room temperature and the solvent removed in vacuo. The residual material was dissolved in H$_2$O and lyophilised to afford H-D-threo-Pse-OH.HCl as a pale yellow solid, which was immediately carried forward to the next step. In a similar manner to that described for the preparation of Fmoc-L-threo-Pse-OH, the crude title product was obtained as a yellow oil (229 mg, 90%). The crude product was dissolved in the minimum volume of EtOAc and dripped into vigorously stirred hexane (120 mL) to afford the title compound (174 mg, 68% overall) as an off-white crystalline solid. M.p.: 127-129° C.; [α]$_D^{22}$ −29.0° (c=1.0, methanol); APcI-MS$^+$ m/z 404.0 (MH$^+$), calcd. 404.4; TLC (EtOAc/AcOH, 99:1); R$_f$=0.27; RP-HPLC (Vydac218TP54, 1 ml/min, 50-100% MeCN in 0.1% aq CF$_3$COOH over 20 min): t$_R$=7.2 min; $^1$H-NMR (d$_6$-DMSO, 250 MHz): δ. 7.88 (2H, d, J=7.2 Hz, Fmoc ArH), 7.68 (1H, d, J=7.2 Hz, Fmoc ArH), 7.63 (1H, d, J=7.5 Hz, Fmoc ArH), 7.22-7.41 (9H, m, ArH), 5.17 (1H, d, J=3.2 Hz, C$^β$H), 4.30 (1H, dd, J=3.3, 9.5 Hz, C$^α$H), 4.01-4.15 (3H, m, Fmoc CH, CH$_2$). HR-MS (FAB) calcd. for C$_{24}$H$_{22}$NO$_5$ (MH$^+$): 404.149798, found: 404.149722.

Addition of Fmoc-Protected Amino Acids to 5-[4-(4-tolyl(chloro)methyl)phenoxy]pentanoyl amino-methylated polystyrene 5-[4-(4-Tolyl(chloro)methyl)phenoxy]pentanoyl aminomethylated polystyrene (0.064 mmol, theoretical loading 0.64 mmol g$^{-1}$; Atkinson, G. E.; Fischer, P. M.; Chan, W. C. *J. Org. Chem.* 2000, 65, 5048-5056) and Fmoc-protected amino acid (0.192 mmol) were suspended in CH$_2$Cl$_2$ (2 mL). Following the addition of Pr$_2^i$NEt (0.128 mmol), the resultant mixture was stirred gently at room temperature for 24 h. The resin was filtered, washed successively with DMF, CH$_2$Cl$_2$ and MeOH, and dried in vacuo.

Addition of Fmoc-Amino Alcohols to 5-[4-(4-tolyl(chloro) methyl)-phenoxy]pentanoyl aminomethylated polystyrene To a mixture of 5-[4-(4-tolyl(chloro)methyl)phenoxy]pentanoyl aminomethylated polystyrene (0.06 mmol, theoretical loading 0.64 mmol g$^{-1}$;) and Fmoc-amino alcohol (0.19 mmol) in ClCH$_2$CH$_2$Cl (3 mL) and THF (1 mL) was added Pr$_2^i$NEt (0.10 mmol). The suspension was then gently agitated at room temperature for 48-72 h. The resin was filtered, washed successively with DMF, CH$_2$Cl$_2$ and MeOH, and dried in vacuo.

Synthesis of Peptides

Amino acyl or peptidyl resin (0.026 mmol) was placed in a reaction column, swollen in DMF for 18 h, and Fmoc-deprotected using 20% piperidine in DMF. The resin was then washed with DMF (10 min, 2.5 mL/min), and the sequence Boc-His(Trt)-Ala/Ser(Bu$^t$)-Lys(Boc)-Arg(Pbf)-Arg(Pbf)-Leu-Ile (SEQ ID NO. 252) was assembled using an automated PepSynthesizer 9050 (MilliGen). Sequential acylation reactions were carried out at ambient temperature for 2 h using appropriate Fmoc-protected amino acids [Fmoc-Ile-OH, 141 mg; Fmoc-Leu-OH, 141 mg; Fmoc-Arg(Pbf)-OH, 260 mg; Fmoc-Lys(Boc)-OH, 187 mg; Fmoc-Ala-OH, 125 mg; Fmoc-Ser(t-Bu)-OH, 153 mg, Fmoc-His(Trt)-OH, 248 mg; 0.40 mmol] and carboxyl-activated using TBTU (128 mg, 0.40 mmol), HOBt (31 mg, 0.20 mmol) and Pr$_2^i$NEt (1.31 mL, 10% in DMF). Repetitive Fmoc-deprotection was achieved using 20% piperidine in DMF (6 min, 2.5 mL/min). After the final Fmoc-deprotection, the terminal amine group was Boc-protected with di-tert-butyl dicarbonate (87 mg, 0.40 mmol). The assembled N-Boc-protected peptidyl-resin was filtered, washed successively with DMF, CH$_2$Cl$_2$ and MeOH, and dried in vacuo. The resin product was suspended in a mixture of Pr$_3^i$SiH (0.1 mL) and H$_2$O (0.4 mL), followed by the addition of CF$_3$COOH (4.5 mL). The reaction mixture was gently stirred at room temperature for 2 h. The suspension was filtered, washed with CF$_3$COOH (5 mL) and the filtrate evaporated to dryness in vacuo. The residual material was triturated with Et$_2$O (15 mL) to yield a white solid. The desired synthetic peptide was lyophilised from H$_2$O overnight, and purified by preparative RP-HPLC.

Dehydration Reaction of Peptides

The N-Boc-protected peptidyl-resin containing a C-terminal Pse residue (0.02 mmol) was swelled in CH$_2$Cl$_2$ (0.5 mL) and THF (0.5 mL) in a 2-necked round-bottomed flask for 1 h under N$_2$. The solution was cooled to −78° C., and Et$_3$N (84 μL, 0.60 mmol) followed by SOCl$_2$ (10 μL, 0.08 mmol) were carefully added to the resin suspension. The mixture was stirred at −78° C. for 3.5 h, after which a further quantity of SOCl$_2$ (10 μL, 0.08 mmol) was added, and the stirred mixture was gradually warmed to −10° C. over a period of 2.5 h. The mixture was then stirred at 5° C. overnight. The resin was filtered, washed successively with DMF, CH$_2$Cl$_2$ and MeOH, and dried in vacuo. The resin product was suspended in a mixture of ethyl methyl sulfide (0.1 mL), Pr$_3^i$SiH (0.1 mL) and H$_2$O (0.4 mL), followed by the addition of CF$_3$COOH (4.4 mL). The suspension was gently stirred at ambient temperature for 2 h. The suspension was filtered, washed with CF$_3$COOH (5 mL) and the filtrate evaporated to dryness in vacuo. The residual material was then triturated with Et$_2$O to yield a yellow solid, which was lyophilised from water (5-10 mL) overnight and purified by preparative RP-HPLC.

Psa-Containing Peptides

A portion of the corresponding Pse-containing peptidyl resin (50 mg, 0.015 mmol, theoretical loading 0.293 mmol/g) was suspended in DMF (1 mL) and treated with Ac$_2$O (14 μL, 0.15 mmol), Pr$_2^i$NEt (5 μL, 0.02 mmol) and 4-(N,N-dimethylamino)pyridine (0.18 mg, 0.0015 mmol). The mixture was gently stirred at room temperature for 24 h. The resin was filtered, washed successively with DMF, CH$_2$Cl$_2$ and MeOH, and dried in vacuo. The resin product (50 mg) upon acidolytic treatment gave the crude product. Pure peptides were obtained after purification by preparative RP-HPLC.

| Compound | SEQ ID No. | Formula | MS[a] $M_r$ | [M + H] | RP-HPLC[b] tg(min) | Purity (%) | Relative activity Kinase Inhibition[c] | Cyclin A Binding[d] |
|---|---|---|---|---|---|---|---|---|
| H-His-Ala-Lys-Arg-<u>Arg</u>-Leu-Ile-Phe-NH$_2$ | 36 | $C_{48}H_{82}N_{18}O_9$ | | | | | 1 | 1 |
| H-His-Ala-Lys-Arg-Arg-Leu-Ile L-Pse OH | 110 | $C_{48}H_{82}N_{18}O_9$ | 1055.9 | 1055.7 | 8.8 | 99 | <0.1 | 0.2 |
| H-His-Ala-Lys-Arg-Arg-Leu-Ile D-Pse OH | 111 | $C_{48}H_{82}N_{18}O_9$ | 1055.9 | 1056.0 | 6.8 | 99 | <0.1 | 0.1 |
| H-His-*Ser*-Lys-Arg-Arg-Leu-Ile L-Pse OH | 112 | $C_{48}H_{82}N_{18}O_{10}$ | 1071.3 | 1074.1 | 8.8 | 99 | <0.1 | <0.1 |
| H-His-*Ser*-Lys-Arg-Arg-Leu-Ile D-Pse OH | 113 | $C_{48}H_{82}N_{18}O_{10}$ | 1071.3 | 1073.0 | 6.8 | 99 | <0.1 | <0.1 |
| H-His-Ala-Lys-Arg-Arg-Leu-Ile L-Psa OH | 114 | $C_{50}H_{84}N_{18}O_{10}$ | 1097.3 | 1098.0 | 11.2 | 99 | 22 | n/d |
| H-His-Ala-Lys-Arg-Arg-Leu-Ile D-Psa OH | 115 | $C_{48}H_{84}N_{18}O_{10}$ | 1097.3 | 1098.0 | 8.4 | 99 | <0.1 | n/d |
| H-His-*Ser*-Lys-Arg-Arg-Leu-Ile L-Psa OH | 116 | $C_{50}H_{84}N_{18}O_{11}$ | 1113.3 | 1114.9 | 10.8 | 99 | <0.1 | n/d |
| H-His-*Ser*-Lys-Arg-Arg-Leu-Ile D-Psa OH | 117 | $C_{50}H_{84}N_{18}O_{11}$ | 1113.3 | 1114.4 | 8 | 99 | <0.1 | n/d |
| H-His-Ala-Lys-Arg-Arg-Leu-Ile *Dhp* OH | 118 | $C_{48}H_{80}N_{18}O_8$ | 1037.3 | 1038.4 | 8.8 | 99 | 3.3 | 0.2 |
| H-His-*Ser*-Lys-Arg-Arg-Leu-Ile *Dhp* OH | 119 | $C_{48}H_{80}N_{18}O_9$ | 1053.3 | 1054.6 | 8.8 | 99 | 0.4 | n/d |
| H-His-Ala-Lys-Arg-Arg-Leu-Ile *Pheol* | 120 | $C_{48}H_{83}N_{17}O_8$ | 1026.3 | 1026.2 | 8.4 | 99 | 0.6 | 1.0 |
| H-His-*Ser*-Lys-Arg-Arg-Leu-Ile *Pheol* | 121 | $C_{48}H_{83}N_{17}O_9$ | 1042.3 | 1041.6 | 8.4 | 95 | 0.2 | <0.1 |

[a] DE MALDI-TOF MS, +ve mode, α-cyano-4-hydroxycinnamic acid matrix, calibration on authentic H-His-Ala-Lys-Arg-Arg-Leu-Ile-Phe-NH$_2$ (SEQ ID No. 36)
[b] Vaydac 218TP54, 1 ml/min, 25° C.; 0-40%, MeCN in 0.1% aq TFA over 20 min, λ = 214 nm
[c] CDK2 / cyclin A kinase assay, pRb substrate, [ATP] = 100 μM
[d] Competitive cyclin A binding assay using immobilized biotinyl Ahx-His Ala-Lys-Arg-Arg Leu Ile Phe-NH$_2$ (SEQ ID No. 186)

As is clear from the results presented above, the Phe[159] residue represents a key determinant in the p21(152-159) pharmacophore: its truncation abolishes activity and certain well-defined substitutions lead to enhanced potency. For this reason, further constriction of the Phe aromatic side chain may lock it into a bio-active conformation and further potency gains may be expected. Such conformational definition can be introduced in many different ways, e.g. through further substitution at $C^\beta$ (as in Psa and Pse), introduction of unsaturation, particularly between $C^\alpha$ and $C^\beta$ (as in Dhp), or by tethering of the aromatic system to the peptide backbone ($C^\alpha$ and NH), as e.g. in Tic (refer structures below).

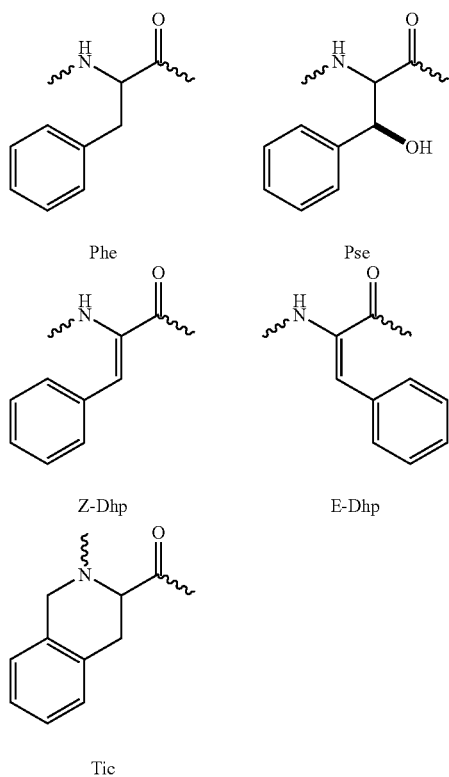

Conformational Constriction of Phenylalanine

The resolution of β-hydroxy-α-amino acids by the action of proteases on a range of N-acyl methyl esters has been described (Chênevert, R.; Létourneau, M.; Thiboutot, S. *Can. J. Chem.* 1990, 68, 960-963). Using a similar method, we resolved N-acetyl-DL-threo-phenylserine methyl ester into enantiomers of high optical purity by α-chymotrypsin-mediated enzymatic hydrolysis. Chymotrypsin is specific for the 2S-enantiomer that is typically found in natural amino acids. $N^\alpha$-Fmoc-L-threo-β-phenylserine and $N^\alpha$-Fmoc-D-threo-β-phenylserine were then synthesised from the resolved enantiomers. In principle the same transformations are applicable in the case of erythro-phenylserine (refer FIG. 3 for stereochemistry of Pse). The protected amino acids were immobilised for standard solid-phase peptide synthesis on a novel synthesis linker (Atkinson, G. E.; Fischer, P. M.; Chan, W. C. *J Org Chem.* 2000, 65, 5048-5056). It was found that the hydroxyl function in Pse did not require temporary protection under the reaction conditions applied (Fischer, P. M.; Retson, K. V.; Tyler, M. I.; Howden, M. E. H. *Intl. J. Peptide Protein Res.* 1991, 38, 491-493).

The peptides with a C-terminal Dhp residue were obtained directly from the corresponding Pse-containing peptides. Thus, protected peptidyl resins were treated with thionyl chloride and triethylamine (Stohlmeyer, M. M.; Tanaka, H.; Wandless, T. J. *J. Am. Chem. Soc.* 1999, 121, 6100-7101), which led to selective dehydration, via a cyclic sulphamidite intermediate, of the hydroxyethylene function in the Pse residue, thus furnishing upon release from the linker-resin the corresponding Dhp peptides. The nature of the reaction mechanism ensured that the intermediate cyclic sulphamidite formed from the threo-configuration of phenylserine, under basic conditions, eliminated $SO_2$ stereospecifically to yield the corresponding Z-Dhp isomer. Peptides H-His-Ser(Ala)-Lys-Arg-Arg-Leu-Ile-Dhp-OH (SEQ ID NO: 460) were typically obtained in >30% purity when analysed by RP-HPLC and purified yields of 20-30%. Conversely, E-Dhp peptides would be obtained by analogous dehydration of erythro-Pse peptides. Protected Pse peptidyl resins were acetylated selectively at the free hydroxyl of the Pse residue to afford the corresponding O-acetylphenylserine (Psa) peptides.

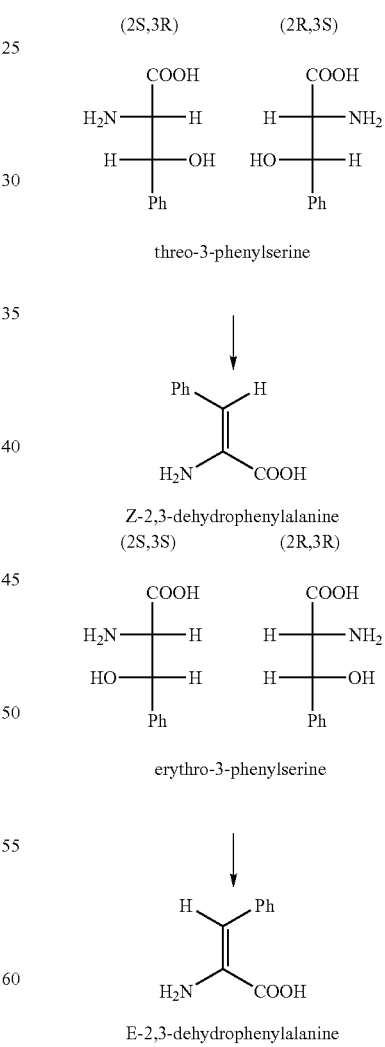

Stereochemistry of 3-phenylserine. The cis (Z) and trans (E) isomers of dehydrophenylalanine are derived from threo- and erythro-phenylserine, respectively, by dehydration.

As far as biological activity is concerned, only the L-Pse/Psa p21(152-159) peptides were able to inhibit CDK2/cyclin A and/or to bind efficiently to cyclin A. Of these, H-His-Ala-Lys-Arg-Arg-Leu-Ile-[L-Psa]-OH (SEQ ID No. 114) was particularly potent. Both Z-Dhp peptides were biologically active; the Ala[153] analogue being more potent then the corresponding Ser[153] peptide. Furthermore, the terminal Phe residue in the p21(152-159) peptides was also replaced with phenylalaninol (Pheol). This substitution was comparatively well-tolerated, showing that the terminal peptide carboxamide (or carboxylate) is not essential in terms of biological activity.

mitted introduction of e.g. Lys154Abu, Arg155Gln, Arg156Cit, Arg156Ser, and Ile158Ala.

Example 22

Multiple Substitutions in p21(152-159)Ser153Ala,Phe159pFPhe

| Compound | SEQ ID No. | Formula | MS[a] $M_r$ | [M + H] | RP-HPLC[b] tg(min) | Purity (%) | Kinase Inhibition[c] | Relative activity Cyclin A Binding[d] |
|---|---|---|---|---|---|---|---|---|
| H-His-Ala-Lys-Arg-Arg-Leu-Ile-Phe-NH$_2$ | 36 | $C_{48}H_{82}N_{18}O_8$ | | | | | 1 | 1 |
| H-*Ala*-*Ala*-*Abu*-Arg Arg Leu Ile-*pFPhe*-NH$_2$ | 122 | $C_{47}H_{74}N_{15}O_8F$ | 948.15 | 948.16 | 18.88 | 99 | 60 | n/d |
| H-*Ala*-*Ala*-Lys-Arg Arg Leu Ile-*pFPhe*-NH$_2$ | 123 | $C_{42}H_{72}N_{13}O_9$ | 922.11 | 922.11 | 1782 | 99 | 80 | n/d |
| H-*Ala*-*Ala*-Lys-Arg *Cit*-Leu Ile-*pFPhe*-NH$_2$ | 124 | $C_{40}H_{73}N_{16}O_9F$ | 992.2 | 922.2 | 16.94 | 99 | 10 | n/d |
| H-*Ala*-*Ala*-Lys-Arg Arg Leu-*Ala*-*pFPhe*-NH$_2$ | 125 | $C_{42}H_{73}N_{16}O_8F$ | 949.14 | 949.69 | 17.89 | 99 | 20 | n/d |
| H-*Ala*-*Ala*-*Abu*-Arg Ser Leu Ile-*pFPhe*-NH$_2$ | 126 | $C_{40}H_{67}N_{12}O_9F$ | 879.04 | 879.05 | 16.56 | 99 | 14 | n/d |
| H-*Ala*-*Ala*-Lys-*Gln*-Arg-Leu Ile-*pFPhe*-NH$_2$ | 127 | $C_{44}H_{75}N_{14}O_9F$ | 963.16 | 963.17 | 20.16 | 99 | 4 | n/d |
| H-Ala-Lys-Arg-Arg-Leu Ile-*pFPhe*-NH$_2$ | 253 | $C_{42}H_{75}N_{15}O_7F$ | 902.15 | 920.14 | 16.6 | 99 | 4 | n/d |

[a]DE MALDI-TOF MS, =ve mode, α-cayno-4-hydroxycinnamic acid matric, calibration on authentic H-His-Ala-Lys-Arg-Arg-Leu-Ile-Phe-NH$_2$ (SEQ ID No. 36)
[b]Vaydac 218TP54, 1 ml/min, 25° C.; 0-40%, MeCN in 0.1% aq TFA over 20 min, λ = 214 nm
[c]CDK2 / cyclin A kinase assay, pRb substrate, [ATP] = 100 μM
[d]Competitive cyclin A binding assay using immobilized biotinyl Ahx-His Ala-Lys-Arg-Arg Leu Ile Phe-NH$_2$ (SEQ ID No. 186)

Example 22

Multiple Substitutions in p21(152-159)Ser153Ala,Phe159pFPhe

It was seen above that certain residue substitution in the p21(152-159) peptides were in fact tolerated, and, in some cases, led to increased potency. Some of these single substitutions were then combined in order to test if combinatorial modifications at various positions in the peptide would be additive and/or synergistic. The results suggest that some synergysm is obtained. E.g., combination of His152Ala and Phe159pFPhe replacements yielded a peptide analogue with about 80-fold increased potency, whereas the same substitutions individually lead to 2.5- and 5-fold potency increase (in terms of cyclin A binding) only. Thus, combination of the His152Ala, Ser153Ala, and Phe159pFPhe modifications per-

Example 23

Cyclic Peptides

Inspection of the appropriate contacts in the complex structure of cyclin A with a p27[KIP1] fragment (Russo, A. A.; Jeffrey, P. D.; Patten, A. K.; Massague, J.; Pavletich, N. P. *Nature* 1996, 382, 325-31).; suggested a starting point for the design of such conformationally constrained peptides. Asn[31] of the p27 sequence apparently participates in H-bonds not only to the cyclin groove, but also in intra-molecular H-bonding to Gly[34]. It was therefore plausible that peptide analogues containing macrocyclic constraints approximating this situation may be bio-active. One such cyclic peptide, in which Asn was replaced with Lys and an amide bond patched between its E-amino group and the carboxyl group of Gly, was designed and modelled (FIG. 3).

While molecular modeling suggested that this approach may work, the question remained whether a synthetic peptide containing the same constraint would indeed be bio-active. For this reason a convenient synthetic route based on an alkanesulfonamide safety-catch linker (Backes, B. J.; Ellman, J. A. *J. Org. Chem.* 1999, 64, 2322-2330) was developed for the synthesis of the desired 'side chain-to-tail' cyclic peptides as set out below;

Synthesis of cyclic peptides

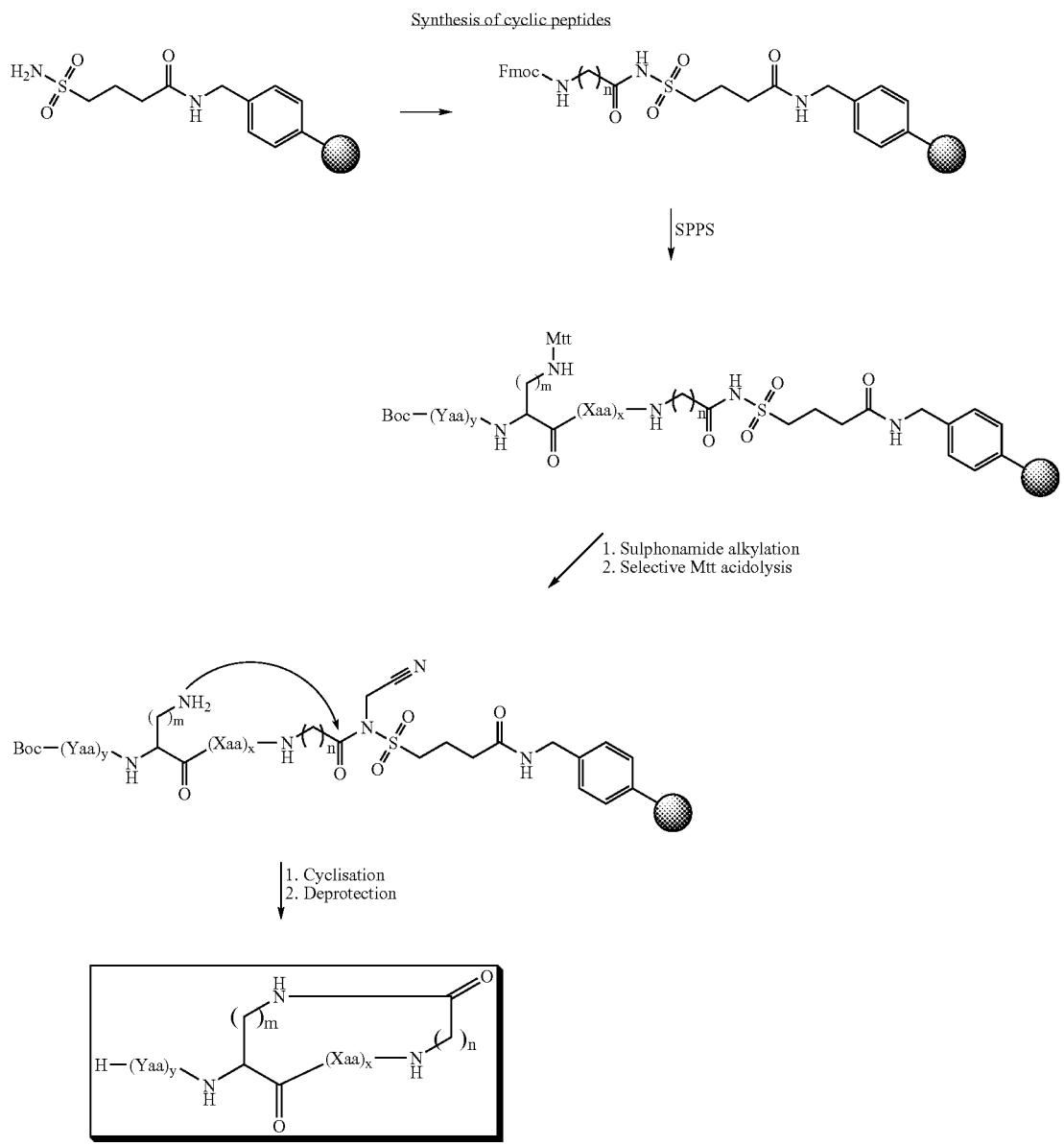

In this method, the immobilised alkanesulfonamide linker is acylated with the desired Fmoc-amino acid, peptide chain assembly is then continued using standard solid-phase peptide synthesis methods. The diamino acid residue which is to participate in the prospective cyclic lactam bond is introduced in an orthogonally protected form, e.g. using an Fmoc-di-amino acid derivative bearing a side-chain Mtt amino protecting group. After complete chain assembly, the sulfonamide linker is activated through alkylation with iodoacetonitrile. The Mtt protecting group is then removed under mild acidolytic conditions. Intramolecular attack of the liberated amino group on the activated acyl sulfonamide function then results in liberation of the protected cyclic peptide from the solid phase. It is isolated, fully deprotected using strong acidolysis, and purified. A similar approach has recently been reported for the synthesis of 'head-to-tail' cyclic peptides (Zhang, Z.; Van Aerschot, A.; Hendrix, C.; Busson, R.; David, F.; Sandra, P.; Herdewijn, P. Tetrahedron 2000, 56, 2513-2522). 'Side chain-to-tail' cyclic peptides can be obtained through various known methods, using either solid phase—(refer, e.g., Mihara, H.; Yamabe, S.; Niidome, T.; Aoyagi, H. Tetrahedron Lett. 1995, 36, 4837-4840) or solution methods (refer, e.g., He, J. X.; Cody, W. L.; Doherty, A. M. Lett.Peptide Sci. 1994, 1, 25-30)

Using the above method, the peptides 5,8-cyclo-[H-His-Ala-Lys-Arg-Lys-Leu-Phe-Gly] (SEQ ID NO. 173) and 5,8-cyclo-[H-His-Ala-Lys-Arg-Orn-Leu-Phe-Gly] (SEQ. ID NO. 174) were then synthesised and characterised. The results clearly show that the cyclic constraint introduced is relevant to the peptide's bioactive conformation. Whereas the analogue containing Lys in position 5 was approximately 2 orders of magnitude less potent than the lead peptide H-His-Ala-Lys-Arg-Arg-Leu-Ile-Phe-NH$_2$, (SEQ ID NO. 36) the corresponding Orn analogue was nearly equipotent with the lead peptide.

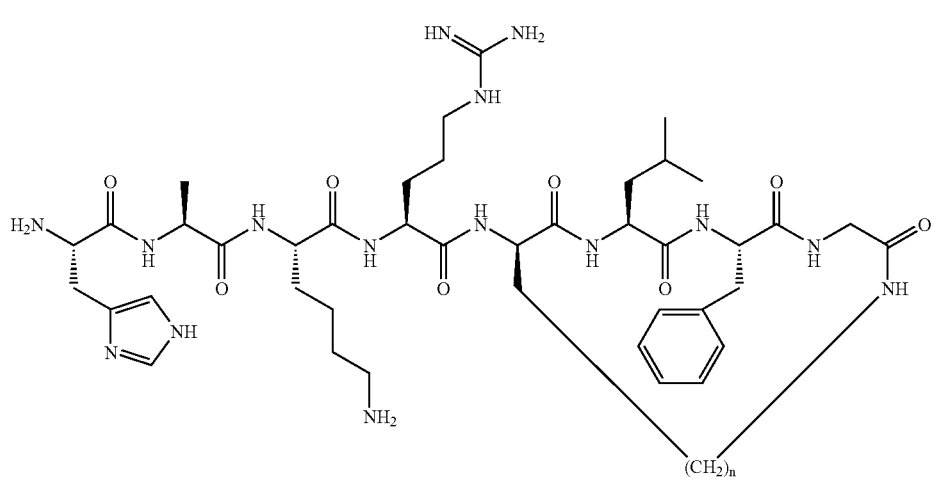

5,8-cyclo-[H-His-Ala-Lys-Arg-Lys-Leu-Phe-Gly] (1, n=3) (SEQ ID NO. 173)

Fmoc-Gly-OH (0.64 g, 2.16 mmol) and 4-sulfamylbutyryl aminomethylpolystyrene resin (Novabiochem; 0.50 g, nominally 0.54 mmol) were suspended in DMF (4.25 mL), and $Pr^i_2NEt$ (0.56 mL, 3.24 mmol) was added. The mixture was stirred for 20 min. After this time, it was cooled to −23° C., and PyBOP (1.13 g, 2.16 mmol) was added in one portion. Stirring was continued overnight, and the reaction was allowed to warm to room temperature during that period. The resin was then washed thoroughly with DMF, drained, and treated with 50% acetic anhydride in $CH_2Cl_2$ (10 mL) for 1 h. After completion, the resin was washed successively with $CH_2Cl_2$, DMF, and $Et_2O$, and was dried. The linear peptide sequence Boc-His(Boc)-Ala-Lys(Boc)-Arg(Pmc)-Lys(Mtt)-Leu-Phe-Gly (SEQ ID NO. 254) was then assembled using an ABI 433A peptide synthesiser, employing standard Fmoc protection strategy chemistry. The final peptidyl resin was washed successively with $CH_2Cl_2$, DMF, and $Et_2O$, and was dried. An aliquot (0.49 g) was swelled in NMP (4 mL) and treated with iodoacetonitrile (0.37 mL, 5.0 mmol) and $Pr^i_2NEt$ (0.24 mL, 1.25 mmol) under $N_2$, for 24 h. After this time, the resin was washed thoroughly with NMP (4×5 min), DMF, $CH_2Cl_2$, and $Et_2O$, before drying. The $Lys^5$ Mtt side-chain protecting group was then removed by treatment with 1.5% $CF_3COOH$, 3% MeOH in 1,2-dichloroethane (3×5 mL, 5 min each), and the resin was then washed with further 1,2-dichloroethane, followed by 20% $Pr^i_2NEt$ in $CH_2Cl_2$ and $Et_2O$. The resin was then dried in vacuo.

The activated and $Lys^5$ side chain-deprotected peptidyl resin (100 mg) was swelled in 1,4-dioxane (2 mL; dried over sodium-benzophenone), and dimethylaminopyridine (10 mg) was added. The mixture was then heated at reflux for 14 h, followed by filtering of the resin, and washing with DMF (2×5 mL, 5 min). The combined filtrate and washings were evaporated, and the residue was treated with 2.5% $Pr_3^iSiH$ in $CF_3COOH$ solution for 1 h. The peptide product was collected by precipitation in ice-cold $Et_2O$, and after washing was dried and fractionated by preparative RP-HPLC (Vydac 218TP1022, 9 mL/min, 13-23% MeCN in 0.1% aq $CF_3COOH$ over 60 min). Fractions containing pure cyclised peptide were pooled and lyophilised to afford title compound (2.2 mg, 2.34 μmol, 6.5% w.r.t. initial resin loading). Anal. RP-HPLC: $t_R$=15.4 min (Vydac 218TP54, 1 mL/min, 25° C., 13-23% MeCN in 0.1% aq $CF_3COOH$ over 20 min), purity>99% ($\lambda$=214 nm). DE MALDI-TOF MS: $[M+H]^+$=937.8, $C_{44}H_{71}N_{15}O_8$ requires 938.14 (positive mode, α-cyano-4-hydroxycinnamic acid matrix. The presence of the 5,8-cyclic structure was verified by inspection of appropriate through-space connectivities in the NMR ROESY spectrum of the peptide.

5,8-cyclo-[H-His-Ala-Lys-Arg-Orn-Leu-Phe-Gly] (1, n=2) (SEQ ID NO. 174)

This compound was prepared in a manner analogous to that described above except that residue position 5 was Orn (Fmoc-Orn(Mtt)-OH was used during chain assembly). A portion of the resin (200 mg) was then treated as above, to give the pure title compound (6.3 mg, 6.81 μmol, 8.9% w.r.t. initial resin loading). Anal. RP-HPLC: $t_R$=14.09 min (Vydac 218TP54, 1 mL/min, 25° C., 15-25% MeCN in 0.1% aq $CF_3COOH$ over 20 min), purity>99% ($\lambda$=214 nm). DE MALDI-TOF MS: $[M+H]^+$=926.4, $C_{43}H_{69}N_{15}O_8$ requires 924.11 (positive mode, α-cyano-4-hydroxycinnamic acid matrix. The presence of the 5,8-cyclic structure was verified by inspection of appropriate through-space connectivities in the NMR ROESY spectrum of the peptide.

| Compound | SEQ ID No. | [Cyclin A] (μg/mL) | Immobilised Ligand[a] | $IC_{50}$ (μM) | Relative Activity |
|---|---|---|---|---|---|
| H-His-Ala-Lys-Arg-Arg-Leu-Ile-Phe-$NH_2$ | 36 | 5 | HAKRRLIF | .03 ± .01 | 1 |
| 5,8-cyclo-[H-His-Ala-Lys-Arg-Lys-Leu-Phe-Gly] | 173 | 5 | HAKRRLIF | 11.1 ± 0.7 | 0.03 |

-continued

| Compound | SEQ ID No. | [Cyclin A] (μg/mL) | Immobilised Ligand[a] | IC$_{50}$] (μM) | Relative Activity |
|---|---|---|---|---|---|
| 5,8-cyclo-[H-His-Ala-Lys-Arg-Orn-Leu-Phe-Gly] | 174 | 5 | HAKRRLIF | 0.7 ± 0.5 | 0.5 |
| H-His-Ala-Lys-Arg-Arg-Leu-Ile-Phe-NH$_2$ | 36 | 10 | HAKRRLIF | 0.1 ± 0.05 | 1 |
| 5,8-cyclo-[H-His-Ala-Lys-Arg-Lys-Leu-Phe-Gly] | 173 | 10 | HAKRRLIF | 16 ± 5 | 0.06 |
| 5,8-cyclo-[H-His-Ala-Lys-Arg-Orn-Leu-Phe-Gly] | 174 | 10 | HAKRRLIF | 0.4 ± 0.2 | 0.25 |
| H-His-Ala-Lys-Arg-Arg-Leu-Ile-Phe-NH$_2$ | 36 | 5 | DFYHSKRRLIFS | 0.09 ± 0.02 | 1 |
| 5,8-cyclo-[H-His-Ala-Lys-Arg-Lys-Leu-Phe-Gly] | 173 | 5 | DFYHSKRRLIFS | 8 ± 1 | 0.01 |
| 5,8-cyclo-[H-His-Ala-Lys-Arg-Orn-Leu-Phe-Gly] | 174 | 5 | DFYHSKRRLIFS | 0.3 ± 0.2 | 0.3 |
| H-His-Ala-Lys-Arg-Arg-Leu-Ile-Phe-NH$_2$ | 36 | 10 | DFYHSKRRLIFS | 1.8 ± 0.9 | 1 |
| 5,8-cyclo-[H-His-Ala-Lys-Arg-Lys-Leu-Phe-Gly] | 173 | 10 | DFYHSKRRLIFS | 22 ± 8 | 0.08 |
| 5,8-cyclo-[H-His-Ala-Lys-Arg-Orn-Leu-Phe-Gly] | 174 | 10 | DFYHSKRRLIFS | 6 ± 7 | 0.3 |

[a]Immobilised ligands HAKRRLIF (SEQ ID No. 42); DFYHSKRRLIFS (SEQ ID No. 13)

Example 24

Further Truncated Peptides

The following truncated peptides were prepared and screened for competitive cyclin A binding in accordance with the methods described above. The results demonstrate that N-terminally truncated analogues of the 8 mer p21-derived peptide H-His-Ala-Lys-Arg-Arg-Leu-Ile-Phe-NH$_2$ (SEQ ID NO. 36), and, to a lesser extent, the p27-derived peptide H-Ser-Ala-Abu-Arg-Arg-Asn-Leu-Phe-Gly-NH$_2$ (SEQ ID NO. 461), retain appreciable cyclin A binding capacity at least down to the C-terminal 4 mer sequences.

Example 24

Further Truncated Peptides

| Compound | SEQ ID No. | Formula | M$_r$ | MS[a] [M + H] | RP-HPLC[b] T$_R$ (min) | Purity (%) | Cyclin A Binding[c] IC$_{50}$ (μM) | Maximum Inhibition (%) |
|---|---|---|---|---|---|---|---|---|
| H-Arg-Leu-Ile-Phe-NH$_2$ | 32 | C$_{27}$H$_{46}$N$_8$O$_4$ | 546.71 | 548.6 | 15.01[iii] | 99 | — | 50 (at 100 μM) |
| H-Arg-Arg-Leu-Ile-Phe-NH$_2$ | 33 | C$_{33}$H$_{58}$N$_{12}$O$_5$ | 702.9 | 704.7 | 13.35[iii] | 99 | 5 | 100 |
| H-Lys-Arg-Arg-Leu-Ile-Phe-NH$_2$ | 34 | C$_{39}$H$_{70}$N$_{14}$O$_6$ | 831.07 | 832.8 | 12.63[iii] | 99 | 5 | 100 |
| H-Ala-Lys-Arg-Arg-Leu-Ile-Phe-NH$_2$ | 35 | C$_{42}$H$_{75}$N$_{15}$O$_7$ | 902.15 | 903.9 | 12.82[iii] | 99 | 2 | 100 |
| H-His-Ala-Lys-Arg-Arg-Leu-Ile-Phe-NH$_2$ | 36 | C$_{48}$H$_{82}$N$_{18}$O$_8$ | 1039.3 | 1040.4 | 12.91[iii] | 99 | 0.3 | 100 |
| H-Asn-Leu-Phe-Gly-NH$_2$ | 37 | C$_{21}$H$_{32}$N$_6$O$_5$ | 448.52 | 449.6 | 18.14[i] | 99 | — | 80 (at 100 μM) |
| H-Arg-Asn-Leu-Phe-Gly-NH$_2$ | 38 | C$_{27}$H$_{44}$N$_{10}$O$_6$ | 604.71 | 605.2 | 17.17[i] | 99 | — | 20 (at 100 μM) |

-continued

| Compound | SEQ ID No. | Formula | $M_r$ | MS[a] [M + H] | RP-HPLC[b] $T_R$(min) | Purity (%) | Cyclin A Binding[c] IC$_{50}$ (μM) | Maximum Inhibition (%) |
|---|---|---|---|---|---|---|---|---|
| H-Abu-Arg-Asn-Leu-Phe-Gly-NH$_2$ | 39 | $C_{31}H_{51}N_{11}O_7$ | 689.81 | 690.9 | 12.87[ii] | 99 | — | — |
| H-Ala-Abu-Arg-Asn-Leu-Phe-Gly-NH$_2$ | 40 | $C_{34}H_{56}N_{12}O_6$ | 760.89 | 761.4 | 13.61[ii] | 99 | 25 | 90 |
| H-Ser-Ala-Abu-Arg-Asn-Leu-Phe-Gly-NH$_2$ | 41 | $C_{37}H_{61}N_{13}O_{10}$ | 847.97 | 849.1 | 14.90[ii] | 99 | 15 | 100 |

[a]DE MALDI-TOF MS, +ve mode. α-cyano-4-hydroxycinnamic acid matrix, calibration on authentic H-His-Ala-Lys-Arg-Arg-Leu-Ile-Phe-NH$_2$ (Seq. ID No. 36)
[b]Vydac218TP54. 1 mL/min, 25 °C., 0-40% MeCN gradient in 0.1% sq TFA over 20 min. λ = 214 nm; [i]20-30%, [ii]23-33%, [iii]25-35%
[c]CDK2 / cyclin A kinase assay, pRb substrate, [ATP] = 100 μM
[d]Competitive cyclin A binding assay using immobilised biotinyl-Ahx-His-Ala-Lys-Arg-Arg-Leu-Ile-Phe-NH$_2$ (Seq. ID No. 186)

Example 25

Peptide Analogues of H-Ala-Ala-Lys-Arg-Arg-Leu-Ile-pFPhe-NH$_2$ (SEQ ID NO. 123)

| Compound | | | | SEQ ID No. | Formula | $M_r$ | MS[a] [M + H]$^+$ | RP-HPLC[b] tg(min) | Purity (%) |
|---|---|---|---|---|---|---|---|---|---|
| H-Ala-Ala-Lys-Arg-Arg-Leu- | Ile- | pFPhe | -NH$_2$ | 123 | $C_{45}H_{79}FN_{16}O_8$ | 991.2 | 991.1 | 12.45 | 90 |
| H-Gly-Ala-Lys-Arg-Arg-Leu- | Ile- | pFPhe | -NH$_2$ | 129 | $C_{44}H_{77}FN_{16}O_8$ | 977.2 | 976.4 | 15.9 | 94 |
| H-Ala-Ala-Lys-hArg-Arg-Leu- | Ile- | pFPhe | -NH$_2$ | 130 | $C_{46}H_{81}FN_{16}O_8$ | 1005.3 | 1004.1 | 12.47 | 85 |
| H-Ala-Ala-Lys-Ser-Arg-Leu- | Ile- | pFPhe | -NH$_2$ | 131 | $C_{42}H_{72}FN_{13}O_9$ | 922.1 | 921.0 | 12.64 | 87 |
| H-Ala-Ala-Lys-Hse-Arg-Leu- | Ile- | pFPhe | -NH$_2$ | 132 | $C_{43}H_{74}FN_{13}O_9$ | 936.1 | 935.5 | 12.68 | 87 |
| H-Ala-Ala-Lys-Arg-Lys-Leu- | Ile- | pFPhe | -NH$_2$ | 133 | $C_{45}H_{79}FN_{14}O_8$ | 963.2 | 962.3 | 12.24 | 90 |
| H-Ala-Ala-Lys-Arg-Orn-Leu- | Ile- | pFPhe | -NH$_2$ | 134 | $C_{44}H_{77}FN_{14}O_8$ | 949.2 | 948.3 | 12.35 | 95 |
| H-Ala-Ala-Lys-Arg-Gln-Leu- | Ile- | pFPhe | -NH$_2$ | 135 | $C_{44}H_{75}FN_{14}O_9$ | 963.2 | 962.6 | 12.58 | 93 |
| H-Ala-Ala-Lys-Arg-Hse-Leu- | Ile- | pFPhe | -NH$_2$ | 136 | $C_{43}H_{74}FN_{13}O_9$ | 936.1 | 934.9 | 12.83 | 90 |
| H-Ala-Ala-Lys-Arg-Thr-Leu- | Ile- | pFPhe | -NH$_2$ | 137 | $C_{43}H_{74}FN_{13}O_9$ | 936.1 | 934.8 | 12.88 | 92 |
| H-Ala-Ala-Lys-Arg-Nva-Leu- | Ile- | pFPhe | -NH$_2$ | 138 | $C_{44}H_{76}FN_{13}O_8$ | 934.2 | 932.6 | 13.74 | 93 |
| H-Ala-Ala-Lys-Arg-Arg-Phg- | Ile- | pFPhe | -NH$_2$ | 139 | $C_{47}H_{75}FN_{16}O_8$ | 934.2 | 1009.8 | 11.42 | 90 |
| H-Ala-Ala-Lys-Arg-Arg-Met- | Ile- | pFPhe | -NH$_2$ | 140 | $C_{44}H_{77}FN_{16}O_8$ | 1011.2 | 1009.2 | 12.04 | 80 |
| H-Ala-Ala-Lys-Arg-Arg-Ala- | Ile- | pFPhe | -NH$_2$ | 141 | $C_{42}H_{73}FN_{16}O_8$ | 1009.3 | 948.1 | 11.43 | 82 |
| H-Ala-Ala-Lys-Arg-Arg-Hof- | Ile- | pFPhe | -NH$_2$ | 142 | $C_{49}H_{79}FN_{16}O_8$ | 949.1 | 1038.0 | 13.37 | 88 |
| H-Ala-Ala-Lys-Arg-Arg-Leu- | Ile- | pFPhe | -NH$_2$ | 123 | $C_{46}H_{81}FN_{16}O_8$ | 1039.3 | 1003.1 | 13.2 | 86 |
| H-Ala-Ala-Lys-Arg-Arg-alIe- | Ile- | pFPhe | -NH$_2$ | 144 | $C_{45}H_{79}FN_{16}O_8$ | 1005.3 | 989.5 | 12.32 | 75 |
| H-Ala-Ala-Lys-Arg-Arg-Leu- | Gly- | pFPhe | -NH$_2$ | 145 | $C_{41}H_{71}FN_{16}O_8$ | 991.2 | 934.6 | 11.25 | 84 |
| H-Ala-Ala-Lys-Arg-Arg-Leu- | βAla- | pFPhe | -NH$_2$ | 146 | $C_{42}H_{73}FN_{16}O_8$ | 935.1 | 947.9 | 14.3 | 94 |
| H-Ala-Ala-Lys-Arg-Arg-Leu- | Pgh- | pFPhe | -NH$_2$ | 147 | $C_{47}H_{75}FN_{16}O_8$ | 949.1 | 1009.7 | 12.8, 14.1 | 88 |

-continued

| Compound | | | SEQ ID No. | Formula | $M_r$ | MS[a] [M + H]+ | RP-HPLC[b] tg(min) | Purity (%) |
|---|---|---|---|---|---|---|---|---|
| H-Ala-Ala-Lys-Arg-Arg-Leu- | Aib- | pFPhe | -NH₂ | 148 | $C_{43}H_{75}FN_{16}O_8$ | 1011.2 | 961.7 | 15.7 | 95 |
| H-Ala-Ala-Lys-Arg-Arg-Leu- | Sar- | pFPhe | -NH₂ | 149 | $C_{42}H_{73}FN_{16}O_8$ | 963.2 | 947.8 | 11.4 | 87 |
| H-Ala-Ala-Lys-Arg-Arg-Leu- | Pro- | pFPhe | -NH₂ | 150 | $C_{44}H_{75}FN_{16}O_8$ | 949.1 | 973.8 | 11.9 | 90 |
| H-Ala-Ala-Lys-Arg-Arg-Leu- | Bug- | pFPhe | -NH₂ | 151 | $C_{45}H_{79}FN_{16}O_8$ | 975.2 | 990.2 | 15.6 | 90 |
| H-Ala-Ala-Lys-Arg-Arg-Leu- | Ser- | pFPhe | -NH₂ | 152 | $C_{42}H_{73}FN_{16}O_9$ | 965.1 | 964.4 | 14.1 | 85 |
| H-Ala-Ala-Lys-Arg-Arg-Leu- | Asp- | pFPhe | -NH₂ | 153 | $C_{43}H_{73}FN_{16}O_{10}$ | 993.2 | 992.4 | 14.2 | 95 |
| H-Ala-Ala-Lys-Arg-Arg-Leu- | Asn- | Phe | -NH₂ | 154 | $C_{43}H_{74}FN_{17}O_9$ | 992.2 | 990.5 | 13.8 | 94 |
| H-Ala-Ala-Lys-Arg-Arg-Leu- | pFPhe- | Phe | -NH₂ | 155 | $C_{48}H_{77}FN_{16}O_8$ | 1025.2 | 1024.1 | 16.8 | 94 |
| H-Ala-Ala-Lys-Arg-Arg-Leu- | diClPhe- | Phe | -NH₂ | 156 | $C_{48}H_{76}Cl_2N_{16}O_8$ | 1076.1 | 1074.9 | 18.9 | 92 |
| H-Ala-Ala-Lys-Arg-Arg-Leu- | pClPhe- | Phe | -NH₂ | 157 | $C_{48}H_{77}ClN_{16}O_8$ | 1041.7 | 1041.1 | 17.8 | 95 |
| H-Ala-Ala-Lys-Arg-Arg-Leu- | mClPhe- | Phe | -NH₂ | 158 | $C_{48}H_{77}ClN_{16}O_8$ | 1041.7 | 1058.1 | 17.9 | 95 |
| H-Ala-Ala-Lys-Arg-Arg-Leu- | oClPhe- | Phe | -NH₂ | 159 | $C_{48}H_{77}ClN_{16}O_8$ | 1041.7 | 1041.0 | 17.2 | 95 |
| H-Ala-Ala-Lys-Arg-Arg-Leu- | pIPhe- | Phe | -NH₂ | 160 | $C_{48}H_{77}IN_{16}O_8$ | 1133.1 | 1132.6 | 18.5 | 95 |
| H-Ala-Ala-Lys-Arg-Arg-Leu- | TyreMe- | Phe | -NH₂ | 161 | $C_{49}H_{89}N_{16}O_8$ | 1037.3 | 1036.7 | 16.4 | 91 |
| H-Ala-Ala-Lys-Arg-Arg-Leu- | Thi- | Phe | -NH₂ | 162 | $C_{46}H_{76}N_{16}O_8S$ | 1013.3 | 1012.7 | 16.1 | 95 |
| H-Ala-Ala-Lys-Arg-Arg-Leu- | Pya- | Phe | -NH₂ | 163 | $C_{47}H_{77}N_{17}O_8$ | 1008.2 | 1007.1 | 13.5 | 86 |
| H-Ala-Ala-Lys-Arg-Arg-Leu- | Ile- | diClPhe | -NH₂ | 164 | $C_{45}H_{78}Cl_2N_{16}O_8$ | 1042.1 | 1005.8 | 18.6 | 91 |
| H-Ala-Ala-Lys-Arg-Arg-Leu- | Ile- | pClPhe | -NH₂ | 165 | $C_{45}H_{79}ClN_{16}O_8$ | 1007.7 | 1004.2 | 17.3 | 88 |
| H-Ala-Ala-Lys-Arg-Arg-Leu- | Ile- | mClPhe | -NH₂ | 166 | $C_{45}H_{79}ClN_{16}O_8$ | 1007.7 | 1006.8 | 17.3 | 88 |
| H-Ala-Ala-Lys-Arg-Arg-Leu- | Ile- | oClPhe | -NH₂ | 167 | $C_{45}H_{79}ClN_{16}O_8$ | 1007.7 | 1007.0 | 16.5 | 84 |
| H-Ala-Ala-Lys-Arg-Arg-Leu- | Ile- | Phg | -NH₂ | 168 | $C_{44}H_{78}N_{16}O_8$ | 959.2 | 958.8 | 14.6, 15.8[c] | 95 |
| H-Ala-Ala-Lys-Arg-Arg-Leu- | Ile- | TyrMe | -NH₂ | 169 | $C_{46}H_{82}N_{16}O_9$ | 1003.3 | 1002.8 | 15.7 | 90 |
| H-Ala-Ala-Lys-Arg-Arg-Leu- | Ile- | Thi | -NH₂ | 170 | $C_{43}H_{78}N_{16}O_8S$ | 979.3 | 978.6 | 15.1 | 87 |
| H-Ala-Ala-Lya-Arg-Arg-Leu- | Ile- | Pya | -NH₂ | 171 | $C_{44}H_{79}N_{17}O_8$ | 974.2 | 973.7 | 11.5 | 90 |
| H-Ala-Ala-Lys-Arg-Arg-Leu- | Ile- | Inc | -NH₂ | 172 | $C_{45}H_{79}FN_{16}O_8$ | 971.2(878.99) | | 16.1 | 95 |

[a] DE MALDI-TOF MS, +ve mode, α-cyano-4-hydroxycinnamic acid matrix, calibration on authentic H-His-Ala-Lys-Arg-Arg-Leu-Ile-Phe-NH₂ (Seq. ID No. 36)
[b] Vydac 218TP54, 1 mL/min, 25° C., 0–40% MeCN in 0.1% aq TFA over 20 min
[c] Mixture of diastereomers (racemic Fmoc-Phg-OH used)

Example 26

Peptide Analogues of H-Ala-Ala-Lys-Arg-Arg-Leu-Phe-Gly-NH₂ (SEQ ID NO. 255)

| Compound | | SEQ ID No. | Formula | $M_r$ | MS[a] [M + H]+ | RP-HPLC[b] tg(min) | Purity (%) |
|---|---|---|---|---|---|---|---|
| H-Ala-Ala-Lys-Arg-Arg-Leu- | Phe-Gly-NH₂ | 255 | $C_{41}H_{72}N_{16}O_8$ | 917.1 | 916.1 | 13.7 | 94 |
| H-Ala-Ala-Lys-hArg-Arg-Leu- | Phe-Gly-NH₂ | 256 | $C_{42}H_{74}N_{16}O_8$ | 931.2 | 929.4 | 13.8 | 93 |

-continued

| Compound | | SEQ ID No. | Formula | $M_r$ | MS[a] [M + H]+ | RP-HPLC[b] tg(min) | Purity (%) |
|---|---|---|---|---|---|---|---|
| H-Ala-Ala-Lys-Ser-Arg-Leu- | Phe-Gly-$NH_2$ | 257 | $C_{38}H_{65}N_{13}O_9$ | 848.0 | 847.4 | 14.1 | 95 |
| H-Ala-Ala-Lys-Hse-Arg-Leu- | Phe-Gly-$NH_2$ | 258 | $C_{39}H_{67}N_{13}O_9$ | 862.0 | 861.1 | 13.9 | 90 |
| H-Ala-Ala-Lys-Arg-Lys-Leu- | Phe-Gly-$NH_2$ | 259 | $C_{41}H_{72}N_{14}O_8$ | 889.1 | 888.8 | 13.5 | 90 |
| H-Ala-Ala-Lys-Arg-Orn-Leu- | Phe-Gly-$NH_2$ | 260 | $C_{40}H_{70}N_{14}O_8$ | 875.1 | 874.6 | 13.5 | 95 |
| H-Ala-Ala-Lys-Arg-Gln-Leu- | Phe-Gly-$NH_2$ | 261 | $C_{40}H_{68}N_{14}O_9$ | 889.1 | 887.7 | 13.7 | 86 |
| H-Ala-Ala-Lys-Arg-Hse-Leu- | Phe-Gly-$NH_2$ | 262 | $C_{39}H_{67}N_{13}O_9$ | 862.0 | 861.3 | 13.9 | 88 |
| H-Ala-Ala-Lys-Arg-Thr-Leu- | Phe-Gly-$NH_2$ | 263 | $C_{39}H_{67}N_{13}O_9$ | 862.0 | 860.4 | 14.3 | 90 |
| H-Ala-Ala-Lys-Arg-Nva-Leu- | Phe-Gly-$NH_2$ | 264 | $C_{40}H_{69}N_{13}O_8$ | 860.1 | 858.7 | 15.6 | 85 |
| H-Ala-Ala-Lys-Arg-Arg-Met- | Phe-Gly-$NH_2$ | 265 | $C_{40}H_{70}N_{16}O_8 S$ | 935.2 | 934.1 | 10.9 | 93 |
| H-Ala-Ala-Lys-Arg-Arg-Ala- | Phe-Gly-$NH_2$ | 266 | $C_{38}H_{66}N_{16}O_8$ | 875.0 | 872.2 | 12.7 | 95 |
| H-Ala-Ala-Lys-Arg-Arg-Hof- | Phe-Gly-$NH_2$ | 267 | $C_{45}H_{72}N_{16}O_8$ | 965.2 | 962.9 | 15.1 | 81 |
| H-Ala-Ala-Lys-Arg-Arg-Hle- | Phe-Gly-$NH_2$ | 268 | $C_{42}H_{74}N_{16}O_8$ | 931.2 | 930.1 | 15.2 | 94 |
| H-Ala-Ala-Lys-Arg-Arg-alle- | Phe-Gly-$NH_2$ | 269 | $C_{41}H_{72}N_{16}O_8$ | 917.1 | 915.9 | 13.2 | 95 |
| H-Ala-Ala-Lys-Arg-Arg-Leu- | Tic-Gly-$NH_2$ | 270 | $C_{42}H_{72}N_{16}O_8$ | 929.1 | 928.3 | 13.7 | 93 |
| H-Ala-Ala-Lys-Arg-Arg-Leu- | Pgh-Gly-$NH_2$ | 271 | $C_{40}H_{70}N_{16}O_8$ | 903.1 | 902.0 | 12.3, 13.7[c] | 95 |
| H-Ala-Ala-Lys-Arg-Arg-Leu- | pFPhe-Gly-$NH_2$ | 272 | $C_{41}H_{71}FN_{16}O_8$ | 935.1 | 933.7 | 14.3 | 95 |
| H-Ala-Ala-Lys-Arg-Arg-Leu- | pIPhe-Gly-$NH_2$ | 273 | $C_{41}H_{71}IN_{16}O_8$ | 1043.0 | 1041.3 | 16.4 | 92 |
| H-Ala-Ala-Lys-Arg-Arg-Leu- | Thi-Gly-$NH_2$ | 274 | $C_{39}H_{70}N_{16}O_8S$ | 923.2 | 920.8 | 13.2 | 96 |
| H-Ala-Ala-Lys-Arg-Arg-Leu- | Pya-Gly-$NH_2$ | 275 | $C_{40}H_{71}N_{17}O_8$ | 918.1 | 915.1 | 9.3 | 90 |
| H-Ala-Ala-Lys-Arg-Arg-Leu- | diClPhe-Gly-$NH_2$ | 276 | $C_{41}H_{70}Cl_2N_{16}O_8$ | 986.0 | 984.2 | 17 | 95 |
| H-Ala-Ala-Lys-Arg-Arg-Leu- | pClPhe-Gly-$NH_2$ | 277 | $C_{41}H_{71}ClN_{16}O_8$ | 951.6 | 950.2 | 15.5 | 95 |
| H-Ala-Ala-Lys-Arg-Arg-Leu- | mClPhe-Gly-$NH_2$ | 278 | $C_{41}H_{71}ClN_{16}O_8$ | 951.6 | 949.8 | 15.5 | 95 |
| H-Ala-Ala-Lys-Arg-Arg-Leu- | oClPhe-Gly-$NH_2$ | 279 | $C_{41}H_{71}ClN_{16}O_8$ | 951.6 | 949.9 | 15 | 95 |
| H-Ala-Ala-Lys-Arg-Arg-Leu- | 1Nap-Gly-$NH_2$ | 280 | $C_{45}H_{74}N_{16}O_8$ | 967.2 | 965.7 | 16.3 | 95 |
| H-Ala-Ala-Lys-Arg-Arg-Leu- | 2Nap-Gly-$NH_2$ | 281 | $C_{45}H_{74}N_{16}O_8$ | 967.2 | 966.1 | 16.4 | 95 |
| H-Ala-Ala-Lys-Arg-Arg-Leu- | Inc-Gly-$NH_2$ | 282 | $C_{41}H_{70}N_{16}O_8$ | 915.1 | 917.8 | 14.36 | 90 |
| H-Ala-Ala-Lys-Arg-Arg-Leu- | Phe-Asp-$NH_2$ | 283 | $C_{43}H_{74}N_{16}O_{10}$ | 975.2 | 972.5 | 13.6 | 95 |
| H-Ala-Ala-Lys-Arg-Arg-Leu- | Phe-Glu-$NH_2$ | 284 | $C_{44}H_{76}N_{16}O_{10}$ | 989.2 | 987.5 | 13.3 | 93 |
| H-Ala-Ala-Lys-Arg-Arg-Leu- | Phe-Ser-$NH_2$ | 285 | $C_{42}H_{74}N_{16}O_9$ | 947.2 | 944.7 | 13.1 | 95 |
| H-Ala-Ala-Lys-Arg-Arg-Leu- | Phe-Asn-$NH_2$ | 286 | $C_{43}H_{75}N_{17}O_9$ | 974.2 | 972.6 | 13.3 | 95 |
| H-Ala-Ala-Lys-Arg-Arg-Leu- | Phe-Gln-$NH_2$ | 287 | $C_{44}H_{77}N_{17}O_9$ | 988.2 | 986.9 | 12.5 | 95 |
| H-Ala-Ala-Lys-Arg-Arg-Leu- | Phe-Lys-$NH_2$ | 288 | $C_{45}H_{81}N_{17}O_8$ | 988.2 | 987.0 | 13.6 | 95 |

[a] DE MALDI-TOF MS, +ve mode, α-cyan-4-hydroxycinnamic acid matrix, calibration on authentic H-Ala-Ala-Lys-Arg-Arg-Leu-Ile-Phe-$NH_2$ (Seq. ID No. 36)
[b] Vydac 218TP54, 1 mL/min, 25° C., 0-40% MeCN in 0.1% aq TFA over 20 min
[c] Mixture of diastereomers (racemic Fmoc-Pgh-OH used)

Example 27

Peptide Pentamers

| Sequence | SEQ ID No. | Binding IC$_{50}$ (μM) Cyclin A | Kinase IC$_{50}$ (μM) CyclinA/CDK2 |
|---|---|---|---|
| Ac- Arg Arg Leu Asn Phe NH$_2$ | 378 | 8.15 | 37.2 |
| Ac- Arg Arg Leu Asn pFF NH$_2$ | 379 | 1.25 | 3.35 |
| Ac- Arg Arg Leu Asn mClF NH$_2$ | 380 | 4.1 | 17.85 |
| Ac- Arg Arg Leu Ala Phe NH$_2$ | 381 | | |
| Ac- Arg Arg Leu Ala pFF NH$_2$ | 382 | 3.7 | 10.45 |
| Ac- Arg Arg Leu Ala mClF NH$_2$ | 383 | 10.125 | 19.4 |
| Ac- Arg Arg Leu Gly Phe NH$_2$ | 384 | | |
| Ac- Arg Arg Leu Gly pFF NH$_2$ | 385 | 11.8 | 23.25 |
| Ac- Arg Arg Leu Gly mClF NH$_2$ | 386 | 25.45 | 29.75 |
| Ac- Arg Arg Ile Asn Phe NH$_2$ | 387 | | |
| Ac- Arg Arg Ile Asn pFF NH$_2$ | 388 | 3.85 | 8.3 |
| Ac- Arg Arg Ile Asn mClF NH$_2$ | 389 | 17.15 | 59.5 |
| Ac- Arg Arg Ile Ala Phe NH$_2$ | 390 | | |
| Ac- Arg Arg Ile Ala pFF NH$_2$ | 391 | 7.75 | 40.35 |
| Ac- Arg Arg Ile Ala mClF NH$_2$ | 392 | 26.15 | >80 |
| Ac- Arg Arg Ile Gly Phe NH$_2$ | 393 | | |
| Ac- Arg Arg Ile Gly pFF NH$_2$ | 394 | | |
| Ac- Arg Arg Val Gly mClF NH$_2$ | 395 | | |
| Ac- Arg Arg Val Asn Phe NH$_2$ | 396 | | |
| Ac- Arg Arg Val Asn pFF NH$_2$ | 397 | | |
| Ac- Arg Arg Val Asn mClF NH$_2$ | 398 | | |
| Ac- Arg Arg Val Ala Phe NH$_2$ | 399 | | |
| Ac- Arg Arg Val Ala pFF NH$_2$ | 400 | | |
| Ac- Arg Arg Val Ala mClF NH$_2$ | 401 | | |
| Ac- Arg Arg Val Gly Phe NH$_2$ | 402 | | |
| Ac- Arg Arg Val Gly pFF NH$_2$ | 403 | | |
| Ac- Arg Arg Val Gly mClF NH$_2$ | 404 | >100 | >80 |
| Ac- Arg Ser Leu Asn Phe NH$_2$ | 405 | | |
| Ac- Arg Ser Leu Asn pFF NH$_2$ | 406 | | |
| Ac- Arg Ser Leu Asn mClF NH$_2$ | 407 | 109.45 | 89.7 |
| Ac- Arg Ser Leu Ala Phe NH$_2$ | 408 | | |
| Ac- Arg Ser Leu Ala pFF NH$_2$ | 409 | | |
| Ac- Arg Ser Leu Ala mClF NH$_2$ | 410 | | |
| Ac- Arg Ser Leu Gly Phe NH$_2$ | 411 | | |
| Ac- Arg Ser Leu Gly pFF NH$_2$ | 412 | | |
| Ac- Arg Ser Leu Gly mClF NH$_2$ | 413 | | |
| Ac- Arg Ser Ile Asn Phe NH$_2$ | 414 | | |
| Ac- Arg Ser Ile Asn pFF NH$_2$ | 415 | | |
| Ac- Arg Ser Ile Asn mClF NH$_2$ | 416 | | |
| Ac- Arg Ser Ile Ala Phe NH$_2$ | 417 | | |
| Ac- Arg Ser Ile Ala pFF NH$_2$ | 418 | | |
| Ac- Arg Ser Ile Ala mClF NH$_2$ | 419 | | |
| Ac- Arg Ser Ile Gly Phe NH$_2$ | 420 | | |
| Ac- Arg Ser Ile Gly pFF NH$_2$ | 421 | | |
| Ac- Arg Ser Ile Gly mClF NH$_2$ | 422 | | |
| Ac- Arg Ser Val Asn Phe NH$_2$ | 423 | | |
| Ac- Arg Ser Val Asn pFF NH$_2$ | 424 | | |
| Ac- Arg Ser Val Asn mClF NH$_2$ | 425 | | |
| Ac- Arg Ser Val Ala Phe NH$_2$ | 426 | | |
| Ac- Arg Ser Val Ala pFF NH$_2$ | 427 | | |
| Ac- Arg Ser Val Ala mClF NH$_2$ | 428 | | |
| Ac- Arg Ser Val Gly Phe NH$_2$ | 429 | | |
| Ac- Arg Ser Val Gly pFF NH$_2$ | 430 | | |
| Ac- Arg Ser Val Gly mClF NH$_2$ | 431 | | |
| Ac- Arg Lys Leu Asn Phe NH$_2$ | 432 | | |
| Ac- Arg Lys Leu Asn pFF NH$_2$ | 433 | | |
| Ac- Arg Lys Leu Asn mClF NH$_2$ | 434 | 17.6 | 24.8 |
| Ac- Arg Lys Leu Ala Phe NH$_2$ | 435 | | |
| Ac- Arg Lys Leu Ala pFF NH$_2$ | 436 | 6.05 | 14.55 |
| Ac- Arg Lys Leu Ala mClF NH$_2$ | 437 | 24.9 | >80 |
| Ac- Arg Lys Leu Gly Phe NH$_2$ | 438 | | |
| Ac- Arg Lys Leu Gly pFF NH$_2$ | 439 | 15.05 | >80 |
| Ac- Arg Lys Leu Gly mClF NH$_2$ | 440 | | |
| Ac- Arg Lys Ile Asn Phe NH$_2$ | 441 | | |
| Ac- Arg Lys Ile Asn pFF NH$_2$ | 442 | 10.35 | 32.95 |
| Ac- Arg Lys Ile Asn mClF NH$_2$ | 443 | | |
| Ac- Arg Lys Ile Ala Phe NH$_2$ | 444 | | |
| Ac- Arg Lys Ile Ala pFF NH$_2$ | 445 | 77.35 | >80 |
| Ac- Arg Lys Ile Ala mClF NH$_2$ | 446 | | |
| Ac- Arg Lys Ile Gly Phe NH$_2$ | 447 | | |
| Ac- Arg Lys Ile Gly pFF NH$_2$ | 448 | | |
| Ac- Arg Lys Ile Gly mClF NH$_2$ | 449 | | |

-continued

| Sequence | SEQ ID No. | Binding IC$_{50}$ (µM) Cyclin A | Kinase IC$_{50}$ (µM) CyclinA/ CDK2 |
|---|---|---|---|
| Ac- Arg Lys Val Asn Phe NH$_2$ | 450 | | |
| Ac- Arg Lys Val Asn pFF NH$_2$ | 451 | | |
| Ac- Arg Lys Val Asn mCIF NH$_2$ | 452 | | |
| Ac- Arg Lys Val Ala Phe NH$_2$ | 453 | | |
| Ac- Arg Lys Val Ala pFF NH$_2$ | 454 | | |
| Ac- Arg Lys Val Ala mCIF NH$_2$ | 455 | | |
| Ac- Arg Lys Val Gly Phe NH$_2$ | 456 | | |
| Ac- Arg Lys Val Gly PFF NH$_2$ | 457 | | |
| Ac- Arg Lys Val Gly mCIF NH$_2$ | 458 | | |
| Ac- Arg Arg Leu Asn pFF NH$_2$ | 295 | 0.72 | 1.55 |
| Ac- Arg Arg Leu Asn pFF NH$_2$ | 379 | 4.65 | 7.95 |
| Ac- Arg Arg Ile Asn pFF NH$_2$ | 304 | 1.25 | 1.45 |
| Ac- Arg Arg Ile Asn pFF NH$_2$ | 388 | 9.75 | 12.6 |
| Ac- Arg Arg Leu Ile pFF NH$_2$ | 375 | 1.55 | 7.85 |
| Ac- Arg Arg Leu Ile pFF NH$_2$ | 459 | 16.00 | 29.8 |
| Ac- Arg Arg Leu Ala pFF NH$_2$ | 298 | 1.00 | 3.15 |
| Ac- Arg Arg Leu Ala pFF NH$_2$ | 382 | 10.73 | 15.45 |

Example 28

Assays

Example of a Cyclin Affinity Capture Method for the Identification of Peptide Inhibitors Peptides were synthesized as described above. Cyclin D1 was expressed in *E coli* BL21(DE3) using PET expression vector and purified from the inclusion bodies. After refolding Cyclin D1 was cross-linked on SulfoLink agarose support (PIERCE). CDK4-6×His (6×His tag disclosed as SEQ ID NO: 462) was expressed in Sf9 insect cells infected with the appropriate baculovirus construct and purified by metal-affinity chromatography (Quiagen). GST-Rb (773-924) was expressed in *E coli* and purified on a Glutathione-Sepharose column according the manufacturers instructions (Pharmacia). CDK4/Cyclin D1 phosphorilation of Rb was determined by incorporation of radio-labeled phosphate in GST-Rb in 96-well format kinase assay. The phosphorylation reaction mixture consisted of 50 mM HEPES pH 7.4, 20 mM MgCl$_2$, 5 mM EDTA, 2 mM DTT, 20mM-gliceroposphate, 2 mM NaF, 1 mM Na$_3$VO$_4$, 0.5 g CDK4, 0.5 g Cyclin D1, 10 1 GST-Rb Sepharose beads, 100 M ATP and 0.2 Ci $^{32}$P-ATP. The reaction was carried out for 30 min at 30 C at constant shaking. The GST-Rb-Sepharose beads were washed with 50 mM HEPES and 1 mM ATP and the radioactivity was measured on Scintillation counter (Topcount, HP).

Three Dimensional Models

As described in Example 4 above, a computer generated model of a preferred peptide of the present invention (HAKRRLIF) (SEQ ID NO. 42) complexed to cyclin A has been generated using AFFINITY (Molecular Simulations Inc.). A representation of this complex is shown in FIG. 4. Using the bond dimension analysis the following cyclin A amino acids have been determined as important in forming associations with this peptide:

| | Cyclin A residues | | |
|---|---|---|---|
| p21 residue | Major Interaction | Intermediate Interaction | Minor Interaction |
| H | E223, E224 | W217, V219, V221 S408, E411 | G222, Y225, I281 |
| A | | Y225 | E223 |
| K | D284 | | E220, V279 |
| R | | I213 | A212, V215, L218 Q406, S408 |
| R | D283 | I213, L214 | M210, L253 |
| L | L253 | G257 | L218, I239, V256 |
| I | | R250, Q254 | |
| F | I206, R211 | T207, L214 | M200 |

These results demonstrate that the p21$^{WAF1}$-derived C-terminal peptides inhibit the phosphorylation of CDK substrates by binding to the cyclin regulatory subunit of the complex. Through the homology of this sequence with the sequences that have been determined crystallographically in complex with cyclins (Brown, N. R.; Noble, M. E.; Endicott, J. A.; Johnson, L. N. *Nat. Cell Biol.* 1999, 1, 438-443; Russo, A. A.; Jeffrey, P. D.; Patten, A. K.; Massague, J.; Pavletich, N. P. *Nature* 1996, 382, 325-31), as well as by virtue of our experimental results, we can conclude that the p21$^{WAF1}$ peptide interacts with the same region of the protein as observed in these structures. The substrate recruitment site from these complexes consists mainly of residues of the α1 and α3 helices, which form a shallow groove on the surface, comprised predominantly of hydrophobic residues. These residues are largely conserved in the A, B, E and D1 cyclins. Analysis of the X-ray crystallographically determined structure of the ternary complex of p27$^{KIP1}$, CDK2 and cyclin A gives considerable insight into the structural basis for the interactions of the p21$^{WAF1}$ peptides examined here. In addition to the available experimentally derived information, a model of cyclin A-bound form of p21(152-159)Ser153Ala has been generated using computational docking procedures. These allow for the complex nature of protein—protein interactions to be delineated in terms of side-chain and backbone flexibility and using a routine employing full molecular mechanics description of non-bonded interactions. The generated model (FIG. 4) gives additional understanding of the molecular basis of the affinity of the peptide for the cyclin groove since it reveals that the residues that are intolerant to substitution and deletion make important contacts with the protein.

Figure 5:
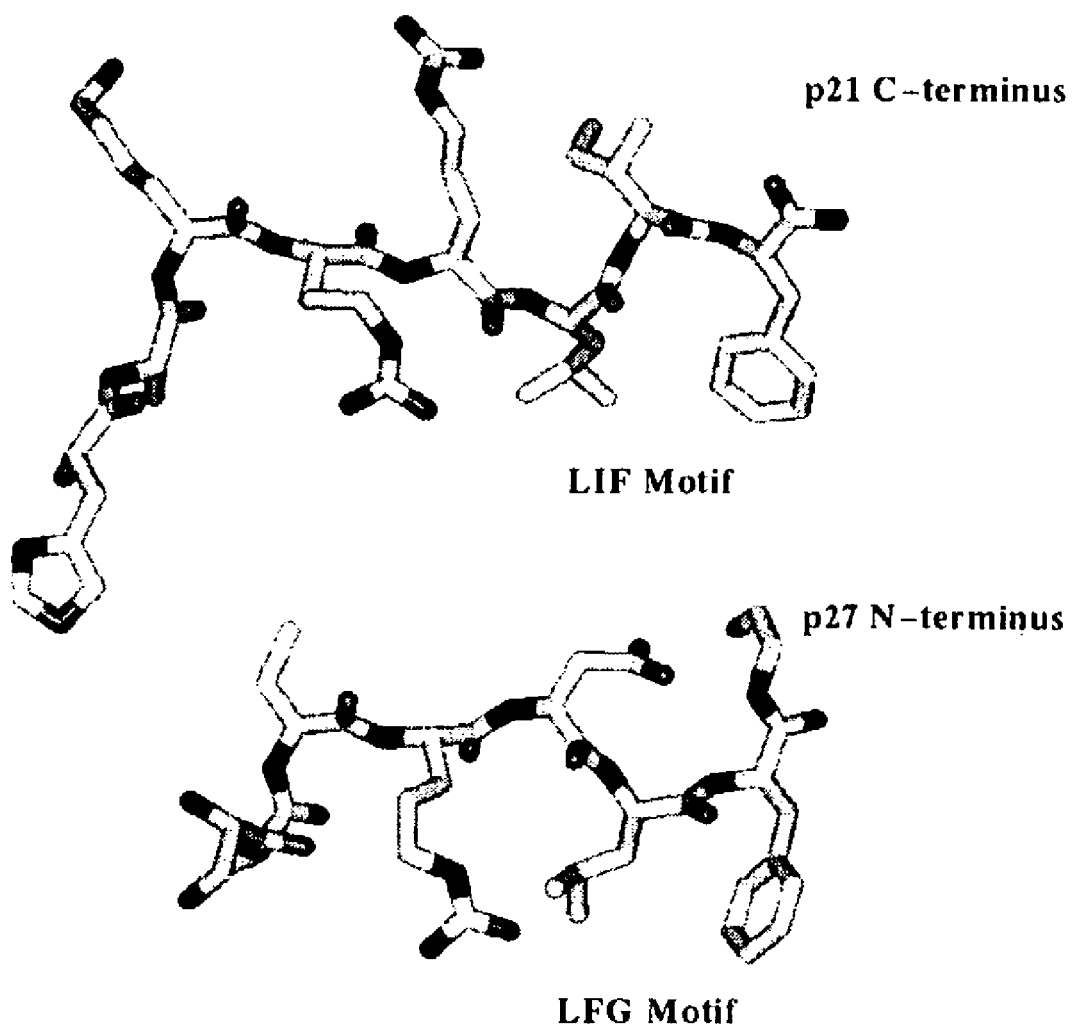
FIG. 5 shows comparison of the conformation of cyclin A-complexed structures of the p21-and p27-derived peptides H-His-Ala-Lys-Arg-Arg-Leu-Ile-Phe (SEQ ID NO. 36) and H-Ser-Ala-Cys-Arg-Asn-Leu-Phe-Gly-NH$_2$ (SEQ ID NO. 180). The positioning of the Leu and Phe side chains of the Leu-Ile-Phe and Leu-Phe-Gly motifs in the groove is remarkably similar, despite the different sequence order of these residues.

As with Examples 12-22, the following discussion relates to observations made in respect of the peptide HAKRRLIF (SEQ ID NO. 42) and all conclusions drawn in respect of potency increasing or decreasing are to be so interpreted. Two immediate conclusions can be drawn from the structure regarding the explanation of the functional significance of residues and which cannot be readily made from the available experimental data. The first is the rationale for the significant potency increase observed in the Ser153Ala substitution and the second is the accommodation of an aromatic residue in either position 7 or 8 of the cyclin binding motif (position 7 in conjunction with Gly at position 8). The basis for this can be ascertained by comparing the X-ray structure of the p27$^{KIP1}$ ternary complex with the binary docked model structure. For the interaction of the LFG motif in the p27 structure, the Leu and Phe residues insert into the hydrophobic pocket formed by Met$^{210}$, Ile$^{213}$, Trp$^{217}$, and Leu$^{253}$ provide the majority of the binding interaction of this region with the cyclin molecule. For the interactions of the LIF motif, the backbone torsion angles of the peptide at positions 6, 7 and 8 adjust in order to allow the Phe side chain to rotate into the hydrophobic pocket and form a high degree of complementarity with the hydrophobic pocket residue of the groove. The Ile side chain at position 7 (158 of p21) rotates out of the pocket to accommodate the Phe and no longer makes any hydrophobic contacts (see FIG. 5). The conformational changes that the peptide undergoes relative to the p27 structure in order to adapt the position 8 Phe residue into the hydrophobic pocket are quite marked. The comparison of the bound peptide structures in FIG. 5 illustrates how the turn structure on the NLFG (SEQ ID NO. 289) sequence in p27 which forms both intra- and inter-molecular hydrogen bonds is no longer present in the p21 peptide structure and is replaced by a more extended backbone conformation.

This observation explains the ability of the spacer residue between the Leu and Phe not only to be tolerated but also to increase affinity significantly as suggested by the observation that HAKRRLIF (SEQ ID NO. 42) is more potent than is the hybrid peptide HAKRRLFG (SEQ ID NO. 44). The ability of position 7 analogues including Ala to retain binding with cyclin A also supports this conclusion. The second observation and explanation that can be extracted from the model is the reason for the ability of the Ala replacement at position 153 dramatically to increase binding. This residue in the model forms hydrophobic contact with a second minor pocket which is made up by the second face of the Trp involved in the major pocket and two other residues. In the docked model, this second minor pocket is more pronounced and forms more complementary interactions with Ala than is observed in the crystal structure. It is apparent from this site that placement of the polar Ser residue in this hydrophobic environment would not be favoured and in fact would destabilise the binding interaction of the p21 peptide for the cyclin.

Further examination of the cyclin-bound p21 complex gives further indications of the nature of the residues that contribute to the affinity of the peptide to the recruitment site and that are different to those in the cyclin binding motif of p27. These include the His at position 1 (Ser$^{27}$ in p27), Lys at position 2 (Cys), and Arg at position 5 (Asn). The Ser to His change from p27 to p21 does not appear to be a critical one since both the Ala replacement peptide (p21(149-160) His152Ala) and the truncated peptide minus the residue at position 1 are essentially equipotent. This result is consistent with the binding model since this residue does not form any contacts with the protein with the exception of an H-bond donation of the terminal amino group. By contrast of the Cys to Lys variant, functional data indicates that the Ala mutant undergoes a two-fold reduction in its ability to phosphorylate pRb. From the calculated model, Lys$^{154}$ forms an ion pair interaction with Asp$^{284}$, thus, suggesting the basis for the potency decrease with this residue. Finally the Asn to Arg (156 in p21) change leads to a six-fold reduction in potency suggesting that the guanidino function of position 5 contributes to the binding interaction. Again the model indicates that this residue plays an important role in forming hydrogen bonds corresponding to those observed to the Asn residue in the p27 structure and thereby contributing to validation of the docked model. In addition, the recently published structure of a p107 peptide bound to cyclin A verifies the model since the homologous Arg in this structure H-bonds to Asp$^{283}$, an interaction which is also observed in the docked complex (Brown, N. R.; Noble, M. E.; Endicott, J. A.; Johnson, L. N. *Nat. Cell Biol.* 1999, 1, 438-443).

Other than those interactions identified as being unique to the peptides of the present invention, there are the residues that are conserved between p27 and the p21 C-terminally optimised peptides that form similar interactions to those observed in the experimentally derived structure. In particular, Arg$^{155}$, forms H-bonding and electrostatic interactions with Asp$^{216}$ and Glu$^{200}$ and Leu$^{157}$ of the hydrophobic motif inserts into the pocket in a similar orientation to that observed in the crystal structure.

In summary, the model structure of the potent CDK2 and CDK4 inhibitor peptide H-His-Ala-Lys-Arg-Arg-Leu-Ile-Phe-NH$_2$ (SEQ ID NO. 36) in complex with CDK2/cyclin A gives considerable insight into the intermolecular interactions involved in cyclin binding and hence into blocking of substrate recruitment. In conjunction with kinase activity data for the series of p21 truncation and substitution analogues, this model clearly defines the sequence and structural requirements of the cyclin binding motif.

Figure 6:
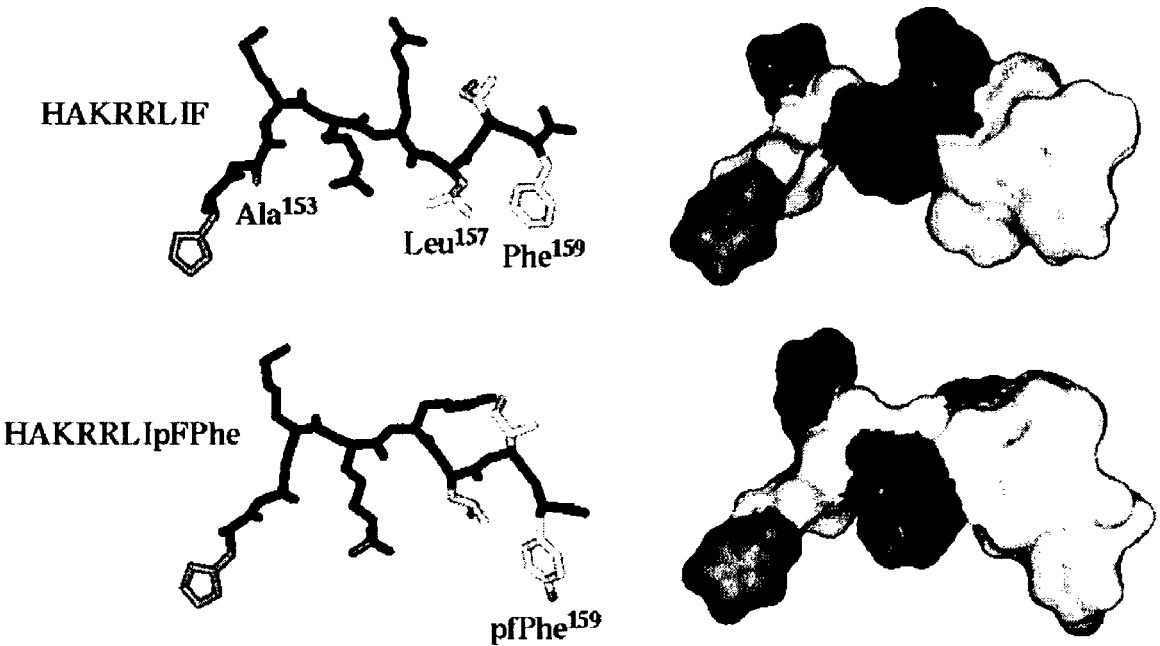
FIG. 6 shows comparison of modeled cyclin A groove-bound conformations of the p21(152-159) Ser153Ala peptides containing either Phe$^{159}$ (top; SEQ ID NO: 42) or pFPhe$^{159}$ (bottom; SEQ ID NO: 103).

The pFPhe$^8$ derivative of the peptide H-His-Ala-Lys-Arg-Arg-Leu-Ile-Phe-NH$_2$ (SEQ ID NO. 36) was found to possess increased activity in binding assays with cyclin A. Molecular modelling docking simulations performed with this analogue (FIG. 6) suggested that the pFPhe derivative inserts deeper into the hydrophobic pocket of the cyclin groove. This appears to result from rearrangement of the residues of the pocket forming more complementary interactions with the pFPhe residue and probably results from the change in charge distribution of the ring relative to the unsubstituted amino acid. This apparent gain in peptide-receptor affinity due to improved hydrophobic interactions of the pFPhe residue suggests that reduction of molecular mass through further N-terminal truncation will be possible without severe loss of biological activity.

REFERENCES

Valerio, R. M., Bray, A. M., Campbell, M., Dipasquale, A., Margellis, C., Rodda, S. J., Geysen, H. M., and Maeji, N.J. (1993) *Int. J. Peptide Protein Res.* 42, 1-9.

Fields. G. B., and Noble, R. L. (1990) *Int. J. Peptide Protein Res.* 35, 161-214.

King, D. S., Fields, C. G., and Fields, G. B. (1990) *Int. J. Peptide Protein Res.* 36, 255-266.

Ball, K. L., Lain, S., Fåhraeus, R., Smythe, C., and Lane, D. P. (1996) *Current Biol.* 7, 71-80.

Harper, J W, Tsai L-H, Zhang, P, Dobrovolski C, Connel-Crowley, (1995) *Cell*, 6:387-400.

Holstein, M, Sidranski, D., Vogelstein, B., Harris, C. (1991) *Science*, 253:49-53.

Lane D P (1992) *Nature* 358:15-16.

Momand,. J., Zambetti, G. P., Olson, D. C., Levine, A. J. (1992) *Cell*, 69:1237-1245.

Deng, C., Zhang, P., Harper, J. W., Elledge S. J., Leder P. (1995) *Cell*, 82: 675-864.

Adams, P., Sellers, W., Sharma, S., Wu, A., Nalin, C., Kaelin W. (1996) *Mol. and Cell. Biol.* 16: 6623-6633.

Chen et al. *Mol Cell Biol* (1996) 16 4673-4682

Lin J. et al., *Mol Cell Biol* (1996) 16 1768-1793

Russo A A et al., Nature (1996) 382: 325-331

Chen, et al., (1995) Nature, 374: 386-388

Flores-Rozas, et al. (1994) Prof. Natl. Acad. Sci. U.S.A., 91: 8655-8659

Luo, et al. (1995) Nature, 375: 159-161

Nakanishi, et al. (1995b) J. Biol. Chem., 270: 17060-17063
Warbrick, et al. (1995) Curr. Biol., 5: 275-282
Waga, et al. (1994) Nature, 369: 574-578

The contents of all references, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A peptide consisting of the formula III or IV:
H'$X_2$K'$R_1$$R_2$L'$X_5$F (formula III) (SEQ ID No. 175) or
H'$X_2$K'$R_1$$R_2$L'F$X_5$ (formula IV) (SEQ ID No. 176),
wherein
H' is nothing, His, D-His, Ala, Thi, Hse, Phe, or Dab;
$X_2$ is Ala, Ser, Abu, Val;
K' is Lys, Arg, or Abu;
$R_1$ is Arg, Lys, or Gln;
$R_2$ forms a cyclic peptide with the C-terminal residue and is either Orn or Lys;
L' is Leu or Ile;
$X_5$ is Ile, Leu, Gly, or Ala; and
F' is Phe, para-fluoroPhe, meta-fluoroPhe, L-Psa, 2-Nap, Dhp, or D-Psa.

2. The peptide according to claim 1, wherein $X_2$ is Ala.

3. The peptide of claim 1 wherein $X_5$ is Gly.

4. A peptide consisting of the formula IV:
H'$X_2$K'$R_1$$R_2$L'F$X_5$ (formula IV) (SEQ ID NO. 176)
wherein:
H' is nothing, His, D-His, Ala, Thi, Hse, Phe, or Dab;
$X_2$ is Ala, Ser, Abu, Val;
K' is Lys, Arg or Abu;
$R_1$ is Arg, Lys or Gln;
$R_2$ is Orn or Lys;
L' is Leu or Ile;
$X_5$ is Ile, Leu Gly or Ala; and
F is Phe, para-fluoro-Phe, meta-fluoro-Phe, L-Psa, 2-Nap, Dhp, or D-Psa;
and wherein said peptide is in cyclic form by virtue of a linkage between the C-terminal residue and the residue 3 upstream to it.

5. The peptide according to claim 4 wherein $X_2$ is Ala.

6. The peptide according to claim 4 wherein $X_5$ is Gly.

7. The peptide according to claim 4 wherein F is para-fluoro-Phe and H' is alanine or nothing.

8. A peptide 5,8-cyclo-[H-His-Ala-Lys-Arg-Lys-Leu-Phe-Gly] (SEQ ID NO: 173).

9. A peptide 5,8-cyclo-[H-His-Ala-Lys-Arg-Orn-Leu-Phe-Gly] (SEQ ID NO: 174).

* * * * *

SEQUENCE LISTING

```
<160> NUMBER OF SEQ ID NOS: 459

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 1

Asp Phe Tyr His Ser Lys Arg Arg Leu Ile Phe
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: 1, 3, 5, 7
<223> OTHER INFORMATION: Xaa is any amino acid
<220> FEATURE:
<221> NAME/KEY: SITE
<222> LOCATION: (2)
<223> OTHER INFORMATION: Xaa may be Ser or Ala or a straight or branched
      chain amino acid
<220> FEATURE:
<221> NAME/KEY: SITE
<222> LOCATION: (4)
<223> OTHER INFORMATION: Xaa is His, Lys or Arg

<400> SEQUENCE: 2

Xaa Xaa Xaa Xaa Xaa Leu Xaa Phe
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (2)
<223> OTHER INFORMATION: Xaa may be Ser or Ala or a straight or branched
      chain amino acid
<220> FEATURE:
<221> NAME/KEY: SITE
<222> LOCATION: (7)
<223> OTHER INFORMATION: Xaa may be any amino acid

<400> SEQUENCE: 3

His Xaa Lys Arg Arg Leu Xaa Phe
 1               5

<210> SEQ ID NO 4
```

```
<211> LENGTH: 13
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: 1, 13
<223> OTHER INFORMATION: Xaa may be any amino acid

<400> SEQUENCE: 4

Xaa Asp Phe Tyr His Ser Lys Arg Arg Leu Ile Phe Xaa
 1               5                  10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 5

Arg Arg Leu Ile Phe
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 6

Lys Arg Arg Leu Ile Phe Ser Lys
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: E2F1
      derived peptide

<400> SEQUENCE: 7

Pro Val Lys Arg Arg Leu Asp Leu
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: E2F1
      derived peptide

<400> SEQUENCE: 8

Pro Val Lys Arg Arg Leu Phe Gly
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: E2F1
```

```
              derived peptide
<220> FEATURE:
<221> NAME/KEY: SITE
<222> LOCATION: (2)
<223> OTHER INFORMATION: Xaa may be any amino acid

<400> SEQUENCE: 9

Arg Xaa Leu Phe

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: E2F1
      derived peptide

<400> SEQUENCE: 10

Arg Arg Leu Phe Gly Glu
  1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: E2F1
      derived peptide
<220> FEATURE:
<221> NAME/KEY: SITE
<222> LOCATION: (1)
<223> OTHER INFORMATION: Xaa may be any amino acid
<220> FEATURE:
<221> NAME/KEY: SITE
<222> LOCATION: (3)
<223> OTHER INFORMATION: Xaa may be any amino acid

<400> SEQUENCE: 11

Xaa Leu Xaa Phe
  1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: E2F1
      derived peptide
<220> FEATURE:
<221> NAME/KEY: SITE
<222> LOCATION: (2)
<223> OTHER INFORMATION: Xaa may be any amino acid
<220> FEATURE:
<221> NAME/KEY: SITE
<222> LOCATION: (4)
<223> OTHER INFORMATION: Xaa may be any amino acid

<400> SEQUENCE: 12

Arg Xaa Leu Xaa Phe
  1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 13
```

```
Asp Phe Tyr His Ser Lys Arg Arg Leu Ile Phe Ser
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 14

```
Thr Asp Phe Tyr His Ser Lys Arg Arg Leu Ile Phe
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 15

```
Ala Phe Tyr His Ser Lys Arg Arg Leu Ile Phe Ser
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 16

```
Asp Ala Tyr His Ser Lys Arg Arg Leu Ile Phe Ser
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 17

```
Asp Phe Ala His Ser Lys Arg Arg Leu Ile Phe Ser
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 18

```
Asp Phe Tyr Ala Ser Lys Arg Arg Leu Ile Phe Ser
1               5                   10
```

<210> SEQ ID NO 19
<211> LENGTH: 12
<212> TYPE: PRT
<213> ORGANISM: Artificial Sequence
<220> FEATURE:

```
<223> OTHER INFORMATION: Description of Artificial Sequence: p21 derived
      peptide

<400> SEQUENCE: 19

Asp Phe Tyr His Ala Lys Arg Arg Leu Ile Phe Ser
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 20

Asp Phe Tyr His Ser Ala Arg Arg Leu Ile Phe Ser
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 21

Asp Phe Tyr His Ser Lys Arg Ala Leu Ile Phe Ser
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 22

Asp Phe Tyr His Ser Lys Arg Arg Leu Ala Phe Ser
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 23

Asp Phe Tyr His Ser Lys Arg Arg Leu Ile Phe Ala
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 24

Phe Tyr His Ser Lys Arg Arg Leu Ile Phe Ser
 1               5                  10
```

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 25

Tyr His Ser Lys Arg Arg Leu Ile Phe Ser
  1               5                  10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 26

His Ser Lys Arg Arg Leu Ile Phe Ser
  1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 27

Phe Tyr His Ser Lys Arg Arg Leu Ile Phe
  1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 28

Tyr His Ser Lys Arg Arg Leu Ile Phe
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 29

His Ser Lys Arg Arg Leu Ile Phe
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 30
```

```
Ser Lys Arg Arg Leu Ile Phe
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 31

Lys Arg Arg Leu Ile Phe
 1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 32

Arg Leu Ile Phe
 1

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 33

Arg Arg Leu Ile Phe
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 34

Lys Arg Arg Leu Ile Phe
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
```

```
          C-terminal Carboxamide

<400> SEQUENCE: 35

Ala Lys Arg Arg Leu Ile Phe
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 36

His Ala Lys Arg Arg Leu Ile Phe
  1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 37

Asn Leu Phe Gly
  1

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 38

Arg Asn Leu Phe Gly
  1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (1)
<223> OTHER INFORMATION: 2-Aminobutyric acid

<400> SEQUENCE: 39

Xaa Arg Asn Leu Phe Gly
  1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (2)
<223> OTHER INFORMATION: 2-Aminobutyric acid

<400> SEQUENCE: 40

Ala Xaa Arg Asn Leu Phe Gly
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (3)
<223> OTHER INFORMATION: 2-Aminobutyric acid

<400> SEQUENCE: 41

Ser Ala Xaa Arg Asn Leu Phe Gly
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 42

His Ala Lys Arg Arg Leu Ile Phe
  1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 43

His Ser Lys Arg Arg Leu Phe Gly
  1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
```

```
<400> SEQUENCE: 44

His Ala Lys Arg Arg Leu Phe Gly
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 45

Lys Ala Cys Arg Arg Leu Phe Gly
 1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide

<400> SEQUENCE: 46

Lys Ala Cys Arg Arg Leu Ile Phe
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 47

Ala Ala Lys Arg Arg Leu Ile Phe
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 48

Ala Lys Arg Arg Leu Ile Phe
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
```

```
<221> NAME/KEY: SITE
<222> LOCATION: (1)
<223> OTHER INFORMATION: Xaa = 3-Pyridylalanine

<400> SEQUENCE: 49

Xaa Ala Lys Arg Arg Leu Ile Phe
 1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (1)
<223> OTHER INFORMATION: Xaa = 2-Thienylalanine

<400> SEQUENCE: 50

Xaa Ala Lys Arg Arg Leu Ile Phe
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (1)
<223> OTHER INFORMATION: Xaa = Homoserine

<400> SEQUENCE: 51

Xaa Ala Lys Arg Arg Leu Ile Phe
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 52

Phe Ala Lys Arg Arg Leu Ile Phe
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
```

```
<220> FEATURE:
<221> NAME/KEY: SITE
<222> LOCATION: (1)
<223> OTHER INFORMATION: Xaa = 1,3-Diaminobutyric acid

<400> SEQUENCE: 53

Xaa Ala Lys Arg Arg Leu Ile Phe
 1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 54

His Gly Lys Arg Arg Leu Ile Phe
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (2)
<223> OTHER INFORMATION: Xaa = 2-Aminobutyric acid

<400> SEQUENCE: 55

His Xaa Lys Arg Arg Leu Ile Phe
 1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (2)
<223> OTHER INFORMATION: Xaa = Norvalin

<400> SEQUENCE: 56

His Xaa Lys Arg Arg Leu Ile Phe
 1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
```

C-terminal Carboxamide
<220> FEATURE:
<221> NAME/KEY: SITE
<222> LOCATION: (2)
<223> OTHER INFORMATION: Xaa = t-Butylglycine

<400> SEQUENCE: 57

His Xaa Lys Arg Arg Leu Ile Phe
 1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 58

His Val Lys Arg Arg Leu Ile Phe
 1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 59

His Ile Lys Arg Arg Leu Ile Phe
 1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (2)
<223> OTHER INFORMATION: Xaa = Phenylglycine

<400> SEQUENCE: 60

His Xaa Lys Arg Arg Leu Ile Phe
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 61

```
His Phe Lys Arg Arg Leu Ile Phe
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 62

His Ala Ala Arg Arg Leu Ile Phe
 1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (3)
<223> OTHER INFORMATION: Xaa = Norleucine

<400> SEQUENCE: 63

His Ala Xaa Arg Arg Leu Ile Phe
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (3)
<223> OTHER INFORMATION: Xaa = 2-Aminobutyric acid

<400> SEQUENCE: 64

His Ala Xaa Arg Arg Leu Ile Phe
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 65

His Ala Leu Arg Arg Leu Ile Phe
 1               5
```

```
<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 66

His Ala Arg Arg Arg Leu Ile Phe
 1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 67

His Ala Lys Ala Arg Leu Ile Phe
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = Citrulline

<400> SEQUENCE: 68

His Ala Lys Xaa Arg Leu Ile Phe
 1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = Homoserine

<400> SEQUENCE: 69

His Ala Lys Xaa Arg Leu Ile Phe
 1               5

<210> SEQ ID NO 70
```

```
<211> LENGTH: 8
<212> TYPE: PRT
<213> ORGANISM: Artificial Sequence
<220> FEATURE:
<223> OTHER INFORMATION: Synthesised with free amino terminus and as the
      C-terminal Carboxamide
<220> FEATURE:
<223> OTHER INFORMATION: Description of Artificial Sequence: p21 derived
      peptide

<400> SEQUENCE: 70

His Ala Lys His Arg Leu Ile Phe
 1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (4)
<223> OTHER INFORMATION: Xaa = Norleucine

<400> SEQUENCE: 71

His Ala Lys Xaa Arg Leu Ile Phe
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 72

His Ala Lys Gln Arg Leu Ile Phe
 1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 73

His Ala Lys Lys Arg Leu Ile Phe
 1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
```

<223> OTHER INFORMATION: Synthesised with free amino terminus and as the
      C-terminal Carboxamide

<400> SEQUENCE: 74

His Ala Lys Arg Ala Leu Ile Phe
  1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 75

His Ala Lys Arg Asn Leu Ile Phe
  1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 76

His Ala Lys Arg Pro Leu Ile Phe
  1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 77

His Ala Lys Arg Ser Leu Ile Phe
  1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = Aminoisobutyric acid

<400> SEQUENCE: 78

His Ala Lys Arg Xaa Leu Ile Phe
  1               5

```
<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (5)
<223> OTHER INFORMATION: Xaa = Sarcosine

<400> SEQUENCE: 79

His Ala Lys Arg Xaa Leu Ile Phe
  1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = Citrulline

<400> SEQUENCE: 80

His Ala Lys Arg Xaa Leu Ile Phe
  1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 81

His Ala Lys Arg Arg Leu Ile Phe
  1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = D-Leu

<400> SEQUENCE: 82

His Ala Lys Arg Arg Xaa Ile Phe
```

-continued

```
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 83

His Ala Lys Arg Arg Ile Ile Phe
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 84

His Ala Lys Arg Arg Val Ile Phe
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (6)
<223> OTHER INFORMATION: Xaa = Norleucine

<400> SEQUENCE: 85

His Ala Lys Arg Arg Xaa Ile Phe
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (6)
<223> OTHER INFORMATION: Xaa = Norvaline

<400> SEQUENCE: 86

His Ala Lys Arg Arg Xaa Ile Phe
1               5
```

```
<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = Cyclohexylalanine

<400> SEQUENCE: 87

His Ala Lys Arg Arg Xaa Ile Phe
  1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 88

His Ala Lys Arg Arg Phe Ile Phe
  1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = 1-Naphthylalanine

<400> SEQUENCE: 89

His Ala Lys Arg Arg Xaa Ile Phe
  1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 90

His Ala Lys Arg Arg Leu Ala Phe
  1               5

<210> SEQ ID NO 91
<211> LENGTH: 8
<212> TYPE: PRT
```

```
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 91

His Ala Lys Arg Arg Leu Leu Phe
 1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 92

His Ala Lys Arg Arg Leu Val Phe
 1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (7)
<223> OTHER INFORMATION: Xaa = Norleucine

<400> SEQUENCE: 93

His Ala Lys Arg Arg Leu Xaa Phe
 1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (7)
<223> OTHER INFORMATION: Xaa = Norvaline

<400> SEQUENCE: 94

His Ala Lys Arg Arg Leu Xaa Phe
 1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: p21 derived
```

```
                                peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = Cyclohexylalanine

<400> SEQUENCE: 95

His Ala Lys Arg Arg Leu Xaa Phe
 1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 96

His Ala Lys Arg Arg Leu Phe Phe
 1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (7)
<223> OTHER INFORMATION: Xaa = 1-Naphthylalanine
<220> FEATURE:
<223> OTHER INFORMATION: Synthesised with free amino terminus and as the
      C-terminal Carboxamide

<400> SEQUENCE: 97

His Ala Lys Arg Arg Leu Xaa Phe
 1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 98

His Ala Lys Arg Arg Leu Phe
 1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
```

C-terminal Carboxamide

<400> SEQUENCE: 99

His Ala Lys Arg Arg Leu Ile Leu
 1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = Cyclohexylalanine

<400> SEQUENCE: 100

His Ala Lys Arg Arg Leu Ile Xaa
 1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = Homophenylalanine

<400> SEQUENCE: 101

His Ala Lys Arg Arg Leu Ile Xaa
 1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 102

His Ala Lys Arg Arg Leu Ile Tyr
 1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE

```
<222> LOCATION: (8)
<223> OTHER INFORMATION: Xaa = p-Fluorophenylalanine

<400> SEQUENCE: 103

His Ala Lys Arg Arg Leu Ile Xaa
 1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = m-Fluorophenylalanine

<400> SEQUENCE: 104

His Ala Lys Arg Arg Leu Ile Xaa
 1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 105

His Ala Lys Arg Arg Leu Ile Trp
 1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = 1-Naphthylalanine

<400> SEQUENCE: 106

His Ala Lys Arg Arg Leu Ile Xaa
 1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
```

```
<221> NAME/KEY: SITE
<222> LOCATION: (8)
<223> OTHER INFORMATION: Xaa = 2-Naphthylalanine

<400> SEQUENCE: 107

His Ala Lys Arg Arg Leu Ile Xaa
 1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 108

His Ala Lys Arg Arg Leu Ile Lys
 1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = 1,2,3,4-Tetrahydroisoquinoline-3-
      carboxylic acid

<400> SEQUENCE: 109

His Ala Lys Arg Arg Leu Ile Xaa
 1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = L-Phenylserine

<400> SEQUENCE: 110

His Ala Lys Arg Arg Leu Ile Xaa
 1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = D-Phenylserine
```

```
<400> SEQUENCE: 111

His Ala Lys Arg Arg Leu Ile Xaa
 1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = L-Phenylserine

<400> SEQUENCE: 112

His Ser Lys Arg Arg Leu Ile Xaa
 1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = D-Phenylserine

<400> SEQUENCE: 113

His Ser Lys Arg Arg Leu Ile Xaa
 1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = L-O-Acetylphenylserine

<400> SEQUENCE: 114

His Ala Lys Arg Arg Leu Ile Xaa
 1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = D-O-Acetylphenylserine

<400> SEQUENCE: 115

His Ala Lys Arg Arg Leu Ile Xaa
 1               5

<210> SEQ ID NO 116
```

```
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = L-O-Acetylphenylserine

<400> SEQUENCE: 116

His Ser Lys Arg Arg Leu Ile Xaa
 1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = D-O-Acetylphenylserine

<400> SEQUENCE: 117

His Ser Lys Arg Arg Leu Ile Xaa
 1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = Dehydrophenylalanine

<400> SEQUENCE: 118

His Ala Lys Arg Arg Leu Ile Xaa
 1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = Dehydrophenylalanine

<400> SEQUENCE: 119

His Ser Lys Arg Arg Leu Ile Xaa
 1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
```

```
<221> NAME/KEY: SITE
<222> LOCATION: (8)
<223> OTHER INFORMATION: Xaa = Phenylalaninol

<400> SEQUENCE: 120

His Ala Lys Arg Arg Leu Ile Xaa
 1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (8)
<223> OTHER INFORMATION: Xaa = Phenylalaninol

<400> SEQUENCE: 121

His Ser Lys Arg Arg Leu Ile Xaa
 1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (3)
<223> OTHER INFORMATION: 2-Aminobutyric acid
<220> FEATURE:
<221> NAME/KEY: SITE
<222> LOCATION: (8)
<223> OTHER INFORMATION: p-Fluorophenylalanine

<400> SEQUENCE: 122

Ala Ala Xaa Arg Arg Leu Ile Xaa
 1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 123

Ala Ala Lys Arg Arg Leu Ile Xaa
 1               5

<210> SEQ ID NO 124
<211> LENGTH: 8
<212> TYPE: PRT
<213> ORGANISM: Artificial Sequence
<220> FEATURE:
```

```
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = Citrulline
<220> FEATURE:
<221> NAME/KEY: SITE
<222> LOCATION: (8)
<223> OTHER INFORMATION: p-Fluorophenylalanine

<400> SEQUENCE: 124

Ala Ala Lys Arg Xaa Leu Ile Xaa
 1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 125

Ala Ala Lys Arg Arg Leu Ala Xaa
 1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (3)
<223> OTHER INFORMATION: 2-Aminobutyric acid
<220> FEATURE:
<221> NAME/KEY: SITE
<222> LOCATION: (8)
<223> OTHER INFORMATION: p-Fluorophenylalanine

<400> SEQUENCE: 126

Ala Ala Xaa Arg Ser Leu Ile Xaa
 1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
```

```
<223> OTHER INFORMATION: p-Fluorophenylalanine

<400> SEQUENCE: 127

Ala Ala Lys Gln Arg Leu Ile Xaa
 1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 128

Ala Ala Lys Arg Arg Leu Ile Xaa
 1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 129

Gly Ala Lys Arg Arg Leu Ile Xaa
 1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Homoarginine
<220> FEATURE:
<221> NAME/KEY: SITE
<222> LOCATION: (8)
<223> OTHER INFORMATION: p-Fluorophenylalanine

<400> SEQUENCE: 130

Ala Ala Lys Xaa Arg Leu Ile Xaa
 1               5

<210> SEQ ID NO 131
<211> LENGTH: 8
<212> TYPE: PRT
<213> ORGANISM: Artificial Sequence
```

-continued

```
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 131

Ala Ala Lys Ser Arg Leu Ile Xaa
 1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = Homoserine
<220> FEATURE:
<221> NAME/KEY: SITE
<222> LOCATION: (8)
<223> OTHER INFORMATION: p-Fluorophenylalanine

<400> SEQUENCE: 132

Ala Ala Lys Xaa Arg Leu Ile Xaa
 1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: p-Fluorophenylalanine

<400> SEQUENCE: 133

Ala Ala Lys Arg Lys Leu Ile Xaa
 1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (5)
<223> OTHER INFORMATION: Xaa = Orn
<220> FEATURE:
<221> NAME/KEY: SITE
```

```
<222> LOCATION: (8)
<223> OTHER INFORMATION: Xaa = p-Fluorophenylalanine

<400> SEQUENCE: 134

Ala Ala Lys Arg Xaa Leu Ile Xaa
 1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 135

Ala Ala Lys Arg Gln Leu Ile Xaa
 1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = Homoserine
<220> FEATURE:
<221> NAME/KEY: SITE
<222> LOCATION: (8)
<223> OTHER INFORMATION: xaa = p-Fluorophenylalanine

<400> SEQUENCE: 136

Ala Ala Lys Arg Xaa Leu Ile Xaa
 1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 137

Ala Ala Lys Arg Thr Leu Ile Xaa
 1               5

<210> SEQ ID NO 138
<211> LENGTH: 8
<212> TYPE: PRT
```

```
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (5)
<223> OTHER INFORMATION: Xaa = Norvaline
<220> FEATURE:
<221> NAME/KEY: SITE
<222> LOCATION: (8)
<223> OTHER INFORMATION: p-Fluorophenylalanine

<400> SEQUENCE: 138

Ala Ala Lys Arg Xaa Leu Ile Xaa
  1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = Phenylglycine
<220> FEATURE:
<221> NAME/KEY: SITE
<222> LOCATION: (8)
<223> OTHER INFORMATION: Xa = p-Fluorophenylalanine

<400> SEQUENCE: 139

Ala Ala Lys Arg Arg Xaa Ile Xaa
  1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 140

Ala Ala Lys Arg Arg Met Ile Xaa
  1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
```

```
<221> NAME/KEY: SITE
<222> LOCATION: (8)
<223> OTHER INFORMATION: Xaa = p-Fluorophenylalanine

<400> SEQUENCE: 141

Ala Ala Lys Arg Arg Ala Ile Xaa
 1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = Homophenylalanine
<220> FEATURE:
<221> NAME/KEY: SITE
<222> LOCATION: (8)
<223> OTHER INFORMATION: Xaa = p-Fluorophenylalanine

<400> SEQUENCE: 142

Ala Ala Lys Arg Arg Xaa Ile Xaa
 1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = hLeu
<220> FEATURE:
<221> NAME/KEY: SITE
<222> LOCATION: (8)
<223> OTHER INFORMATION: Xa = p-Fluorophenylalanine

<400> SEQUENCE: 143

Ala Ala Lys Arg Arg Xaa Ile Xaa
 1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = allo-Isoleucine
<220> FEATURE:
<221> NAME/KEY: SITE
<222> LOCATION: (8)
<223> OTHER INFORMATION: Xaa = p-Fluorophenylalanine
```

```
<400> SEQUENCE: 144

Ala Ala Lys Arg Arg Xaa Ile Xaa
 1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 145

Ala Ala Lys Arg Arg Leu Gly Xaa
 1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (7)
<223> OTHER INFORMATION: Xaa = beta-Ala
<220> FEATURE:
<221> NAME/KEY: SITE
<222> LOCATION: (8)
<223> OTHER INFORMATION: Xaa = p-Fluorophenylalanine

<400> SEQUENCE: 146

Ala Ala Lys Arg Arg Leu Xaa Xaa
 1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = Phenylglycine
<220> FEATURE:
<221> NAME/KEY: SITE
<222> LOCATION: (8)
<223> OTHER INFORMATION: p-Fluorophenylalanine

<400> SEQUENCE: 147

Ala Ala Lys Arg Arg Leu Xaa Xaa
 1               5

<210> SEQ ID NO 148
<211> LENGTH: 8
```

```
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = Aminoisobutyric acid
<220> FEATURE:
<221> NAME/KEY: SITE
<222> LOCATION: (8)
<223> OTHER INFORMATION: Xaa = p-Fluorophenylalanine

<400> SEQUENCE: 148

Ala Ala Lys Arg Arg Leu Xaa Xaa
  1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (7)
<223> OTHER INFORMATION: Xaa = Sarcosine
<220> FEATURE:
<221> NAME/KEY: SITE
<222> LOCATION: (8)
<223> OTHER INFORMATION: Xaa = p-Fluorophenylalanine

<400> SEQUENCE: 149

Ala Ala Lys Arg Arg Leu Xaa Xaa
  1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 150

Ala Ala Lys Arg Arg Leu Pro Xaa
  1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
```

```
<220> FEATURE:
<221> NAME/KEY: SITE
<222> LOCATION: (7)
<223> OTHER INFORMATION: Xaa = t-Butylglycine
<220> FEATURE:
<221> NAME/KEY: SITE
<222> LOCATION: (8)
<223> OTHER INFORMATION: Xaa = p-Fluorophenylalanine

<400> SEQUENCE: 151

Ala Ala Lys Arg Arg Leu Xaa Xaa
 1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 152

Ala Ala Lys Arg Arg Leu Ser Xaa
 1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 153

Ala Ala Lys Arg Arg Leu Asp Xaa
 1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophenylalanine

<400> SEQUENCE: 154

Ala Ala Lys Arg Arg Leu Asn Xaa
 1               5

<210> SEQ ID NO 155
```

```
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Fluorophenylalanine

<400> SEQUENCE: 155

Ala Ala Lys Arg Arg Leu Xaa Phe
  1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = m,p-Dichlorophenylalanine

<400> SEQUENCE: 156

Ala Ala Lys Arg Arg Leu Xaa Phe
  1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Chlorophenylalanine

<400> SEQUENCE: 157

Ala Ala Lys Arg Arg Leu Xaa Phe
  1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = m-Chlorophenylalanine

<400> SEQUENCE: 158
```

Ala Ala Lys Arg Arg Leu Xaa Phe
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = o-Chlorophenylalanine

<400> SEQUENCE: 159

Ala Ala Lys Arg Arg Leu Xaa Phe
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Iodophenylalanine

<400> SEQUENCE: 160

Ala Ala Lys Arg Arg Leu Xaa Phe
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = O-Methyltyrosine

<400> SEQUENCE: 161

Ala Ala Lys Arg Arg Leu Xaa Phe
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE

```
<222> LOCATION: (7)
<223> OTHER INFORMATION: Xaa = 2-Thienylalanine

<400> SEQUENCE: 162

Ala Ala Lys Arg Arg Leu Xaa Phe
 1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 3-Pyridylalanine

<400> SEQUENCE: 163

Ala Ala Lys Arg Arg Leu Xaa Phe
 1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = m,p-Dichlorophenylalanine

<400> SEQUENCE: 164

Ala Ala Lys Arg Arg Leu Ile Xaa
 1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Chlorophenylalanine

<400> SEQUENCE: 165

Ala Ala Lys Arg Arg Leu Ile Xaa
 1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
```

```
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = m-Chlorophenylalanine

<400> SEQUENCE: 166

Ala Ala Lys Arg Arg Leu Ile Xaa
 1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = o-Chlorophenylalanine

<400> SEQUENCE: 167

Ala Ala Lys Arg Arg Leu Ile Xaa
 1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = Phenylglycine

<400> SEQUENCE: 168

Ala Ala Lys Arg Arg Leu Ile Xaa
 1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = O-Methyltyrosine

<400> SEQUENCE: 169

Ala Ala Lys Arg Arg Leu Ile Xaa
 1               5

<210> SEQ ID NO 170
<211> LENGTH: 8
```

```
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = 2-Thienylalanine

<400> SEQUENCE: 170

Ala Ala Lys Arg Arg Leu Ile Xaa
  1               5

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = 3-Pyridylalanine

<400> SEQUENCE: 171

Ala Ala Lys Arg Arg Leu Ile Xaa
  1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = 2-Indolecarboxylic acid

<400> SEQUENCE: 172

Ala Ala Lys Arg Arg Leu Ile Xaa
  1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Cyclic peptide (5,8-cyclo-)

<400> SEQUENCE: 173

His Ala Lys Arg Lys Leu Phe Gly
  1               5

<210> SEQ ID NO 174
<211> LENGTH: 8
```

```
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Cyclic peptide (5,8-cyclo-)
<220> FEATURE:
<221> NAME/KEY: MOD_RES
<222> LOCATION: (5)
<223> OTHER INFORMATION: Xaa = Orn

<400> SEQUENCE: 174

His Ala Lys Arg Xaa Leu Phe Gly
 1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (2)
<223> OTHER INFORMATION: Xaa may be Ser or Ala or a straight or branched
      chain amino acid
<220> FEATURE:
<221> NAME/KEY: SITE
<222> LOCATION: (3)
<223> OTHER INFORMATION: Xaa may be Ser or Ala or 2-aminobutyric acid
<220> FEATURE:
<221> NAME/KEY: SITE
<222> LOCATION: (4)
<223> OTHER INFORMATION: Xaa may be Arg or Lys or Gln
<220> FEATURE:
<221> NAME/KEY: SITE
<222> LOCATION: (5)
<223> OTHER INFORMATION: Xaa may be Arg or Ser or Citrulline or forms a
      cyclic peptide with C-terminal residue
<220> FEATURE:
<221> NAME/KEY: SITE
<222> LOCATION: (6)
<223> OTHER INFORMATION: Xaa may be Leu or Ile
<220> FEATURE:
<221> NAME/KEY: SITE
<222> LOCATION: (7)
<223> OTHER INFORMATION: Xaa may be Ile or Leu or Gly or Ala
<220> FEATURE:
<221> NAME/KEY: SITE
<222> LOCATION: (8)
<223> OTHER INFORMATION: Xaa may be Phe, p-fluorphenylalanine,
      m-fluorphenylalanine L-O-Acetylphenylserine, 2-Naphtylalanine,
      Dehydrophenylalanine D-O-Acetylphenylserine

<400> SEQUENCE: 175

His Xaa Xaa Xaa Xaa Xaa Xaa Xaa
 1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (2)
<223> OTHER INFORMATION: Xaa may be Ser or Ala or a straight or branched
      chain amino acid
<220> FEATURE:
<221> NAME/KEY: SITE
<222> LOCATION: (3)
```

```
<223> OTHER INFORMATION: Xaa may be Ser or Ala or 2-aminobutyric acid
<220> FEATURE:
<221> NAME/KEY: SITE
<222> LOCATION: (4)
<223> OTHER INFORMATION: Xaa may be Arg or Lys or Gln
<220> FEATURE:
<221> NAME/KEY: SITE
<222> LOCATION: (5)
<223> OTHER INFORMATION: Xaa may be Arg or Ser or Citrulline or forms a
      cyclic peptide with C-terminal residue
<220> FEATURE:
<221> NAME/KEY: SITE
<222> LOCATION: (6)
<223> OTHER INFORMATION: Xaa may be Leu or Ile
<220> FEATURE:
<221> NAME/KEY: SITE
<222> LOCATION: (7)
<223> OTHER INFORMATION: Xaa may be Phe, p-fluorphenylalanine,
      m-fluorphenylalanine L-O-Acetylphenylserine, 2-Naphtylalanine,
      Dehydrophenylalanine D-O-Acetylphenylserine
<220> FEATURE:
<221> NAME/KEY: SITE
<222> LOCATION: (8)
<223> OTHER INFORMATION: Xaa may be Ile or Leu or Gly or Ala

<400> SEQUENCE: 176

His Xaa Xaa Xaa Xaa Xaa Xaa Xaa
 1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Fluorophenylalanine

<400> SEQUENCE: 177

Ala Lys Arg Arg Leu Ile Xaa

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: p27 derived
      peptide

<400> SEQUENCE: 178

Ser Ala Cys Arg Asn Leu Phe Gly
 1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Modelled
      cyclic peptide

<400> SEQUENCE: 179

Ser Ala Cys Arg Lys Leu Phe Gly
 1               5
```

```
<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 180

Ser Ala Cys Arg Asn Leu Phe Gly
 1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (1)
<223> OTHER INFORMATION: Xaa may be Ser or Ala or a straight or branched
      chain amino acid
<220> FEATURE:
<221> NAME/KEY: SITE
<222> LOCATION: (6)
<223> OTHER INFORMATION: Xaa may be Ile or Leu or Gly or Ala

<400> SEQUENCE: 181

Xaa Lys Arg Arg Leu Xaa Phe
 1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (2)
<223> OTHER INFORMATION: Xaa may be Ser or Ala or a straight or branched
      chain amino acid
<220> FEATURE:
<221> NAME/KEY: SITE
<222> LOCATION: (8)
<223> OTHER INFORMATION: Xaa may be Ile or Leu or Gly or Ala

<400> SEQUENCE: 182

His Xaa Xaa Xaa Xaa Xaa Xaa Xaa
 1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (1)
<223> OTHER INFORMATION: Xaa = D-His

<400> SEQUENCE: 183
```

```
Xaa Ala Lys Arg Arg Leu Ile Phe
  1               5
```

<210> SEQ ID NO 184
<211> LENGTH: 4
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (3)
<223> OTHER INFORMATION: Xaa may be any amino acid

<400> SEQUENCE: 184

```
Arg Leu Xaa Phe
  1
```

<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: (4)
<223> OTHER INFORMATION: Xaa may be any amino acid

<400> SEQUENCE: 185

```
Arg Leu Xaa Phe
  1
```

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (1)
<223> OTHER INFORMATION: Xaa = epsilon-aminohexanoic acid

<400> SEQUENCE: 186

```
Xaa His Ala Lys Arg Arg Leu Ile Phe
  1               5
```

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 187

```
Thr Ser Met Thr Asp Phe Tyr His Ser Lys Arg Arg Leu Ile Phe Ser
  1               5                  10                  15

Lys Arg Lys Pro
```

```
<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 188

Thr Ser Met Thr Asp Phe Tyr His Ser Lys Arg Arg
 1               5                  10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 189

Ser Met Thr Asp Phe Tyr His Ser Lys Arg Arg Leu
 1               5                  10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 190

Met Thr Asp Phe Tyr His Ser Lys Arg Arg Leu Ile
 1               5                  10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 191

Thr Asp Phe Tyr His Ser Lys Arg Arg Leu Ile Phe
 1               5                  10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
```

```
<223> OTHER INFORMATION: Synthesised with free amino terminus and as the
      C-terminal Carboxamide

<400> SEQUENCE: 192

Asp Phe Tyr His Ser Lys Arg Arg Leu Ile Phe Ser
 1               5                  10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 193

Phe Tyr His Ser Lys Arg Arg Leu Ile Phe Ser Lys
 1               5                  10

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 194

Tyr His Ser Lys Arg Arg Leu Ile Phe Ser Lys Arg
 1               5                  10

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 195

His Ser Lys Arg Arg Leu Ile Phe Ser Lys Arg Lys
 1               5                  10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 196

Ser Lys Arg Arg Leu Ile Phe Ser Lys Arg Lys Pro
 1               5                  10

<210> SEQ ID NO 197
<211> LENGTH: 12
```

```
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 197

Ala Phe Tyr His Ser Lys Arg Arg Leu Ile Phe Ser
 1               5                  10

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 198

Asp Ala Tyr His Ser Lys Arg Arg Leu Ile Phe Ser
 1               5                  10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 199

Asp Phe Ala His Ser Lys Arg Arg Leu Ile Phe Ser
 1               5                  10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 200

Asp Phe Tyr Ala Ser Lys Arg Arg Leu Ile Phe Ser
 1               5                  10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 201
```

```
Asp Phe Tyr His Ala Lys Arg Arg Leu Ile Phe Ser
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 202

Asp Phe Tyr His Ser Ala Arg Arg Leu Ile Phe Ser
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 203

Asp Phe Tyr His Ser Lys Ala Arg Leu Ile Phe Ser
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 204

Asp Phe Tyr His Ser Lys Arg Ala Leu Ile Phe Ser
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 205

Asp Phe Tyr His Ser Lys Arg Arg Ala Ile Phe Ser
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
```

```
<220> FEATURE:
<223> OTHER INFORMATION: Synthesised with free amino terminus and as the
      C-terminal Carboxamide

<400> SEQUENCE: 206

Asp Phe Tyr His Ser Lys Arg Arg Leu Ala Phe Ser
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 207

Asp Phe Tyr His Ser Lys Arg Arg Leu Ile Ala Ser
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 208

Asp Phe Tyr His Ser Lys Arg Arg Leu Ile Phe Ala
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 209

Phe Tyr His Ser Lys Arg Arg Leu Ile Phe Ser
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 210

Tyr His Ser Lys Arg Arg Leu Ile Phe Ser
1               5                   10

<210> SEQ ID NO 211
```

```
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 211

His Ser Lys Arg Arg Leu Ile Phe Ser
 1               5

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 212

Asp Phe Tyr Ala Ser Lys Arg Arg Leu Ile Phe
 1               5                  10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 213

Asp Phe Tyr His Ser Lys Arg Arg Leu Ile
 1               5                  10

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 214

Asp Phe Tyr His Ser Lys Arg Arg Leu
 1               5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 215
```

```
Asp Phe Tyr His Ser Lys Arg Arg
  1               5
```

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 216

```
Asp Phe Tyr His Ser Lys Arg
  1               5
```

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 217

```
Asp Phe Tyr His Ser Lys
  1               5
```

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 218

```
Phe Tyr His Ser Lys Arg Arg Leu Ile Phe
  1               5                  10
```

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 219

```
Phe Tyr His Ser Lys Arg Arg Leu Ile
  1               5
```

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: p21 derived

```
        peptide
<220> FEATURE:
<223> OTHER INFORMATION: Synthesised with free amino terminus and as the
      C-terminal Carboxamide

<400> SEQUENCE: 220

Phe Tyr His Ser Lys Arg Arg Leu
 1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 221

Phe Tyr His Ser Lys Arg Arg
 1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 222

Phe Tyr His Ser Lys Arg
 1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 223

Tyr His Ser Lys Arg Arg Leu Ile Phe
 1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 224

Tyr His Ser Lys Arg Arg Leu Ile
 1               5
```

```
<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 225

Tyr His Ser Lys Arg Arg Leu
 1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 226

Tyr His Ser Lys Arg Arg
 1               5

<210> SEQ ID NO 227
<211> LENGTH: 5
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 227

Tyr His Ser Lys Arg
 1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 228

His Ser Lys Arg Arg Leu Ile Phe
 1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
```

```
<400> SEQUENCE: 229

Ser Lys Arg Arg Leu Ile Phe
  1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 230

His Ser Lys Arg Arg Leu Ile
  1               5

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 231

His Ser Lys Arg Arg Leu
  1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 232

Lys Arg Arg Leu Ile Phe Ser Lys
  1               5

<210> SEQ ID NO 233
<211> LENGTH: 4
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<221> NAME/KEY: SITE
<222> LOCATION: 1, 2
<223> OTHER INFORMATION: Xaa = any basic amino acid

<400> SEQUENCE: 233

Xaa Xaa Arg Leu
  1

<210> SEQ ID NO 234
<211> LENGTH: 8
<212> TYPE: PRT
<213> ORGANISM: Artificial Sequence
```

```
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: 3
<223> OTHER INFORMATION: Xaa = 2-Aminobutyric acid

<400> SEQUENCE: 234

Lys Ala Xaa Arg Arg Leu Ile Phe
  1               5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 235

His Ser Lys Arg Arg Leu Phe Gly
  1               5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 236

His Ser Lys Arg Arg Leu Asp Leu
  1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide

<400> SEQUENCE: 237

His Ala Lys Arg Arg Leu Phe Gly
  1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
```

```
<400> SEQUENCE: 238

Pro Val Lys Arg Arg Leu Asp Leu
 1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: p107
      peptide
<220> FEATURE:
<223> OTHER INFORMATION: Synthesised with free amino terminus and as the
      C-terminal Carboxamide

<400> SEQUENCE: 239

Ser Ala Lys Arg Arg Leu Phe Gly
 1               5

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: 3
<223> OTHER INFORMATION: Xaa = 2-Aminobutyric acid

<400> SEQUENCE: 240

Lys Ala Xaa Arg Arg Leu Phe Gly
 1               5

<210> SEQ ID NO 241
<211> LENGTH: 12
<212> TYPE: PRT
<213> ORGANISM: Artificial Sequence
<220> FEATURE:
<221> NAME/KEY: SITE
<222> LOCATION: (1)
<223> OTHER INFORMATION: Xaa = e-Aminohexanoic acid
<220> FEATURE:
<223> OTHER INFORMATION: Description of Artificial Sequence: Immobilised
      peptide
<220> FEATURE:
<223> OTHER INFORMATION: Synthesised with free amino terminus and as the
      C-terminal Carboxamide

<400> SEQUENCE: 241

Xaa Asp Phe Tyr His Ser Lys Arg Arg Leu Ile Phe
 1               5                   10

<210> SEQ ID NO 242
<211> LENGTH: 11
<212> TYPE: PRT
<213> ORGANISM: Artificial Sequence
<220> FEATURE:
<223> OTHER INFORMATION: Description of Artificial Sequence: pRb-derived
      peptide
<220> FEATURE:
<223> OTHER INFORMATION: Synthesised with free amino terminus and as the
      C-terminal Carboxamide

<400> SEQUENCE: 242

Asp Phe Tyr His Ala Lys Arg Arg Leu Ile Phe
```

-continued

```
                 1               5                  10
```

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: pRb-derived
      peptide
<220> FEATURE:
<223> OTHER INFORMATION: Synthesised with free amino terminus and as the
      C-terminal Carboxamide

<400> SEQUENCE: 243

```
Ser Asn Pro Pro Lys Pro Leu Lys Lys Leu Arg Phe Asp Ile Glu
 1               5                  10                  15
```

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: pRb-derived
      peptide
<220> FEATURE:
<223> OTHER INFORMATION: Synthesised with free amino terminus and as the
      C-terminal Carboxamide

<400> SEQUENCE: 244

```
Lys Pro Leu Lys Lys Leu Arg Phe
 1               5
```

<210> SEQ ID NO 245
<211> LENGTH: 9
<212> TYPE: PRT
<213> ORGANISM: Artificial Sequence
<220> FEATURE:
<221> NAME/KEY: SITE
<222> LOCATION: (1)
<223> OTHER INFORMATION: Xaa = e-Aminohexanoic acid
<220> FEATURE:
<223> OTHER INFORMATION: Description of Artificial Sequence: Immobilised
      peptide
<220> FEATURE:
<223> OTHER INFORMATION: Synthesised with free amino terminus and as the
      C-terminal Carboxamide

<400> SEQUENCE: 245

```
Xaa Lys Pro Leu Lys Lys Leu Arg Phe
 1               5
```

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (2)
<223> OTHER INFORMATION: Xaa = D- Ala

<400> SEQUENCE: 246

```
His Xaa Lys Arg Arg Leu Ile Phe
 1               5
```

```
<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (3)
<223> OTHER INFORMATION: Xaa = D- Lys

<400> SEQUENCE: 247

His Ala Xaa Arg Arg Leu Ile Phe
  1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = D-Arg

<400> SEQUENCE: 248

His Ala Lys Xaa Arg Leu Ile Phe
  1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = D-Arg

<400> SEQUENCE: 249

His Ala Lys Arg Xaa Leu Ile Phe
  1               5

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = D-Ile

<400> SEQUENCE: 250
```

His Ala Lys Arg Arg Leu Xaa Phe
 1               5

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = D-Phe

<400> SEQUENCE: 251

His Ala Lys Arg Arg Leu Ile Xaa
 1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with N-terminal t-butyloxycarbonyl
<220> FEATURE:
<221> NAME/KEY: SITE
<222> LOCATION: (1)
<223> OTHER INFORMATION: Xaa = trityl-His
<220> FEATURE:
<221> NAME/KEY: SITE
<222> LOCATION: (2)
<223> OTHER INFORMATION: Xaa = But-Ala or But-Ser
<220> FEATURE:
<221> NAME/KEY: SITE
<222> LOCATION: (3)
<223> OTHER INFORMATION: Xaa = t-butyloxycarbonyl-Lys
<220> FEATURE:
<221> NAME/KEY: SITE
<222> LOCATION: (4)
<223> OTHER INFORMATION: Xaa = 2,2,4,6,7-Pentamethyldihydrobenzofuran-
      5-sulfonyl Arg
<220> FEATURE:
<221> NAME/KEY: SITE
<222> LOCATION: (5)
<223> OTHER INFORMATION: Xaa = 2,2,4,6,7-Pentamethyldihydrobenzofuran-
      5-sulfonyl Arg

<400> SEQUENCE: 252

Xaa Xaa Xaa Xaa Xaa Leu Ile
 1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with free amino terminus and as the
      C-terminal Carboxamide
<220> FEATURE:
<221> NAME/KEY: SITE
<222> LOCATION: (8)
<223> OTHER INFORMATION: Xaa = p-Fluorophnylalanine

```
<400> SEQUENCE: 253

Ala Lys Arg Arg Leu Ile Xaa
 1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: p21 derived
      peptide
<220> FEATURE:
<223> OTHER INFORMATION: Synthesised with N-terminal t-butyloxycarbonyl
<220> FEATURE:
<221> NAME/KEY: SITE
<222> LOCATION: (1)
<223> OTHER INFORMATION: Xaa = t-butyloxycarbonyl-His
<220> FEATURE:
<221> NAME/KEY: SITE
<222> LOCATION: (3)
<223> OTHER INFORMATION: Xaa = t-butyloxycarbonyl-Lys
<220> FEATURE:
<221> NAME/KEY: SITE
<222> LOCATION: (4)
<223> OTHER INFORMATION: Xaa = 2,2,5,7,8-Pentamethylchroman-6-sulfonyl
      Arg
<220> FEATURE:
<221> NAME/KEY: SITE
<222> LOCATION: (5)
<223> OTHER INFORMATION: Xaa = 4-methyltrityl-Lys

<400> SEQUENCE: 254

Xaa Ala Xaa Xaa Xaa Leu Phe Gly
 1               5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 255

Ala Ala Lys Arg Arg Leu Phe Gly
 1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = Homoarginine

<400> SEQUENCE: 256

Ala Ala Lys Xaa Arg Leu Phe Gly
 1               5

<210> SEQ ID NO 257
<211> LENGTH: 8
```

```
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 257

Ala Ala Lys Ser Arg Leu Phe Gly
  1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (4)
<223> OTHER INFORMATION: Xaa = Homoserine

<400> SEQUENCE: 258

Ala Ala Lys Xaa Arg Leu Phe Gly
  1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 259

Ala Ala Lys Arg Lys Leu Phe Gly
  1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (5)
<223> OTHER INFORMATION: Orn

<400> SEQUENCE: 260

Ala Ala Lys Arg Xaa Leu Phe Gly
  1               5

<210> SEQ ID NO 261
<211> LENGTH: 8
<212> TYPE: PRT
<213> ORGANISM: Artificial Sequence
<220> FEATURE:
```

```
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 261

Ala Ala Lys Arg Gln Leu Phe Gly
 1               5

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (5)
<223> OTHER INFORMATION: Xaa = Homoserine

<400> SEQUENCE: 262

Ala Ala Lys Arg Xaa Leu Phe Gly
 1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 263

Ala Ala Lys Arg Thr Leu Phe Gly
 1               5

<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: MOD_RES
<222> LOCATION: (5)
<223> OTHER INFORMATION: Norvaline

<400> SEQUENCE: 264

Ala Ala Lys Arg Xaa Leu Phe Gly
 1               5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
```

<223> OTHER INFORMATION: Synthesised with free amino terminus and as the
      C-terminal Carboxamide

<400> SEQUENCE: 265

Ala Ala Lys Arg Arg Met Phe Gly
 1               5

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 266

Ala Ala Lys Arg Arg Ala Phe Gly
 1               5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = Homophenylalanine

<400> SEQUENCE: 267

Ala Ala Lys Arg Arg Xaa Phe Gly
 1               5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (6)
<223> OTHER INFORMATION: Xaa = Hle

<400> SEQUENCE: 268

Ala Ala Lys Arg Arg Xaa Phe Gly
 1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:

```
<221> NAME/KEY: SITE
<222> LOCATION: (6)
<223> OTHER INFORMATION: Xaa = allo-Isoleucine

<400> SEQUENCE: 269

Ala Ala Lys Arg Arg Xaa Phe Gly
  1               5

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 1,2,3,4-Tetrahydroisoquinoline-3-
      carboxylic acid

<400> SEQUENCE: 270

Ala Ala Lys Arg Arg Leu Xaa Gly
  1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = Phenylglycine

<400> SEQUENCE: 271

Ala Ala Lys Arg Arg Leu Xaa Gly
  1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Fluorophenylalanine

<400> SEQUENCE: 272

Ala Ala Lys Arg Arg Leu Xaa Gly
  1               5

<210> SEQ ID NO 273
<211> LENGTH: 8
<212> TYPE: PRT
<213> ORGANISM: Artificial Sequence
<220> FEATURE:
```

```
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Iodophenylalanine

<400> SEQUENCE: 273

Ala Ala Lys Arg Arg Leu Xaa Gly
 1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 2-Thienylalanine

<400> SEQUENCE: 274

Ala Ala Lys Arg Arg Leu Xaa Gly
 1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 3-Pyridylalanine

<400> SEQUENCE: 275

Ala Ala Lys Arg Arg Leu Xaa Gly
 1               5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = m,p-Dichlorophenylalanine

<400> SEQUENCE: 276

Ala Ala Lys Arg Arg Leu Xaa Gly
 1               5
```

```
<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = p-Chlorophenylalanine

<400> SEQUENCE: 277

Ala Ala Lys Arg Arg Leu Xaa Gly
 1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = m-Chlorophenylalanine

<400> SEQUENCE: 278

Ala Ala Lys Arg Arg Leu Xaa Gly
 1               5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = o-Chlorophenylalanine

<400> SEQUENCE: 279

Ala Ala Lys Arg Arg Leu Xaa Gly
 1               5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 1-Naphthylalanine

<400> SEQUENCE: 280
```

```
Ala Ala Lys Arg Arg Leu Xaa Gly
  1               5
```

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 2-Naphthylalanine

<400> SEQUENCE: 281

```
Ala Ala Lys Arg Arg Leu Xaa Gly
  1               5
```

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide
<220> FEATURE:
<221> NAME/KEY: SITE
<222> LOCATION: (7)
<223> OTHER INFORMATION: Xaa = 2-Indolecarboxylic acid

<400> SEQUENCE: 282

```
Ala Ala Lys Arg Arg Leu Xaa Gly
  1               5
```

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 283

```
Ala Ala Lys Arg Arg Leu Phe Asp
  1               5
```

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 284

```
Ala Ala Lys Arg Arg Leu Phe Glu
  1               5
```

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 285

Ala Ala Lys Arg Arg Leu Phe Ser
 1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 286

Ala Ala Lys Arg Arg Leu Phe Asn
 1               5

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 287

Ala Ala Lys Arg Arg Leu Phe Gln
 1               5

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Peptide
      analogue
<220> FEATURE:
<223> OTHER INFORMATION: Synthesised with free amino terminus and as the
      C-terminal Carboxamide

<400> SEQUENCE: 288

Ala Ala Lys Arg Arg Leu Phe Lys
 1               5

<210> SEQ ID NO 289
<211> LENGTH: 4
<212> TYPE: PRT
<213> ORGANISM: Artificial Sequence
<220> FEATURE:
<223> OTHER INFORMATION: Description of Artificial Sequence: p27
      derived peptide

<400> SEQUENCE: 289

Asn Leu Phe Gly
 1

<210> SEQ ID NO 290
<211> LENGTH: 8
<212> TYPE: PRT
<213> ORGANISM: Artificial Sequence
<220> FEATURE:
<223> OTHER INFORMATION: p21 derived peptide
<220> FEATURE:
<221> NAME/KEY: VARIANT
<222> LOCATION: 3
<223> OTHER INFORMATION: Xaa = 2-Aminobutyric acid

<400> SEQUENCE: 290

Ala Ala Xaa Arg Ser Leu Ile Gly
 1               5

<210> SEQ ID NO 291
<211> LENGTH: 8
<212> TYPE: PRT
<213> ORGANISM: Artificial Sequence
<220> FEATURE:
<223> OTHER INFORMATION: p21 derived peptide
<220> FEATURE:
<221> NAME/KEY: VARIANT
<222> LOCATION: 3
<223> OTHER INFORMATION: Xaa = 2-Aminobutyric acid
<220> FEATURE:
<221> NAME/KEY: VARIANT
<222> LOCATION: 7
<223> OTHER INFORMATION: Xaa = meta-chlorophenylalanine
<220> FEATURE:
<221> NAME/KEY: VARIANT
<222> LOCATION: 8
<223> OTHER INFORMATION: Xaa = para-fluorophenylaline

<400> SEQUENCE: 291

Ala Ala Xaa Arg Ser Leu Xaa Xaa
 1               5

<210> SEQ ID NO 292
<211> LENGTH: 8
<212> TYPE: PRT
<213> ORGANISM: Artificial Sequence
<220> FEATURE:
<223> OTHER INFORMATION: p21 derived peptide
<220> FEATURE:
<221> NAME/KEY: VARIANT
<222> LOCATION: 3
<223> OTHER INFORMATION: Xaa = 2-Aminobutyric acid
<220> FEATURE:
<221> NAME/KEY: VARIANT
<222> LOCATION: 7
<223> OTHER INFORMATION: Xaa = meta-chlorophenylalanine

<400> SEQUENCE: 292

Ala Ala Xaa Arg Ser Leu Xaa Gly
 1               5

<210> SEQ ID NO 293
<211> LENGTH: 5
<212> TYPE: PRT
<213> ORGANISM: Artificial Sequence
<220> FEATURE:
<223> OTHER INFORMATION: p21 derived peptide
<220> FEATURE:
<221> NAME/KEY: VARIANT
<222> LOCATION: 2
<223> OTHER INFORMATION: Xaa = Arg, Ser or Lys
<220> FEATURE:

```
<221> NAME/KEY: VARIANT
<222> LOCATION: 3
<223> OTHER INFORMATION: Xaa = Leu, Ile or Val
<220> FEATURE:
<221> NAME/KEY: VARIANT
<222> LOCATION: 4
<223> OTHER INFORMATION: Xaa = Asp, Ala, Gly or Val
<220> FEATURE:
<221> NAME/KEY: VARIANT
<222> LOCATION: 5
<223> OTHER INFORMATION: Xaa = Phe

<400> SEQUENCE: 293

Arg Xaa Xaa Xaa Xaa
 1               5

<210> SEQ ID NO 294
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 294

Arg Arg Leu Asn Phe
 1               5

<210> SEQ ID NO 295
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 295

Arg Arg Leu Asn Xaa
 1               5

<210> SEQ ID NO 296
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 296

Arg Arg Leu Asn Xaa
 1               5

<210> SEQ ID NO 297
<211> LENGTH: 5
<212> TYPE: PRT
<213> ORGANISM: Artificial Sequence
<220> FEATURE:
```

```
<223> OTHER INFORMATION: p21 derived peptide
<220> FEATURE:
<223> OTHER INFORMATION: Synthesised with free amino terminus and as the
      C-terminal Carboxamide

<400> SEQUENCE: 297

Arg Arg Leu Ala Phe
1               5

<210> SEQ ID NO 298
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 298

Arg Arg Leu Ala Xaa
1               5

<210> SEQ ID NO 299
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 299

Arg Arg Leu Ala Xaa
1               5

<210> SEQ ID NO 300
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 300

Arg Arg Leu Gly Phe
1               5

<210> SEQ ID NO 301
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
```

```
<223> OTHER INFORMATION: Xaa = pFF

<400> SEQUENCE: 301

Arg Arg Leu Gly Xaa
 1               5

<210> SEQ ID NO 302
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 302

Arg Arg Leu Gly Xaa
 1               5

<210> SEQ ID NO 303
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 303

Arg Arg Ile Asn Phe
 1               5

<210> SEQ ID NO 304
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 304

Arg Arg Ile Asn Xaa
 1               5

<210> SEQ ID NO 305
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 305
```

```
Arg Arg Ile Asn Xaa
 1               5

<210> SEQ ID NO 306
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 306

Arg Arg Ile Ala Phe
 1               5

<210> SEQ ID NO 307
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 307

Arg Arg Ile Ala Xaa
 1               5

<210> SEQ ID NO 308
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 308

Arg Arg Ile Ala Xaa
 1               5

<210> SEQ ID NO 309
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 309

Arg Arg Ile Gly Phe
 1               5

<210> SEQ ID NO 310
<211> LENGTH: 5
```

```
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 310

Arg Arg Ile Gly Xaa
1               5

<210> SEQ ID NO 311
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY:
<220> FEATURE:
<221> NAME/KEY: VARIANT
<222> LOCATION: 5
<223> OTHER INFORMATION: Xaa = mClF

<400> SEQUENCE: 311

Arg Arg Ile Gly Xaa
1               5

<210> SEQ ID NO 312
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 312

Arg Arg Val Asn Phe
1               5

<210> SEQ ID NO 313
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY:
<220> FEATURE:
<221> NAME/KEY: VARIANT
<222> LOCATION: 5
<223> OTHER INFORMATION: Xaa = pFF

<400> SEQUENCE: 313

Arg Arg Val Asn Xaa
1               5

<210> SEQ ID NO 314
```

```
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY:
<220> FEATURE:
<221> NAME/KEY: VARIANT
<222> LOCATION: 5
<223> OTHER INFORMATION: Xaa = mClF

<400> SEQUENCE: 314

Arg Arg Val Asn Xaa
1               5

<210> SEQ ID NO 315
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 315

Arg Arg Val Ala Phe
1               5

<210> SEQ ID NO 316
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY:
<220> FEATURE:
<221> NAME/KEY: VARIANT
<222> LOCATION: 5
<223> OTHER INFORMATION: Xaa = pFF

<400> SEQUENCE: 316

Arg Arg Val Ala Xaa
1               5

<210> SEQ ID NO 317
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY:
<220> FEATURE:
<221> NAME/KEY: VARIANT
<222> LOCATION: 5
<223> OTHER INFORMATION: Xaa = mClF

<400> SEQUENCE: 317

Arg Arg Val Ala Xaa
1               5
```

```
<210> SEQ ID NO 318
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 318

Arg Arg Val Gly Phe
1               5

<210> SEQ ID NO 319
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 319

Arg Arg Val Gly Xaa
1               5

<210> SEQ ID NO 320
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 320

Arg Arg Val Gly Xaa
1               5

<210> SEQ ID NO 321
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 321

Arg Ser Leu Asn Phe
1               5

<210> SEQ ID NO 322
<211> LENGTH: 5
<212> TYPE: PRT
<213> ORGANISM: Artificial Sequence
<220> FEATURE:
```

```
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 322

Arg Ser Leu Asn Xaa
1               5

<210> SEQ ID NO 323
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 323

Arg Ser Leu Asn Xaa
1               5

<210> SEQ ID NO 324
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 324

Arg Ser Leu Ala Phe
1               5

<210> SEQ ID NO 325
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 325

Arg Ser Leu Ala Xaa
1               5

<210> SEQ ID NO 326
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
```

```
                   C-terminal Carboxamide
<220> FEATURE:
<221> NAME/KEY: VARIANT
<222> LOCATION: 5
<223> OTHER INFORMATION: Xaa = mClF

<400> SEQUENCE: 326

Arg Ser Leu Ala Xaa
1               5

<210> SEQ ID NO 327
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 327

Arg Ser Leu Gly Phe
1               5

<210> SEQ ID NO 328
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 328

Arg Ser Leu Gly Xaa
1               5

<210> SEQ ID NO 329
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 329

Arg Ser Leu Gly Xaa
1               5

<210> SEQ ID NO 330
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 330
```

Arg Ser Ile Asn Phe
1               5

<210> SEQ ID NO 331
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 331

Arg Ser Ile Asn Xaa
1               5

<210> SEQ ID NO 332
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 332

Arg Ser Ile Asn Xaa
1               5

<210> SEQ ID NO 333
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 333

Arg Ser Ile Ala Phe
1               5

<210> SEQ ID NO 334
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 334

Arg Ser Ile Ala Xaa
1               5

```
<210> SEQ ID NO 335
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 335

Arg Ser Ile Ala Xaa
 1               5

<210> SEQ ID NO 336
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 336

Arg Ser Ile Gly Phe
 1               5

<210> SEQ ID NO 337
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 337

Arg Ser Ile Gly Xaa
 1               5

<210> SEQ ID NO 338
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 338

Arg Ser Ile Gly Xaa
 1               5

<210> SEQ ID NO 339
```

```
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 339

Arg Ser Val Asn Phe
1               5

<210> SEQ ID NO 340
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 340

Arg Ser Val Asn Xaa
1               5

<210> SEQ ID NO 341
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 341

Arg Ser Val Asn Xaa
1               5

<210> SEQ ID NO 342
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 342

Arg Ser Val Ala Phe
1               5

<210> SEQ ID NO 343
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
```

-continued

```
      C-terminal Carboxamide
<220> FEATURE:
<221> NAME/KEY: VARIANT
<222> LOCATION: 5
<223> OTHER INFORMATION: Xaa = pFF

<400> SEQUENCE: 343

Arg Ser Val Ala Xaa
 1               5

<210> SEQ ID NO 344
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 344

Arg Ser Val Ala Xaa
 1               5

<210> SEQ ID NO 345
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 345

Arg Ser Val Gly Phe
 1               5

<210> SEQ ID NO 346
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 346

Arg Ser Val Gly Xaa
 1               5

<210> SEQ ID NO 347
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
```

```
<222> LOCATION: 5
<223> OTHER INFORMATION: Xaa = mClF

<400> SEQUENCE: 347

Arg Ser Val Gly Xaa
 1               5

<210> SEQ ID NO 348
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 348

Arg Lys Leu Asn Phe
 1               5

<210> SEQ ID NO 349
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 349

Arg Lys Leu Asn Xaa
 1               5

<210> SEQ ID NO 350
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 350

Arg Lys Leu Asn Xaa
 1               5

<210> SEQ ID NO 351
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 351

Arg Lys Leu Ala Phe
 1               5
```

```
<210> SEQ ID NO 352
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 352

Arg Lys Leu Ala Xaa
 1               5

<210> SEQ ID NO 353
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 353

Arg Lys Leu Ala Xaa
 1               5

<210> SEQ ID NO 354
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 354

Arg Lys Leu Gly Phe
 1               5

<210> SEQ ID NO 355
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 355

Arg Lys Leu Gly Xaa
 1               5

<210> SEQ ID NO 356
```

```
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 356

Arg Lys Leu Gly Xaa
 1               5

<210> SEQ ID NO 357
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 357

Arg Lys Ile Asn Phe
 1               5

<210> SEQ ID NO 358
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 358

Arg Lys Ile Asn Xaa
 1               5

<210> SEQ ID NO 359
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 359

Arg Lys Ile Asn Xaa
 1               5

<210> SEQ ID NO 360
<211> LENGTH: 5
<212> TYPE: PRT
<213> ORGANISM: Artificial Sequence
```

```
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 360

Arg Lys Ile Ala Phe
1               5

<210> SEQ ID NO 361
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 361

Arg Lys Ile Ala Xaa
1               5

<210> SEQ ID NO 362
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 362

Arg Lys Ile Ala Xaa
1               5

<210> SEQ ID NO 363
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 363

Arg Lys Ile Gly Phe
1               5

<210> SEQ ID NO 364
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
```

```
<222> LOCATION: 5
<223> OTHER INFORMATION: Xaa = pFF

<400> SEQUENCE: 364

Arg Lys Ile Gly Xaa
 1               5

<210> SEQ ID NO 365
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 365

Arg Lys Ile Gly Xaa
 1               5

<210> SEQ ID NO 366
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 366

Arg Lys Val Asn Phe
 1               5

<210> SEQ ID NO 367
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 367

Arg Lys Val Asn Xaa
 1               5

<210> SEQ ID NO 368
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF
```

-continued

```
<400> SEQUENCE: 368

Arg Lys Val Asn Xaa
1               5

<210> SEQ ID NO 369
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 369

Arg Lys Val Ala Phe
1               5

<210> SEQ ID NO 370
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 370

Arg Lys Val Ala Xaa
1               5

<210> SEQ ID NO 371
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 371

Arg Lys Val Ala Xaa
1               5

<210> SEQ ID NO 372
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 372

Arg Lys Val Gly Phe
1               5

<210> SEQ ID NO 373
```

```
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 373

Arg Lys Val Gly Xaa
 1               5

<210> SEQ ID NO 374
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = mClF

<400> SEQUENCE: 374

Arg Lys Val Gly Xaa
 1               5

<210> SEQ ID NO 375
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 5
<223> OTHER INFORMATION: Xaa = pFF

<400> SEQUENCE: 375

Arg Arg Leu Ile Xaa
 1               5

<210> SEQ ID NO 376
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide
<220> FEATURE:
<221> NAME/KEY: VARIANT
<222> LOCATION: 1
<223> OTHER INFORMATION: Xaa = Citrulline
<220> FEATURE:
<221> NAME/KEY: VARIANT
<222> LOCATION: 2
<223> OTHER INFORMATION: Xaa = Citrulline
<220> FEATURE:
<221> NAME/KEY: VARIANT
<222> LOCATION: 5
```

```
<223> OTHER INFORMATION: Xaa = pFF

<400> SEQUENCE: 376

Xaa Xaa Leu Ile Xaa
 1               5

<210> SEQ ID NO 377
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with free amino terminus and as the
      C-terminal Carboxamide

<400> SEQUENCE: 377

Arg Arg Leu Ile Phe
 1               5

<210> SEQ ID NO 378
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 378

Arg Arg Leu Asn Phe
 1               5

<210> SEQ ID NO 379
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 379

Arg Arg Leu Asn Xaa
 1               5

<210> SEQ ID NO 380
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 380

Arg Arg Leu Asn Xaa
 1               5
```

<210> SEQ ID NO 381
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 381

Arg Arg Leu Ala Phe
 1               5

<210> SEQ ID NO 382
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 382

Arg Arg Leu Ala Xaa
 1               5

<210> SEQ ID NO 383
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 383

Arg Arg Leu Ala Xaa
 1               5

<210> SEQ ID NO 384
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 384

Arg Arg Leu Gly Phe
 1               5

<210> SEQ ID NO 385
<211> LENGTH: 5
<212> TYPE: PRT
<213> ORGANISM: Artificial Sequence
<220> FEATURE:
<223> OTHER INFORMATION: p21 derived peptide

```
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 385

Arg Arg Leu Gly Xaa
1               5

<210> SEQ ID NO 386
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 386

Arg Arg Leu Gly Xaa
1               5

<210> SEQ ID NO 387
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 387

Arg Arg Ile Asn Phe
1               5

<210> SEQ ID NO 388
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 388

Arg Arg Ile Asn Xaa
1               5

<210> SEQ ID NO 389
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
```

```
<220> FEATURE:
<221> NAME/KEY: VARIANT
<222> LOCATION: 5
<223> OTHER INFORMATION: Xaa = mClF

<400> SEQUENCE: 389

Arg Arg Ile Asn Xaa
1               5

<210> SEQ ID NO 390
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 390

Arg Arg Ile Ala Phe
1               5

<210> SEQ ID NO 391
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 391

Arg Arg Ile Ala Xaa
1               5

<210> SEQ ID NO 392
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 392

Arg Arg Ile Ala Xaa
1               5

<210> SEQ ID NO 393
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 393
```

```
Arg Arg Ile Gly Phe
 1               5

<210> SEQ ID NO 394
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 394

Arg Arg Ile Gly Xaa
 1               5

<210> SEQ ID NO 395
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 395

Arg Arg Ile Gly Xaa
 1               5

<210> SEQ ID NO 396
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 396

Arg Arg Val Asn Phe
 1               5

<210> SEQ ID NO 397
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 397

Arg Arg Val Asn Xaa
 1               5
```

```
<210> SEQ ID NO 398
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 398

Arg Arg Val Asn Xaa
1               5

<210> SEQ ID NO 399
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 399

Arg Arg Val Ala Phe
1               5

<210> SEQ ID NO 400
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 400

Arg Arg Val Ala Xaa
1               5

<210> SEQ ID NO 401
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 401

Arg Arg Val Ala Xaa
1               5

<210> SEQ ID NO 402
<211> LENGTH: 5
```

```
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 402

Arg Arg Val Gly Phe
 1               5

<210> SEQ ID NO 403
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 403

Arg Arg Val Gly Xaa
 1               5

<210> SEQ ID NO 404
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 404

Arg Arg Val Gly Xaa
 1               5

<210> SEQ ID NO 405
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 405

Arg Ser Leu Asn Phe
 1               5

<210> SEQ ID NO 406
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
```

```
-continued

<220> FEATURE:
<221> NAME/KEY: VARIANT
<222> LOCATION: 5
<223> OTHER INFORMATION: Xaa = pFF

<400> SEQUENCE: 406

Arg Ser Leu Asn Xaa
1               5

<210> SEQ ID NO 407
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 407

Arg Ser Leu Asn Xaa
1               5

<210> SEQ ID NO 408
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 408

Arg Ser Leu Ala Phe
1               5

<210> SEQ ID NO 409
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 409

Arg Ser Leu Ala Xaa
1               5

<210> SEQ ID NO 410
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
```

```
<223> OTHER INFORMATION: Xaa = mClF

<400> SEQUENCE: 410

Arg Ser Leu Ala Xaa
1               5

<210> SEQ ID NO 411
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 411

Arg Ser Leu Gly Phe
1               5

<210> SEQ ID NO 412
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 412

Arg Ser Leu Gly Xaa
1               5

<210> SEQ ID NO 413
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 413

Arg Ser Leu Gly Xaa
1               5

<210> SEQ ID NO 414
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 414

Arg Ser Ile Asn Phe
1               5
```

```
<210> SEQ ID NO 415
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 415

Arg Ser Ile Asn Xaa
1               5

<210> SEQ ID NO 416
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 416

Arg Ser Ile Asn Xaa
1               5

<210> SEQ ID NO 417
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 417

Arg Ser Ile Ala Phe
1               5

<210> SEQ ID NO 418
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 418

Arg Ser Ile Ala Xaa
1               5

<210> SEQ ID NO 419
<211> LENGTH: 5
```

```
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 419

Arg Ser Ile Ala Xaa
1               5

<210> SEQ ID NO 420
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 420

Arg Ser Ile Gly Phe
1               5

<210> SEQ ID NO 421
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 421

Arg Ser Ile Gly Xaa
1               5

<210> SEQ ID NO 422
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 422

Arg Ser Ile Gly Xaa
1               5

<210> SEQ ID NO 423
<211> LENGTH: 5
<212> TYPE: PRT
<213> ORGANISM: Artificial Sequence
<220> FEATURE:
```

```
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 423

Arg Ser Val Asn Phe
 1               5

<210> SEQ ID NO 424
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 424

Arg Ser Val Asn Xaa
 1               5

<210> SEQ ID NO 425
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 425

Arg Ser Val Asn Xaa
 1               5

<210> SEQ ID NO 426
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 426

Arg Ser Val Ala Phe
 1               5

<210> SEQ ID NO 427
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
```

<223> OTHER INFORMATION: Xaa = pFF

<400> SEQUENCE: 427

Arg Ser Val Ala Xaa
1               5

<210> SEQ ID NO 428
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 428

Arg Ser Val Ala Xaa
1               5

<210> SEQ ID NO 429
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 429

Arg Ser Val Gly Phe
1               5

<210> SEQ ID NO 430
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 430

Arg Ser Val Gly Xaa
1               5

<210> SEQ ID NO 431
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 431

Arg Ser Val Gly Xaa
1               5

<210> SEQ ID NO 432
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 432

Arg Lys Leu Asn Phe
1               5

<210> SEQ ID NO 433
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 433

Arg Lys Leu Asn Xaa
1               5

<210> SEQ ID NO 434
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 434

Arg Lys Leu Asn Xaa
1               5

<210> SEQ ID NO 435
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 435

Arg Lys Leu Ala Phe
1               5

<210> SEQ ID NO 436
<211> LENGTH: 5

```
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 436

Arg Lys Leu Ala Xaa
1               5

<210> SEQ ID NO 437
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 437

Arg Lys Leu Ala Xaa
1               5

<210> SEQ ID NO 438
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 438

Arg Lys Leu Gly Phe
1               5

<210> SEQ ID NO 439
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 439

Arg Lys Leu Gly Xaa
1               5

<210> SEQ ID NO 440
<211> LENGTH: 5
<212> TYPE: PRT
<213> ORGANISM: Artificial Sequence
<220> FEATURE:
```

```
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 440

Arg Lys Leu Gly Xaa
 1               5

<210> SEQ ID NO 441
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 441

Arg Lys Ile Asn Phe
 1               5

<210> SEQ ID NO 442
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 442

Arg Lys Ile Asn Xaa
 1               5

<210> SEQ ID NO 443
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 443

Arg Lys Ile Asn Xaa
 1               5

<210> SEQ ID NO 444
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
``` and as the C-teminal Carboxamide

<400> SEQUENCE: 444

Arg Lys Ile Ala Phe
1               5

<210> SEQ ID NO 445
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 445

Arg Lys Ile Ala Xaa
1               5

<210> SEQ ID NO 446
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 446

Arg Lys Ile Ala Xaa
1               5

<210> SEQ ID NO 447
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 447

Arg Lys Ile Gly Phe
1               5

<210> SEQ ID NO 448
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 448

```
Arg Lys Ile Gly Xaa
1               5

<210> SEQ ID NO 449
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 449

Arg Lys Ile Gly Xaa
1               5

<210> SEQ ID NO 450
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 450

Arg Lys Val Asn Phe
1               5

<210> SEQ ID NO 451
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 451

Arg Lys Val Asn Xaa
1               5

<210> SEQ ID NO 452
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 452

Arg Lys Val Asn Xaa
1               5
```

```
<210> SEQ ID NO 453
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 453

Arg Lys Val Ala Phe
 1               5

<210> SEQ ID NO 454
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 454

Arg Lys Val Ala Xaa
 1               5

<210> SEQ ID NO 455
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 455

Arg Lys Val Ala Xaa
 1               5

<210> SEQ ID NO 456
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide

<400> SEQUENCE: 456

Arg Lys Val Gly Phe
 1               5

<210> SEQ ID NO 457
<211> LENGTH: 5
<212> TYPE: PRT
<213> ORGANISM: Artificial Sequence
<220> FEATURE:
<223> OTHER INFORMATION: p21 derived peptide
<220> FEATURE:
```

```
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 457

Arg Lys Val Gly Xaa
 1               5

<210> SEQ ID NO 458
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = mClF

<400> SEQUENCE: 458

Arg Lys Val Gly Xaa
 1               5

<210> SEQ ID NO 459
<211> LENGTH: 5
<212> TYPE: PRT
<213> ORGANISM: Artificial Sequence
<220> FEATURE:
<223> OTHER INFORMATION: p21 derived peptide
<220> FEATURE:
<223> OTHER INFORMATION: Synthesised with amino terminal as acetylated
      and as the C-teminal Carboxamide
<220> FEATURE:
<221> NAME/KEY: VARIANT
<222> LOCATION: 5
<223> OTHER INFORMATION: Xaa = pFF

<400> SEQUENCE: 459

Arg Arg Leu Ile Xaa
 1               5
```